(12) United States Patent
Kühnert et al.

(10) Patent No.: US 9,168,259 B2
(45) Date of Patent: Oct. 27, 2015

(54) SUBSTITUTED 6-AMINO-NICOTINAMIDES AS KCNQ2/3 MODULATORS

(75) Inventors: Sven Kühnert, Düren (DE); Gregor Bahrenberg, Monschau-Konzen (DE); Achim Kless, Aachen (DE); Wolfgang Schröder, Aachen (DE); Simon Lucas, Aachen (DE)

(73) Assignee: GRÜNENTHAL GMBH, Aachen (DE)

( * ) Notice: Subject to any disclaimer, the term of this patent is extended or adjusted under 35 U.S.C. 154(b) by 108 days.

(21) Appl. No.: 13/449,472

(22) Filed: Apr. 18, 2012

(65) Prior Publication Data

US 2012/0258947 A1    Oct. 11, 2012

Related U.S. Application Data

(63) Continuation-in-part of application No. 13/276,464, filed on Oct. 19, 2011, now Pat. No. 8,552,200.

(60) Provisional application No. 61/394,868, filed on Oct. 20, 2010.

(30) Foreign Application Priority Data

Oct. 20, 2010   (EP) ..................................... 10013811

(51) Int. Cl.
| | |
|---|---|
| *A61K 31/5377* | (2006.01) |
| *C07D 413/04* | (2006.01) |
| *A61K 31/541* | (2006.01) |
| *C07D 213/82* | (2006.01) |
| *C07D 401/04* | (2006.01) |
| *C07D 401/14* | (2006.01) |
| *C07D 405/12* | (2006.01) |
| *C07D 413/14* | (2006.01) |
| *A61K 31/455* | (2006.01) |
| *C07D 401/12* | (2006.01) |
| *C07D 417/04* | (2006.01) |

(52) U.S. Cl.
CPC ............. *A61K 31/541* (2013.01); *A61K 31/455* (2013.01); *A61K 31/5377* (2013.01); *C07D 213/82* (2013.01); *C07D 401/04* (2013.01); *C07D 401/12* (2013.01); *C07D 401/14* (2013.01); *C07D 405/12* (2013.01); *C07D 413/04* (2013.01); *C07D 413/14* (2013.01); *C07D 417/04* (2013.01)

(58) Field of Classification Search
CPC .......................... C07D 413/04; A61K 31/5377
USPC .......................................... 514/235.5; 544/124
See application file for complete search history.

(56) References Cited

U.S. PATENT DOCUMENTS

| | | | |
|---|---|---|---|
| 7,625,900 B2 | 12/2009 | Merla et al. | |
| 7,812,020 B2 * | 10/2010 | Tornoe et al. | ............... 514/235.5 |
| 8,178,684 B2 | 5/2012 | Kuhnert et al. | |
| 8,466,181 B2 * | 6/2013 | Thomas | ........................ 514/359 |
| 2002/0128277 A1 | 9/2002 | Dworetzky et al. | |
| 2010/0105722 A1 | 4/2010 | Kuehnert et al. | |
| 2010/0234377 A1 * | 9/2010 | Aicher et al. | .............. 514/235.8 |

FOREIGN PATENT DOCUMENTS

| | | |
|---|---|---|
| DE | 25 13 949 A1 | 10/1976 |
| DE | 2513949 A1 | 10/1976 |
| GB | 791599 A | 3/1958 |
| GB | 896720 A | 5/1962 |
| GB | 1 420 987 | 1/1976 |
| GB | 1420987 | 1/1976 |
| GB | 1495124 | 12/1977 |
| WO | 2002 066036 A1 | 8/2002 |
| WO | 02066036 A1 | 8/2002 |
| WO | 2008 046582 A1 | 4/2008 |
| WO | 2008046582 A1 | 4/2008 |
| WO | 2010046108 A1 | 4/2010 |
| WO | WO2010094644 * | 8/2010 |
| WO | 2010102809 A1 | 9/2010 |
| WO | WO 2012/052167 | 4/2012 |

OTHER PUBLICATIONS

Exhibit I, Starting material Search result, p. 1-25, (2013).*
Improper Markush, Fed. Reg. v.76(27) p. 7162-7715, slide 1, 64-67 (2011).*
Menet et al. "Novel triazolopyridine . . . " CA152-192130 (2010).*
Patani et al. "bioisosterism . . . " p. 3147, 3170 (1966).*
Bosmans et al. "preparation of N-piperidi . . . " CA142:114101 (2005).*
Wickenden et al. "KCNQ potassium . . . " Exp. Opin. Ther. Patents 14(4) [.457-469 (2004).*
Bennett, G.J. and Xie, Y.K., A peripheral mononeuropathy in rat that produces disorders of pain sensation like those seen in man, Pain 1988, 33(1), 87-107.
Kim, S. H. and Chung, J.M., An experimental model for peripheral neuropathy produced by segmental spinal nerve ligation in the rat, Pain 1992, 50(3), 355-363.
Ravin, Louis. Preformulation. Chapter 76. In Remington's Pharmaceutical Sciences, 17th Ed, 1985.
Disanto, Anthony. Bioavailability and Bioequivalency Testing. Chapter 77. In Remington's Pharmaceutical Sciences, 17th Ed, 1985.
Knevel, Adelbert. Separation. Chapter 78. In Remington's Pharmaceutical Sciences, 17th Ed, 1985.
Phillips, G. Briggs. Sterilization. Chapter 79. In Remington's Pharmaceutical Sciences, 17th Ed, 1985.
Siegel, Frederick. Tonicity, Osmoticity, Osmolality, and Osmolarity. Chapter 80. In Remington's Pharmaceutical Sciences, 17th Ed, 1985.
Giles et al. Plastic Packaging Materials. Chapter 81. In Remington's Pharmaceutical Sciences, 17th Ed, 1985.
Lintner, Carl. Stability of Pharmaceutical Products. Chapter 82. In Remington's Pharmaceutical Sciences, 17th Ed, 1985.
Erskine, Jr., Clyde. Quality Assurance and Control. Chapter 83. In Remington's Pharmaceutical Sciences, 17th Ed, 1985.

(Continued)

*Primary Examiner* — Celia Chang
(74) *Attorney, Agent, or Firm* — Norris McLaughlin & Marcus, P.A.

(57) ABSTRACT

Substituted 6-amino-nicotinamides, pharmaceutical compositions containing these compounds and also use of these compounds in the treatment and/or prophylaxis of pain and further diseases and/or disorders.

14 Claims, No Drawings

(56) References Cited

OTHER PUBLICATIONS

Nairn, J.G., Solutions, Emulsion, Suspensions and Extractives. Chapter 84. In Remington's Pharmaceutical Sciences, 17th Ed, 1985.
Avis, Kenneth. Parenteral Preparations. Chapter 85. In Remington's Pharmaceutical Sciences, 17th Ed, 1985.
Turco et al. Intravenous Admixtures. Chapter 86. In Remington's Pharmaceutical Sciences, 17th Ed, 1985.
Mullins, John. Ophthalmic Preparations. Chapter 87. In Remington's Pharmaceutical Sciences, 17th Ed, 1985.
Block, Lawrence. Medicated Applications. Chapter 88. In Remington's Pharmaceutical Sciences, 17th Ed, 1985.
Rippie, Edward. Powders. Chapter 89. In Remington's Pharmaceutical Sciences, 17th Ed, 1985.
King et al. Oral Solid Dosage Forms. Chapter 90. In Remington's Pharmaceutical Sciences, 17th Ed, 1985.
Porter, Stuart. Coating of Pharmaceutical Dosage Forms. Chapter 91. In Remington's Pharmaceutical Sciences, 17th Ed, 1985.
Longer et al. Sustained-Release Drug Delivery Systems. Chapter 92. In Remington's Pharmaceutical Sciences, 17th Ed, 1985.
Sciarra et al. Aerosols. Chapter 93. In Remington's Pharmaceutical Sciences, 17th Ed, 1985.
Passmore et al. KCNQ/M Currents in Sensory Neurons: Significance for Pain Therapy. J. Neurosci. 2003; 23(18): 7227-36.
Blackburn-Munro and Jensen. The anticonvulsant retigabine attenuates nociceptive behaviours in rat models of persistent and neuropathic pain. Eur J Pharmacol. 2003; 460(2-3); 109-16.
Dost et al., The anti-hyperalgesic activity of retigabine is mediated by KCNQ potassium channel activation. Naunyn Schmiedebergs Arch Pharmacol 2004; 369(4): 382-390.
Gribkoff, Valentin. The therapeutic potential of neuronal KCNQ channel modulators Expert Opin Ther Targets 2003; 7 (6): 737-748.
Korsgaard et al. Anxiolytic effects of Maxipost (BMS-204352) and retigabine via activation of neuronal Kv7 channels. J Pharmacol Exp Ther. 2005, 14(1): 282-92.
Wickenden et al. KCNQ potassium channels: drug targets for the treatment of epilepsy and pain. Expert Opin Ther Pat 2004; 14(4): 457-469.
Gribkoff, Valentin. The therapeutic potential of neuronal K V 7 (KCNQ) channel modulators: an update. Expert Opin Ther Targets 2008, 12(5): 565-81.
Miceli et al., Molecular pharmacology and therapeutic potential of neuronal Kv7-modulating drugs. Curr Opin Pharmacol 2008, 8(1): 65-74.
Streng et al., Urodynamic effects of the K+ channel (KCNQ) opener retigabine in freely moving, conscious rats. J Urol 2004; 172: 2054-2058.
Hansen et al., The neuronal KCNQ channel opener retigabine inhibits locomotor activity and reduces forebrain excitatory responses to the psychostimulants cocaine, methylphenidate and phencyclidine. Eur J Pharmacol 2007, 570 (1-3): 77-88.
Dencker et al., Effect of the new antiepileptic drug retigabine in a rodent model of mania. Epilepsy Behav 2008, 12(1): 49-53.
Richter et al., Antidystonic effects of Kv7 (KCNQ) channel openers in the dtsz mutant, an animal model of primary paroxysmal dystonia. Br J Pharmacol 2006, 149(6): 747-53.
D'Amour and Smith. A method for determining loss of pain sensation. J. Pharm. Exp. Ther. 72, 74 79 (1941).
D. Dubuisson et al., The formalin test: a quantitative study of the analgesic effects of morphine, mepiridine, and brain stem stimulation in rats and cats. Pain 1977, 4, 161-174.
De Sarro et al., Influence of retigabine on the anticonvulsant activity of some antiepileptic drugs against audiogenic seizures in DBA/2 mice. Naunyn-Schmiedeberg's Arch. Pharmacol. 2001, 363, 330-336.
Honkanen, "Preparation of Various Sterically Hindered Compounds with Local Anesthetic Activity;" Ann Acad Sci Fen A2 Chem; pp. 5-80, 99; 1960 (English abstract attached).
International Search Report for related PCT/EP2013/001135 mailed Sep. 5, 2013.
SciFinder Search Report I, pp. 1-7 (2014).
SciFinder Search Report II, pp. 1-10 (2014).
SciFinder Search Report III, pp. 1-14 (2014).
SciFinder Search Report IV, pp. 1-55 (2014).
Sigma-Aldrich Catalog, pp. 152 and 3040 (2008).

\* cited by examiner

SUBSTITUTED 6-AMINO-NICOTINAMIDES AS KCNQ2/3 MODULATORS

This application is a continuation-in-part of U.S. Non-Provisional patent application Ser. No. 13/276,464, filed Oct. 19, 2011, now pending, which, in turn, claims priority of U.S. Provisional Patent Application No. 61/394,868, filed Oct. 20, 2010, and European Patent Application No. 10 013 811.4, filed Oct. 20, 2010. The contents of all three prior applications are incorporated herein fully by reference.

The invention relates to substituted 6-amino-nicotinamides, to pharmaceutical compositions containing these compounds and also to these compounds for use in the treatment and/or prophylaxis of pain and further diseases and/or disorders.

The treatment of pain, in particular of neuropathic pain, is of great importance in medicine. There is a worldwide need for effective pain therapies. The urgent need for action for a target-orientated treatment of chronic and non-chronic states of pain appropriate for the patient, by which is to be understood the successful and satisfactory treatment of pain for the patient, is also documented in the large number of scientific works which have recently been published in the field of applied analgesics and of fundamental research into nociception.

A pathophysiological feature of chronic pain is the over-excitability of neurons. Neuronal excitability is influenced decisively by the activity of $K^+$ channels, since these determine decisively the resting membrane potential of the cell and therefore the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarization of the cell membrane and, accompanying this, to a decrease in the electrical excitability of these neurons. KCNQ2/3-expressing neurons of the dorsal root ganglia are involved in the transmission of nociceptive stimuli from the periphery into the spinal marrow (Passmore et al., J. Neurosci. 2003; 23(18): 7227-36).

It has accordingly been possible to detect an analgesic activity in preclinical neuropathy and inflammatory pain models for the KCNQ2/3 agonist retigabine (Blackburn-Munro and Jensen, Eur J Pharmacol. 2003; 460(2-3); 109-16; post et al., Naunyn Schmiedebergs Arch Pharmacol 2004; 369(4): 382-390).

The KCNQ2/3 $K^+$ channel thus represents a suitable starting point for the treatment of pain; in particular of pain selected from the group consisting of chronic pain, acute pain, neuropathic pain, inflammatory pain, visceral pain and muscular pain (Nielsen et al., Eur J Pharmacol. 2004; 487(1-3): 93-103), in particular of neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety (Korsgaard et al., J Pharmacol Exp Ther. 2005, 14(1): 282-92), epilepsy (Wickenden et al., Expert Opin Ther Pat 2004; 14(4): 457-469; Gribkoff, Expert Opin Ther Targets 2008, 12(5): 565-81; Miceli et al., Curr Opin Pharmacol 2008, 8(1): 65-74), urinary incontinence (Streng et al., J Urol 2004; 172: 2054-2058), dependency (Hansen et al., Eur J Pharmacol 2007, 570(1-3): 77-88), mania/bipolar disorders (Dencker et al., Epilepsy Behav 2008, 12(1): 49-53) and dystonia-associated dyskinesias (Richter et al., Br J Pharmacol 2006, 149(6): 747-53).

Substituted compounds that have an affinity for the KCNQ2/3 $K^+$ channel are e.g. known from the prior art (WO 2008/046582, WO 2010/046108, WO 2010/102809 and WO 2002/066036).

DE 25 13 949 and GB 1 420 987 disclose substituted nicotinamides and derivatives thereof as coupling components for the preparation of azo dyes.

There is a demand for further compounds having comparable or better properties, not only with regard to affinity to KCNQ2/3 $K^+$ channels per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example. A weak or non-existent interaction with transporter molecules, which are involved in the ingestion and the excretion of pharmaceutical compositions, is also to be regarded as an indication of improved bioavailability and at most low interactions of pharmaceutical compositions. Furthermore, the interactions with the enzymes involved in the decomposition and the excretion of pharmaceutical compositions should also be as low as possible, as such test results also suggest that at most low interactions, or no interactions at all, of pharmaceutical compositions are to be expected.

In addition, it may be advantageous if the compounds show a high selectivity towards other receptors of the KCNQ family (specificity), e.g. towards KCNQ1, KCNQ3/5 or KCNQ4. A high selectivity may have a positive effect on the side effects profile: for example it is known that compounds which (also) have an affinity to KCNQ1 are likely to have a potential for cardial side effects. Therefore, a high selectivity towards KCNQ1 may be desirable. However, it may also be advantageous for the compounds to show a high selectivity towards other receptors. For instance, it may be advantageous for the compounds to show a low affinity for the hERG ion channel or the L-type calcium ion channel (phenylalkylamine-, benzothiazepin-, dihydropyridine-binding site) since these receptors are known to possibly have a potential for cardial side effects. Further, an improved selectivity towards binding to other endogenic proteins (i.e. receptors or enzymes) may result in a better side effects profile and, consequently to an improved tolerance.

It was therefore an object of the invention to provide new compounds having advantages over the compounds of the prior art. These compounds should be suitable in particular as pharmacological active ingredients in pharmaceutical compositions, preferably in pharmaceutical compositions for the treatment and/or prophylaxis of disorders and/or diseases which are mediated, at least in part, by KCNQ2/3 $K^+$ channels.

That object is achieved by the subject-matter described herein.

It has been found, surprisingly, that substituted compounds of the general formula (I) given below are suitable for the treatment of pain. It has also been found, surprisingly, that substituted compounds of the general formula (I) given below also have an excellent affinity for the KCNQ2/3 $K^+$ channel and are therefore suitable for the prophylaxis and/or treatment of disorders and/or diseases that are mediated at least in part by KCNQ2/3 $K^+$ channels. The substituted compounds thereby act as modulators, i.e. agonists or antagonists, of the KCNQ2/3 $K^+$ channel.

The present invention therefore relates to a substituted compound of general formula (I),

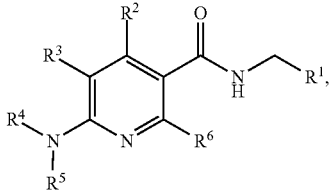

wherein
$R^1$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;
$R^2$ represents F; Cl; Br; I; CN; $CF_3$; C(=O)H; $NO_2$; $OCF_3$; $SCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a S(=O)$_2$—O—$C_{1-4}$-aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;
$R^3$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;
$R^4$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged, preferably in each case bridged, via a $C_{1-8}$ aliphatic group, which in turn may be unsubstituted or mono- or polysubstituted;
on the condition that if $R^4$ denotes a 3 to 10 membered heterocycloaliphatic residue or a heteroaryl, the 3 to 10 membered heterocycloaliphatic residue or the heteroaryl is linked via a carbon atom;
$R^5$ denotes H or a $C_{1-10}$-aliphatic residue, preferably a $C_{1-4}$-aliphatic residue, unsubstituted or mono- or polysubstituted;
or
$R^4$ and $R^5$ form together with the nitrogen atom connecting them a 3 to 10 membered heterocycloaliphatic residue, preferably a 4 to 7 membered heterocycloaliphatic residue, unsubstituted or mono- or polysubstituted, which may optionally be condensed with aryl or heteroaryl, preferably selected from the group consisting of phenyl, pyridyl and thienyl, wherein the aryl or heteroaryl residues condensed in this way can for their part be respectively unsubstituted or mono- or polysubstituted;
$R^6$ represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
on the condition that if $R^6$ denotes a 3 to 10 membered heterocycloaliphatic residue, the 3 to 10 membered heterocycloaliphatic residue is linked via a carbon atom,
or
denotes S—$R^7$, O—$R^8$ or N($R^9R^{10}$),
wherein
$R^7$ and $R^8$ in each case represent a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
on the condition that if $R^7$ or $R^8$ denotes a 3 to 10 membered heterocycloaliphatic residue, the 3 to 10 membered heterocycloaliphatic residue is linked via a carbon atom,
$R^9$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
on the condition that if $R^9$ denotes a 3 to 10 membered heterocycloaliphatic residue, the 3 to 10 membered heterocycloaliphatic residue is linked via a carbon atom;
$R^{10}$ denotes H or a $C_{1-10}$-aliphatic residue, preferably a $C_{1-4}$-aliphatic residue, unsubstituted or mono- or polysubstituted;
or
$R^9$ and $R^{10}$ form together with the nitrogen atom connecting them a 3 to 10 membered heterocycloaliphatic residue, preferably a 4 to 7 membered heterocycloaliphatic residue, unsubstituted or mono- or polysubstituted; which may optionally be condensed with aryl or heteroaryl, wherein the aryl or heteroaryl residues condensed in this way can for their part be respectively unsubstituted or mono- or polysubstituted;
in which an "aliphatic group" and an "aliphatic residue" can in each case be branched or unbranched, saturated or unsaturated,
in which a "cycloaliphatic residue" and a "heterocycloaliphatic residue" can in each case be saturated or unsaturated,
in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue$)_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue$)_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, $NO_2$, $NH_2$,

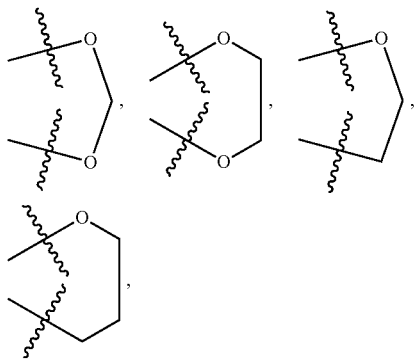

an $NH(C_{1-4}$ aliphatic residue), an $N(C_{1-4}$ aliphatic residue)$_2$, an NH—C(=O)—$C_{1-4}$ aliphatic residue, an NH—S(=O)$_2$—$C_{1-4}$ aliphatic residue, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, C(=O)H, C(=O)OH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, benzyl, aryl, heteroaryl, C(=O)—$NH_2$, a C(=O)—NH($C_{1-4}$ aliphatic residue), and a C(=O)—N($C_{1-4}$ aliphatic residue)$_2$;

with the exception of the following compounds
N-butyl-4-methyl-2,6-bis(methylamino)nicotinamide and
N-butyl-2,6-bis(butylamino)-4-methylnicotinamide,
in the form of the free compounds, the racemate, the enantiomers, diastereomers, mixtures of the enantiomers or diastereomers in any mixing ratio, or of an individual enantiomer or diastereomer, or in the form of the salts of physiologically acceptable acids or bases, or in the form of the solvates, in particular hydrates.

The terms "$C_{1-10}$-aliphatic residue", "$C_{2-10}$-aliphatic residue", "$C_{1-8}$-aliphatic residue", "$C_{1-6}$-aliphatic residue", "$C_{2-6}$-aliphatic residue" and "$C_{1-4}$-aliphatic residue" and "$C_{1-2}$-aliphatic residue" comprise in the sense of this invention acyclic saturated or unsaturated aliphatic hydrocarbon residues, which can be branched or unbranched and also unsubstituted or mono- or polysubstituted, containing 1 to 10, or 2 to 10, or 1 to 8, or 1 to 6, or 2 to 6, or 1 to 4 or 1 to 2 carbon atoms, respectively, i.e. $C_{1-10}$ alkanyls, $C_{2-10}$ alkenyls and $C_{2-10}$ alkynyls as well as $C_{2-10}$ alkanyls as well as $C_{1-8}$ alkanyls, $C_{2-8}$ alkenyls and $C_{2-8}$ alkynyls as well as $C_{1-6}$ alkanyls, $C_{2-6}$ alkenyls, $C_{2-6}$ alkenyls and $C_{2-6}$ alkynyls as well as $C_{1-4}$ alkanyls, $C_{2-4}$ alkenyls and $C_{2-4}$ alkynyls, as well as $C_{1-2}$ alkanyls, $C_2$-alkenyls and $C_2$ alkynyls, respectively. In this case, alkenyls comprise at least one C—C double bond (a C=C-bond) and alkynyls comprise at least one C—C triple bond (a C≡C-bond). Preferably, aliphatic residues are selected from the group consisting of alkanyl (alkyl) and alkenyl residues, more preferably are alkanyl residues. Preferred $C_{1-10}$ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl and n-decyl. Preferred $C_{2-10}$ alkanyl residues are selected from the group consisting of ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl and n-decyl. Preferred $C_{1-8}$ alkanyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl and n-octyl. Preferred $C_{1-6}$ alkanyl residues are selected from the group consisting of methyl, ethyl, n-propyl, 2-propyl, n-butyl, isobutyl, sec.-butyl, tert.-butyl, n-pentyl, isopentyl, neopentyl and n-hexyl. Preferred $C_{2-6}$ alkanyl residues are selected from the group consisting of ethyl, n-propyl, 2-propyl, n-butyl, isobutyl, sec.-butyl, tert.-butyl, n-pentyl, isopentyl, neopentyl and n-hexyl. Preferred $C_{1-4}$ alkanyl residues are selected from the group consisting of methyl, ethyl, n-propyl, 2-propyl, n-butyl, isobutyl, sec.-butyl and tert.-butyl. Preferred $C_{2-10}$ alkenyl residues are selected from the group consisting of ethenyl (vinyl), propenyl (—$CH_2$CH=$CH_2$, —CH=CH—$CH_3$, —C(=$CH_2$)—$CH_3$), butenyl, pentenyl, hexenyl heptenyl, octenyl, nonenyl and decenyl. Preferred $C_{2-8}$ alkenyl residues are selected from the group consisting of ethenyl (vinyl), propenyl (—$CH_2$CH=$CH_2$, —CH=CH—$CH_3$, —C(=$CH_2$)—$CH_3$), butenyl, pentenyl, hexenyl heptenyl and octenyl. Preferred $C_{2-6}$ alkenyl residues are selected from the group consisting of ethenyl (vinyl), propenyl (—$CH_2$CH=$CH_2$, —CH=CH—$CH_3$, —C(=$CH_2$)—$CH_3$), butenyl, pentenyl and hexenyl. Preferred $C_{2-4}$ alkenyl residues are selected from the group consisting of ethenyl (vinyl), propenyl (—$CH_2$CH=$CH_2$, —CH=CH—$CH_3$, —C(=$CH_2$)—$CH_3$) and butenyl. Preferred $C_{2-10}$ alkynyl residues are selected from the group consisting of ethynyl, propynyl (—$CH_2$—C≡CH, —C≡C—$CH_3$), butynyl, pentynyl, hexynyl, heptynyl, octynyl, nonynyl and decynyl. Preferred $C_{2-10}$ alkynyl residues are selected from the group consisting of ethynyl, propynyl (—$CH_2$—C≡CH, —C≡C—CH₃), butynyl, pentynyl, hexynyl, heptynyl and octynyl. Preferred C$_{2-6}$ alkynyl residues are selected from the group consisting of ethynyl, propynyl (—CH₂—C≡CH, —C≡C—CH₃), butynyl, pentynyl and hexynyl Preferred C$_{2-4}$ alkynyl residues are selected from the group consisting of ethynyl, propynyl (—CH₂—C≡CH, —C≡C—CH₃) and butynyl.

The terms "C$_{3-6}$-cycloaliphatic residue" and "C$_{3-10}$-cycloaliphatic residue" mean for the purposes of this invention cyclic aliphatic hydrocarbons containing 3, 4, 5 or 6 carbon atoms and 3, 4, 5, 6, 7, 8, 9 or 10 carbon atoms, respectively, wherein the hydrocarbons in each case can be saturated or unsaturated (but not aromatic), unsubstituted or mono- or polysubstituted. The cycloaliphatic residues can be bound to the respective superordinate general structure via any desired and possible ring member of the cycloaliphatic residue. The cycloaliphatic residues can also be condensed with further saturated, (partially) unsaturated, (hetero)cyclic, aromatic or heteroaromatic ring systems, i.e. with cycloaliphatic, heterocycloaliphatic, aryl or heteroaryl residues which can in turn be unsubstituted or mono- or polysubstituted. C$_{3-10}$ cycloaliphatic residue can furthermore be singly or multiply bridged such as, for example, in the case of adamantyl, bicyclo[2.2.1]heptyl or bicyclo[2.2.2]octyl, or preferably also in the case of bicyclo[1.1.1]pentyl. Preferred C$_{3-10}$ cycloaliphatic residues are selected from the group consisting of cyclopropyl, cyclobutyl, cyclopentyl, cyclohexyl, cycloheptyl, cyclooctyl, cyclononyl, cyclodecyl, adamantyl,

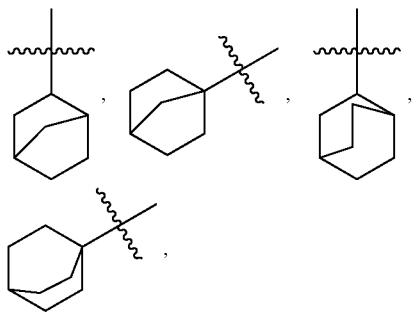

cyclopentenyl, cyclohexenyl, cycloheptenyl and cyclooctenyl. Preferred C$_{3-6}$ cycloaliphatic residues are selected from the group consisting of cyclopropyl, cyclobutyl, cyclopentyl, cyclohexyl, cyclopentenyl and cyclohexenyl.

The terms "3-6-membered heterocycloaliphatic residue", "4-7-membered heterocycloaliphatic residue" and "3-10-membered heterocycloaliphatic residue" mean for the purposes of this invention heterocycloaliphatic saturated or unsaturated (but not aromatic) residues having 3-6, i.e. 3, 4, 5 or 6 ring members, and 4-7, i.e. 4, 5, 6 or 7 ring members, and 3-10, i.e. 3, 4, 5, 6, 7, 8, 9 or 10 ring members, respectively, in which in each case at least one, if appropriate also two or three carbon atoms are replaced by a heteroatom or a heteroatom group each selected independently of one another from the group consisting of O, S, S(=O)₂, N, NH and N(C$_{1-8}$ alkyl), preferably N(CH₃), wherein the ring members can be unsubstituted or mono- or polysubstituted. The heterocycloaliphatic residue can be bound to the superordinate general structure via any desired and possible ring member of the heterocycloaliphatic residue if not indicated otherwise. The heterocycloaliphatic residues can also be condensed with further saturated, (partially) unsaturated (hetero)cycloaliphatic or aromatic or heteroaromatic ring systems, i.e. with cycloaliphatic, heterocycloaliphatic, aryl or heteroaryl residues, which can in turn be unsubstituted or mono- or polysubstituted. The term "condensed" also optionally includes spirocycles, i.e. an at least bicyclic ring system, wherein the heterocycloaliphatic residue is connected through just one (spiro)atom with a further saturated, (partially) unsaturated (hetero)cycloaliphatic or aromatic or heteroaromatic ring system. Example of such spirocycles are e.g.

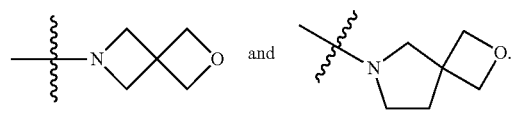

The heterocycloaliphatic residues can furthermore optionally be singly or multiply bridged with a C$_1$- or C$_2$-aliphatic group such as, for example, in the case of

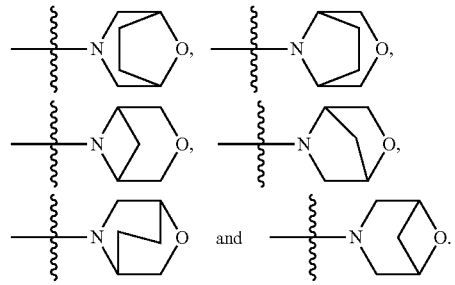

Preferred heterocycloaliphatic residues are selected from the group consisting of azetidinyl, aziridinyl, azepanyl, azocanyl, diazepanyl, dithiolanyl, dihydroquinolinyl, dihydropyrrolyl, dioxanyl, dioxolanyl, dioxepanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, oxazepanyl, pyrrolidinyl, piperazinyl, 4-methylpiperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolo-pyridinyl, thiazolidinyl, tetrahydroimidazo[1,2-a]pyrazinyl, octahydropyrrolo[1,2-a]pyrazinyl and thiomorpholinyl. More preferred heterocycloaliphatic residues are pyrrolidinyl, piperidinyl, oxazepanyl, azetidinyl, morpholinyl, piperazinyl, tetrahydroquinolinyl, tetrahydroisoquinolinyl, dihydroindolinyl, and dihydroisoindolyl. Most preferred heterocycloaliphatic residues are pyrrolidinyl, piperidinyl, oxazepanyl, azetidinyl, tetrahydroquinolinyl, tetrahydroisoquinolinyl, dihydroindolinyl, and dihydroisoindolyl.

The term "aryl" means for the purpose of this invention aromatic hydrocarbons having 6 to 14 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cycloaliphatic, aromatic or heteroaromatic ring systems, i.e. with a cycloaliphatic, heterocycloaliphatic, aryl or heteroaryl residue, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue. The heteroaryl can also be part of a bi- or polycyclic system having up to 14 ring members, wherein the ring system can be formed with further saturated, (partially) unsaturated, (hetero)cycloaliphatic or aromatic or heteroaromatic rings, i.e. with a cycloaliphatic, heterocycloaliphatic, aryl or heteroaryl residue, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl. Furyl, pyridyl, oxazolyl, thiazolyl and thienyl are particularly preferred.

The terms "aryl, heteroaryl, a heterocycloaliphatic residue, or a cycloaliphatic residue bridged via a $C_{1-4}$-aliphatic group or via a $C_{1-8}$-aliphatic group" mean for the purpose of the invention that the expressions "aryl, heteroaryl, heterocycloaliphatic residue and cycloaliphatic residue" have the above-defined meanings and are bound to the respective superordinate general structure via a $C_{1-4}$-aliphatic group or via a $C_{1-8}$-aliphatic group, respectively. The $C_{1-4}$ aliphatic group and the $C_{1-8}$-aliphatic group can in all cases be branched or unbranched, unsubstituted or mono- or polysubstituted. The $C_{1-4}$ aliphatic group can in all cases be furthermore saturated or unsaturated, i.e. can be a $C_{1-4}$ alkylene group, a $C_{2-4}$ alkenylene group or a $C_{2-4}$ alkynylene group. The same applies to a $C_{1-8}$-aliphatic group, i.e. a $C_{1-8}$-aliphatic group can in all cases be furthermore saturated or unsaturated, i.e. can be a $C_{1-8}$-alkylene group, a $C_{2-8}$ alkenylene group or a $C_{2-8}$ alkynylene group. Preferably, the $C_{1-4}$-aliphatic group is a $C_{1-4}$ alkylene group or a $C_{2-4}$ alkenylene group, more preferably a $C_{1-4}$ alkylene group. Preferably, the $C_{1-8}$-aliphatic group is a $C_{1-8}$ alkylene group or a $C_{2-8}$ alkenylene group, more preferably a $C_{1-8}$ alkylene group. Preferred $C_{1-4}$ alkylene groups are selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, and —$C(CH_3)(CH_2CH_3)$—. Preferred $C_{2-4}$ alkenylene groups are selected from the group consisting of —$CH$=$CH$—, —$CH$=$CH$—$CH_2$—, —$C(CH_3)$=$CH_2$—, —$CH$=$CH$—$CH_2$—$CH_2$—, —$CH_2$—$CH$=$CH$—$CH_2$—, —$CH$=$CH$—$CH$=$CH$—, —$C(CH_3)$=$CH$—$CH_2$—, —$CH$=$C(CH_3)$—$CH_2$—, —$C(CH_3)$=$C(CH_3)$— and —$C(CH_2CH_3)$=$CH$—. Preferred $C_{2-4}$ alkynylene groups are selected from the group consisting of —$C$≡$C$—, —$C$≡$C$—$CH_2$—, —$C$≡$C$—$CH_2$—$CH_2$—, —$C$≡$C$—$CH(CH_3)$—, —$CH_2$—$C$≡$C$—$CH_2$— and —$C$≡$C$—$C$≡$C$—. Preferred $C_{1-8}$ alkylene groups are selected from the group consisting of —$CH_2$—, —$CH_2$—$CH_2$—, —$CH(CH_3)$—, —$CH_2$—$CH_2$—$CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—$CH_2$—$CH(CH_3)$—, —$CH(CH_3)$—$CH(CH_3)$—$CH_2$—, —$C(CH_3)_2$—$CH_2$—$CH_2$—, —$CH_2$—$C(CH_3)_2$—$CH_2$—, —$CH(CH_2CH_3)$—$CH_2$—$CH_2$—, —$CH_2$—$CH(CH_2CH_3)$—$CH_2$—, —$C(CH_3)_2$—$CH(CH_3)$—, —$CH(CH_2CH_3)$—$CH(CH_3)$—, —$C(CH_3)(CH_2CH_3)$—$CH_2$—, —$CH(CH_2CH_2CH_3)$—$CH_2$—, —$C(CH_2CH_2CH_3)$—$CH_2$—, —$CH(CH_2CH_2CH_2CH_3)$—, —$C(CH_3)(CH_2CH_2CH_3)$—, —$C(CH_2CH_3)_2$— and —$CH_2$—$(CH_2)_4$—$CH_2$—. Preferred $C_{2-8}$ alkenylene groups are selected from the group consisting of —$CH$=$CH$—, —$CH$=$CH$—$CH_2$—, —$C(CH_3)$=$CH_2$—, —$CH$=$CH$—$CH_2$—$CH_2$—, —$CH_2$—$CH$=$CH$—$CH_2$—, —$CH$=$CH$—$CH$=$CH$—, —$C(CH_3)$=$CH$—$CH_2$—, —$CH$=$C(CH_3)$—$CH_2$—, —$C(CH_3)$=$C(CH_3)$—, —$C(CH_2CH_3)$=$CH$—, —$CH$=$CH$—$CH_2$—$CH_2$—$CH_2$—, —$CH_2$—$CH$=$CH$—$CH_2$—$CH_2$—, —$CH$=$CH$—$CH$—$CH_2$—$CH_2$— and —$CH$=$CH$—$CH$—$CH$=$CH_2$—. Preferred $C_{2-8}$ alkynylene groups are selected from the group consisting of —$C$≡$C$—, —$C$≡$C$—$CH_2$—, —$C$≡$C$—$CH_2$—$CH_2$—, —$C$≡$C$—$CH(CH_3)$—, —$CH_2$—$C$≡$C$—$CH_2$—, —$C$≡$C$—$C$≡$C$—, —$C$≡$C$—$C(CH_3)_2$—, —$C$≡$C$—$CH_2$—$CH_2$—$CH_2$—, —$CH_2$—$C$≡$C$—$CH_2$—$CH_2$—, —$C$≡$C$—$C$≡$C$—$CH_2$— and —$C$≡$C$—$CH_2$—$C$≡$C$.

In relation to "aliphatic residue" and "aliphatic group" the term "mono- or polysubstituted" refers in the sense of this invention, with respect to the corresponding residues or groups, to the single substitution or multiple substitution, e.g. disubstitution, trisubstitution and tetrasubstitution, of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue)$_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$. The term "polysubstituted" with respect to polysubstituted residues and groups includes the polysubstitution of these residues and groups either on different or on the same atoms, for example trisubstituted on the same carbon atom, as in the case of $CF_3$ or $CH_2CF_3$, or at various points, as in the case of $CH(OH)$—$CH$=$CH$—$CHCl_2$. A substituent can if appropriate for its part in turn be mono- or polysubstituted. The multiple substitution can be carried out using the same or using different substituents.

In relation to "cycloaliphatic residue" and "heterocycloaliphatic residue" the term "mono- or polysubstituted" refers in the sense of this invention, with respect to the corresponding residues, to the single substitution or multiple substitution, e.g. disubstitution, trisubstitution and tetrasubstitution, of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue$)_2$, a $NH$—$C$(=$O$)—$C_{1-4}$ aliphatic residue, a $NH$—$S$(=$O$)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, $S$(=$O$)$_2$OH, a $S$(=$O$)$_2$—$C_{1-4}$-aliphatic residue, a $S$(=$O$)$_2$—O—$C_{1-4}$-aliphatic residue, a $S$(=$O$)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$. The term "polysubstituted" with respect to polysubstituted residues and groups includes the polysubstitution of these residues and groups either on different or on the same atoms, for example disubstituted on the same carbon atom, as in the case of 1,1-difluorocyclohexyl, or at various points, as in the case of 1-chloro-3-fluorocyclohexyl. A substituent can if appropriate for its part in turn be mono- or polysubstituted. The multiple substitution can be carried out using the same or using different substituents.

Preferred substituents of "aliphatic residue" and "aliphatic group" are selected from the group consisting of F, Cl, Br, I, $NO_2$, $NH_2$, an $NH(C_{1-4}$ aliphatic residue), an $N(C_{1-4}$ aliphatic residue)$_2$, =O, OH, $OCF_3$, a O—$C_{1-4}$-aliphatic residue, SH, $SCF_3$, a S—$C_{1-4}$-aliphatic residue, a $S$(=$O$)$_2$—$C_{1-4}$-aliphatic residue, a $S$(=$O$)$_2$—NH—$C_{1-4}$-aliphatic residue, CN, $CF_3$, a $C_{1-4}$-aliphatic residue, a C(=O)—$C_{1-4}$-aliphatic residue, a C(=O)—O—$C_{1-4}$-aliphatic residue, $CONH_2$, a C(=O)—NH($C_{1-4}$ aliphatic residue), and a C(=O)—N($C_{1-4}$ aliphatic residue)$_2$.

Preferred substituents of "cycloaliphatic residue" and "heterocycloaliphatic residue" are selected from the group consisting of F, Cl, Br, I, $NO_2$, $NH_2$, an $NH(C_{1-4}$ aliphatic residue), an $N(C_{1-4}$ aliphatic residue)$_2$, =O, OH, $OCF_3$, a O—$C_{1-4}$-aliphatic residue, SH, $SCF_3$, a S—$C_{1-4}$-aliphatic residue, a $S$(=$O$)$_2$—$C_{1-4}$-aliphatic residue, a $S$(=$O$)$_2$—NH—$C_{1-4}$-aliphatic residue, CN, $CF_3$, a $C_{1-4}$-aliphatic residue, a C(=O)—$C_{1-4}$-aliphatic residue, a C(=O)—O—$C_{1-4}$-aliphatic residue, $CONH_2$, a C(=O)—NH($C_{1-4}$ aliphatic residue), and a C(=O)—N($C_{1-4}$ aliphatic residue)$_2$.

In relation to "aryl" and "heteroaryl" the term "mono- or polysubstituted" refers in the sense of this invention to the single substitution or multiple substitution, e.g. disubstitution, trisubstitution and tetrasubstitution, of one or more hydrogen atoms each independently of another by at least one substituent selected from the group consisting of F, Cl, Br, I, $NO_2$, $NH_2$,

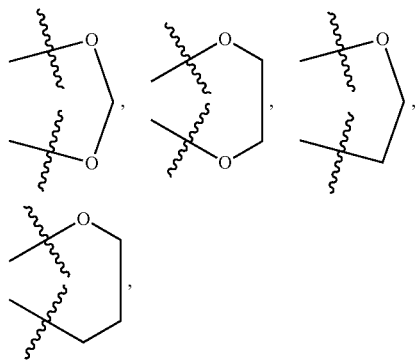

an $NH(C_{1-4}$ aliphatic residue), an $N(C_{1-4}$ aliphatic residue)$_2$, an $NH$—C(=O)—$C_{1-4}$ aliphatic residue, an $NH$—$S$(=$O$)$_2$—$C_{1-4}$ aliphatic residue, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, $S$(=$O$)$_2$OH, a $S$(=$O$)$_2$—$C_{1-4}$-aliphatic residue, a $S$(=$O$)$_2$—O—$C_{1-4}$-aliphatic residue, a $S$(=$O$)$_2$—NH—$C_{1-4}$-aliphatic residue, CN, $CF_3$, C(=O)H, C(=O)OH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, benzyl, aryl, heteroaryl, C(=O)—$NH_2$, a C(=O)—NH($C_{1-4}$ aliphatic residue), and a C(=O)—N($C_{1-4}$ aliphatic residue)$_2$ on one or if appropriate different atoms, wherein a substituent can if appropriate for its part in turn be mono- or polysubstituted. The multiple substitution is carried out employing the same or using different substituents.

Preferred substituents of "aryl" and "heteroaryl" are selected from the group consisting of F, Cl, Br, I, $NO_2$, $NH_2$,

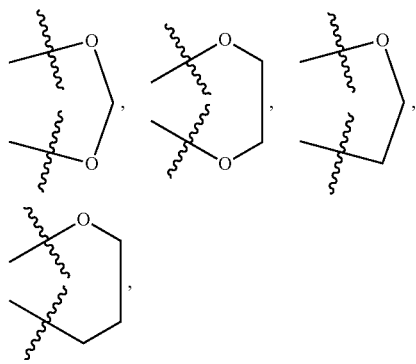

an $NH(C_{1-4}$ aliphatic residue), an $N(C_{1-4}$ aliphatic residue)$_2$, an $NH$—C(=O)—$C_{1-4}$ aliphatic residue, an $NH$—$S$(=$O$)$_2$—$C_{1-4}$ aliphatic residue, OH, $OCF_3$, a O—$C_{1-4}$-aliphatic residue, SH, $SCF_3$, a S—$C_{1-4}$-aliphatic residue, $S$(=$O$)$_2$OH, a $S$(=$O$)$_2$—$C_{1-4}$-aliphatic residue, a $S$(=$O$)$_2$—NH—$C_{1-4}$-aliphatic residue, CN, $CF_3$, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, $CONH_2$, a C(=O)—NH($C_{1-4}$ aliphatic residue), a C(=O)—N($C_{1-4}$ aliphatic residue)$_2$, aryl, preferably phenyl, or benzyl, in each case unsubstituted or mono- or polysubstituted with at least one substituent selected from the group consisting of F, Cl, Br, I, CN, $CF_3$, $CH_3$, $C_2H_5$, iso-propyl, tert.-butyl, C(=O)—OH, C(=O)—$CH_3$, C(=O)—$C_2H_5$, C(=O)—O—$CH_3$ and C(=O)—O—

$C_2H_5$, O—$CH_3$, $OCF_3$, O—$CH_2$—OH, O—$CH_2$—O—$CH_3$, SH, S—$CH_3$, $SCF_3$, $NO_2$, $NH_2$, $N(CH_3)_2$, $N(CH_3)(C_2H_5)$ and $N(C_2H_5)_2$, heteroaryl, preferably pyridyl, thienyl, furyl, thiazolyl or oxazolyl, in each case unsubstituted or mono- or polysubstituted with at least one substituent selected from the group consisting of F, Cl, Br, I, CN, $CF_3$, $CH_3$, $C_2H_5$, isopropyl, tert.-butyl, C(=O)—OH, C(=O)—$CH_3$, C(=O)—$C_2H_5$, C(=O)—O—$CH_3$ and C(=O)—O—$C_2H_5$, O—$CH_3$, $OCF_3$, O—$CH_2$—OH, O—$CH_2$—O—$CH_3$, SH, S—$CH_3$, $SCF_3$, $NO_2$, $NH_2$, $N(CH_3)_2$, $N(CH_3)(C_2H_5)$ and $N(C_2H_5)_2$.

The compounds according to the invention are defined by substituents, for example by $R^1$, $R^2$ and $R^3$ ($1^{st}$ generation substituents) which are for their part if appropriate substituted ($2^{nd}$ generation substituents). Depending on the definition, these substituents of the substituents can for their part be resubstituted ($3^{rd}$ generation substituents). If, for example, $R^1$=a $C_{1-10}$ aliphatic residue ($1^{st}$ generation substituent), then the $C_{1-10}$ aliphatic residue can for its part be substituted, for example with a NH—$C_{1-4}$ aliphatic residue ($2^{nd}$ generation substituent). This produces the functional group $R^1$=($C_{1-10}$ aliphatic residue-NH—$C_{1-4}$ aliphatic residue). The NH—$C_{1-4}$ aliphatic residue can then for its part be resubstituted, for example with Cl ($3^{rd}$ generation substituent). Overall, this produces the functional group $R^1$=$C_{1-10}$ aliphatic residue-NH—$C_{1-4}$ aliphatic residue, wherein the $C_{1-4}$ aliphatic residue of the NH—$C_{1-4}$ aliphatic residue is substituted by Cl.

However, in a preferred embodiment, the $3^{rd}$ generation substituents may not be resubstituted, i.e. there are then no $4^{th}$ generation substituents.

In another preferred embodiment, the $2^{nd}$ generation substituents may not be resubstituted, i.e. there are then not even any $3^{rd}$ generation substituents. In other words, in this embodiment, in the case of general formula (I), for example, the functional groups for $R^1$ to $R^6$ can each if appropriate be substituted; however, the respective substituents may then for their part not be resubstituted.

In some cases, the compounds according to the invention are defined by substituents which are or carry an aryl or heteroaryl residue, respectively unsubstituted or mono- or polysubstituted, or which form together with the carbon atom(s) or heteroatom(s) connecting them, as the ring member or as the ring members, a ring, for example an aryl or heteroaryl, in each case unsubstituted or mono- or polysubstituted. Both these aryl or heteroaryl residues and the (hetero)aromatic ring systems formed in this way can if appropriate be condensed with a cycloaliphatic, preferably a $C_{3-6}$ cycloaliphatic residue, or heterocycloaliphatic residue, preferably a 3 to 6 membered heterocycloaliphatic residue, or with aryl or heteroaryl, e.g. with a $C_{3-6}$ cycloaliphatic residue such as cyclopentyl, or a 3 to 6 membered heterocycloaliphatic residue such as morpholinyl, or an aryl such as phenyl, or a heteroaryl such as pyridyl, wherein the cycloaliphatic or heterocycloaliphatic residues, aryl or heteroaryl residues condensed in this way can for their part be respectively unsubstituted or mono- or polysubstituted.

In some cases, the compounds according to the invention are defined by substituents which are or carry a cycloaliphatic residue or a heterocycloaliphatic residue, respectively, in each case unsubstituted or mono- or polysubstituted, or which form together with the carbon atom(s) or heteroatom(s) connecting them, as the ring member or as the ring members, a ring, for example a cycloaliphatic or a heterocycloaliphatic ring system. Both these cycloaliphatic or heterocycloaliphatic ring systems and the (hetero)cycloaliphatic ring systems formed in this manner can if appropriate be condensed with aryl or heteroaryl, preferably selected from the group consisting of phenyl, pyridyl and thienyl, or with a cycloaliphatic residue, preferably a $C_{3-6}$ cycloaliphatic residue, or a heterocycloaliphatic residue, preferably a 3 to 6 membered heterocycloaliphatic residue, e.g. with an aryl such as phenyl, or a heteroaryl such as pyridyl, or a cycloaliphatic residue such as cyclohexyl, or a heterocycloaliphatic residue such as morpholinyl, wherein the aryl or heteroaryl residues or cycloaliphatic or heterocycloaliphatic residues condensed in this way can for their part be respectively unsubstituted or mono- or polysubstituted.

Within the scope of the present invention, the symbol

used in the formulae denotes a link of a corresponding residue to the respective superordinate general structure.

If a residue occurs multiply within a molecule, then this residue can have respectively different meanings for various substituents: if, for example, both $R^2$ and $R^3$ denote a 3 to 6 membered heterocycloaliphatic residue, then the 3 to 6 membered heterocycloaliphatic residue can e.g. represent morpholinyl for $R^2$ and can represent piperazinyl for $R^3$.

The term "salts of physiologically acceptable acids" refers in the sense of this invention to salts of the respective active ingredient with inorganic or organic acids which are physiologically acceptable—in particular when used in human beings and/or other mammals. Hydrochloride is particularly preferred. Examples of physiologically acceptable acids are: hydrochloric acid, hydrobromic acid, sulphuric acid, methanesulphonic acid, p-toluenesulphonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulphonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred.

The term "salts of physiologically acceptable bases" refers in the sense of this invention to salts of the respective compound according to the invention—as an anion, e.g. upon deprotonation of a suitable functional group—with at least one cation or base—preferably with at least one inorganic cation—which are physiologically acceptable—in particular when used in human beings and/or other mammals. Particularly preferred are the salts of the alkali and alkaline earth metals, in particular (mono-) or (di)sodium, (mono-) or (di)potassium, magnesium or calcium salts, but also ammonium salts $[NH_xR_{4-x}]^+$, in which x=0, 1, 2, 3 or 4 and R represents a branched or unbranched $C_{1-4}$ aliphatic residue.

Particularly preferred is also a compound according to general formula (I), wherein the particular radicals $R^1$-$R^6$ have the meanings described herein in connection with the compounds according to the invention and preferred embodiments thereof with the additional exception of the following compounds
N-ethyl-2,6-bis(butylamino)-4-methylnicotinamide,
N-(2-methoxyethyl)-2,6-bis(2-methoxyethylamino)-4-methylnicotinamide and
N-butyl-2,6-bis(butylamino)-4-propylnicotinamide.

In another particularly preferred embodiment of the compound according to general formula (I) radicals $R^1$, $R^2$, $R^3$, $R^4$, $R^5$ and $R^6$ have the meanings described herein in connection with the compounds according to the invention and preferred embodiments thereof, with the proviso that $R^1$ comprises at least 4 atoms selected from the group consisting of carbon and heteroatoms, preferably at least 4 atoms selected from the group consisting of carbon atoms and heteroatoms selected from the group consisting of N, O and S.

The present invention further relates to a substituted compound of general formula (I),

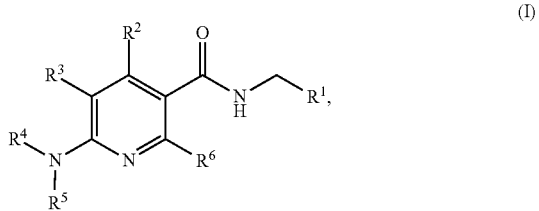

(I)

wherein
$R^1$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

$R^2$ represents F; Cl; Br; I; CN; $CF_3$; C(=O)H; $NO_2$; $OCF_3$; $SCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a S(=O)$_2$—O—$C_{1-4}$-aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^3$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^4$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged, preferably in each case bridged, via a $C_{1-8}$ aliphatic group, which in turn may be unsubstituted or mono- or polysubstituted;

on the condition that if $R^4$ denotes a 3 to 10 membered heterocycloaliphatic residue or a heteroaryl, the 3 to 10 membered heterocycloaliphatic residue or the heteroaryl is linked via a carbon atom;

$R^5$ denotes H or a $C_{1-10}$-aliphatic residue, preferably a $C_{1-4}$-aliphatic residue, unsubstituted or mono- or polysubstituted;
or
$R^4$ and $R^5$ form together with the nitrogen atom connecting them a 3 to 10 membered heterocycloaliphatic residue, preferably a 4 to 7 membered heterocycloaliphatic residue, unsubstituted or mono- or polysubstituted, $R^6$ represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
on the condition that if $R^6$ denotes a 3 to 10 membered heterocycloaliphatic residue, the 3 to 10 membered heterocycloaliphatic residue is linked via a carbon atom,
or
denotes S—$R^7$, O—$R^8$ or N($R^9R^{10}$),
wherein
$R^7$ and $R^8$ in each case represent a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
on the condition that if $R^7$ or $R^8$ denotes a 3 to 10 membered heterocycloaliphatic residue, the 3 to 10 membered heterocycloaliphatic residue is linked via a carbon atom, $R^9$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
on the condition that if $R^9$ denotes a 3 to 10 membered heterocycloaliphatic residue, the 3 to 10 membered heterocycloaliphatic residue is linked via a carbon atom;

$R^{10}$ denotes a $C_{1-10}$-aliphatic residue, preferably a $C_{1-4}$-aliphatic residue, unsubstituted or mono- or polysubstituted;
or
$R^9$ and $R^{10}$ form together with the nitrogen atom connecting them a 3 to 10 membered heterocycloaliphatic residue, preferably a 4 to 7 membered heterocycloaliphatic residue, unsubstituted or mono- or polysubstituted;
in which an "aliphatic group" and an "aliphatic residue" can in each case be branched or unbranched, saturated or unsaturated,
in which a "cycloaliphatic residue" and a "heterocycloaliphatic residue" can in each case be saturated or unsaturated,
in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an NH($C_{1-4}$ aliphatic residue), an N($C_{1-4}$ aliphatic residue)$_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C (=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, CN, CF$_3$, CHO, COOH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, C(=O)—NH$_2$, a C(=O)—NH(C$_{1-4}$ aliphatic residue), and a C(=O)—N(C$_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, NO$_2$, NH$_2$, an NH(C$_{1-4}$ aliphatic residue), an N(C$_{1-4}$ aliphatic residue)$_2$, a NH—C(=O)—C$_{1-4}$ aliphatic residue, a NH—S(=O)$_2$—C$_{1-4}$ aliphatic residue, =O, OH, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, CN, CF$_3$, CHO, COOH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, C(=O)—NH$_2$, a C(=O)—NH(C$_{1-4}$ aliphatic residue), and a C(=O)—N(C$_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO$_2$, NH$_2$,

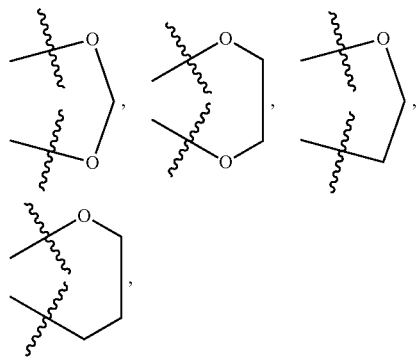

an NH(C$_{1-4}$ aliphatic residue), an N(C$_{1-4}$ aliphatic residue)$_2$, an NH—C(=O)—C$_{1-4}$ aliphatic residue, an NH—S(=O)$_2$—C$_{1-4}$ aliphatic residue, OH, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—NH—C$_{1-4}$-aliphatic residue, CN, CF$_3$, C(=O)H, C(=O)OH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, benzyl, aryl, heteroaryl, C(=O)—NH$_2$, a C(=O)—NH(C$_{1-4}$ aliphatic residue), and a C(=O)—N(C$_{1-4}$ aliphatic residue)$_2$;

in the form of the free compounds, the racemate, the enantiomers, diastereomers, mixtures of the enantiomers or diastereomers in any mixing ratio, or of an individual enantiomer or diastereomer, or in the form of the salts of physiologically acceptable acids or bases, or in the form of the solvates, in particular hydrates.

In another preferred embodiment of the compound according to formula (I), preferred substituents of "cycloaliphatic residue" and "heterocycloaliphatic residue" are selected from the group consisting of F, Cl, Br, I, NO$_2$, NH$_2$, an NH(C$_{1-4}$ aliphatic residue), an N(C$_{1-4}$ aliphatic residue)$_2$, a NH—C(=O)—C$_{1-4}$ aliphatic residue, a NH—S(=O)$_2$—C$_{1-4}$ aliphatic residue, =O, OH, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, CN, CF$_3$, CHO, COOH, a C$_{1-4}$-aliphatic residue, CH$_2$OH, CH$_2$—OCH$_3$, C$_2$H$_4$—OH, C$_2$H$_4$—OCH$_3$ CH$_2$—CF$_3$, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, C(=O)—NH$_2$, a C(=O)—NH(C$_{1-4}$ aliphatic residue), and a C(=O)—N(C$_{1-4}$ aliphatic residue)$_2$.

In another preferred embodiment of the compound according to formula (I), preferred substituents of "aryl" and "heteroaryl" are selected from the group consisting of F, Cl, Br, I, NO$_2$, NH$_2$,

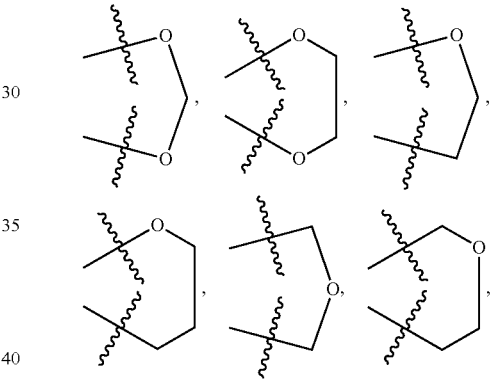

an NH(C$_{1-4}$ aliphatic residue), an N(C$_{1-4}$ aliphatic residue)$_2$, an NH—C(=O)—C$_{1-4}$ aliphatic residue, an NH—S(=O)$_2$—C$_{1-4}$ aliphatic residue, OH, OCFH$_2$, OCF$_2$H, OCF$_3$, a O—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—NH—C$_{1-4}$-aliphatic residue, CN, CF$_3$, CF$_2$H, CHF$_2$, a C$_{1-4}$-aliphatic residue, CH$_2$OH, CH$_2$—OCH$_3$, C$_2$H$_4$—OH, C$_2$H$_4$—OCH$_3$, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, CONH$_2$, a C(=O)—NH(C$_{1-4}$ aliphatic residue), a C(=O)—N(C$_{1-4}$ aliphatic residue)$_2$, aryl, preferably phenyl, or benzyl, in each case unsubstituted or mono- or polysubstituted with at least one substituent selected from the group consisting of F, Cl, Br, I, CN, CF$_3$, CH$_3$, C$_2$H$_5$, iso-propyl, tert.-butyl, C(=O)—OH, C(=O)—CH$_3$, C(=O)—C$_2$H$_5$, C(=O)—O—CH$_3$ and C(=O)—O—C$_2$H$_5$, O—CH$_3$, OCF$_3$, O—CH$_2$—OH, O—CH$_2$—O—CH$_3$, SH, S—CH$_3$, SCF$_3$, NO$_2$, NH$_2$, N(CH$_3$)$_2$, N(CH$_3$)(C$_2$H$_5$) and N(C$_2$H$_5$)$_2$, heteroaryl, preferably pyridyl, thienyl, furyl, thiazolyl or oxazolyl, in each case unsubstituted or mono- or polysubstituted with at least one substituent selected from the group consisting of F, Cl, Br, I, CN, CF$_3$, CH$_3$, C$_2$H$_5$, iso-propyl, tert.-butyl, C(=O)—OH, C(=O)—CH$_3$, C(=O)—C$_2$H$_5$, C(=O)—O—CH$_3$ and C(=O)—O—C$_2$H$_5$, O—CH$_3$, OCF$_3$, O—CH$_2$—OH, O—CH$_2$—O—CH$_3$, SH, S—CH$_3$, SCF$_3$, NO$_2$, NH$_2$, N(CH$_3$)$_2$, N(CH$_3$)(C$_2$H$_5$) and N(C$_2$H$_5$)$_2$.

In yet another preferred embodiment of the compound according to general formula (I) the particular radicals $R^1$-$R^5$ have the meanings described herein in connection with the compounds according to the invention and preferred embodiments thereof and $R^6$ represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^6$ denotes a 3 to 10 membered heterocycloaliphatic residue, the 3 to 10 membered heterocycloaliphatic residue is linked via a carbon atom, or denotes S—$R^7$ or O—$R^8$ wherein $R^7$ and $R^8$ in each case represent a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^7$ or $R^8$ denotes a 3 to 10 membered heterocycloaliphatic residue, the 3 to 10 membered heterocycloaliphatic residue is linked via a carbon atom.

In another preferred embodiment of the present invention the compound according to general formula (I) has the general formula (I-a)

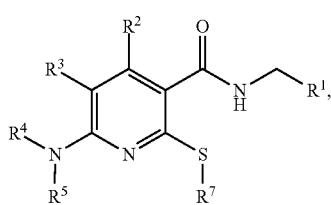

(I-a)

wherein the particular radicals $R^1$-$R^5$ and $R^7$ have the meanings described herein in connection with the compounds according to the invention and preferred embodiments thereof.

In another preferred embodiment of the present invention the compound according to general formula (I) has the general formula (I-b)

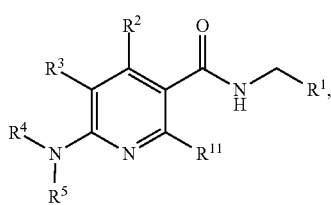

(I-b)

wherein the particular radicals $R^1$-$R^5$ have the meanings described herein in connection with the compounds according to the invention and preferred embodiments thereof, $R^{11}$ represents O—$R^8$ or N($R^9R^{10}$), wherein $R^8$, $R^9$ and $R^{10}$ have the meanings described herein in connection with the compounds according to the invention and preferred embodiments thereof, or represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{11}$ denotes a 3 to 10 membered heterocycloaliphatic residue, the binding is carried out via a carbon atom of the 3 to 10 membered heterocycloaliphatic residue.

In a particular preferred embodiment of the present invention, radical $R^{11}$ in general formula (I-b) and radical $R^6$ in general formula (I) represents O—$R^8$, wherein $R^8$ has the meanings described herein in connection with the compounds according to the invention and preferred embodiments thereof.

In another particular preferred embodiment of the present invention, radical $R^{11}$ in general formula (I-b) and radical $R^6$ in general formula (I) represents N($R^9R^{10}$), wherein $R^9$ and $R^{10}$ have the meanings described herein in connection with the compounds according to the invention and preferred embodiments thereof.

In yet another particular preferred embodiment of the present invention, radical $R^{11}$ in general formula (I-b) and radical $R^6$ in general formula (I) represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{11}$ denotes a 3 to 10 membered heterocycloaliphatic residue, the binding is carried out via a carbon atom of the 3 to 10 membered heterocycloaliphatic residue.

Another preferred embodiment of the compound according to general formula (I) has the general formula (I-c),

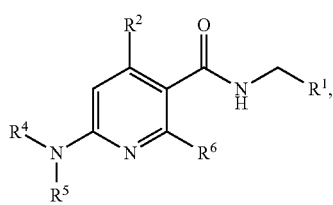

(I-c)

wherein the particular radicals $R^1$, $R^2$, $R^4$, $R^5$ and $R^6$ have the meanings described herein in connection with the compounds according to the invention and preferred embodiments thereof.

Another preferred embodiment of the compound according to general formula (I) has the general formula (I-e) or (I-f),

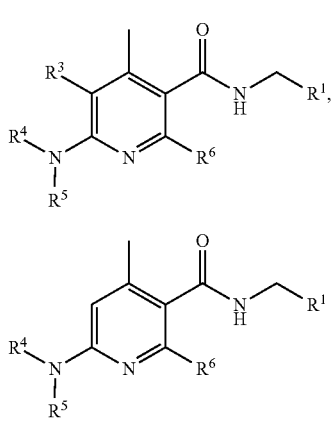

(I-e)

(I-f)

wherein the particular radicals $R^1$, $R^3$, $R^4$, $R^5$ and $R^6$ or $R^1$, $R^4$, $R^5$ and $R^6$, respectively, have the meanings described herein in connection with the compounds according to the invention and preferred embodiments thereof.

In yet another preferred embodiment of the compound according to general formula (I) radicals $R^2$, $R^3$, $R^4$, $R^5$ and $R^6$ have the meanings described herein in connection with the compounds according to the invention and preferred embodiments thereof, and $R^1$ represents aryl or heteroaryl, in each case unsubstituted or mono- or polysubstituted.

In case $R^4$ and $R^5$ of the compound of general formula (I) form together with the nitrogen atom connecting them a 3 to 10 membered heterocycloaliphatic residue, preferably a 4 to 7 membered heterocycloaliphatic residue, unsubstituted or mono- or polysubstituted, said heterocycloaliphatic residue may optionally be condensed with aryl or heteroaryl or with a $C_{3-10}$ cycloaliphatic residue or with a 3 to 10 membered heterocycloaliphatic residue, wherein the aryl, heteroaryl, $C_{3-10}$ cycloaliphatic or 3 to 10 membered heterocycloaliphatic residues condensed in this way can for their part be respectively unsubstituted or mono- or polysubstituted. Preferably, said heterocycloaliphatic residue formed by $R^4$ and $R^5$ of the compound of general formula (I) together with the nitrogen atom connecting them may optionally be condensed with aryl or heteroaryl, wherein the aryl, or heteroaryl, preferably selected from the group consisting of phenyl, pyridyl and thienyl condensed in this way can for their part be respectively unsubstituted or mono- or polysubstituted.

Particularly preferably, in case $R^4$ and $R^5$ form together with the nitrogen atom connecting them a 3 to 10 membered heterocycloaliphatic residue, preferably a 4 to 7 membered heterocycloaliphatic residue, unsubstituted or mono- or polysubstituted, said heterocycloaliphatic residue may optionally be condensed with aryl or heteroaryl, preferably selected from the group consisting of phenyl, pyridyl and thienyl, wherein the aryl or heteroaryl residues condensed in this way can for their part be respectively unsubstituted or mono- or polysubstituted.

In case $R^9$ and $R^{10}$ of the compound of general formula (I) form together with the nitrogen atom connecting them a 3 to 10 membered heterocycloaliphatic residue, preferably a 4 to 7 membered heterocycloaliphatic residue, unsubstituted or mono- or polysubstituted, said heterocycloaliphatic residue may optionally be condensed with aryl or heteroaryl or with a $C_{3-10}$ cycloaliphatic residue or with a 3 to 10 membered heterocycloaliphatic residue, wherein the aryl, heteroaryl, $C_{3-10}$ cycloaliphatic or 3 to 10 membered heterocycloaliphatic residues condensed in this way can for their part be respectively unsubstituted or mono- or polysubstituted. Preferably, said heterocycloaliphatic residue formed by $R^9$ and $R^{10}$ of the compound of general formula (I) together with the nitrogen atom connecting them may optionally be condensed with aryl or heteroaryl, wherein the aryl, or heteroaryl, preferably selected from the group consisting of phenyl, pyridyl and thienyl condensed in this way can for their part be respectively unsubstituted or mono- or polysubstituted.

Particularly preferably, in case $R^9$ and $R^{10}$ form together with the nitrogen atom connecting them a 3 to 10 membered heterocycloaliphatic residue, preferably a 4 to 7 membered heterocycloaliphatic residue, unsubstituted or mono- or polysubstituted, said heterocycloaliphatic residue may optionally be condensed with aryl or heteroaryl, preferably selected from the group consisting of phenyl, pyridyl and thienyl, wherein the aryl or heteroaryl residues condensed in this way can for their part be respectively unsubstituted or mono- or polysubstituted.

Yet another preferred embodiment of present invention is a compound according to general formula (I), wherein $R^1$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, $=$O, an O—$C_{1-4}$-aliphatic residue, $OCF_3$, SH, $SCF_3$, a S—$C_{1-4}$-aliphatic residue, a $S(=O)_2$—$C_{1-4}$-aliphatic residue, $CF_3$, CN, a $C_{1-4}$-aliphatic residue and $C(=O)$—OH, preferably denotes a $C_{1-10}$-aliphatic residue, more preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, $=$O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and $C(=O)$—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, $=$O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, $C(=O)$—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, $=$O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, a S(=O)$_2$—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

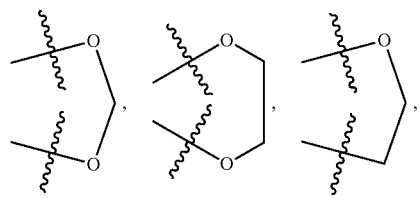

benzyl, phenyl, thienyl, pyridyl, furyl, thiazolyl and oxazolyl, preferably in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

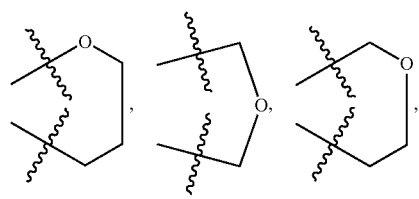

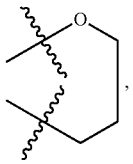

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the aryl or the heteroaryl residue may in each case be optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN and C(=O)—OH, R$^2$ represents F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue, wherein the C$_{1-4}$ aliphatic residue may be in each case be unsubstituted or mono- or polysubstituted; a C$_{3-6}$-cycloaliphatic residue or a 3 to 6 membered heterocycloaliphatic residue, in each case unsubstituted or mono- or polysubstituted and in each case optionally bridged via a C$_{1-4}$ aliphatic group, which in turn may be unsubstituted or mono- or polysubstituted, preferably represents F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue; a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a C$_{1-4}$-aliphatic residue and an O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, $R^3$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue, wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue;

a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, $R^4$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^4$ denotes a 3 to 10 membered heterocycloaliphatic residue, the 3 to 10 membered heterocycloaliphatic residue is linked via a carbon atom, or denotes an aryl or heteroaryl, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

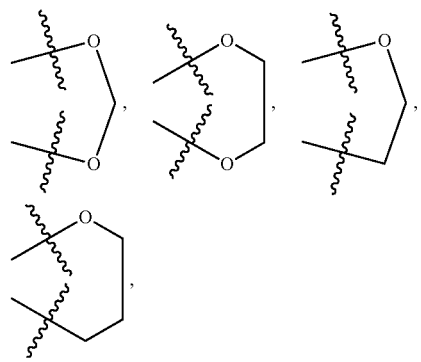

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the aryl or the heteroaryl residue may in each case be optionally bridged, preferably in each case is bridged, via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN and C(=O)—OH, R$^5$ denotes H or a C$_{1-10}$-aliphatic residue, preferably a C$_{1-4}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or R$^4$ and R$^5$ form together with the nitrogen atom connecting them a 3 to 10 membered heterocycloaliphatic residue, preferably a 4 to 7 membered heterocycloaliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, =O, OCF$_3$, CF$_3$ and an unsubstituted O—C$_{1-4}$-aliphatic residue, preferably selected from the group consisting of F, Cl, Br, I, OH, OCF$_3$, CF$_3$ and an unsubstituted O—C$_{1-4}$-aliphatic residue and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the 3 to 10 membered heterocycloaliphatic residue formed by R$^4$ and R$^5$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

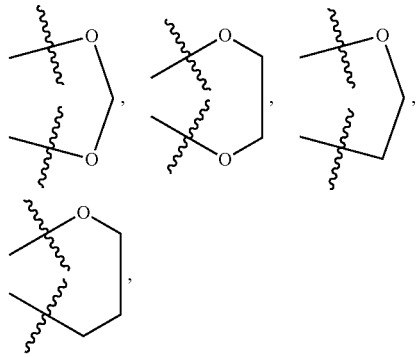

benzyl, phenyl, thienyl, pyridyl, furyl, thiazolyl and oxazolyl, and wherein the 3 to 10 membered heterocycloaliphatic residue formed by R$^4$ and R$^5$ together with the nitrogen atom connecting them may optionally be condensed with a C$_{3-10}$ cycloaliphatic residue or a 3 to 10 membered heterocycloaliphatic residue, wherein the C$_{3-10}$ cycloaliphatic residue or the 3 to 10 membered heterocycloaliphatic residue condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, =O, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue, benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, R$^6$ denotes a C$_{2-10}$-aliphatic residue, preferably a C$_{2-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue and C(=O)—OH,
  wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue,
or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, and C(=O)—OH,
  wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
  and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH,
on the condition that if R$^6$ denotes a 3 to 10 membered heterocycloaliphatic residue, the 3 to 10 membered heterocycloaliphatic residue is linked via a carbon atom,
or
R$^6$ denotes S—R$^7$, O—R$^8$ or N(R$^9$R$^{10}$),
  wherein
  R$^7$ and R$^8$ in each case represent a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue and C(=O)—OH,
    wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue,
  or in each case represent a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue,
    wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
    wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH,
    and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH,
  on the condition that if R$^7$ or R$^8$ denotes a 3 to 10 membered heterocycloaliphatic residue, the 3 to 10 membered heterocycloaliphatic residue is linked via a carbon atom of the 3 to 10 membered heterocycloaliphatic residue,
  R$^9$ denotes a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue, a C(=O)—O—C$_{1-4}$-aliphatic residue, and C(=O)—OH,
    wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue,
  or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C(=O)—O—C$_{1-4}$-aliphatic residue a C$_{3-6}$ cycloaliphatic residue, and a 3 to 6 membered heterocycloaliphatic residue,
    wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
    wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH,
    and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, a C(=O)—O—C$_{1-4}$-aliphatic residue, OCF$_3$, SH, SCF$_3$, a S—C$_{1-4}$ aliphatic residue, CF$_3$, CN, a C$_{1-4}$-aliphatic residue and C(=O)—OH, on the condition that if R$^9$ denotes a 3 to 10 membered heterocycloaliphatic residue, the 3 to 10 membered heterocycloaliphatic residue is linked via a carbon atom of the 3 to 10 membered heterocycloaliphatic residue, R$^{10}$ denotes H or a C$_{1-10}$-aliphatic residue, preferably a C$_{1-4}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH; preferably denotes a C$_{1-10}$-aliphatic residue, more preferably a C$_{1-4}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or R$^9$ and R$^{10}$ form together with the nitrogen atom connecting them a 3 to 10 membered heterocycloaliphatic residue, preferably a 3 to 6 membered heterocycloaliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the 3 to 10 membered heterocycloaliphatic residue formed by R$^9$ and R$^{10}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

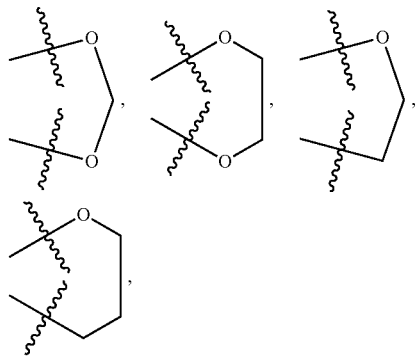

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH.

In a preferred embodiment of the compound according to general formula (I), the residue R$^1$ denotes a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, a S(=O)$_2$—C$_{1-4}$-aliphatic residue, CF$_3$, CN, a C$_{1-4}$-aliphatic residue and C(=O)—OH, preferably denotes a C$_{1-10}$-aliphatic residue, more preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, a S(=O)$_2$—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

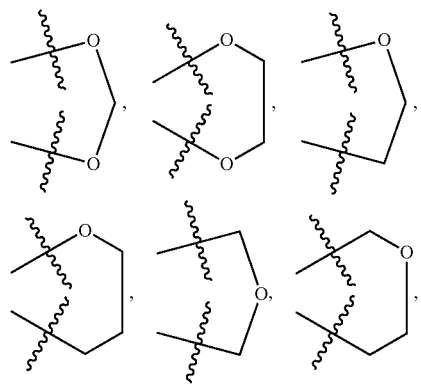

benzyl, phenyl, thienyl, pyridyl, furyl, thiazolyl and oxazolyl, preferably in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

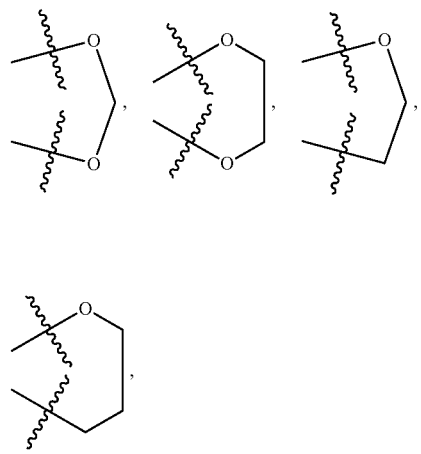

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the aryl or the heteroaryl residue may in each case be optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN and C(=O)—OH.

In a further preferred embodiment of the compound according to general formula (I), the residue $R^1$ represents the partial structure (T1)

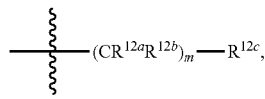
(T1)

wherein
m denotes 0, 1, 2, 3 or 4, preferably denotes 0, 1, 2 or 3, more preferably denotes 0, 1, or 2,
$R^{12a}$ and $R^{12b}$ each independently of one another represent H, F, Cl, Br, I, $NO_2$, $NH_2$, a $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$ aliphatic residue or C(=O)—OH, or together denote =O, preferably each independently of one another represent H, F, Cl, Br, I, $NH_2$, a $NH(C_{1-4}$ aliphatic residue), a $N(C_{1-4}$ aliphatic residue)$_2$, OH, O—$C_{1-4}$ aliphatic residue or a $C_{1-4}$ aliphatic residue, or together denote =O, more preferably each independently of one another represent H, F, Cl, Br, I, OH, an O—$C_{1-4}$ aliphatic residue or a $C_{1-4}$ aliphatic residue, or together denote =O,
even more preferably each independently of one another represent H, F, OH, an O—$C_{1-4}$ aliphatic residue or a $C_{1-4}$ aliphatic residue, or together denote =O, and
$R^{12c}$ denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, a $S(=O)_2$—$C_{1-4}$ aliphatic residue, $CF_3$, CN, a $C_{1-4}$-aliphatic residue and C(=O)—OH, preferably denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue and a 3 to 6 membered heterocycloaliphatic residue, preferably when m is ≠0,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes—preferably when m is 0 or 2, more preferably when m is 0—an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, a $S(=O)_2$—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

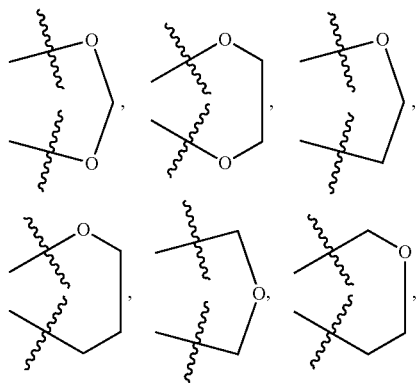

benzyl, phenyl, thienyl, pyridyl, furyl, thiazolyl and oxazolyl, preferably denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

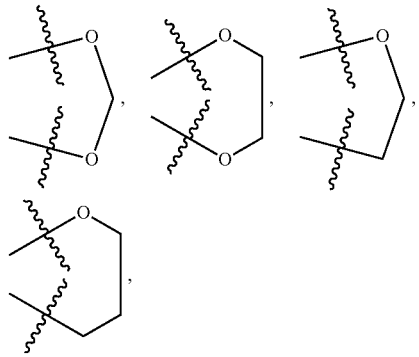

benzyl, phenyl, thienyl, pyridyl, furyl, thiazolyl and oxazolyl, preferably when m is =O,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH.

Preferably,

R$^1$ represents the partial structure (T1),
wherein
m denotes 0, 1, 2 or 3, preferably denotes 0, 1 or 2,
R$^{12a}$ and R$^{12b}$ each independently of one another represent H, F, Cl, Br, I, OH, an O—C$_{1-4}$ aliphatic residue or a C$_{1-4}$ aliphatic residue, or together denote =O,
preferably each independently of one another represent H, F, OH, a O—C$_{1-2}$ aliphatic residue or a C$_{1-2}$ aliphatic residue, or together denote =O, and
R$^{12c}$ denotes a C$_{1-4}$ aliphatic residue, unsubstituted or mono- or polysubstituted with at least one substituent selected from the group consisting of F, Cl, Br, I, OH, =O, an O—C$_{1-4}$ aliphatic residue, OCF$_3$, CF$_3$, CN, a C$_{1-4}$-aliphatic residue, a S(=O)$_2$—C$_{1-4}$-aliphatic residue and C(=O)—OH, preferably denotes a C$_{1-4}$ aliphatic residue, unsubstituted or mono- or polysubstituted with at least one substituent selected from the group consisting of F, Cl, Br, I, OH, =O, an O—C$_{1-4}$ aliphatic residue, OCF$_3$, CF$_3$, a C$_{1-4}$-aliphatic residue and C(=O)—OH,
or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—C$_{1-4}$ aliphatic residue, OCF$_3$, CF$_3$, a C$_{1-4}$-aliphatic residue, C(=O)—OH, a C$_{3-6}$ cycloaliphatic residue, and a 3 to 6 membered heterocycloaliphatic residue,
wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$, a C$_{1-4}$-aliphatic residue and C(=O)—OH,
or denotes—preferably when m is 0 or 2, more preferably when m is 0—an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, SH, SCF$_3$, a S—C$_{1-4}$ aliphatic residue, a S(=O)$_2$—C$_{1-4}$ aliphatic residue, NO$_2$, N(C$_{1-4}$ aliphatic residue)$_2$, CF$_3$, CN, a C$_{1-4}$- aliphatic residue, C(=O)—OH, C(=O)—CH$_3$, C(=O)—C$_2$H$_5$, C(=O)—O—CH$_3$, C(=O)—O—C$_2$H$_5$,

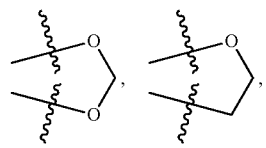 [SMILES: *OCO* ; *CCO*]

a C$_{3-6}$ cycloaliphatic residue, a 3 to 6 membered heterocycloaliphatic residue, benzyl, phenyl, thienyl, pyridyl, furyl, thiazolyl or oxazolyl, preferably denotes an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$, C(=O)—O—C$_2$H$_5$, a C$_{3-6}$ cycloaliphatic residue, a 3 to 6 membered heterocycloaliphatic residue, benzyl, phenyl, thienyl, pyridyl, furyl, thiazolyl or oxazolyl, preferably when m is 0,
wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$,
wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$ a C$_{1-4}$-aliphatic residue and C(=O)—OH.

More preferably,
R$^1$ represents the partial structure (T1),
wherein
m denotes 0, 1, or 2 or 3, preferably denotes 0, 1 or 2,
R$^{12a}$ and R$^{12b}$ each independently of one another represent H, F, Cl, Br, I, OH, an O—C$_{1-4}$ aliphatic residue or a C$_{1-4}$ aliphatic residue, or together denote =O, preferably each independently of one another represent H, F, OH, a O—C$_{1-2}$ aliphatic residue or a C$_{1-2}$ aliphatic residue, or together denote =O, and
R$^{12c}$ denotes a C$_{1-4}$ aliphatic residue, unsubstituted or mono- or polysubstituted with at least one substituent selected from the group consisting of F, Cl, Br, I, OH, an O—C$_{1-4}$ aliphatic residue, CF$_3$, CN, a S(=O)$_2$—C$_{1-4}$-aliphatic residue and a C$_{1-4}$-aliphatic residue, preferably denotes a C$_{1-4}$ aliphatic residue, unsubstituted or mono- or polysubstituted with at least one substituent selected from the group consisting of F, Cl, Br, I, an O—C$_{1-4}$ aliphatic residue, CF$_3$, and a C$_{1-4}$-aliphatic residue,
wherein the C$_{1-4}$-aliphatic residue in each case may be unsubstituted or mono- or polysubstituted with at least one substituent selected from the group consisting of F, Cl, CF$_3$ and an unsubstituted O—C$_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue, or denotes—preferably when m is 0 or 2, more preferably when m is 0—an aryl or heteroaryl, in each case unsubstituted or mono- or polysubstituted with at least one substituent selected from the group consisting of F, Cl, Br, I, OH, an O—$C_{1-4}$ aliphatic residue, $OCF_2H$, $OCF_3$, $CF_3$, CN, a $C_{1-4}$-aliphatic residue, C(=O)—$CH_3$, C(=O)—$C_2H_5$, $CH_2$—OH, $CH_2$—$OCH_3$, $S(=O)_2$—$CH_3$, $CF_3$, $NO_2$, N($C_{1-4}$ aliphatic residue)$_2$,

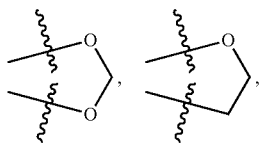 [SMILES: *OCO* ; *CCO*]

C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl or pyridyl, preferably denotes—preferably when m is 0 or 2, more preferably when m is 0—an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$ a $C_{1-4}$-aliphatic residue and C(=O)—OH.

In a further preferred embodiment of the compound according to general formula (I), the residue $R^1$ represents the partial structure (T1), wherein m is 0, 1 or 2, preferably 0 or 2, more preferably 2, and $R^{12a}$ and $R^{12b}$ each independently of one another represent H, F, OH, a O—$C_{1-4}$ aliphatic residue or a $C_{1-4}$ aliphatic residue or together denote =O; preferably H, F, OH, $CH_3$ or $OCH_3$ or together denote =O;

$R^{12c}$ denotes a $C_{1-4}$ aliphatic residue, unsubstituted or mono- or polysubstituted with at least one substituent selected from the group consisting of F, Cl, Br, I, CN, OH, an unsubstituted O—$C_{1-4}$ aliphatic residue, an unsubstituted $S(=O)_2$—$C_{1-4}$ aliphatic residue, $CF_3$, and an unsubstituted $C_{1-4}$-aliphatic residue, preferably denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or wherein m is 0 or 2, more preferably 0, and $R^{12a}$ and $R^{12b}$ each independently of one another represent H, F, OH, a O—$C_{1-4}$ aliphatic residue or a $C_{1-4}$ aliphatic residue; preferably H, F, OH, $CH_3$ or $OCH_3$; and $R^{12c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $OCF_2H$, $CH_2$—OH, $CH_2$—$OCH_3$, $S(=O)_2$—$CH_3$, $SCF_3$, $NO_2$, N($C_{1-4}$ aliphatic residue)$_2$,

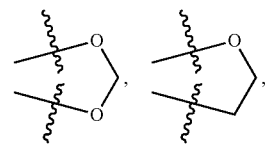 [SMILES: *OCO* ; *CCO*]

$CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl, preferably denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl, wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$.

Preferably, $R^1$ represents the partial structure (T1), wherein m is 0, 1 or 2, preferably 0 or 2, more preferably 2, and $R^{12a}$ and $R^{12b}$ each independently of one another represent H, F, OH, $CH_3$ or $OCH_3$ or together denote =O, more preferably H, F, OH or $CH_3$, even more preferably H, $R^{12c}$ denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, CN, OH, $S(=O)_2$—$CH_3$, an unsubstituted O—$C_{1-4}$ aliphatic residue, preferably O-methyl and O-tert.-butyl, and $CF_3$, preferably denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, an unsubstituted O—$C_{1-4}$ aliphatic residue, preferably O-methyl and O-tert.-butyl, and $CF_3$ or denotes a $C_{3-10}$-cycloaliphatic residue or a 3 to 10 membered heterocycloaliphatic residue, preferably cyclopropyl, cyclopentyl, cyclohexyl, morpholinyl, oxetanyl, or tetrahydropyranyl, in each case unsubstituted or mono- or polysubstituted with at least one substituent selected from the group consisting of F, Cl, Br, I, an unsubstituted O—$C_{1-4}$ aliphatic residue, preferably O-methyl and O-ethyl, $CF_3$, and an unsubstituted $C_{1-4}$-aliphatic residue, preferably methyl or ethyl, or wherein m is 0 or 2, more preferably 0, and $R^{12a}$ and $R^{12b}$ each independently of one another represent H, F, OH, $CH_3$ or $OCH_3$; preferably H, OH or $CH_3$, and $R^{12c}$ denotes an aryl or heteroaryl, preferably phenyl or pyridyl, in each case unsubstituted or mono- or polysubstituted with at least one substituent selected from the group consisting of F, Cl, Br, I, OH, an O—$C_{1-4}$ aliphatic residue, preferably $OCH_3$, $OCF_3$, $OCF_2H$, $CH_2$—OH, $CH_2$—$OCH_3$, $S(=O)_2$—$CH_3$, $SCF_3$, $NO_2$, $N(CH_3)_2$,

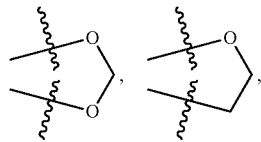

$CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl, preferably denotes an aryl or heteroaryl, preferably phenyl or pyridyl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl, wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$.

Particularly preferred is a compound according to general formula (I) which has the following general formula (I-d):

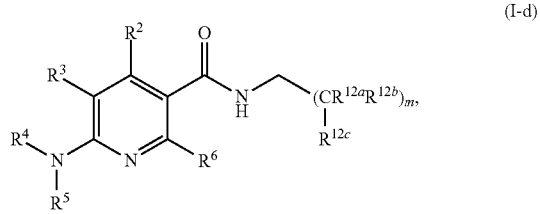

(I-d)

wherein the particular radicals and parameters have the meanings described herein in connection with the compounds according to the invention and preferred embodiments thereof.

In a preferred embodiment of the compound according to general formula (I), the residue $R^2$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted.

Preferably, $R^2$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

More preferably, $R^2$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, cyclopropyl, cyclobutyl, cyclopentyl, cyclohexyl, pyrrolidinyl, piperazinyl, 4-methylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an $C_{1-4}$ aliphatic group, which in turn may be unsubstituted or mono- or polysubstituted with at least one substituent selected from the group consisting of F, Cl, OH, an unsubstituted $C_{1-4}$-aliphatic residue and an unsubstituted O—$C_{1-4}$-aliphatic residue.

Even more preferably, $R^2$ represents F; Cl; Br; I; CN; $CF_3$; $NO_2$; $OCF_3$; $SCF_3$; methyl; ethyl; n-propyl; iso-propyl; n-butyl; sec.-butyl; tert.-butyl; $CH_2$—OH; $CH_2$—O—$CH_3$; $CH_2$—$CH_2$—OH; $CH_2$—$CH_2$—$OCH_3$; O-methyl; O-ethyl; O—$(CH_2)_2$—O—$CH_3$; O—$(CH_2)_2$—OH; S-Methyl; S-ethyl; cyclopropyl, cyclobutyl, cyclopentyl, and cyclohexyl; preferably represents F; Cl; Br; I; CN; $CF_3$; $NO_2$; $OCF_3$; $SCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; S-ethyl; cyclopropyl, cyclobutyl, cyclopentyl, and cyclohexyl Still more preferably, $R^2$ is selected from the group consisting of F; Cl; $CF_3$; CN; $SCF_3$; $OCF_3$; $CH_3$; $C_2H_5$; n-propyl; iso-propyl; t-butyl; $CH_2$—OH; $CH_2$—O—$CH_3$; cyclopropyl; O—$CH_3$ and O—$C_2H_5$; preferably is selected from the group consisting of F; Cl; $CF_3$; CN; $SCF_3$; $OCF_3$; $CH_3$; $C_2H_5$; n-propyl; iso-propyl; t-butyl; cyclopropyl; O—$CH_3$ and O—$C_2H_5$;

In particular, $R^2$ is selected from the group consisting of F; Cl; $CF_3$; $CH_3$; $C_2H_5$, iso-propyl; $CH_2$—O—$CH_3$; cyclopropyl; and O—$CH_3$; preferably is selected from the group consisting of F; Cl; $CF_3$; $CH_3$; $C_2H_5$, iso-propyl; cyclopropyl; and O—$CH_3$;

More particular, $R^2$ is selected from the group consisting of $CF_3$; $CH_3$; $C_2H_5$, iso-propyl; $CH_2$—O—$CH_3$; and O—$CH_3$; preferably is selected from the group consisting of $CH_3$; $C_2H_5$, iso-propyl; $CH_2$—O—$CH_3$; and O—$CH_3$;

In a particular preferred embodiment of the compound according to general formula (I), the residue $R^2$ denotes $CH_3$ or $CF_3$, most preferably $R^2$ denotes $CH_3$.

In a further preferred embodiment of the compound according to general formula (I), the residue $R^3$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue,
wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue;
a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue,
wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue,
and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

Preferably, $R^3$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue,
wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue.

More preferably, $R^3$ represents H; F; Cl; Br; I; CN; $CF_3$; $SCF_3$; $NO_2$; $OCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; or S-Ethyl.

Even more preferably $R^3$ represents H; F; Cl; Br; I; CN; $CF_3$; $SCF_3$; $OCF_3$; methyl; ethyl; O-methyl; or O-ethyl, preferably represents H; F; Cl; Br; I; $CF_3$; $SCF_3$; $OCF_3$; methyl; ethyl; O-methyl; or O-ethyl, Still more preferably $R^3$ represents H; F; Cl; Br; CN; $CF_3$; $SCF_3$; $OCF_3$; O-methyl or methyl, preferably represents H; F; Cl; $CF_3$; $SCF_3$; $OCF_3$; O-methyl or methyl.

In particular $R^3$ represents H; F; Cl; Br; CN; or methyl, preferably H, F, Cl, Br or CN, more preferably H, Cl or Br, most preferably H.

In a further preferred embodiment of the compound according to general formula (I), the residue $R^4$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O)—OH,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, a C(=O)—O—C$_{1-4}$-aliphatic residue, OCF$_3$, SH, SCF$_3$, a S—C$_{1-4}$ aliphatic residue, CF$_3$, CN, a C$_{1-4}$-aliphatic residue and C(=O)—OH, on the condition that if R$^4$ denotes a 3 to 10 membered heterocycloaliphatic residue, the 3 to 10 membered heterocycloaliphatic residue is linked via a carbon atom, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

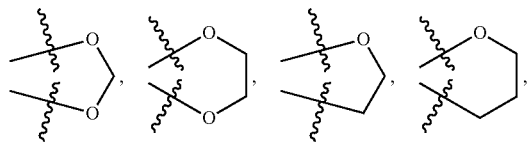 [SMILES: *OCO* ; *OCCO* ; *CCO* ; *CCCO*]

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the aryl or the heteroaryl residue may in each case be optionally bridged, preferably in each case is bridged, via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN and C(=O)—OH, R$^5$ denotes H or a C$_{1-10}$-aliphatic residue, preferably a C$_{1-4}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or R$^4$ and R$^5$ form together with the nitrogen atom connecting them a 3 to 10 membered heterocycloaliphatic residue, preferably a 4 to 7 membered heterocycloaliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, =O, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the 3 to 10 membered heterocycloaliphatic residue formed by R$^4$ and R$^5$ together with the nitrogen atom connecting them may optionally be condensed with aryl or heteroaryl, preferably with phenyl, pyridyl or thienyl, wherein the aryl or heteroaryl residues condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

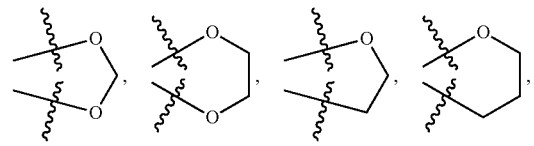 [SMILES: *OCO* ; *OCCO* ; *CCO* ; *CCCO*]

benzyl, phenyl, thienyl, pyridyl, furyl, thiazolyl and oxazolyl, and wherein the 3 to 10 membered heterocycloaliphatic residue formed by R$^4$ and R$^5$ together with the nitrogen atom connecting them may optionally be condensed with a C$_{3-10}$ cycloaliphatic residue or a 3 to 10 membered heterocycloaliphatic residue, wherein the C$_{3-10}$ cycloaliphatic residue or a 3 to 10 membered heterocycloaliphatic residue condensed in this way can for their part be respectively unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, =O, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.

In a further preferred embodiment of the compound according to general formula (I), the residue $R^4$ represents the partial structure (T2)

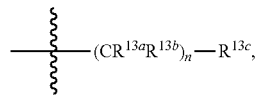

(T2)

wherein
n denotes 0, 1, 2, or 3, preferably denotes 1, 2 or 3, more preferably denotes 1 or 2, even more preferably denotes 1, $R^{13a}$ and $R^{13b}$ each independently of one another represent H, F, Cl, Br, I, $NO_2$, $NH_2$, a $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$ aliphatic residue or C(=O)—OH, or together denote =O, preferably each independently of one another represent H, F, Cl, Br, I, $NH_2$, a $NH(C_{1-4}$ aliphatic residue), a $N(C_{1-4}$ aliphatic residue)$_2$, OH, O—$C_{1-4}$ aliphatic residue or a $C_{1-4}$ aliphatic residue or together denote =O, more preferably each independently of one another represent H, F, Cl, Br, I, an O—$C_{1-4}$ aliphatic residue or a $C_{1-4}$ aliphatic residue or together denote =O,
even more preferably each independently of one another represent H, F, an O—$C_{1-4}$ aliphatic residue or a $C_{1-4}$ aliphatic residue or together denote =O, and
$R^{13c}$ denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes—preferably when n is ≠0, more preferably when n is 1—a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes—preferably when n is ≠0, more preferably when n is 1, —an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

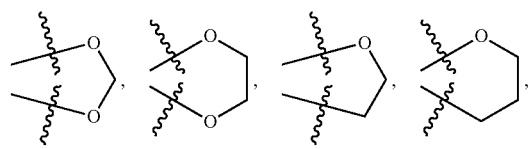 [SMILES: *OCO* ; *OCCO* ; *CCO* ; *CCCO*]

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, $R^5$ denotes H or a $C_{1-10}$-aliphatic residue, preferably a $C_{1-6}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or $R^4$ and $R^5$ form together with the nitrogen atom connecting them a 3 to 10 membered heterocycloaliphatic residue, preferably a 4 to 7 membered heterocycloaliphatic residue, or preferably selected from the group consisting of morpholinyl, piperidinyl, pyrrolidinyl, azetidinyl, piperazinyl, 4-methylpiperazinyl, oxazepanyl, thiomorpholinyl, azepanyl,

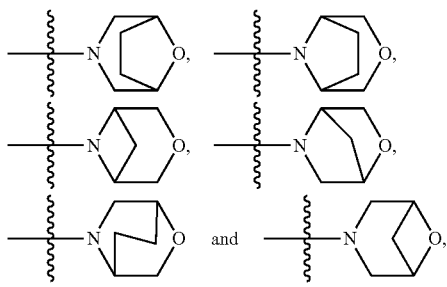

more preferably selected from the group consisting of morpholinyl, piperidinyl, pyrrolidinyl, azetidinyl, piperazinyl, 4-methylpiperazinyl, oxazepanyl, in each case unsubstituted or mono- or polysubstituted with at least one substituent selected from the group consisting of F, Cl, Br, I, $NO_2$, OH, =O, C(=O)—OH, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, a $C_{3-6}$ cycloaliphatic residue, preferably cyclopropyl, cyclobutyl or cyclopentyl, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, =O, OH, $CF_3$ and an unsubstituted O—$C_{1-4}$-aliphatic residue, preferably selected from the group consisting of F, Cl, Br, I, OH, $CF_3$ and an unsubstituted O—$C_{1-4}$-aliphatic residue, wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the 3 to 10 membered heterocycloaliphatic residue formed by $R^4$ and $R^5$ together with the nitrogen atom connecting them may optionally be condensed with aryl or heteroaryl, preferably with phenyl, pyridyl or thienyl, wherein the aryl or heteroaryl residues condensed in this way can for their part be respectively unsubstituted or mono- or polysubstituted with at least one substituent selected from the group consisting of F, Cl, Br, I, $NO_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, a 3 to 6 membered heterocycloaliphatic residue,

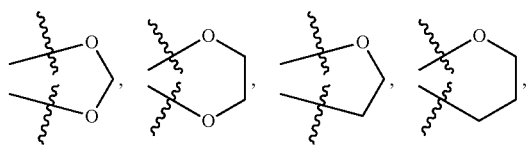 [SMILES: *OCO* ; *OCCO* ; *CCO* ; *CCCO*]

benzyl, phenyl, thienyl, and pyridyl, and wherein the 3 to 10 membered heterocycloaliphatic residue formed by $R^4$ and $R^5$ together with the nitrogen atom connecting them may optionally be condensed with a $C_{3-10}$ cycloaliphatic residue, preferably cyclopropyl, cyclobutyl or cycclopentyl, or a 3 to 10 membered heterocycloaliphatic residue, preferably oxetanyl or oxiranyl, wherein the $C_{3-10}$ cycloaliphatic residue or the 3 to 10 membered heterocycloaliphatic residue condensed in this way can for their part be respectively unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, =O, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, and pyridyl, may in each case may be unsubstituted or mono- or polysubstituted with at least one substituent selected from the group consisting of F, Cl, Br, I, $NO_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, and C(=O)—OH, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.

Preferably, $R^4$ represents the partial structure (T2),
wherein
n denotes 0, 1, 2, or 3, preferably denotes 1, 2 or 3, more preferably denotes 1 or 2, even more preferably denotes 1,
$R^{13a}$ and $R^{13b}$ each independently of one another represent H, F, Cl, Br, I, an O—$C_{1-4}$ aliphatic residue or a $C_{1-4}$ aliphatic residue or together denote =O, preferably each independently of one another represent H, F, a O—$C_{1-2}$ aliphatic residue or a $C_{1-2}$ aliphatic residue or together denote =O, and $R^{13c}$ denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, OCF$_3$, CF$_3$, a $C_{1-4}$-aliphatic residue and C(=O)—OH, or denotes—preferably when n is ≠0, more preferably when n is 1-a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, CF$_3$, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, OCF$_3$, CF$_3$, a $C_{1-4}$-aliphatic residue and C(=O)—OH, or denotes—preferably when n is ≠0, more preferably when n is 1—an aryl or heteroaryl, in each case unsubstituted or mono- or polysubstituted with at least one substituent selected from the group consisting of F, Cl, Br, I, OH, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue, C(=O)—OH, C(=O)—CH$_3$, C(=O)—$C_2H_5$, C(=O)—O—CH$_3$ and C(=O)—O—$C_2H_5$, a $C_{3-6}$ cycloaliphatic residue, a 3 to 6 membered heterocycloaliphatic residue, benzyl, phenyl, thienyl, pyridyl, furyl, thiazolyl or oxazolyl, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, OCF$_3$, CF$_3$, CN, a $C_{1-4}$-aliphatic residue, C(=O)—OH, C(=O)—CH$_3$, C(=O)—$C_2H_5$, C(=O)—O—CH$_3$ and C(=O)—O—$C_2H_5$, preferably with at least one substituent selected from the group consisting of F, Cl, CH$_3$, O—CH$_3$, CF$_3$ and OCF$_3$, wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, OCF$_3$, CF$_3$ a $C_{1-4}$-aliphatic residue and C(=O)—OH, $R^5$ denotes H or a $C_{1-6}$-aliphatic residue, preferably a $C_{1-4}$-aliphatic residue, unsubstituted or mono- or polysubstituted with at least one substituent selected from the group consisting of F, Cl, Br, I, NO$_2$, OH, =O, an O—$C_{1-4}$ aliphatic residue, OCF$_3$, SH, SCF$_3$, a S—$C_{1-4}$ aliphatic residue, CF$_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue, or $R^4$ and $R^5$ form together with the nitrogen atom connecting them a 3 to 10 membered heterocycloaliphatic residue, preferably a 4 to 7 membered heterocycloaliphatic residue, or preferably selected from the group consisting of morpholinyl, piperidinyl, pyrrolidinyl, azetidinyl, piperazinyl, 4-methylpiperazinyl, oxazepanyl, thiomorpholinyl, azepanyl,

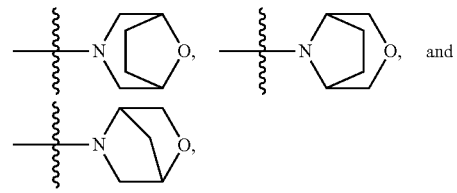

more preferably selected from the group consisting of morpholinyl, piperidinyl, pyrrolidinyl, azetidinyl, piperazinyl, 4-methylpiperazinyl, oxazepanyl, unsubstituted or mono- or polysubstituted with at least one substituent selected from the group consisting of F, Cl, Br, I, OH, =O, C(=O)—OH, an O—$C_{1-4}$ aliphatic residue, OCF$_3$, SCF$_3$, a S—$C_{1-4}$ aliphatic residue, CF$_3$, and a $C_{1-4}$-aliphatic residue, and a $C_{3-6}$ cycloaliphatic residue, preferably cyclopropyl, cyclobutyl or cyclopentyl, wherein the $C_{1-4}$-aliphatic residue in each case may be unsubstituted or mono- or polysubstituted with at least one substituent selected from the group consisting of F, Cl, Br, I, OH, =O, CF$_3$ and an unsubstituted O—$C_{1-4}$-aliphatic residue, preferably selected from the group consisting of F, Cl, Br, I, OH, CF$_3$ and an unsubstituted O—$C_{1-4}$-aliphatic residue, wherein the $C_{3-6}$ cycloaliphatic residue may in each case may be unsubstituted or mono- or polysubstituted with at least one substituent selected from the group consisting of F, Cl, Br, I, OH, =O, an O—$C_{1-4}$ aliphatic residue, OCF$_3$, SCF$_3$, a S—$C_{1-4}$ aliphatic residue, CF$_3$, CN, a $C_{1-4}$-aliphatic residue and C(=O)—OH, and wherein the 3 to 10 membered heterocycloaliphatic residue formed by $R^4$ and $R^5$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, OH, an O—$C_{1-4}$ aliphatic residue, OCF$_3$, SCF$_3$, a S—$C_{1-4}$ aliphatic residue, CF$_3$, a $C_{1-4}$-aliphatic residue, C(=O)—OH, a $C_{3-6}$ cycloaliphatic residue, benzyl, phenyl, thienyl, and pyridyl, and wherein the 3 to 10 membered heterocycloaliphatic residue formed by $R^4$ and $R^5$ together with the nitrogen atom connecting them may optionally be condensed with a $C_{3-10}$ cycloaliphatic residue, preferably cyclopropyl, cyclobutyl or cyclopentyl, or a 3 to 10 membered heterocycloaliphatic residue, preferably oxetanyl or oxiranyl, wherein the $C_{3-10}$ cycloaliphatic residue or the 3 to 10 membered heterocycloaliphatic residue condensed in this way can for their part be respectively unsubstituted or mono- or polysubstituted with at least one substituent selected from the group consisting of F, Cl, Br, I, =O, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, and pyridyl, may in each case may be unsubstituted or mono- or polysubstituted with at least one substituent selected from the group consisting of F, Cl, Br, I, OH, an O—$C_{1-4}$ aliphatic residue, $OCF_3$, O—$CH_2$—OH, O—$CH_2$—O—$CH_3$, $SCF_3$, a S—$C_{1-4}$ aliphatic residue, $CF_3$, CN, a $C_{1-4}$-aliphatic residue, and C(=O)—OH, and wherein the $C_{3-6}$ cycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, $CF_3$, a $C_{1-4}$-aliphatic residue and C(=O)—OH.

More preferably, $R^4$ represents the partial structure (T2), wherein n denotes 0, 1, 2 or 3, preferably denotes 1 or 2, more preferably denotes 1, $R^{13a}$ and $R^{13b}$ each independently of one another represent H, F, Cl, Br, I, an O—$C_{1-4}$ aliphatic residue or a $C_{1-4}$ aliphatic residue or together denote =O, preferably each independently of one another represent H, F, a O—$C_{1-2}$ aliphatic residue or a $C_{1-2}$ aliphatic residue or together denote =O, and $R^{13c}$ denotes a $C_{1-4}$ aliphatic residue, unsubstituted or mono- or polysubstituted with at least one substituent selected from the group consisting of F, Cl, Br, I, =O, an O—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue, or denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$ a $C_{1-4}$-aliphatic residue and C(=O)—OH, $R^5$ denotes H or an unsubstituted $C_{1-4}$-aliphatic residue or a $C_{1-4}$-aliphatic residue monosubstituted with O-methyl, wherein the $C_{1-4}$-aliphatic residue is in each case preferably selected from the group consisting of methyl, ethyl, n-propyl, 2-propyl, n-butyl, isobutyl, sec.-butyl and tert.-butyl, more preferably selected from the group consisting of methyl and ethyl, or $R^4$ and $R^5$ form together with the nitrogen atom connecting them a 3 to 10 membered heterocycloaliphatic residue, more preferably selected from the group consisting of morpholinyl, piperidinyl, pyrrolidinyl, azetidinyl, piperazinyl, 4-methylpiperazinyl, oxazepanyl, thiomorpholinyl, azepanyl,

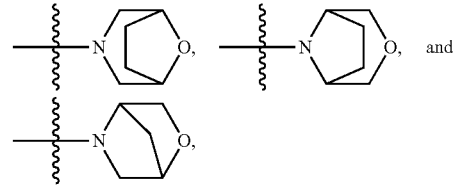

in each case unsubstituted or mono- or polysubstituted with at least one substituent selected from the group consisting of F, Cl, Br, I, OH, =O, C(=O)—OH, an O—$C_{1-4}$ aliphatic residue, $OCF_3$, $SCF_3$, a S—$C_{1-4}$ aliphatic residue, $CF_3$, and a $C_{1-4}$-aliphatic residue, cyclopropyl, cyclobutyl and cyclopentyl, wherein the $C_{1-4}$-aliphatic residue is in each case unsubstituted or mono- or polysubstituted with at least one substituent selected from the group consisting of F, Cl, OH, =O, $CF_3$ and an unsubstituted O—$C_{1-4}$-aliphatic residue, preferably is in each case unsubstituted, and wherein the 3 to 10 membered heterocycloaliphatic residue formed by $R^4$ and $R^5$ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, Br, I, OH, an O—$C_{1-4}$ aliphatic residue, $OCF_3$, $SCF_3$, a $C_{1-4}$ aliphatic residue, $CF_3$, a $C_{1-4}$-aliphatic residue, C(=O)—OH, and a $C_{3-6}$ cycloaliphatic residue, wherein the $C_{1-4}$-aliphatic residue in each case may be unsubstituted or mono- or polysubstituted with at least one substituent selected from the group consisting of F, Cl, OH, $OCF_3$, $CF_3$ and an unsubstituted O—$C_{1-4}$-aliphatic residue, and wherein the $C_{3-6}$ cycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, $CF_3$, a $C_{1-4}$-aliphatic residue and C(=O)—OH, and wherein the 3 to 10 membered heterocycloaliphatic residue formed by $R^4$ and $R^5$ together with the nitrogen atom connecting them may optionally be condensed with a $C_{3-6}$ cycloaliphatic residue, preferably cyclopropyl, cyclobutyl or cycclopentyl, or a 4 to 7 membered heterocycloaliphatic residue, preferably oxetanyl or oxiranyl, wherein the $C_{3-6}$ cycloaliphatic residue or the 4 to 7 membered heterocycloaliphatic residue condensed in this way can for their part be respectively unsubstituted or mono- or polysubstituted with at least one substituent selected from the group consisting of F, Cl, Br, I, =O, OH, an O—$C_{1-4}$-aliphatic residue, $OCF_3$, $SCF_3$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$.

Even more preferably, $R^4$ represents the partial structure (T2),
wherein
n denotes 0, 1, 2 or 3, preferably denotes 1 or 2, more preferably denotes 1,
$R^{13a}$ and $R^{13b}$ each independently of one another represent H, F, a O—$C_{1-4}$ aliphatic residue or a $C_{1-4}$ aliphatic residue or together denote =O; preferably each independently of one another represent H, F, $CH_3$ or $OCH_3$ or together denote =O;
$R^{13c}$ denotes a $C_{1-4}$ aliphatic residue, unsubstituted or mono- or polysubstituted with at least one substituent selected from the group consisting of F, Cl, Br, I, =O, an unsubstituted O—$C_{1-4}$ aliphatic residue, $CF_3$, and an unsubstituted $C_{1-4}$-aliphatic residue,
or denotes a $C_{3-10}$-cycloaliphatic residue, preferably selected from the group consisting of cyclopropyl, cyclobutyl, cyclopentyl and cyclohexyl, or a 3 to 10 membered heterocycloaliphatic residue, preferably selected from the group consisting of pyrrolidinyl, morpholinyl, piperazinyl, piperidinyl and tetrahydropyranyl, more preferably tetrahydropyranyl, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or denotes an aryl or heteroaryl, preferably phenyl or pyridyl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl,
wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, $R^5$ denotes H or an unsubstituted $C_{1-4}$-aliphatic residue or a $C_{1-4}$-aliphatic residue, which is monosubstituted with $OCH_3$, preferably H, methyl, ethyl, n-propyl, 2-propyl, n-butyl, isobutyl, sec.-butyl or tert.-butyl or $CH_2$—$OCH_3$, $C_2H_4$—$OCH_3$ or $C_3H_6$—$OCH_3$, more preferably H, methyl or ethyl, preferably denotes H or an unsubstituted $C_{1-4}$-aliphatic residue, preferably H, methyl, ethyl, n-propyl, 2-propyl, n-butyl, isobutyl, sec.-butyl or tert.-butyl, more preferably H, methyl or ethyl, or $R^4$ and $R^5$ form together with the nitrogen atom connecting them a morpholinyl, piperidinyl, pyrrolidinyl, azetidinyl, piperazinyl, 4-methylpiperazinyl, oxazepanyl, thiomorpholinyl, azepanyl,

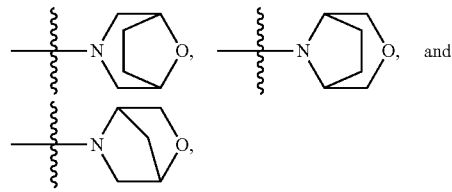

tetrahydroquinolinyl, tetrahydroisoquinolinyl, tetrahydroimidazo[1,2-a]pyrazinyl, octahydropyrrolo[1,2-a] pyrazinyl,

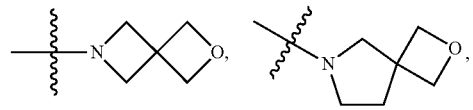 [SMILES: *N1CC2(COC2)C1 ; *N1CCC2(COC2)C1]

dihydroindolinyl, or dihydroisoindolyl, preferably a morpholinyl, piperidinyl, pyrrolidinyl, azetidinyl, piperazinyl, 4-methylpiperazinyl, oxazepanyl, tetrahydroquinolinyl, tetrahydroisoquinolinyl, dihydroindolinyl, or dihydroisoindolyl, in each case unsubstituted or mono- or polysubstituted with at least one substituent selected from the group consisting of F, Cl, Br, I, OH, =O, C(=O)— OH, an O—$C_{1-4}$ aliphatic residue, $OCF_3$, $SCF_3$, a S—$C_{1-4}$ aliphatic residue, $CF_3$, and a $C_{1-4}$-aliphatic residue, cyclopropyl, cyclobutyl and cyclopentyl,
wherein the $C_{1-4}$-aliphatic residue is in each case unsubstituted or mono- or polysubstituted with at least one substituent selected from the group consisting of F, OH, =O, $CF_3$ and an unsubstituted O—$C_{1-4}$-aliphatic residue, preferably is in each case unsubstituted.

Still more preferably, $R^4$ represents the partial structure (T2),
wherein
n denotes 0, 1, 2 or 3, preferably denotes 1 or 2, more preferably denotes 1,
$R^{13a}$ and $R^{13b}$ each independently of one another represent H, F, $CH_3$ or $OCH_3$ or together denote =O, preferably each independently of one another represent H or $CH_3$, more preferably H,
$R^{13c}$ denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, =O, an unsubstituted O—$C_{1-4}$ aliphatic residue, and $CF_3$,
or denotes cyclopropyl, cyclobutyl, cyclopentyl or cyclohexyl, pyrrolidinyl, morpholinyl, piperazinyl, piperidinyl and tetrahydropyranyl, more preferably tetrahydropyranyl or morpholinyl, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or denotes an aryl or heteroaryl, preferably phenyl or pyridyl, more preferably phenyl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, and a $C_{1-4}$-aliphatic residue, $R^5$ denotes H, methyl or ethyl or $C_2H_4OCH_3$ or $C_3H_6OCH_3$, more preferably H or methyl or ethyl, even more preferably methyl, or $R^4$ and $R^5$ form together with the nitrogen atom connecting them a morpholinyl, piperidinyl, pyrrolidinyl, azetidinyl, oxazepanyl, tetrahydroquinolinyl, tetrahydroisoquinolinyl, thiomorpholinyl, azepanyl,

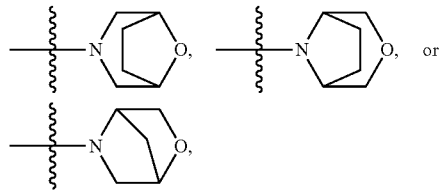

tetrahydroimidazo[1,2-a]pyrazinyl, octahydropyrrolo[1,2-a]pyrazinyl,

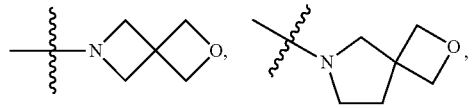 [SMILES: *N1CC2(COC2)C1 ; *N1CCC2(COC2)C1]

dihydroindolinyl, or dihydroisoindolyl, preferably a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, more preferably a morpholinyl, piperidinyl, pyrrolidinyl, azetidinyl, oxazepanyl, tetrahydroquinolinyl, tetrahydroisoquinolinyl, more preferably a morpholinyl, oxazepanyl, tetrahydroquinolinyl, or tetrahydroisoquinolinyl, in each case unsubstituted or mono- or polysubstituted with at least one substituent selected from the group consisting of F, Cl, OH, =O, C(=O)—OH, C(=O)—$CH_3$, C(=O)—$OCH_3$, O-methyl, O-ethyl, $OCF_3$, $SCF_3$, $CF_3$, methyl, $CH_2CF_3$, $CH_2OH$, $CH_2$—$OCH_3$, $CH_2CH_2$—$OCH_3$, ethyl, n-propyl, 2-propyl, cyclopropyl, and cyclobutyl, preferably selected from the group consisting of F, Cl, OH, =O, C(=O)—OH, O-methyl, O-ethyl, $OCF_3$, $SCF_3$, $CF_3$, methyl, ethyl, n-propyl, 2-propyl, cyclopropyl, and cyclobutyl In a preferred embodiment of the compound according to general formula (I), the residue $R^6$ denotes a $C_{2-10}$-aliphatic residue, preferably a $C_{2-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^6$ denotes a 3 to 10 membered heterocycloaliphatic residue, the binding is carried out via a carbon atom of the 3 to 10 membered heterocycloaliphatic residue, or $R^6$ denotes S—$R^7$, O—$R^8$ or N($R^9R^{10}$), wherein $R^7$ and $R^8$ in each case represent a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or in each case represent a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^7$ or $R^8$ denotes a 3 to 10 membered heterocycloaliphatic residue, the binding is carried out via a carbon atom of the 3 to 10 membered heterocycloaliphatic residue, $R^9$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^9$ denotes a 3 to 10 membered heterocycloaliphatic residue, the binding is carried out via a carbon atom of the 3 to 10 membered heterocycloaliphatic residue, $R^{10}$ denotes H or a $C_{1-10}$-aliphatic residue, preferably a $C_{1-4}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, preferably denotes a $C_{1-10}$-aliphatic residue, more preferably a $C_{1-4}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or $R^9$ and $R^{10}$ form together with the nitrogen atom connecting them a 3 to 10 membered heterocycloaliphatic residue, preferably a 3 to 6 membered heterocycloaliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the 3 to 10 membered heterocycloaliphatic residue formed by $R^9$ and $R^{10}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

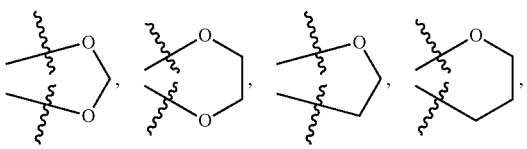 [SMILES: *OCO* ; *OCCO* ; *CCO* ; *CCCO*]

benzyl, phenyl, thienyl, pyridyl, furyl, thiazolyl and oxazolyl,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, $C(=O)$—OH, $C(=O)$—$CH_3$, $C(=O)$—$C_2H_5$, $C(=O)$—O—$CH_3$ and $C(=O)$—O—$C_2H_5$, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and $C(=O)$—OH.

Preferably,
$R^6$ denotes a $C_{2-10}$-aliphatic residue, preferably a $C_{2-6}$-aliphatic residue, unsubstituted or mono- or polysubstituted with at least one substituent selected from the group consisting of F, Cl, Br, I, $NO_2$, OH, =O, an O—$C_{1-4}$-aliphatic residue, $OCF_3$, SH, $SCF_3$, a S—$C_{1-4}$-aliphatic residue, a $C(=O)$—O—$C_{1-4}$-aliphatic residue, $CF_3$, CN, and a $C_{1-4}$-aliphatic residue
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, a $C(=O)$—O—$C_{1-4}$-aliphatic residue, $CF_3$, CN, a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, OH, =O, an O—$C_{1-4}$ aliphatic residue, a $C(=O)$—O—$C_{1-4}$ aliphatic residue, $OCF_3$, SH, $SCF_3$, a S—$C_{1-4}$ aliphatic residue, $CF_3$, CN, and a $C_{1-4}$-aliphatic residue.
  on the condition that if $R^6$ denotes a 3 to 10 membered heterocycloaliphatic residue, the 3 to 10 membered heterocycloaliphatic residue is linked via a carbon atom,
or
$R^6$ denotes S—$R^7$ or O—$R^8$
  wherein
  $R^7$ and $R^8$ in each case represent a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, an $NH(C_{1-4}$ aliphatic residue), an $N(C_{1-4}$ aliphatic residue)$_2$, a $C(=O)$—O—$C_{1-4}$-aliphatic residue, $CF_3$, and a $C_{1-4}$-aliphatic residue,
    wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue,
  or in each case denote a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a $C(=O)$—O—$C_{1-4}$-aliphatic residue, a S—$C_{1-4}$ aliphatic residue, $CF_3$, and a $C_{1-4}$-aliphatic residue,
    wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue,
  and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a $C(=O)$—O—$C_{1-4}$-aliphatic residue, $CF_3$, CN, and a $C_{1-4}$-aliphatic residue.
  on the condition that if $R^7$ or $R^8$ denotes a 3 to 10 membered heterocycloaliphatic residue, the 3 to 10 membered heterocycloaliphatic residue is linked via a carbon atom,
or
$R^6$ denotes $N(R^9R^{10})$,
  wherein
  $R^9$ denotes a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, a $C(=O)$—O—$C_{1-4}$-aliphatic residue, $CF_3$, and a $C_{1-4}$-aliphatic residue,
    wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue,
  or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a $C(=O)$—O—$C_{1-4}$-aliphatic residue, a S—$C_{1-4}$ aliphatic residue, $CF_3$, and a $C_{1-4}$-aliphatic residue,
    wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, OH, =O, an O—C$_{1-4}$ aliphatic residue, OCF$_3$, SH, SCF$_3$, a S—C$_{1-4}$ aliphatic residue, a C(=O)—O—C$_{1-4}$-aliphatic residue, CF$_3$, CN, and a C$_{1-4}$-aliphatic residue, on the condition that if R$^9$ denotes a 3 to 10 membered heterocycloaliphatic residue, the 3 to 10 membered heterocycloaliphatic residue is linked via a carbon atom, and wherein R$^{10}$ denotes H or a C$_{1-10}$-aliphatic residue, preferably a C$_{1-6}$-aliphatic residue, unsubstituted or mono- or polysubstituted with at least one substituent selected from the group consisting of F, Cl, Br, I, NO$_2$, OH, =O, an O—C$_{1-4}$ aliphatic residue, OCF$_3$, SH, SCF$_3$, a S—C$_{1-4}$ aliphatic residue, CF$_3$, CN, and a C$_{1-4}$-aliphatic residue, preferably denotes a C$_{1-10}$-aliphatic residue, more preferably a C$_{1-6}$-aliphatic residue, unsubstituted or mono- or polysubstituted with at least one substituent selected from the group consisting of F, Cl, Br, I, NO$_2$, OH, =O, an O—C$_{1-4}$ aliphatic residue, OCF$_3$, SH, SCF$_3$, a S—C$_{1-4}$ aliphatic residue, CF$_3$, CN, and a C$_{1-4}$-aliphatic residue wherein the C$_{1-4}$-aliphatic residue in each case may be unsubstituted or mono- or polysubstituted with at least one substituent selected from the group consisting of F, Cl, Br, I, OH, CF$_3$ and an unsubstituted O—C$_{1-4}$-aliphatic residue, or R$^9$ and R$^{10}$ form together with the nitrogen atom connecting them a 3 to 10 membered heterocycloaliphatic residue, preferably a 3 to 6 membered heterocycloaliphatic residue, more preferably selected from the group consisting of morpholinyl, piperidinyl, pyrrolidinyl, azetidinyl and piperazinyl, unsubstituted or mono- or polysubstituted with at least one substituent selected from the group consisting of F, Cl, Br, I, NO$_2$, OH, =O, an O—C$_{1-4}$ aliphatic residue, OCF$_3$, SH, SCF$_3$, a S—C$_{1-4}$ aliphatic residue, CF$_3$, CN, and a C$_{1-4}$-aliphatic residue, wherein the C$_{1-4}$-aliphatic residue in each case may be unsubstituted or mono- or polysubstituted with at least one substituent selected from the group consisting of F, Cl, Br, I, OH, CF$_3$ and an unsubstituted O—C$_{1-4}$-aliphatic residue, and wherein the 3 to 10 membered heterocycloaliphatic residue formed by R$^9$ and R$^{10}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, NO$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, a 3 to 6 membered heterocycloaliphatic residue,

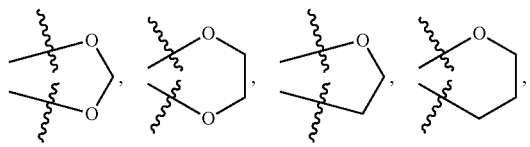 [SMILES: *OCO* ; *OCCO* ; *CCO* ; *CCCO*]

benzyl, phenyl, thienyl, and pyridyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, and pyridyl, may in each case may be unsubstituted or mono- or polysubstituted with at least one substituent selected from the group consisting of F, Cl, Br, I, NO$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, and C(=O)—OH, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH.

More preferably,

R$^6$ denotes a C$_{2-8}$-aliphatic residue, unsubstituted or mono- or polysubstituted with at least one substituent selected from the group consisting of F, Cl, Br, I, OH, =O, an O—C$_{1-4}$-aliphatic residue, OCF$_3$, SH, SCF$_3$, a S—C$_{1-4}$-aliphatic residue, a C(=O)—O—C$_{1-4}$-aliphatic residue, CF$_3$, and a C$_{1-4}$-aliphatic residue wherein the C$_{1-4}$-aliphatic residue in each case may be unsubstituted or mono- or polysubstituted with at least one substituent selected from the group consisting of F, Cl, Br, I, OH, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—C$_{1-4}$ aliphatic residue, OCF$_3$, SCF$_3$, a C(=O)—O—C$_{1-4}$-aliphatic residue, a S—C$_{1-4}$ aliphatic residue, CF$_3$, and a C$_{1-4}$-aliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, OH, =O, an O—C$_{1-4}$ aliphatic residue, OCF$_3$, SH, SCF$_3$, a S—C$_{1-4}$ aliphatic residue, a C(=O)—O—C$_{1-4}$-aliphatic residue, CF$_3$, CN, and a C$_{1-4}$-aliphatic residue.

on the condition that if $R^6$ denotes a 3 to 10 membered heterocycloaliphatic residue, the 3 to 10 membered heterocycloaliphatic residue is linked via a carbon atom, or $R^6$ denotes S—$R^7$ or O—$R^8$ wherein $R^7$ and $R^8$ in each case denote a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, an $NH(C_{1-4}$ aliphatic residue), an $N(C_{1-4}$ aliphatic residue)$_2$, $CF_3$, a C(=O)—O—$C_{1-4}$-aliphatic residue, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or in each case denote a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue may be bridged, preferably is bridged, via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue, on the condition that if $R^7$ or $R^8$ denotes a 3 to 10 membered heterocycloaliphatic residue, the 3 to 10 membered heterocycloaliphatic residue is linked via a carbon atom, or $R^6$ denotes $N(R^9R^{10})$, wherein $R^9$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, $CF_3$, a C(=O)—O—$C_{1-4}$-aliphatic residue, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue may in each case be bridged, preferably is bridged, via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue, on the condition that if $R^9$ denotes a 3 to 10 membered heterocycloaliphatic residue, the 3 to 10 membered heterocycloaliphatic residue is linked via a carbon atom, and $R^{10}$ denotes H or a $C_{1-6}$-aliphatic residue, preferably a $C_{1-4}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, preferably denotes a $C_{1-6}$-aliphatic residue, more preferably a $C_{1-4}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or $R^9$ and $R^{10}$ form together with the nitrogen atom connecting them a 3 to 10 membered heterocycloaliphatic residue, preferably selected from the group consisting of morpholinyl, piperidinyl, pyrrolidinyl, azetidinyl and piperazinyl, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, and wherein the 3 to 10 membered heterocycloaliphatic residue formed by $R^9$ and $R^{10}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, $NO_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, residue,

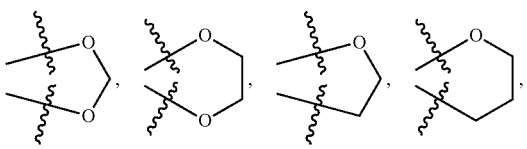 [SMILES: *OCO* ; *OCCO* ; *CCO* ; *CCCO*]

benzyl, phenyl, thienyl, and pyridyl,
wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, and wherein benzyl, phenyl, thienyl, and pyridyl, may in each case may be unsubstituted or mono- or polysubstituted with at least one substituent selected from the group consisting of F, Cl, Br, I, $NO_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, and C(=O)—OH.

Even more preferably, $R^6$ denotes a $C_{2-6}$-aliphatic residue, unsubstituted or mono- or polysubstituted with at least one substituent selected from the group consisting of F, Cl, Br, I, OH, =O, an O—$C_{1-4}$ aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue wherein the $C_{1-4}$-aliphatic residue in each case is unsubstituted, or denotes a $C_{3-10}$-cycloaliphatic residue, preferably a $C_{3-6}$-cycloaliphatic residue, or a 3 to 10 membered heterocycloaliphatic residue, preferably a 3 to 6 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with OH or an unsubstituted O—$C_{1-4}$-aliphatic residue.

and wherein the $C_{3-10}$-cycloaliphatic residue or the 3 to 10 membered heterocycloaliphatic residue may in each case optionally bridged via a unsubstituted $C_{1-4}$ aliphatic group, on the condition that if $R^6$ denotes a 3 to 10 membered heterocycloaliphatic residue, the 3 to 10 membered heterocycloaliphatic residue is linked via a carbon atom, or
$R^6$ denotes S—$R^7$ or O—$R^8$
wherein
$R^7$ and $R^8$ in each case denote a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, an NH($C_{1-4}$ aliphatic residue), an N($C_{1-4}$ aliphatic residue)$_2$, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or in each case denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue in each case may be bridged, preferably is bridged, via an unsubstituted $C_{1-8}$ aliphatic group, preferably an unsubstituted $C_{1-4}$ aliphatic group, on the condition that if $R^7$ or $R^8$ denotes a 3 to 10 membered heterocycloaliphatic residue, the 3 to 10 membered heterocycloaliphatic residue is linked via a carbon atom, or
$R^6$ denotes N($R^9R^{10}$),
wherein
$R^9$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue is in each case bridged via a unsubstituted $C_{1-8}$ aliphatic group, preferably an unsubstituted $C_{1-4}$ aliphatic group, on the condition that if $R^9$ denotes a 3 to 10 membered heterocycloaliphatic residue, the 3 to 10 membered heterocycloaliphatic residue is linked via a carbon atom, and
$R^{10}$ denotes H or an unsubstituted $C_{1-4}$-aliphatic residue, preferably selected from the group consisting of methyl, ethyl, n-propyl, 2-propyl, n-butyl, isobutyl, sec.-butyl and tert.-butyl, more preferably selected from the group consisting of methyl and ethyl, preferably denotes an unsubstituted $C_{1-4}$-aliphatic residue, preferably selected from the group consisting of methyl, ethyl, n-propyl, 2-propyl, n-butyl, isobutyl, sec.-butyl and tert.-butyl, more preferably selected from the group consisting of methyl and ethyl or
$R^9$ and $R^{10}$ form together with the nitrogen atom connecting them a 3 to 6 membered heterocycloaliphatic residue, preferably selected from the group consisting of morpholinyl, piperidinyl, pyrrolidinyl, and azetidinyl, unsubstituted or mono- or polysubstituted with at least one substituent selected from the group consisting of F, Cl, Br, I, NO$_2$, OH, =O, an O—C$_{1-4}$ aliphatic residue, OCF$_3$, SH, SCF$_3$, a S—C$_{1-4}$ aliphatic residue, CF$_3$, CN, and a C$_{1-4}$-aliphatic residue,
wherein the C$_{1-4}$-aliphatic residue in each case may be unsubstituted or mono- or polysubstituted with at least one substituent selected from the group consisting of F, Cl, Br, I, OH, CF$_3$ and an unsubstituted O—C$_{1-4}$-aliphatic residue,
and wherein the 3 to 6 membered heterocycloaliphatic residue formed by R$^9$ and R$^{10}$ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, Br, I, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, residue, benzyl, phenyl, and pyridyl,
wherein the C$_{1-4}$-aliphatic residue in each case may be unsubstituted or mono- or polysubstituted with at least one substituent selected from the group consisting of F, Cl, OH, and an unsubstituted O—C$_{1-4}$-aliphatic residue, and
wherein benzyl, phenyl, and pyridyl, may in each case may be unsubstituted or mono- or polysubstituted with at least one substituent selected from the group consisting of F, Cl, Br, I, OCH$_3$, OCF$_3$, O—CH$_2$—OH, O—CH$_2$—O—CH$_3$, SH, SCF$_3$, CF$_3$, and a C$_{1-4}$-aliphatic residue.

Still more preferably,

R$^6$ denotes a C$_{2-6}$-aliphatic residue, preferably selected from the group consisting of ethyl, n-propyl, 2-propyl, n-butyl, isobutyl, sec.-butyl, tert.-butyl, n-pentyl, isopentyl, neopentyl, n-hexyl, ethenyl and propenyl (—CH$_2$CH=CH$_2$, —CH=CH—CH$_3$, —C(=CH$_2$)—CH$_3$), unsubstituted or mono- or polysubstituted with at least one substituent selected from the group consisting of F, Cl, Br, I, OH, =O, an O—C$_{1-4}$-aliphatic residue, a C(=O)—O—C$_{1-4}$-aliphatic residue, OCF$_3$, SH, SCF$_3$, a S—C$_{1-4}$-aliphatic residue, CF$_3$, and a C$_{1-4}$-aliphatic residue, preferably in each case unsubstituted or mono- or polysubstituted with at least one substituent selected from the group consisting of F, Cl, OH, an O—C$_{1-4}$-aliphatic residue, CF$_3$, and a C$_{1-4}$-aliphatic residue, more preferably in each case unsubstituted or mono- or polysubstituted with at least one substituent selected from the group consisting of F, Cl, and an O—C$_{1-4}$-aliphatic residue, preferably O-methyl, even more preferably in each case unsubstituted,
wherein the C$_{1-4}$-aliphatic residue in each case is unsubstituted,
or denotes a C$_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of piperidinyl (preferably piperidin-4-yl or piperidin-3-yl), tetrahydrofuranyl, and tetrahydropyranyl, in each case unsubstituted or mono- or polysubstituted with at least one substituent selected from the group consisting of F, Cl, Br, I, OH, =O, an O—C$_{1-4}$-aliphatic residue, a C(=O)—O—C$_{1-4}$-aliphatic residue, OCF$_3$, SH, SCF$_3$, a S—C$_{1-4}$-aliphatic residue, CF$_3$, and a C$_{1-4}$-aliphatic residue, preferably in each case unsubstituted or mono- or polysubstituted with at least one substituent selected from the group consisting of F, Cl, OH, an O—C$_{1-4}$-aliphatic residue, CF$_3$, and a C$_{1-4}$-aliphatic residue, more preferably in each case unsubstituted or mono- or polysubstituted with at least one substituent selected from the group consisting of F, Cl, and an O—C$_{1-4}$-aliphatic residue, preferably O-methyl, even more preferably in each case unsubstituted,
wherein the C$_{1-4}$-aliphatic residue in each case is unsubstituted,
and wherein the C$_{3-6}$-cycloaliphatic residue or the 3 to 6 membered heterocycloaliphatic residue may in each case optionally bridged via an unsubstituted C$_{1-4}$ aliphatic group, preferably via an unsubstituted C$_{1-2}$ aliphatic group, on the condition that if R$^6$ a 3 to 6 membered heterocycloaliphatic residue, the 3 to 6 membered heterocycloaliphatic residue is linked via a carbon atom, or R$^6$ denotes S—R$^7$ or O—R$^8$
wherein
R$^7$ and R$^8$ in each case denote a C$_{1-6}$-aliphatic residue, preferably selected from the group consisting of methyl, ethyl, n-propyl, 2-propyl, n-butyl, isobutyl, sec.-butyl, tert.-butyl, n-pentyl, isopentyl, neopentyl, n-hexyl, ethenyl and propenyl (—CH$_2$CH=CH$_2$, —CH=CH—CH$_3$, —C(=CH$_2$)—CH$_3$), unsubstituted or mono- or polysubstituted with at least one substituent selected from the group consisting of F, Cl, Br, I, OH, =O, an O—C$_{1-4}$-aliphatic residue, a C(=O)—O—C$_{1-4}$-aliphatic residue, OCF$_3$, SH, SCF$_3$, a S—C$_{1-4}$-aliphatic residue, an NH(C$_{1-4}$ aliphatic residue), an N(C$_{1-4}$ aliphatic residue)$_2$, CF$_3$, and a C$_{1-4}$-aliphatic residue, more preferably in each case unsubstituted or mono- or polysubstituted with at least one substituent selected from the group consisting of F, Cl, OH, and an O—C$_{1-4}$-aliphatic residue,
wherein the C$_{1-4}$-aliphatic residue in each case is unsubstituted,
or denotes a C$_{3-6}$-cycloaliphatic residue, preferably cyclopropyl, or a 3 to 6 membered heterocycloaliphatic residue, preferably oxetanyl, in each case unsubstituted or mono- or polysubstituted with at least one substituent selected from the group consisting of F, Cl, Br, I, OH, =O, an O—C$_{1-4}$ aliphatic residue, OCF$_3$, SCF$_3$, a S—C$_{1-4}$ aliphatic residue, a C(=O)—O—C$_{1-4}$-aliphatic residue, CF$_3$, and a C$_{1-4}$-aliphatic residue, preferably in each case unsubstituted or mono- or polysubstituted with at least one substituent selected from the group consisting of F, Cl, OH, an O—C$_{1-4}$-aliphatic residue, CF$_3$, and a C$_{1-4}$-aliphatic residue,
wherein the C$_{1-4}$-aliphatic residue in each case may be unsubstituted or mono- or polysubstituted with OH or an unsubstituted O—C$_{1-4}$-aliphatic residue,
and wherein the C$_{3-10}$-cycloaliphatic residue or the 3 to 10 membered heterocycloaliphatic residue in each case may be bridged, preferably is bridged, via an unsubstituted C$_{1-4}$ aliphatic group,
on the condition that if R$^7$ or R$^8$ denotes a 3 to 10 membered heterocycloaliphatic residue, the 3 to 10 membered heterocycloaliphatic residue is linked via a carbon atom, or R$^6$ denotes N(R$^9$R$^{10}$),
wherein
R$^9$ denotes a C$_{1-6}$-aliphatic residue, unsubstituted or mono- or polysubstituted with at least one substituent selected from the group consisting of F, Cl, Br, I, OH, =O, an O—C$_{1-4}$-aliphatic residue, a C(=O)—O—C$_{1-4}$-aliphatic residue, OCF$_3$, SH, SCF$_3$, a S—C$_{1-4}$-aliphatic residue, CF$_3$, and a C$_{1-4}$-aliphatic residue, preferably an unsubstituted C$_{1-6}$-aliphatic residue, more preferably selected from the group consisting of methyl, ethyl, n-propyl, 2-propyl, n-butyl, isobutyl, sec.-butyl, tert.-butyl, n-pentyl, isopentyl, neopentyl, and n-hexyl, wherein the $C_{1-4}$-aliphatic residue in each case is unsubstituted,
or denotes a $C_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of piperidinyl (preferably piperidin-4-yl or piperidin-3-yl), tetrahydrofuranyl, and tetrahydropyranyl, in each case unsubstituted or mono- or polysubstituted with at least one substituent selected from the group consisting of F, Cl, a $C_{1-4}$-aliphatic residue and an O—$C_{1-4}$-aliphatic residue, even more preferably in each case unsubstituted,
wherein the $C_{1-4}$-aliphatic residue in each case is unsubstituted,
and wherein the $C_{3-6}$-cycloaliphatic residue or the 3 to 6 membered heterocycloaliphatic residue may in each case optionally bridged via an unsubstituted $C_{1-4}$ aliphatic group,
on the condition that if $R^9$ denotes a 3 to 6 membered heterocycloaliphatic residue, the 3 to 10 membered heterocycloaliphatic residue is linked via a carbon atom,
$R^{10}$ denotes H or an unsubstituted $C_{1-4}$-aliphatic residue, preferably represents an unsubstituted $C_{1-4}$-aliphatic residue, or denotes H, methyl, ethyl, n-propyl, 2-propyl, n-butyl, isobutyl, sec.-butyl or tert.-butyl, preferably denotes methyl, ethyl, n-propyl, 2-propyl, n-butyl, isobutyl, sec.-butyl or tert.-butyl,
or
$R^9$ and $R^{10}$ form together with the nitrogen atom connecting them a morpholinyl, piperidinyl, pyrrolidinyl, or azetidinyl, in each case unsubstituted or mono- or polysubstituted with at least one substituent selected from the group consisting of F, Cl, Br, I, OH, an O—$C_{1-4}$ aliphatic residue, and a $C_{1-4}$-aliphatic residue
wherein the $C_{1-4}$-aliphatic residue in each case may be unsubstituted or mono- or polysubstituted with OH or an unsubstituted O—$C_{1-4}$-aliphatic residue.
Most preferred,
$R^6$ denotes ethyl, n-propyl, 2-propyl, n-butyl, isobutyl, sec.-butyl, tert.-butyl, n-pentyl, isopentyl, neopentyl, n-hexyl, ethenyl or propenyl (—$CH_2CH=CH_2$, —$CH=CH$—$CH_3$, —$C(=CH_2)$—$CH_3$), in each case unsubstituted or mono- or polysubstituted with at least one substituent selected from the group consisting of F, Cl, OH, an O—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, and an O—$C_{1-4}$-aliphatic residue, preferably O-methyl, more preferably in each case unsubstituted,
wherein the $C_{1-4}$-aliphatic residue in each case is unsubstituted,
or denotes cyclopropyl, cyclobutyl, cyclopentyl and cyclohexyl, piperidinyl, tetrahydrofuranyl, or tetrahydropyranyl, preferably denotes cyclopropyl or tetrahydropyranyl, more preferably cyclopropyl, in each case unsubstituted or mono- or polysubstituted with at least one substituent selected from the group consisting of F, Cl, OH, an O—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, and an O—$C_{1-4}$-aliphatic residue, preferably O-methyl, more preferably in each case unsubstituted,
wherein the $C_{1-4}$-aliphatic residue in each case is unsubstituted,
and wherein cyclopropyl, cyclobutyl, cyclopentyl and cyclohexyl, piperidinyl, tetrahydrofuranyl, and tetrahydropyranyl may in each case be optionally bridged via an unsubstituted $C_{1-4}$ aliphatic group, preferably via an unsubstituted $C_{1-2}$ aliphatic group,
on the condition that if $R^6$ denotes piperidinyl, tetrahydrofuranyl, or tetrahydropyranyl, piperidinyl, tetrahydrofuranyl, or tetrahydropyranyl is linked via a carbon atom,
or
$R^6$ denotes S—$R^7$ or O—$R^8$
wherein
$R^7$ and $R^8$ in each case denote methyl, ethyl, n-propyl, 2-propyl, n-butyl, isobutyl, sec.-butyl, tert.-butyl, n-pentyl, isopentyl, neopentyl, n-hexyl, ethenyl and propenyl (—$CH_2CH=CH_2$, —$CH=CH$—$CH_3$, —$C(=CH_2)$—$CH_3$), in each case unsubstituted or mono- or polysubstituted with at least one substituent selected from the group consisting of F, Cl, OH, N($C_{1-4}$ aliphatic residue)$_2$ and an O—$C_{1-4}$-aliphatic residue,
wherein the $C_{1-4}$-aliphatic residue in each case is unsubstituted,
or in each case denote cyclopropyl, cyclobutyl, cyclopentyl cyclohexyl, oxetanyl, piperidinyl, tetrahydrofuranyl, or tetrahydropyranyl, preferably cyclopropyl or oxetanyl, in each case unsubstituted or mono- or polysubstituted with at least one substituent selected from the group consisting of F, Cl, OH, an O—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, and an O—$C_{1-4}$-aliphatic residue, more preferably in each case unsubstituted,
wherein the $C_{1-4}$-aliphatic residue in each case is unsubstituted,
and wherein cyclopropyl, cyclobutyl, cyclopentyl and cyclohexyl, oxetanyl, piperidinyl, tetrahydrofuranyl, and tetrahydropyranyl may in each case be optionally bridged via an unsubstituted $C_{1-4}$ aliphatic group,
on the condition that if $R^7$ or $R^8$ denotes piperidinyl, oxetanyl, tetrahydrofuranyl, or tetrahydropyranyl, each of these residues is linked via a carbon atom,
or
$R^6$ denotes N($R^9R^{10}$),
wherein
$R^9$ denotes a $C_{1-6}$-aliphatic residue, unsubstituted or mono- or polysubstituted with at least one substituent selected from the group consisting of F, Cl, =O, OH, and O-methyl, preferably unsubstituted or mono- or polysubstituted with at least one substituent selected from the group consisting of F, Cl, and O-methyl, more preferably unsubstituted or mono- or polysubstituted with at least one substituent selected from the group consisting of F and O-methyl, preferably denotes an unsubstituted $C_{1-6}$-aliphatic residue, more preferably selected from the group consisting of methyl, ethyl, n-propyl, 2-propyl, n-butyl, isobutyl, sec.-butyl, tert.-butyl, n-pentyl, isopentyl, neopentyl, and n-hexyl,
$R^{10}$ denotes H, methyl, ethyl, n-propyl, 2-propyl, n-butyl, isobutyl, sec.-butyl or tert.-butyl, preferably methyl, ethyl, n-propyl, 2-propyl, n-butyl, isobutyl, sec.-butyl or tert.-butyl, more preferably methyl or ethyl,
or
$R^9$ and $R^{10}$ form together with the nitrogen atom connecting them a morpholinyl, piperidinyl, pyrrolidinyl, or azetidinyl, in each case unsubstituted or mono- or polysubstituted with at least one substituent selected from the group consisting of F, Cl, Br, I, OH, an O—$C_{1-4}$ aliphatic residue, and a $C_{1-4}$-aliphatic residue, more preferably unsubstituted or mono- or polysubstituted with at least one substituent selected from the group consisting of F, Cl and a O—$C_{1-4}$ aliphatic residue, preferably form together with the nitrogen atom connecting them a morpholinyl, piperidinyl, pyrrolidinyl, or azetidinyl, in each case unsubstituted.

In particular, $R^6$ denotes ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, ethenyl or propenyl (—$CH_2CH$=$CH_2$, —$CH$=$CH$—$CH_3$, —$C(=CH_2)$—$CH_3$), $CH_2$—$OCH_3$, $C_2H_4$—$OCH_3$, $C_3H_6$—$OCH_3$, cyclopropyl, cyclobutyl, or tetrahydropyranyl, in each case unsubstituted, or $R^6$ denotes S—$R^7$ or O—$R^8$
wherein $R^7$ and $R^8$ in each case denote methyl, ethyl, n-propyl, 2-propyl, n-butyl, isobutyl, sec.-butyl, tert.-butyl, n-pentyl, isopentyl, neopentyl, or n-hexyl, in each case unsubstituted or mono- or polysubstituted with at least one substituent selected from the group consisting of F, Cl, OH, a N($C_{1-4}$ aliphatic residue)$_2$, and an O—$C_{1-4}$-aliphatic residue, preferably with at least one substituent selected from the group consisting of F, OH, N($CH_3$)$_2$, O-methyl and O-ethyl, or in each case denote $CH_2$-cyclopropyl or oxetanyl, preferably, $R^7$ and $R^8$ in each case denote methyl, ethyl, n-propyl, 2-propyl, n-butyl, isobutyl, sec.-butyl, tert.-butyl, n-pentyl, isopentyl, neopentyl, or n-hexyl, $CH_2$—$CH_2$—F, $CH_2CHF_2$, $CH_2$—$OCH_3$, $CH_2CH_2$—$OCH_3$, $CH_2CH_2$—$N(CH_3)_2$, $CH_2$-cyclopropyl or oxetanyl,
wherein the $C_{1-4}$-aliphatic residue in each case is unsubstituted, or $R^6$ denotes N($R^9R^{10}$),
wherein
$R^9$ denotes methyl, ethyl, C(=O)—$CH_3$, n-propyl, 2-propyl, n-butyl, isobutyl, sec.-butyl, tert.-butyl, n-pentyl, isopentyl, neopentyl, or n-hexyl,
$R^{10}$ denotes H, methyl or ethyl, preferably methyl or ethyl, or $R^9$ and $R^{10}$ form together with the nitrogen atom connecting them a morpholinyl, piperidinyl, pyrrolidinyl, or azetidinyl, in each case unsubstituted.

Particularly preferred is a compound according to general formula (I), wherein
$R^1$ represents the partial structure (T1),

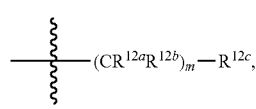

(T1)

wherein
m is 0, 1 or 2, preferably 0 or 2, more preferably 2, and
$R^{12a}$ and $R^{12b}$ each independently of one another represent H, F, OH, $CH_3$ or $OCH_3$ or together denote =O, more preferably H, F, OH or $CH_3$, even more preferably H,
$R^{12c}$ denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, CN, OH, S(=O)$_2$—$CH_3$, an unsubstituted O—$C_{1-4}$ aliphatic residue, preferably O-methyl and O-tert.-butyl, and $CF_3$, preferably denotes a $C_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, an unsubstituted O—$C_{1-4}$ aliphatic residue, preferably O-methyl and O-tert.-butyl, and $CF_3$, or denotes a $C_{3-10}$-cycloaliphatic residue or a 3 to 10 membered heterocycloaliphatic residue, preferably cyclopropyl, cyclopentyl, cyclohexyl, morpholinyl, oxetanyl or tetrahydropyranyl, in each case unsubstituted or mono- or polysubstituted with at least one substituent selected from the group consisting of F, Cl, Br, I, an unsubstituted O—$C_{1-4}$ aliphatic residue, preferably O-methyl and O-ethyl, $CF_3$, and an unsubstituted $C_{1-4}$-aliphatic residue, preferably methyl or ethyl, or wherein
m is 0 or 2, more preferably 0, and
$R^{12a}$ and $R^{12b}$ each independently of one another represent H, F, $CH_3$ or $OCH_3$; and
$R^{12c}$ denotes an aryl or heteroaryl, preferably phenyl or pyridyl, in each case unsubstituted or mono- or polysubstituted with at least one substituent selected from the group consisting of F, Cl, Br, I, OH, an O—$C_{1-4}$ aliphatic residue, $OCF_3$, $OCF_2H$, $CH_2$—OH, $CH_2$—$OCH_3$, S(=O)$_2$—$CH_3$, $SCF_3$, $NO_2$, N($CH_3$)$_2$,

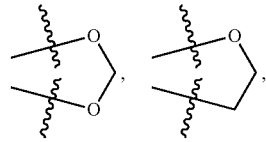 [SMILES: *OCO* ; *CCO*]

$CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl, preferably denotes an aryl or heteroaryl, preferably phenyl or pyridyl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl,
wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, $R^2$ represents F; Cl; Br; I; CN; $CF_3$; $NO_2$; $OCF_3$; $SCF_3$; methyl; ethyl; n-propyl; iso-propyl; n-butyl; sec.-butyl; tert.-butyl; $CH_2$—OH; $CH_2$—O—$CH_3$; $CH_2$—$CH_2$—OH; $CH_2$—$CH_2$—$OCH_3$; O-methyl; O-ethyl; O—($CH_2$)$_2$—O—$CH_3$; O—($CH_2$)$_2$—OH; S-Methyl; S-Ethyl; cyclopropyl, cyclobutyl, cyclopentyl, or cyclohexyl; preferably represents F; Cl; Br; I; CN; $CF_3$; $NO_2$; $OCF_3$; $SCF_3$; methyl; ethyl; n-propyl; iso-propyl; n-butyl; sec.-butyl; tert.-butyl; $CH_2$—OH; O-methyl; O-ethyl; O—($CH_2$)$_2$—O—$CH_3$; O—($CH_2$)$_2$—OH; S-Methyl; S-Ethyl; cyclopropyl, cyclobutyl, cyclopentyl, or cyclohexyl, $R^3$ represents H; F; Cl; Br; I; CN; $CF_3$; $SCF_3$; $NO_2$; $OCF_3$; methyl; ethyl; n-propyl; iso-propyl; n-butyl; sec.-butyl;

tert.-butyl; O-methyl; O-ethyl; O—(CH$_2$)$_2$—O—CH$_3$; O—(CH$_2$)$_2$—OH; S-Methyl; or S-Ethyl, R$^4$ represents the partial structure (T2)

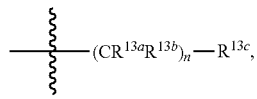

(T2)

wherein n denotes 0, 1, 2 or 3, preferably denotes 1 or 2, more preferably denotes 1, R$^{13a}$ and R$^{13b}$ each independently of one another represent H, F, CH$_3$ or OCH$_3$, or together denote =O, preferably each independently of one another represent H or CH$_3$, more preferably H, R$^{13c}$ denotes a C$_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, =O, an unsubstituted aliphatic residue, and CF$_3$, or denotes cyclopropyl, cyclobutyl, cyclopentyl or cyclohexyl, pyrrolidinyl, morpholinyl, piperazinyl, piperidinyl and tetrahydropyranyl, more preferably tetrahydropyranyl or morpholinyl, in each case unsubstituted or mono- or polysubstituted with at least one substituent selected from the group consisting of F, Cl, Br, I, an unsubstituted aliphatic residue, CF$_3$, and an unsubstituted C$_{1-4}$-aliphatic residue, or denotes an aryl or heteroaryl, preferably phenyl or pyridyl, more preferably phenyl, in each case unsubstituted or mono- or polysubstituted with at least one substituent selected from the group consisting of F, Cl, Br, I, OH, an O—C$_{1-4}$ aliphatic residue, OCF$_3$, CF$_3$, CN, and a C$_{1-4}$-aliphatic residue, R$^5$ denotes H, methyl or ethyl, C$_2$H$_4$OCH$_3$ or C$_3$H$_6$OCH$_3$, more preferably H or methyl, even more preferably methyl, or R$^4$ and R$^5$ form together with the nitrogen atom connecting them a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, preferably a morpholinyl, piperidinyl, pyrrolidinyl, azetidinyl, oxazepanyl, tetrahydroquinolinyl, tetrahydroisoquinolinyl, thiomorpholinyl, azepanyl,

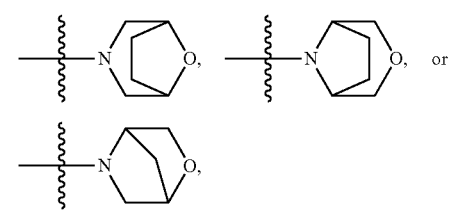

tetrahydroimidazo[1,2-a]pyrazinyl, octahydropyrrolo[1,2-a]pyrazinyl,

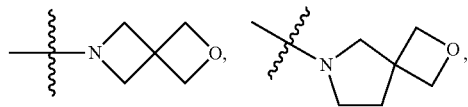 [SMILES: *N1CC2(COC2)C1 ; *N1CCC2(COC2)C1]

dihydroindolinyl, or dihydroisoindolyl, preferably a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, more preferably a morpholinyl, oxazepanyl, tetrahydroquinolinyl, or tetrahydroisoquinolinyl, in each case unsubstituted or mono- or polysubstituted with at least one substituent selected from the group consisting of F, Cl, OH, =O, C(=O)—OH, O-methyl, O-ethyl, OCF$_3$, SCF$_3$, CF$_3$, C(=O)—CH$_3$, C(=O)—OCH$_3$, CH$_2$CF$_3$, CH$_2$OH, CH$_2$—OCH$_3$, CH$_2$CH$_2$—OCH$_3$, methyl, ethyl, n-propyl, 2-propyl, cyclopropyl, and cyclobutyl, preferably selected from the group consisting of F, Cl, OH, =O, C(=O)—OH, O-methyl, O-ethyl, OCF$_3$, SCF$_3$, CF$_3$, methyl, ethyl, n-propyl, 2-propyl, cyclopropyl, and cyclobutyl, R$^6$ denotes ethyl, n-propyl, 2-propyl, n-butyl, isobutyl, sec.-butyl, tert.-butyl, n-pentyl, isopentyl, neopentyl, n-hexyl, CH$_2$—CH(CH$_3$)(C$_2$H$_5$), C(CH$_3$)$_2$(C$_2$H$_5$), ethenyl or propenyl (—CH$_2$CH=CH$_2$, —CH=CH—CH$_3$, —C(=CH$_2$)—CH$_3$), CH$_2$—OCH$_3$, C$_2$H$_4$—OCH$_3$, C$_3$H$_6$—OCH$_3$, cyclopropyl, cyclobutyl, or tetrahydropyranyl, in each case unsubstituted, or R$^6$ denotes S—R$^7$ or O—R$^8$ wherein R$^7$ and R$^8$ in each case denote methyl, ethyl, n-propyl, 2-propyl, n-butyl, isobutyl, sec.-butyl, tert.-butyl, n-pentyl, isopentyl, neopentyl, or n-hexyl, in each case unsubstituted or mono- or polysubstituted with at least one substituent selected from the group consisting of F, Cl, OH, a N(C$_{1-4}$ aliphatic residue)$_2$, and an O—C$_{1-4}$-aliphatic residue, preferably with at least one substituent selected from the group consisting of F, OH, N(CH$_3$)$_2$, O-methyl and O-ethyl, or in each case denote CH$_2$-cyclopropyl or oxetanyl, preferably, R$^7$ and R$^8$ in each case denote methyl, ethyl, n-propyl, 2-propyl, n-butyl, isobutyl, sec.-butyl, tert.-butyl, n-pentyl, isopentyl, neopentyl, or n-hexyl, CH$_2$—CH$_2$—F, CH$_2$CHF$_2$, CH$_2$—OCH$_3$, CH$_2$CH$_2$—OCH$_3$, CH$_2$CH$_2$—N(CH$_3$)$_2$, CH$_2$-cyclopropyl or oxetanyl, wherein the C$_{1-4}$-aliphatic residue in each case is unsubstituted, or R$^6$ denotes N(R$^9$R$^{10}$), wherein R$^9$ denotes methyl, C(=O)—CH$_3$, ethyl, n-propyl, 2-propyl, n-butyl, isobutyl, sec.-butyl, tert.-butyl, n-pentyl, isopentyl, neopentyl, or n-hexyl, R$^{10}$ denotes H, methyl or ethyl, preferably methyl or ethyl, or R$^9$ and R$^{10}$ form together with the nitrogen atom connecting them a morpholinyl, piperidinyl, pyrrolidinyl, or azetidinyl, in each case unsubstituted.

In another particularly preferred embodiment of the compound according to general formula (I), R$^1$ represents phenyl or pyridyl, preferably phenyl, in each case unsubstituted or mono- or disubstituted with at least one substituent selected from the group consisting of F, Cl, Br, OH, OCH$_3$, OCF$_3$, CF$_3$, and CH$_3$, R$^2$ represents H; CF$_3$; methyl; ethyl; iso-propyl; O-methyl; or cyclopropyl, R³ represents H; F; Cl; Br; I; CN; CF₃; methyl; or O-methyl;

R⁴ and R⁵ form together with the nitrogen atom connecting them a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, in each case unsubstituted;

R⁶ denotes ethyl, n-propyl, 2-propyl (iso-propyl), tert.-butyl, cyclopropyl, cyclobutyl or cyclopentyl or tetrahydropyranyl, or R⁶ denotes S—R⁷ or O—R⁸ wherein R⁷ and R⁸ in each case denote methyl, ethyl, 2-propyl, or tert.-butyl.

or

R⁶ denotes N(R⁹R¹⁰), wherein

R⁹ denotes methyl, ethyl, n-propyl, 2-propyl, or tert.-butyl,

R¹⁰ denotes H, methyl or ethyl, preferably methyl or ethyl, or

R⁹ and R¹⁰ form together with the nitrogen atom connecting them a morpholinyl, piperidinyl, pyrrolidinyl, or azetidinyl.

Especially particularly preferred are compounds according to general formula (I) selected from the group comprising:

1 N-[(3,5-Difluoro-phenyl)-methyl]-2-ethylsulfanyl-4-methyl-6-morpholin-4-yl-pyridine-3-carboxylic acid amide;
2 Ethylsulfanyl-N-[(3-fluorophenyl)-methyl]-4-methyl-6-morpholin-4-yl-pyridine-3-carboxylic acid amide;
3 N-[(3,5-Difluoro-phenyl)-methyl]-2-methoxy-4-methyl-6-morpholin-4-yl-pyridine-3-carboxylic acid amide;
4 2-Ethylsulfanyl-N-[(4-fluorophenyl)-methyl]-4-methyl-6-morpholin-4-yl-pyridine-3-carboxylic acid amide;
5 2-Ethylsulfanyl-N-[(3-fluorophenyl)-methyl]-4-methyl-6-[methyl-(tetrahydro-pyran-2-yl-methyl)-amino]-pyridine-3-carboxylic acid amide;
6 2-Ethylsulfanyl-N-[(3-fluorophenyl)-methyl]-6-(3-methoxy-azetidin-1-yl)-4-methyl-pyridine-3-carboxylic acid amide;
7 2-Ethylsulfanyl-N-[(3-fluorophenyl)-methyl]-6-(3-hydroxy-azetidin-1-yl)-4-methyl-pyridine-3-carboxylic acid amide;
8 2-Ethylsulfanyl-N-[(3-fluorophenyl)-methyl]-6-[(4-fluorophenyl)-methylamino]-4-methyl-pyridine-3-carboxylic acid amide;
9 N-[(3-Fluorophenyl)-methyl]-4-methyl-6-morpholin-4-yl-2-[(E)-prop-1-enyl]pyridine-3-carboxylic acid amide;
10 N-[(3-Fluorophenyl)-methyl]-4-methyl-6-morpholin-4-yl-2-propyl-pyridine-3-carboxylic acid amide;
11 2-Ethylsulfanyl-N-[(3-fluorophenyl)-methyl]-6-morpholin-4-yl-4-(trifluoromethyl)-pyridine-3-carboxylic acid amide;
12 N-[(3-Fluorophenyl)-methyl]-4-methyl-2,6-dimorpholin-4-yl-pyridine-3-carboxylic acid amide;
13 1-[6-Ethylsulfanyl-5-[(3-fluorophenyl)-methyl-carbamoyl]-4-methyl-pyridin-2-yl]-piperidine-4-carboxylic acid methyl ester;
14 1-[6-Ethylsulfanyl-5-[(3-fluorophenyl)-methyl-carbamoyl]-4-methyl-pyridin-2-yl]-piperidine-4-carboxylic acid;
15 2-Ethylsulfanyl-N-[(3-fluorophenyl)-methyl]-6-(4-hydroxy-piperidin-1-yl)-4-methyl-pyridine-3-carboxylic acid amide;
16 2-Ethylsulfanyl-N-[(3-fluorophenyl)-methyl]-4-methyl-6-(4-oxo-piperidin-1-yl)-pyridine-3-carboxylic acid amide;
17 2-Ethylsulfanyl-N-[(4-fluoro-2-methoxy-phenyl)methyl]-4-methyl-6-morpholin-4-yl-pyridine-3-carboxylic acid amide;
18 2-Ethylsulfanyl-N-[(4-fluoro-2-hydroxy-phenyl)methyl]-4-methyl-6-morpholin-4-yl-pyridine-3-carboxylic acid amide;
19 N-[(3-Fluorophenyl)-methyl]-2-methoxy-4-methyl-6-morpholin-4-yl-pyridine-3-carboxylic acid amide;
20 2-Ethylamino-N-[(3-fluorophenyl)-methyl]-4-methyl-6-morpholin-4-yl-pyridine-3-carboxylic acid amide;
21 N-[(3-Fluorophenyl)-methyl]-2-(2-methoxy-ethoxy)-4-methyl-6-morpholin-4-yl-pyridine-3-carboxylic acid amide;
22 2-Ethyl-N-[(3-fluorophenyl)-methyl]-4-methyl-6-morpholin-4-yl-pyridine-3-carboxylic acid amide;
23 N-[(3-Fluorophenyl)-methyl]-2-isopropyl-4-methyl-6-morpholin-4-yl-pyridine-3-carboxylic acid amide;
24 N-[(3-Fluorophenyl)-methyl]-4-methyl-6-morpholin-4-yl-2-pyrrolidin-1-yl-pyridine-3-carboxylic acid amide;
25 2-Ethylsulfanyl-N-[(3-fluorophenyl)-methyl]-4-methyl-6-pyrrolidin-1-yl-pyridine-3-carboxylic acid amide;
26 2-Ethylsulfanyl-N-[(3-fluorophenyl)-methyl]-4-methyl-6-(1,2,3,4-tetrahydro-isoquinolin-2-yl)-pyridine-3-carboxylic acid amide;
27 2-Ethylsulfanyl-N-[(3-fluorophenyl)-methyl]-4-methyl-6-[6-(trifluoromethyl)-1,2,3,4-tetrahydro-isoquinolin-2-yl]pyridine-3-carboxylic acid amide;
28 N-[(4-Fluorophenyl)-methyl]-4-methyl-6-morpholin-4-yl-2-[(E)-prop-1-enyl]pyridine-3-carboxylic acid amide;
29 N-[(4-Fluorophenyl)-methyl]-4-methyl-6-morpholin-4-yl-2-propyl-pyridine-3-carboxylic acid amide
30 2-Ethylsulfanyl-N-[(3-fluorophenyl)-methyl]-6-(3-methoxy-pyrrolidin-1-yl)-4-methyl-pyridine-3-carboxylic acid amide;
31 2-Ethylsulfanyl-N-[(3-fluorophenyl)-methyl]-4-methyl-6-(4-methyl-piperazin-1-yl)-pyridine-3-carboxylic acid amide;
32 2-Ethylsulfanyl-N-[(3-fluorophenyl)-methyl]-4-methyl-6-piperidin-1-yl-pyridine-3-carboxylic acid amide;
33 6-Dimethylamino-2-ethylsulfanyl-N-[(3-fluorophenyl)-methyl]-4-methyl-pyridine-3-carboxylic acid amide;
34 2-Ethylsulfanyl-N-[(3-fluorophenyl)-methyl]-4-methyl-6-methylamino-pyridine-3-carboxylic acid amide;
35 2-Ethylsulfanyl-N-[(3-fluorophenyl)-methyl]-6-(2-methoxy-ethyl-methyl-amino)-4-methyl-pyridine-3-carboxylic acid amide;
36 2-Ethylsulfanyl-N-[(3-fluorophenyl)-methyl]-6-(2-methoxy-ethylamino)-4-methyl-pyridine-3-carboxylic acid amide;
37 N-[(3-Fluorophenyl)-methyl]-2-(isopropylsulfanyl)-4-methyl-6-morpholin-4-yl-pyridine-3-carboxylic acid amide;
38 2-Ethoxy-N-[(3-fluorophenyl)-methyl]-4-methyl-6-morpholin-4-yl-pyridine-3-carboxylic acid amide;
39 N-[(4-Fluorophenyl)-methyl]-2-methoxy-4-methyl-6-morpholin-4-yl-pyridine-3-carboxylic acid amide;
40 N-[(3-Fluorophenyl)-methyl]-4-methyl-2-methylsulfanyl-6-morpholin-4-yl-pyridine-3-carboxylic acid amide;
41 N-[(3,4-Difluoro-phenyl)-methyl]-2-ethylsulfanyl-4-methyl-6-morpholin-4-yl-pyridine-3-carboxylic acid amide;
42 2-Ethylsulfanyl-4-methyl-N-(3-methyl-butyl)-6-morpholin-4-yl-pyridine-3-carboxylic acid amide;
43 N-(Cyclopentyl-methyl)-2-ethylsulfanyl-4-methyl-6-morpholin-4-yl-pyridine-3-carboxylic acid amide;
44 N-(2-Cyclopentyl-ethyl)-2-ethylsulfanyl-4-methyl-6-morpholin-4-yl-pyridine-3-carboxylic acid amide;
45 2-Ethylsulfanyl-N-[(6-fluoro-pyridin-2-yl)-methyl]-4-methyl-6-morpholin-4-yl-pyridine-3-carboxylic acid amide;

46 2-Ethylsulfanyl-N-[(5-fluoro-pyridin-2-yl)-methyl]-4-methyl-6-morpholin-4-yl-pyridine-3-carboxylic acid amide;
47 N-(2,2-Dimethyl-propyl)-2-ethylsulfanyl-4-methyl-6-morpholin-4-yl-pyridine-3-carboxylic acid amide;
48 2-Ethylsulfanyl-N-[(3-fluorophenyl)-methyl]-4-methyl-6-(2-methyl-morpholin-4-yl)-pyridine-3-carboxylic acid amide;
49 2-Ethylsulfanyl-N-[(3-fluorophenyl)-methyl]-6-(4-methoxy-piperidin-1-yl)-4-methyl-pyridine-3-carboxylic acid amide;
50 2-Ethylsulfanyl-4-methyl-6-morpholin-4-yl-N-[(2-phenyl-phenyl)-methyl]-pyridine-3-carboxylic acid amide;
51 2-Ethylsulfanyl-4-methyl-6-morpholin-4-yl-N-[[2-(trifluoromethyl)-phenyl]methyl]-pyridine-3-carboxylic acid amide;
52 2-Ethylsulfanyl-N-[(3-fluorophenyl)-methyl]-6-[(4-fluorophenyl)-methyl-methyl-amino]-4-methyl-pyridine-3-carboxylic acid amide;
53 2-Ethylsulfanyl-4-methyl-6-morpholin-4-yl-N-(3-phenyl-propyl)-pyridine-3-carboxylic acid amide;
54 2-Ethylsulfanyl-4-methyl-6-morpholin-4-yl-N-phenethyl-pyridine-3-carboxylic acid amide;
55 N-Benzyl-2-ethylsulfanyl-4-methyl-6-morpholin-4-yl-pyridine-3-carboxylic acid amide
56 N-[(3-Fluorophenyl)-methyl]-4-methyl-6-morpholin-4-yl-2-(propylsulfanyl)-pyridine-3-carboxylic acid amide;
57 2-(Butylsulfanyl)-N-[(3-fluorophenyl)-methyl]-4-methyl-6-morpholin-4-yl-pyridine-3-carboxylic acid amide;
58 2-Ethylsulfanyl-5-fluoro-N-[(3-fluorophenyl)-methyl]-4-methyl-6-morpholin-4-yl-pyridine-3-carboxylic acid amide;
59 2-Ethylsulfanyl-4-methyl-6-morpholin-4-yl-N-[[3-(trifluoromethyl)phenyl]methyl]-pyridine-3-carboxylic acid amide;
60 2-Ethylsulfanyl-4-methyl-6-morpholin-4-yl-N-[[4-(trifluoromethyl)-phenyl]methyl]-pyridine-3-carboxylic acid amide;
61 2-Ethylsulfanyl-N-[(3-fluorophenyl)-methyl]-4-methyl-6-[methyl-(tetrahydro-pyran-4-yl-methyl)-amino]-pyridine-3-carboxylic acid amide;
62 N-[(3-Fluorophenyl)-methyl]-4-methyl-2-(2-methyl-propylsulfanyl)-6-morpholin-4-yl-pyridine-3-carboxylic acid amide;
63 N-[(3-Fluorophenyl)-methyl]-2-(2-methoxy-ethylsulfanyl)-4-methyl-6-morpholin-4-yl-pyridine-3-carboxylic acid amide;
64 2-Ethoxy-N-[(4-fluorophenyl)-methyl]-4-methyl-6-morpholin-4-yl-pyridine-3-carboxylic acid amide;
65 2-Dimethylamino-N-[(3-fluorophenyl)-methyl]-4-methyl-6-morpholin-4-yl-pyridine-3-carboxylic acid amide;
66 6-(2,6-Dimethyl-morpholin-4-yl)-2-ethylsulfanyl-N-[(3-fluorophenyl)-methyl]-4-methyl-pyridine-3-carboxylic acid amide;
67 N-(4,4-Dimethyl-pentyl)-2-ethylsulfanyl-4-methyl-6-morpholin-4-yl-pyridine-3-carboxylic acid amide;
68 2-Ethylsulfanyl-4-methyl-6-morpholin-4-yl-N-(2-tetrahydro-pyran-2-yl-ethyl)-pyridine-3-carboxylic acid amide;
69 2-Ethylsulfanyl-4-methyl-6-morpholin-4-yl-N-(tetrahydro-pyran-2-yl-methyl)-pyridine-3-carboxylic acid amide;
70 2-Ethylsulfanyl-N-[(3-fluorophenyl)-methyl]-4-methyl-6-(4-methyl-piperidin-1-yl)-pyridine-3-carboxylic acid amide;
71 2-Ethylsulfanyl-N-[[2-(4-fluorophenyl)-phenyl]-methyl]-4-methyl-6-morpholin-4-yl-pyridine-3-carboxylic acid amide;
72 2-[[6-Ethylsulfanyl-5-[(3-fluorophenyl)-methyl-carbamoyl]-4-methyl-pyridin-2-yl]-methyl-amino]-acetic acid ethyl ester;
73 6-(4-Cyclopropyl-piperazin-1-yl)-2-ethylsulfanyl-N-[(3-fluorophenyl)-methyl]-4-methyl-pyridine-3-carboxylic acid amide;
74 6-(4,4-Dimethyl-piperidin-1-yl)-2-ethylsulfanyl-N-[(3-fluorophenyl)-methyl]-4-methyl-pyridine-3-carboxylic acid amide;
75 2-Ethylsulfanyl-4-methyl-6-morpholin-4-yl-N-[[4-(trifluoromethylsulfanyl)-phenyl]-methyl]-pyridine-3-carboxylic acid amide;
76 N-(Cyclohexyl-methyl)-2-ethylsulfanyl-4-methyl-6-morpholin-4-yl-pyridine-3-carboxylic acid amide;
77 2-Ethylsulfanyl-N-(2-methoxy-ethyl)-4-methyl-6-morpholin-4-yl-pyridine-3-carboxylic acid amide;
78 2-Ethylsulfanyl-N-(3-methoxy-propyl)-4-methyl-6-morpholin-4-yl-pyridine-3-carboxylic acid amide;
79 2-Ethylsulfanyl-4-methyl-N-(4-methyl-pentyl)-6-morpholin-4-yl-pyridine-3-carboxylic acid amide;
80 N-Butyl-2-ethylsulfanyl-4-methyl-6-morpholin-4-yl-pyridine-3-carboxylic acid amide;
81 2-Ethylsulfanyl-4-methyl-6-morpholin-4-yl-N-pentyl-pyridine-3-carboxylic acid amide;
82 2-Ethylsulfanyl-N-[[4-fluoro-3-(trifluoromethyl)-phenyl]-methyl]-4-methyl-6-morpholin-4-yl-pyridine-3-carboxylic acid amide;
83 N-(2-tert-Butoxy-ethyl)-2-ethylsulfanyl-4-methyl-6-morpholin-4-yl-pyridine-3-carboxylic acid amide;
84 2-Ethylsulfanyl-4-methyl-6-morpholin-4-yl-N-(4,4,4-trifluoro-butyl)-pyridine-3-carboxylic acid amide;
85 2-Ethylsulfanyl-N-[[4-fluoro-2-(4-fluorophenyl)-phenyl]-methyl]-4-methyl-6-morpholin-4-yl-pyridine-3-carboxylic acid amide;
86 N-(4,4-Dimethyl-pentyl)-2-methoxy-4-methyl-6-morpholin-4-yl-pyridine-3-carboxylic acid amide;
87 N-[(3,4-Difluoro-phenyl)-methyl]-2-methoxy-4-methyl-6-morpholin-4-yl-pyridine-3-carboxylic acid amide;
88 2-Methoxy-4-methyl-6-morpholin-4-yl-N-[(2-phenyl-phenyl)-methyl]-pyridine-3-carboxylic acid amide;
89 N-(4,4-Dimethyl-pentyl)-2-ethoxy-4-methyl-6-morpholin-4-yl-pyridine-3-carboxylic acid amide;
90 N-[(3,5-Difluoro-phenyl)-methyl]-2-ethoxy-4-methyl-6-morpholin-4-yl-pyridine-3-carboxylic acid amide;
91 N-[(3,4-Difluoro-phenyl)-methyl]-2-ethoxy-4-methyl-6-morpholin-4-yl-pyridine-3-carboxylic acid amide;
92 2-Ethoxy-4-methyl-6-morpholin-4-yl-N-[(2-phenyl-phenyl)-methyl]-pyridine-3-carboxylic acid amide;
93 2-Ethylsulfanyl-N-[[3-fluoro-5-(trifluoromethyl)-phenyl]-methyl]-4-methyl-6-morpholin-4-yl-pyridine-3-carboxylic acid amide;
94 2-Ethylsulfanyl-N-[[2-fluoro-3-(trifluoromethyl)-phenyl]-methyl]-4-methyl-6-morpholin-4-yl-pyridine-3-carboxylic acid amide;
95 2-Ethylsulfanyl-N-[[2-fluoro-5-(trifluoromethyl)-phenyl]-methyl]-4-methyl-6-morpholin-4-yl-pyridine-3-carboxylic acid amide;
96 2-Ethylsulfanyl-N-[(3-fluorophenyl)-methyl]-4-methyl-6-([1,4]oxazepan-4-yl)-pyridine-3-carboxylic acid amide;
97 2-Ethylsulfanyl-4-methyl-6-morpholin-4-yl-N-[[4-(trifluoromethyloxy)-phenyl]methyl]-pyridine-3-carboxylic acid amide;
98 N-[(3-Fluorophenyl)-methyl]-2-methoxy-4-methyl-6-([1,4]oxazepan-4-yl)-pyridine-3-carboxylic acid amide;

99 2-Ethoxy-N-[(3-fluorophenyl)-methyl]-4-methyl-6-([1,4]oxazepan-4-yl)-pyridine-3-carboxylic acid amide;
100 N-[(2,3-Difluoro-phenyl)-methyl]-2-ethylsulfanyl-4-methyl-6-morpholin-4-yl-pyridine-3-carboxylic acid amide;
101 N-[(2,5-Difluoro-phenyl)-methyl]-2-ethylsulfanyl-4-methyl-6-morpholin-4-yl-pyridine-3-carboxylic acid amide;
102 N-[(3-Cyano-phenyl)-methyl]-2-ethylsulfanyl-4-methyl-6-morpholin-4-yl-pyridine-3-carboxylic acid amide;
103 2-Ethylsulfanyl-N-(2-isopropoxy-ethyl)-4-methyl-6-morpholin-4-yl-pyridine-3-carboxylic acid amide;
104 N-(3,3-Dimethyl-butyl)-2-ethylsulfanyl-4-methyl-6-morpholin-4-yl-pyridine-3-carboxylic acid amide;
105 N-(3-Cyclopentyl-propyl)-2-ethylsulfanyl-4-methyl-6-morpholin-4-yl-pyridine-3-carboxylic acid amide;
106 N-(2-Cyclohexyl-ethyl)-2-ethylsulfanyl-4-methyl-6-morpholin-4-yl-pyridine-3-carboxylic acid amide;
107 N-[(2,4-Difluoro-phenyl)-methyl]-2-ethylsulfanyl-4-methyl-6-morpholin-4-yl-pyridine-3-carboxylic acid amide;
108 2-Ethylsulfanyl-N-[3-(4-fluorophenyl)-propyl]-4-methyl-6-morpholin-4-yl-pyridine-3-carboxylic acid amide;
109 2-Ethylsulfanyl-4-methyl-6-morpholin-4-yl-N-(3-pyridin-2-yl-propyl)-pyridine-3-carboxylic acid amide;
110 2-Butoxy-N-[(3-fluorophenyl)-methyl]-4-methyl-6-morpholin-4-yl-pyridine-3-carboxylic acid amide;
111 N-[(3-Fluorophenyl)-methyl]-4-methyl-6-morpholin-4-yl-2-propoxy-pyridine-3-carboxylic acid amide;
112 2-Ethylsulfanyl-N-[(3-fluorophenyl)-methyl]-4-methyl-6-(3-oxo-azetidin-1-yl)-pyridine-3-carboxylic acid amide;
113 2-Ethylsulfanyl-N-[3-(3-fluorophenyl)-propyl]-4-methyl-6-morpholin-4-yl-pyridine-3-carboxylic acid amide;
114 2-Ethylsulfanyl-4-methyl-6-morpholin-4-yl-N-(3-pyridin-3-yl-propyl)-pyridine-3-carboxylic acid amide;
115 2-Ethylsulfanyl-4-methyl-6-morpholin-4-yl-N-(3-pyridin-4-yl-propyl)-pyridine-3-carboxylic acid amide;
116 N-(5,5-Dimethyl-hexyl)-2-ethylsulfanyl-4-methyl-6-morpholin-4-yl-pyridine-3-carboxylic acid amide;
117 2-Methoxy-4-methyl-6-morpholin-4-yl-N-[[4-(trifluoromethyl)-phenyl]-methyl]pyridine-3-carboxylic acid amide;
118 2-Ethylsulfanyl-N-[(3-fluorophenyl)-methyl]-4-methyl-6-[methyl-(pyridin-4-yl-methyl)-amino]-pyridine-3-carboxylic acid amide;
119 2-Ethylsulfanyl-N-[(3-fluorophenyl)-methyl]-4-methyl-6-[methyl-(pyridin-3-yl-methyl)-amino]-pyridine-3-carboxylic acid amide;
120 2-Ethylsulfanyl-6-[(4-fluoro-benzoyl)-methyl-amino]-N-[(3-fluorophenyl)-methyl]-4-methyl-pyridine-3-carboxylic acid amide;
121 2-Ethylsulfanyl-N-[(3-fluorophenyl)-methyl]-4-methyl-6-[methyl-(pyridin-2-yl-methyl)-amino]-pyridine-3-carboxylic acid amide;
122 2-Ethylsulfanyl-N-[(3-fluorophenyl)-methyl]-4-methyl-6-(pyridin-3-yl-methylamino)-pyridine-3-carboxylic acid amide;
123 6-(Acetyl-methyl-amino)-2-ethylsulfanyl-N-[(3-fluorophenyl)-methyl]-4-methyl-pyridine-3-carboxylic acid amide;
124 N-[(4-Chlorophenyl)-methyl]-2-ethylsulfanyl-4-methyl-6-morpholin-4-yl-pyridine-3-carboxylic acid amide;
125 N-[(3-Chlorophenyl)-methyl]-2-ethylsulfanyl-4-methyl-6-morpholin-4-yl-pyridine-3-carboxylic acid amide;
126 6-[Bis(2-methoxy-ethyl)-amino]-2-ethylsulfanyl-N-[(3-fluorophenyl)-methyl]-4-methyl-pyridine-3-carboxylic acid amide;
127 2-(Ethyl-methyl-amino)-N-[(3-fluorophenyl)-methyl]-4-methyl-6-morpholin-4-yl-pyridine-3-carboxylic acid amide;
128 2-Ethylsulfanyl-N-[(3-fluorophenyl)-methyl]-6-(3-methoxy-propyl-methyl-amino)-4-methyl-pyridine-3-carboxylic acid amide;
129 2-Ethylsulfanyl-N-[3-(2-fluorophenyl)-propyl]-4-methyl-6-morpholin-4-yl-pyridine-3-carboxylic acid amide;
130 2-Ethylsulfanyl-4-methyl-6-morpholin-4-yl-N-[[3-(trifluoromethyloxy)-phenyl]methyl]-pyridine-3-carboxylic acid amide;
131 2-Ethylsulfanyl-N-[[3-(methoxymethyl)-phenyl]-methyl]-4-methyl-6-morpholin-4-yl-pyridine-3-carboxylic acid amide;
132 2-Ethoxy-4-methyl-6-morpholin-4-yl-N-[[4-(trifluoromethyl)-phenyl]-methyl]pyridine-3-carboxylic acid amide;
133 2-Ethoxy-4-methyl-6-morpholin-4-yl-N-(4,4,4-trifluoro-butyl)-pyridine-3-carboxylic acid amide;
134 N-(1,3-Benzodioxol-5-yl-methyl)-2-ethylsulfanyl-4-methyl-6-morpholin-4-yl-pyridine-3-carboxylic acid amide;
135 2-Ethylsulfanyl-N-[[2-fluoro-4-(trifluoromethyl)-phenyl]-methyl]-4-methyl-6-morpholin-4-yl-pyridine-3-carboxylic acid amide;
136 6-(Azepan-1-yl)-2-ethylsulfanyl-N-[(3-fluorophenyl)-methyl]-4-methyl-pyridine-3-carboxylic acid amide;
137 2-Ethylsulfanyl-N-[(4-methoxyphenyl)-methyl]-4-methyl-6-morpholin-4-yl-pyridine-3-carboxylic acid amide;
138 (2S)-2-Ethylsulfanyl-N-[(3-fluorophenyl)-methyl]-4-methyl-6-(2-methyl-morpholin-4-yl)-pyridine-3-carboxylic acid amide;
139 (2R)-2-Ethylsulfanyl-N-[(3-fluorophenyl)-methyl]-4-methyl-6-(2-methyl-morpholin-4-yl)-pyridine-3-carboxylic acid amide;
140 2-Methoxy-4-methyl-6-morpholin-4-yl-N-(4,4,4-trifluoro-butyl)-pyridine-3-carboxylic acid amide;
141 N-(3-Cyclopropyl-propyl)-2-ethylsulfanyl-4-methyl-6-morpholin-4-yl-pyridine-3-carboxylic acid amide;
142 2-Ethylsulfanyl-N-[[3-fluoro-4-(trifluoromethyl)-phenyl]-methyl]-4-methyl-6-morpholin-4-yl-pyridine-3-carboxylic acid amide;
143 2-Ethylsulfanyl-N-[(3-fluorophenyl)-methyl]-4-methyl-6-(3-oxo-piperazin-1-yl)-pyridine-3-carboxylic acid amide;
144 6-(4-Acetyl-piperazin-1-yl)-2-ethylsulfanyl-N-[(3-fluorophenyl)-methyl]-4-methyl-pyridine-3-carboxylic acid amide;
145 N-[(4-Cyano-phenyl)-methyl]-2-ethylsulfanyl-4-methyl-6-morpholin-4-yl-pyridine-3-carboxylic acid amide;
146 2-Ethylsulfanyl-N-[[4-(methoxymethyl)-phenyl]-methyl]-4-methyl-6-morpholin-4-yl-pyridine-3-carboxylic acid amide;
147 2-Ethylsulfanyl-N-[[3-fluoro-4-(methoxymethyl)-phenyl]-methyl]-4-methyl-6-morpholin-4-yl-pyridine-3-carboxylic acid amide;
148 N-[(4-Dimethylaminophenyl)-methyl]-2-ethylsulfanyl-4-methyl-6-morpholin-4-yl-pyridine-3-carboxylic acid amide;
149 2-Ethylsulfanyl-N-[[4-fluoro-3-(methoxymethyl)-phenyl]-methyl]-4-methyl-6-morpholin-4-yl-pyridine-3-carboxylic acid amide;
150 2-Ethylsulfanyl-N-[(3-fluorophenyl)-methyl]-4-methyl-6-(4-methyl-3-oxo-piperazin-1-yl)-pyridine-3-carboxylic acid amide;

151 2-Ethylsulfanyl-N-[(3-fluorophenyl)-methyl]-4-methyl-6-(6-oxa-2-azaspiro[3.3]heptan-2-yl)-pyridine-3-carboxylic acid amide;

152 N-(4,4-Dimethyl-pentyl)-4-methyl-2-methylsulfanyl-6-morpholin-4-yl-pyridine-3-carboxylic acid amide;

153 4-Methyl-2-methylsulfanyl-6-morpholin-4-yl-N-(4,4,4-trifluoro-butyl)-pyridine-3-carboxylic acid amide;

154 N-[(4-Fluorophenyl)-methyl]-4-methyl-2-methylsulfanyl-6-morpholin-4-yl-pyridine-3-carboxylic acid amide;

155 N-[(3,4-Difluoro-phenyl)-methyl]-4-methyl-2-methylsulfanyl-6-morpholin-4-yl-pyridine-3-carboxylic acid amide;

156 N-[(3,5-Difluoro-phenyl)-methyl]-4-methyl-2-methylsulfanyl-6-morpholin-4-yl-pyridine-3-carboxylic acid amide;

157 4-Methyl-2-methylsulfanyl-6-morpholin-4-yl-N-[[4-(trifluoromethyl)-phenyl]-methyl]-pyridine-3-carboxylic acid amide;

158 2-Ethylsulfanyl-N-[(3-fluorophenyl)-methyl]-4-methyl-6-(6-oxo-2,3,4,7,8,8a-hexahydro-1H-pyrrolo[1,2-a]pyrazin-2-yl)-pyridine-3-carboxylic acid amide;

159 2-Ethylsulfanyl-N-[(3-fluorophenyl)-methyl]-4-methyl-6-(3-oxa-6-azabicyclo[2.2.1]heptan-6-yl)-pyridine-3-carboxylic acid amide;

160 N-(3-Cyano-propyl)-2-ethylsulfanyl-4-methyl-6-morpholin-4-yl-pyridine-3-carboxylic acid amide;

161 2-Ethylsulfanyl-4-methyl-6-morpholin-4-yl-N-(p-tolylmethyl)-pyridine-3-carboxylic acid amide;

162 2-Ethylsulfanyl-4-methyl-N-(3-methylsulfonyl-propyl)-6-morpholin-4-yl-pyridine-3-carboxylic acid amide;

163 N-(4-Cyano-butyl)-2-ethylsulfanyl-4-methyl-6-morpholin-4-yl-pyridine-3-carboxylic acid amide;

164 2-Ethylsulfanyl-4-methyl-6-morpholin-4-yl-N-(m-tolyl-methyl)-pyridine-3-carboxylic acid amide;

165 N-[(4-Chlorophenyl)-methyl]-2-methoxy-4-methyl-6-morpholin-4-yl-pyridine-3-carboxylic acid amide;

166 N-[(4-Chlorophenyl)-methyl]-2-ethoxy-4-methyl-6-morpholin-4-yl-pyridine-3-carboxylic acid amide;

167 6-(2-Ethyl-morpholin-4-yl)-2-ethylsulfanyl-N-[(3-fluorophenyl)-methyl]-4-methyl-pyridine-3-carboxylic acid amide;

168 N-[(4-Chlorophenyl)-methyl]-4-methyl-2-methylsulfanyl-6-morpholin-4-yl-pyridine-3-carboxylic acid amide;

169 N-[(4-Fluorophenyl)-methyl]-2-isopropyl-4-methyl-6-[(3R)-3-methyl-morpholin-4-yl]-pyridine-3-carboxylic acid amide;

170 2-Ethylsulfanyl-N-[(3-fluorophenyl)-methyl]-4-methyl-6-(methyl-pyridin-2-yl-amino)-pyridine-3-carboxylic acid amide;

171 2-Ethylsulfanyl-N-[(3-fluorophenyl)-methyl]-4-methyl-6-(methyl-pyridin-3-yl-amino)-pyridine-3-carboxylic acid amide;

172 2-Dimethylamino-N-[(4-fluorophenyl)-methyl]-4-methyl-6-[(3R)-3-methyl-morpholin-4-yl]-pyridine-3-carboxylic acid amide;

173 2-(Ethyl-methyl-amino)-N-[(4-fluorophenyl)-methyl]-4-methyl-6-[(3R)-3-methyl-morpholin-4-yl]-pyridine-3-carboxylic acid amide;

174 2-(Ethyl-methyl-amino)-N-[(4-fluorophenyl)-methyl]-4-methyl-6-morpholin-4-yl-pyridine-3-carboxylic acid amide;

175 2-Ethylsulfanyl-N-[(3-fluorophenyl)-methyl]-4-methyl-6-[methyl-(tetrahydro-pyran-3-yl-methyl)-amino]-pyridine-3-carboxylic acid amide;

176 N-[(4-Fluorophenyl)-methyl]-4-methyl-6-[(3R)-3-methyl-morpholin-4-yl]-2-methylsulfanyl-pyridine-3-carboxylic acid amide;

177 2-Ethylsulfanyl-N-[(4-fluorophenyl)-methyl]-4-methyl-6-[(3R)-3-methyl-morpholin-4-yl]-pyridine-3-carboxylic acid amide;

178 6-(3-Ethyl-morpholin-4-yl)-2-ethylsulfanyl-N-[(3-fluorophenyl)-methyl]-4-methyl-pyridine-3-carboxylic acid amide;

179 2-Ethylsulfanyl-N-[(3-fluorophenyl)-methyl]-6-[(3R)-3-(methoxymethyl)-morpholin-4-yl]-4-methyl-pyridine-3-carboxylic acid amide;

180 2-Ethylsulfanyl-N-[(3-fluorophenyl)-methyl]-6-[(3S)-3-(methoxymethyl)-morpholin-4-yl]-4-methyl-pyridine-3-carboxylic acid amide;

181 N-[(4-Fluorophenyl)-methyl]-2-methoxy-4-methyl-6-[(3R)-3-methyl-morpholin-4-yl]-pyridine-3-carboxylic acid amide;

182 2-Ethoxy-N-[(4-fluorophenyl)-methyl]-4-methyl-6-[(3R)-3-methyl-morpholin-4-yl]-pyridine-3-carboxylic acid amide;

183 2-Dimethylamino-N-(4,4-dimethyl-pentyl)-4-methyl-6-[(3R)-3-methyl-morpholin-4-yl]-pyridine-3-carboxylic acid amide;

184 N-(4,4-Dimethyl-pentyl)-2-(ethyl-methyl-amino)-4-methyl-6-[(3R)-3-methyl-morpholin-4-yl]-pyridine-3-carboxylic acid amide;

185 N-(4,4-Dimethyl-pentyl)-2-isopropyl-4-methyl-6-[(3R)-3-methyl-morpholin-4-yl]-pyridine-3-carboxylic acid amide;

186 N-(4,4-Dimethyl-pentyl)-2-methoxy-4-methyl-6-[(3R)-3-methyl-morpholin-4-yl]-pyridine-3-carboxylic acid amide;

187 N-(4,4-Dimethyl-pentyl)-2-ethoxy-4-methyl-6-[(3R)-3-methyl-morpholin-4-yl]-pyridine-3-carboxylic acid amide;

188 2-(Ethyl-methyl-amino)-4-methyl-6-morpholin-4-yl-N-[[4-(trifluoromethyl)-phenyl]-methyl]pyridine-3-carboxylic acid amide;

189 N-(4,4-Dimethyl-pentyl)-2-(ethyl-methyl-amino)-4-methyl-6-morpholin-4-yl-pyridine-3-carboxylic acid amide;

190 2-(Ethyl-methyl-amino)-4-methyl-6-morpholin-4-yl-N-(4,4,4-trifluoro-butyl)-pyridine-3-carboxylic acid amide;

191 N-[(4-Chlorophenyl)-methyl]-2-(ethyl-methyl-amino)-4-methyl-6-morpholin-4-yl-pyridine-3-carboxylic acid amide;

192 N-(4,4-Dimethyl-pentyl)-4-methyl-6-[(3R)-3-methyl-morpholin-4-yl]-2-methylsulfanyl-pyridine-3-carboxylic acid amide;

193 N-(4,4-Dimethyl-pentyl)-2-ethylsulfanyl-4-methyl-6-[(3R)-3-methyl-morpholin-4-yl]-pyridine-3-carboxylic acid amide;

194 N-[(4-Fluorophenyl)-methyl]-4-methyl-6-[(3R)-3-methyl-morpholin-4-yl]-2-(1-methyl-propyl)-pyridine-3-carboxylic acid amide;

195 N-(4,4-Dimethyl-pentyl)-4-methyl-6-[(3R)-3-methyl-morpholin-4-yl]-2-(1-methyl-propyl)-pyridine-3-carboxylic acid amide;

196 2-Cyclopropyl-N-[(4-fluorophenyl)-methyl]-4-methyl-6-[(3R)-3-methyl-morpholin-4-yl]-pyridine-3-carboxylic acid amide;

197 N-[(4-Fluorophenyl)-methyl]-4-methyl-6-[(3R)-3-methyl-morpholin-4-yl]-2-propyl-pyridine-3-carboxylic acid amide;

198 2-Cyclopropyl-N-(4,4-dimethyl-pentyl)-4-methyl-6-[(3R)-3-methyl-morpholin-4-yl]-pyridine-3-carboxylic acid amide;

199 N-(4,4-Dimethyl-pentyl)-4-methyl-6-[(3R)-3-methyl-morpholin-4-yl]-2-propyl-pyridine-3-carboxylic acid amide;
200 2-Ethylsulfanyl-N-[(3-fluorophenyl)-methyl]-4-methyl-6-(methyl-pyridin-4-yl-amino)-pyridine-3-carboxylic acid amide;
201 2-Ethylsulfanyl-N-[(4-fluoro-3-methyl-phenyl)-methyl]-4-methyl-6-morpholin-4-yl-pyridine-3-carboxylic acid amide;
202 2-Ethylsulfanyl-N-(2-hydroxy-3-phenyl-propyl)-4-methyl-6-morpholin-4-yl-pyridine-3-carboxylic acid amide;
203 N-[(3,4-Difluoro-phenyl)-methyl]-2-(ethyl-methyl-amino)-4-methyl-6-morpholin-4-yl-pyridine-3-carboxylic acid amide;
204 N-[(3,5-Difluoro-phenyl)-methyl]-2-(ethyl-methyl-amino)-4-methyl-6-morpholin-4-yl-pyridine-3-carboxylic acid amide;
205 2-Dimethylamino-N-[(4-fluorophenyl)-methyl]-4-methyl-6-morpholin-4-yl-pyridine-3-carboxylic acid amide;
206 N-[(3,4-Difluoro-phenyl)-methyl]-2-dimethylamino-4-methyl-6-morpholin-4-yl-pyridine-3-carboxylic acid amide;
207 N-[(4-Chlorophenyl)-methyl]-2-ethylsulfanyl-4-methyl-6-[(3R)-3-methyl-morpholin-4-yl]-pyridine-3-carboxylic acid amide;
208 N-[(3,5-Dimethyl-phenyl)-methyl]-2-ethylsulfanyl-4-methyl-6-morpholin-4-yl-pyridine-3-carboxylic acid amide;
209 2-Ethylsulfanyl-N-heptyl-4-methyl-6-morpholin-4-yl-pyridine-3-carboxylic acid amide;
210 6-Dimethylamino-N-(4,4-dimethyl-pentyl)-2-ethylsulfanyl-4-methyl-pyridine-3-carboxylic acid amide;
211 N-(4,4-Dimethyl-pentyl)-2-ethylsulfanyl-6-(2-methoxy-ethyl-methyl-amino)-4-methyl-pyridine-3-carboxylic acid amide;
212 N-(4,4-Dimethyl-pentyl)-2-ethylsulfanyl-6-(3-methoxy-propyl-methyl-amino)-4-methyl-pyridine-3-carboxylic acid amide;
213 2-Ethylsulfanyl-N-[(3-fluorophenyl)-methyl]-4-methyl-6-(3-propyl-morpholin-4-yl)-pyridine-3-carboxylic acid amide;
214 N-[(3-Fluorophenyl)-methyl]-2-methoxy-4-methyl-6-[(3R)-3-methyl-morpholin-4-yl]-pyridine-3-carboxylic acid amide;
215 N-[(4-Chlorophenyl)-methyl]-2-methoxy-4-methyl-6-[(3R)-3-methyl-morpholin-4-yl]-pyridine-3-carboxylic acid amide;
216 N-[(3-Fluorophenyl)-methyl]-4-methyl-2-(1-methyl-propyl)-6-morpholin-4-yl-pyridine-3-carboxylic acid amide;
217 2-Ethylsulfanyl-N-hexyl-4-methyl-6-morpholin-4-yl-pyridine-3-carboxylic acid amide;
218 N-(4,4-Dimethyl-pentyl)-2-ethylsulfanyl-4-methyl-6-(methyl-tetrahydro-furan-3-yl-amino)-pyridine-3-carboxylic acid amide;
219 N-(4,4-Dimethyl-pentyl)-2-ethylsulfanyl-4-methyl-6-(2-methyl-morpholin-4-yl)-pyridine-3-carboxylic acid amide;
220 2-tert-Butyl-N-(4,4-dimethyl-pentyl)-4-methyl-6-morpholin-4-yl-pyridine-3-carboxylic acid amide;
221 N-(4,4-Dimethyl-pentyl)-4-methyl-2-(1-methyl-propyl)-6-morpholin-4-yl-pyridine-3-carboxylic acid amide;
222 2-Ethylsulfanyl-N-[(3-fluorophenyl)-methyl]-4-methyl-6-(2-oxa-6-azaspiro[3.4]octan-6-yl)-pyridine-3-carboxylic acid amide;
223 2-Ethylsulfanyl-N-[(3-fluorophenyl)-methyl]-6-[(2R)-2-(methoxymethyl)-morpholin-4-yl]-4-methyl-pyridine-3-carboxylic acid amide;
224 2-Ethylsulfanyl-N-[(3-fluorophenyl)-methyl]-6-[(2S)-2-(methoxymethyl)-morpholin-4-yl]-4-methyl-pyridine-3-carboxylic acid amide;
225 N-[(3,4-Difluoro-phenyl)-methyl]-2-ethylsulfanyl-4-methyl-6-[(3R)-3-methyl-morpholin-4-yl]-pyridine-3-carboxylic acid amide;
226 N-[(3,4-Difluoro-phenyl)-methyl]-2-methoxy-4-methyl-6-[(3R)-3-methyl-morpholin-4-yl]-pyridine-3-carboxylic acid amide;
227 2-Ethylsulfanyl-N-(3-hydroxy-3-phenyl-propyl)-4-methyl-6-morpholin-4-yl-pyridine-3-carboxylic acid amide;
228 2-Ethylsulfanyl-N-(2-hydroxy-4-methyl-pentyl)-4-methyl-6-morpholin-4-yl-pyridine-3-carboxylic acid amide;
229 2-Ethylsulfanyl-N-[(3-fluorophenyl)-methyl]-6-[2-(2-methoxy-ethyl)-morpholin-4-yl]-4-methyl-pyridine-3-carboxylic acid amide;
230 2-Ethylsulfanyl-N-(5-hydroxy-4,4-dimethyl-pentyl)-4-methyl-6-morpholin-4-yl-pyridine-3-carboxylic acid amide;
231 2-Ethylsulfanyl-4-methyl-N-[(3-methylsulfonyl-phenyl)-methyl]-6-morpholin-4-yl-pyridine-3-carboxylic acid amide;
232 2-Ethylsulfanyl-N-[(3-fluorophenyl)-methyl]-4-methyl-6-[2-(trifluoromethyl)-5,6,7,8-tetrahydro-[1,6]naphthyridin-6-yl]-pyridine-3-carboxylic acid amide;
233 N-[(3,5-Difluoro-phenyl)-methyl]-2-ethylsulfanyl-4-methyl-6-[(3R)-3-methyl-morpholin-4-yl]-pyridine-3-carboxylic acid amide;
234 N-[(3,5-Difluoro-phenyl)-methyl]-2-methoxy-4-methyl-6-[(3R)-3-methyl-morpholin-4-yl]-pyridine-3-carboxylic acid amide;
235 2-Ethylsulfanyl-4-methyl-6-[(3R)-3-methyl-morpholin-4-yl]-N-(4,4,4-trifluoro-butyl)-pyridine-3-carboxylic acid amide;
236 2-Methoxy-4-methyl-6-[(3R)-3-methyl-morpholin-4-yl]-N-(4,4,4-trifluoro-butyl)-pyridine-3-carboxylic acid amide;
237 2-Ethylsulfanyl-4-methyl-6-[(3R)-3-methyl-morpholin-4-yl]-N-[[4-(trifluoromethyl)-phenyl]-methyl]-pyridine-3-carboxylic acid amide;
238 2-Methoxy-4-methyl-6-[(3R)-3-methyl-morpholin-4-yl]-N-[[4-(trifluoromethyl)-phenyl]-methyl]pyridine-3-carboxylic acid amide;
239 2-Ethylsulfanyl-N-[(3-fluorophenyl)-methyl]-6-[3-(methoxymethyl)-azetidin-1-yl]-4-methyl-pyridine-3-carboxylic acid amide;
240 6-(2,5-Dimethyl-morpholin-4-yl)-2-ethylsulfanyl-N-[(3-fluorophenyl)-methyl]-4-methyl-pyridine-3-carboxylic acid amide;
241 2-Dimethylamino-4-methyl-6-morpholin-4-yl-N-[[4-(trifluoromethyl)-phenyl]-methyl]-pyridine-3-carboxylic acid amide;
242 N-[(3,5-Difluoro-phenyl)-methyl]-2-dimethylamino-4-methyl-6-morpholin-4-yl-pyridine-3-carboxylic acid amide;
243 2-Ethylsulfanyl-N-[(3-fluorophenyl)-methyl]-4-methyl-6-[2-(trifluoromethyl)-5,6,7,8-tetrahydro-imidazo[1,2-a]pyrazin-7-yl]-pyridine-3-carboxylic acid amide;
244 N-[(4-Chlorophenyl)-methyl]-2-dimethylamino-4-methyl-6-morpholin-4-yl-pyridine-3-carboxylic acid amide;
245 2-Dimethylamino-N-(4,4-dimethyl-pentyl)-4-methyl-6-morpholin-4-yl-pyridine-3-carboxylic acid amide;
246 2-Dimethylamino-4-methyl-6-morpholin-4-yl-N-(4,4,4-trifluoro-butyl)-pyridine-3-carboxylic acid amide;

247 2-Ethylsulfanyl-4-methyl-N-[(4-methylsulfonyl-phenyl)-methyl]-6-morpholin-4-yl-pyridine-3-carboxylic acid amide;
248 2-Ethylsulfanyl-N-[(4-fluorophenyl)-methyl]-6-[(3R)-3-(methoxymethyl)-morpholin-4-yl]-4-methyl-pyridine-3-carboxylic acid amide;
249 2-Ethylsulfanyl-N-[(4-fluorophenyl)-methyl]-6-[(3S)-3-(methoxymethyl)-morpholin-4-yl]-4-methyl-pyridine-3-carboxylic acid amide;
250 2-tert-Butyl-N-[(3-fluorophenyl)-methyl]-4-methyl-6-morpholin-4-yl-pyridine-3-carboxylic acid amide;
251 2-Ethylsulfanyl-N-[(3-fluorophenyl)-methyl]-4-methyl-6-[4-(2,2,2-trifluoro-ethyl)-piperazin-1-yl]-pyridine-3-carboxylic acid amide;
252 6-(2,2-Dimethyl-morpholin-4-yl)-2-ethylsulfanyl-N-[(3-fluorophenyl)-methyl]-4-methyl-pyridine-3-carboxylic acid amide;
253 2-Ethylsulfanyl-N-[(3-fluorophenyl)-methyl]-4-methyl-6-[methyl-(2-oxo-propyl)-amino]-pyridine-3-carboxylic acid amide;
254 N-[(4-Chlorophenyl)-methyl]-2-ethylsulfanyl-6-[(2R)-2-(methoxymethyl)-morpholin-4-yl]-4-methyl-pyridine-3-carboxylic acid amide;
255 N-[(4-Chlorophenyl)-methyl]-2-ethylsulfanyl-6-[(2S)-2-(methoxymethyl)-morpholin-4-yl]-4-methyl-pyridine-3-carboxylic acid amide;
256 N-[(4-Chlorophenyl)-methyl]-2-ethylsulfanyl-6-[(3R)-3-(methoxymethyl)-morpholin-4-yl]-4-methyl-pyridine-3-carboxylic acid amide;
257 N-[(4-Chlorophenyl)-methyl]-2-ethylsulfanyl-6-[(3S)-3-(methoxymethyl)-morpholin-4-yl]-4-methyl-pyridine-3-carboxylic acid amide;
258 2-Ethylsulfanyl-N-[(3-fluorophenyl)-methyl]-4-methyl-6-(methyl-tetrahydro-pyran-4-yl-amino)-pyridine-3-carboxylic acid amide;
259 2-Ethylsulfanyl-N-[(3-fluorophenyl)-methyl]-6-[(4-methoxy-cyclohexyl)-methyl-amino]-4-methyl-pyridine-3-carboxylic acid amide;
260 2-Ethylsulfanyl-N-[(3-fluorophenyl)-methyl]-4-methyl-6-[2-(trifluoromethyl)-morpholin-4-yl]-pyridine-3-carboxylic acid amide;
261 2-Ethylsulfanyl-N-[(3-fluorophenyl)-methyl]-4-methyl-6-(methyl-tetrahydro-pyran-3-yl-amino)-pyridine-3-carboxylic acid amide;
262 6-(3,5-Dimethyl-morpholin-4-yl)-2-ethylsulfanyl-N-[(3-fluorophenyl)-methyl]-4-methyl-pyridine-3-carboxylic acid amide;
263 2-Ethylsulfanyl-N-[(3-fluorophenyl)-methyl]-6-[(3S)-3-(hydroxymethyl)-morpholin-4-yl]-4-methyl-pyridine-3-carboxylic acid amide;
264 2-Ethylsulfanyl-N-[(3-fluorophenyl)-methyl]-6-[(3R)-3-(hydroxymethyl)-morpholin-4-yl]-4-methyl-pyridine-3-carboxylic acid amide;
265 N-[(4-Chlorophenyl)-methyl]-2-isopropyl-4-methyl-6-[(3R)-3-methyl-morpholin-4-yl]-pyridine-3-carboxylic acid amide;
266 N-[(4-Chlorophenyl)-methyl]-4-methyl-6-[(3R)-3-methyl-morpholin-4-yl]-2-propyl-pyridine-3-carboxylic acid amide;
267 2-Ethylsulfanyl-N-(3-hydroxy-4,4-dimethyl-pentyl)-4-methyl-6-morpholin-4-yl-pyridine-3-carboxylic acid amide;
268 N-[(4-Cyano-3-fluoro-phenyl)-methyl]-2-ethylsulfanyl-4-methyl-6-morpholin-4-yl-pyridine-3-carboxylic acid amide;
269 N-[(4-Chlorophenyl)-methyl]-2-(2-fluoro-ethoxy)-4-methyl-6-morpholin-4-yl-pyridine-3-carboxylic acid amide;
270 N-[(4-Chlorophenyl)-methyl]-2-(2,2-difluoro-ethoxy)-4-methyl-6-morpholin-4-yl-pyridine-3-carboxylic acid amide;
271 N-[(4-Chlorophenyl)-methyl]-2-(cyclopropyl-methoxy)-4-methyl-6-morpholin-4-yl-pyridine-3-carboxylic acid amide;
272 2-(2,2-Difluoro-ethoxy)-N-[(4-fluorophenyl)-methyl]-4-methyl-6-morpholin-4-yl-pyridine-3-carboxylic acid amide;
273 N-[(4-Chlorophenyl)-methyl]-2-ethoxy-4-methyl-6-[(3R)-3-methyl-morpholin-4-yl]-pyridine-3-carboxylic acid amide;
274 N-(4,4-Dimethyl-pentyl)-2-ethylsulfanyl-4-methyl-6-[(2S)-2-methyl-morpholin-4-yl]-pyridine-3-carboxylic acid amide;
275 N-(4,4-Dimethyl-pentyl)-2-ethylsulfanyl-4-methyl-6-[(2R)-2-methyl-morpholin-4-yl]-pyridine-3-carboxylic acid amide;
276 2-(Cyclopropyl-methoxy)-N-[(4-fluorophenyl)-methyl]-4-methyl-6-morpholin-4-yl-pyridine-3-carboxylic acid amide;
277 N-[(4-Chlorophenyl)-methyl]-2-isopropyl-6-[(3S)-3-(methoxymethyl)-morpholin-4-yl]-4-methyl-pyridine-3-carboxylic acid amide;
278 N-(4,4-Dimethyl-pentyl)-4-methyl-2-(2-methyl-butyl)-6-morpholin-4-yl-pyridine-3-carboxylic acid amide;
279 N-(4,4-Dimethyl-pentyl)-2-(1,1-dimethyl-propyl)-4-methyl-6-morpholin-4-yl-pyridine-3-carboxylic acid amide;
280 N-(4,4-Dimethyl-pentyl)-2-ethylsulfanyl-4-methyl-6-(methyl-tetrahydro-pyran-3-yl-amino)-pyridine-3-carboxylic acid amide;
281 2-Ethylsulfanyl-4-methyl-6-morpholin-4-yl-N-[(4-nitrophenyl)-methyl]-pyridine-3-carboxylic acid amide;
282 N-[(4-Chlorophenyl)-methyl]-2-cyclopropyl-4-methyl-6-[(3R)-3-methyl-morpholin-4-yl]-pyridine-3-carboxylic acid amide;
283 N-[(4-Chlorophenyl)-methyl]-2-(2-dimethylaminoethyloxy)-4-methyl-6-morpholin-4-yl-pyridine-3-carboxylic acid amide;
284 2-Ethylsulfanyl-N-[(4-fluoro-3-methoxy-phenyl)-methyl]-4-methyl-6-morpholin-4-yl-pyridine-3-carboxylic acid amide;
285 N-[(4-Chlorophenyl)-methyl]-2-isopropyl-6-[(2S)-2-(methoxymethyl)-morpholin-4-yl]-4-methyl-pyridine-3-carboxylic acid amide;
286 2-Ethylsulfanyl-N-(3-hydroxy-4-methyl-pentyl)-4-methyl-6-morpholin-4-yl-pyridine-3-carboxylic acid amide;
287 2-Ethylsulfanyl-N-[(3-fluoro-4-methoxy-phenyl)-methyl]-4-methyl-6-morpholin-4-yl-pyridine-3-carboxylic acid amide;
288 N-[[4-(Difluoro-methoxy)-phenyl]-methyl]-2-ethylsulfanyl-4-methyl-6-morpholin-4-yl-pyridine-3-carboxylic acid amide;
289 N-(1,3-Dihydro-isobenzofuran-5-yl-methyl)-2-ethylsulfanyl-4-methyl-6-morpholin-4-yl-pyridine-3-carboxylic acid amide;
290 N-[(4-Chlorophenyl)-methyl]-2-cyclopropyl-6-[(2S)-2-(methoxymethyl)-morpholin-4-yl]-4-methyl-pyridine-3-carboxylic acid amide;
291 2-Ethylsulfanyl-N-[(3-fluorophenyl)-methyl]-6-[(2S)-2-(hydroxymethyl)-morpholin-4-yl]-4-methyl-pyridine-3-carboxylic acid amide;

292 2-Ethylsulfanyl-N-[(3-fluorophenyl)-methyl]-6-[(2R)-2-(hydroxymethyl)-morpholin-4-yl]-4-methyl-pyridine-3-carboxylic acid amide;
293 6-(Benzyl-methyl-amino)-2-ethylsulfanyl-N-[(3-fluorophenyl)-methyl]-4-methyl-pyridine-3-carboxylic acid amide;
294 2-Ethylsulfanyl-N-[(3-fluorophenyl)-methyl]-4-methyl-6-[methyl-(tetrahydro-furan-2-yl-methyl)-amino]-pyridine-3-carboxylic acid amide;
295 2-Ethylsulfanyl-N-[(3-fluorophenyl)-methyl]-4-methyl-6-[(3R)-3-methyl-morpholin-4-yl]-pyridine-3-carboxylic acid amide;
296 2-Ethylsulfanyl-N-[(3-fluorophenyl)-methyl]-4-methyl-6-[(3S)-3-methyl-morpholin-4-yl]-pyridine-3-carboxylic acid amide;
297 2-Ethylsulfanyl-N-[(3-fluorophenyl)-methyl]-4-methyl-6-[methyl-[[4-(trifluoromethyl)-phenyl]-methyl]-amino]-pyridine-3-carboxylic acid amide;
298 6-(1,1-Dioxo-[1,4]thiazinan-4-yl)-2-ethylsulfanyl-N-[(3-fluorophenyl)-methyl]-4-methyl-pyridine-3-carboxylic acid amide;
299 6-(Azetidin-1-yl)-2-ethylsulfanyl-N-[(3-fluorophenyl)-methyl]-4-methyl-pyridine-3-carboxylic acid amide;
301 2-Ethylsulfanyl-N-[(3-fluorophenyl)-methyl]-4-methyl-6-(methyl-tetrahydro-furan-3-yl-amino)-pyridine-3-carboxylic acid amide;
302 2-Ethylsulfanyl-N-[(3-fluorophenyl)-methyl]-4-methyl-6-(N-methyl-anilino)-pyridine-3-carboxylic acid amide;
303 6-(2,3-Dihydro-1H-isoindol-2-yl)-2-ethylsulfanyl-N-[(3-fluorophenyl)-methyl]-4-methyl-pyridine-3-carboxylic acid amide;
304 2-Ethylsulfanyl-N-[(3-fluorophenyl)-methyl]-4-methyl-6-(1,2,3,4-tetrahydro-quinolin-1-yl)-pyridine-3-carboxylic acid amide;
305 6-(2,3-Dihydro-1H-indol-1-yl)-2-ethylsulfanyl-N-[(3-fluorophenyl)-methyl]-4-methyl-pyridine-3-carboxylic acid amide;
306 2-Ethylsulfanyl-4-methyl-6-morpholin-4-yl-N-(2,4,4-trimethyl-pentyl)-pyridine-3-carboxylic acid amide;
307 2-Ethylsulfanyl-N-[(3-fluorophenyl)-methyl]-6-[(3-methoxy-cyclohexyl)-methyl-amino]-4-methyl-pyridine-3-carboxylic acid amide;
308 N-(4,4-Difluoro-pentyl)-2-ethylsulfanyl-4-methyl-6-morpholin-4-yl-pyridine-3-carboxylic acid amide;
309 N-[(4-Fluorophenyl)-methyl]-2-isopropyl-4-methyl-6-morpholin-4-yl-pyridine-3-carboxylic acid amide;
310 N-[(3,4-Difluoro-phenyl)-methyl]-2-isopropyl-4-methyl-6-morpholin-4-yl-pyridine-3-carboxylic acid amide;
311 2-Isopropyl-4-methyl-6-morpholin-4-yl-N-[[4-(trifluoromethyl)-phenyl]-methyl]pyridine-3-carboxylic acid amide;
312 2-Ethylsulfanyl-N-[(3-fluorophenyl)-methyl]-4-methyl-6-(3-oxo-morpholin-4-yl)-pyridine-3-carboxylic acid amide;
313 N-(4,4-Dimethyl-pentyl)-4-methyl-6-morpholin-4-yl-2-propyl-pyridine-3-carboxylic acid amide;
314 N-(4,4-Dimethyl-pentyl)-2-isopropyl-4-methyl-6-morpholin-4-yl-pyridine-3-carboxylic acid amide;
315 2-Isopropyl-4-methyl-6-morpholin-4-yl-N-(4,4,4-trifluoro-butyl)-pyridine-3-carboxylic acid amide;
316 N-[(3,5-Difluoro-phenyl)-methyl]-2-isopropyl-4-methyl-6-morpholin-4-yl-pyridine-3-carboxylic acid amide;
317 N-[(3-Fluorophenyl)-methyl]-4-methyl-6-morpholin-4-yl-2-(oxetan-3-yloxy)-pyridine-3-carboxylic acid amide;
318 2-Ethylsulfanyl-N-(4-methoxy-4-methyl-pentyl)-4-methyl-6-morpholin-4-yl-pyridine-3-carboxylic acid amide;
319 2-Ethylsulfanyl-N-(4-fluoro-4-methyl-pentyl)-4-methyl-6-morpholin-4-yl-pyridine-3-carboxylic acid amide;
320 4-Methyl-6-morpholin-4-yl-2-propyl-N-(4,4,4-trifluoro-butyl)-pyridine-3-carboxylic acid amide;
321 N-[(3,4-Difluoro-phenyl)-methyl]-4-methyl-6-morpholin-4-yl-2-propyl-pyridine-3-carboxylic acid amide;
322 N-[(3,5-Difluoro-phenyl)-methyl]-4-methyl-6-morpholin-4-yl-2-propyl-pyridine-3-carboxylic acid amide;
323 4-Methyl-6-morpholin-4-yl-2-propyl-N-[[4-(trifluoromethyl)-phenyl]-methyl]pyridine-3-carboxylic acid amide;
324 N-(4,4-Dimethyl-2-oxo-pentyl)-2-ethylsulfanyl-4-methyl-6-morpholin-4-yl-pyridine-3-carboxylic acid amide;
325 2-Ethylsulfanyl-N-[(3-fluorophenyl)-methyl]-4-methyl-6-(8-oxa-3-azabicyclo[3.2.1]octan-3-yl)-pyridine-3-carboxylic acid amide;
326 N-[(4-Chlorophenyl)-methyl]-4-methyl-6-morpholin-4-yl-2-propyl-pyridine-3-carboxylic acid amide;
327 N-[(4-Chlorophenyl)-methyl]-2-isopropyl-4-methyl-6-morpholin-4-yl-pyridine-3-carboxylic acid amide;
328 2-Cyclopropyl-N-(4,4-dimethyl-pentyl)-4-methyl-6-morpholin-4-yl-pyridine-3-carboxylic acid amide;
329 2-Cyclopropyl-4-methyl-6-morpholin-4-yl-N-(4,4,4-trifluoro-butyl)-pyridine-3-carboxylic acid amide;
330 2-Cyclopropyl-N-[(3-fluorophenyl)-methyl]-4-methyl-6-morpholin-4-yl-pyridine-3-carboxylic acid amide;
331 2-Cyclopropyl-N-[(4-fluorophenyl)-methyl]-4-methyl-6-morpholin-4-yl-pyridine-3-carboxylic acid amide;
332 2-Cyclopropyl-N-[(3,4-difluoro-phenyl)-methyl]-4-methyl-6-morpholin-4-yl-pyridine-3-carboxylic acid amide;
333 2-Cyclopropyl-N-[(3,5-difluoro-phenyl)-methyl]-4-methyl-6-morpholin-4-yl-pyridine-3-carboxylic acid amide;
334 2-Cyclopropyl-4-methyl-6-morpholin-4-yl-N-[[4-(trifluoromethyl)-phenyl]-methyl]-pyridine-3-carboxylic acid amide;
335 N-[(4-Chlorophenyl)-methyl]-2-cyclopropyl-4-methyl-6-morpholin-4-yl-pyridine-3-carboxylic acid amide;
336 2-Ethylsulfanyl-N-[(3-fluorophenyl)-methyl]-4-methoxy-6-morpholin-4-yl-pyridine-3-carboxylic acid amide;
337 N-(4,4-Dimethyl-pentyl)-2-(2-methoxy-ethylsulfanyl)-4-methyl-6-morpholin-4-yl-pyridine-3-carboxylic acid amide;
338 2-Ethylsulfanyl-N-[(3-fluorophenyl)-methyl]-6-[(4-fluorophenyl)-methyl-(3-methoxy-propyl)-amino]-4-methyl-pyridine-3-carboxylic acid amide;
339 2-Ethylsulfanyl-4-methyl-6-morpholin-4-yl-N-(3,4,4-trimethyl-pentyl)-pyridine-3-carboxylic acid amide;
340 2-Ethylsulfanyl-N-[(3-fluorophenyl)-methyl]-6-[3-(2-methoxy-ethyl)-morpholin-4-yl]-4-methyl-pyridine-3-carboxylic acid amide;
341 2-(Acetyl-methyl-amino)-N-[(3-fluorophenyl)-methyl]-4-methyl-6-morpholin-4-yl-pyridine-3-carboxylic acid amide;
342 2-Ethylsulfanyl-N-[(3-fluorophenyl)-methyl]-6-[(4-fluorophenyl)-methyl-(2-methoxy-ethyl)-amino]-4-methyl-pyridine-3-carboxylic acid amide;
343 2-Ethylsulfanyl-4-methyl-N-[3-(3-methyl-oxetan-3-yl)-propyl]-6-morpholin-4-yl-pyridine-3-carboxylic acid amide;
344 N-(4,4-Dimethyl-pent-2-ynyl)-2-ethylsulfanyl-4-methyl-6-morpholin-4-yl-pyridine-3-carboxylic acid amide;
345 2-Ethylsulfanyl-N-[(3-fluorophenyl)-methyl]-4-methyl-6-(3-oxa-8-azabicyclo[3.2.1]octan-8-yl)-pyridine-3-carboxylic acid amide;
346 2-Ethylsulfanyl-N-[(3-fluorophenyl)-methyl]-4-(methoxymethyl)-6-morpholin-4-yl-pyridine-3-carboxylic acid amide;

347 N-[(4-Chlorophenyl)-methyl]-4-methyl-2-(1-methyl-propyl)-6-morpholin-4-yl-pyridine-3-carboxylic acid amide;
348 N-(4,4-Dimethyl-hexyl)-2-ethylsulfanyl-4-methyl-6-morpholin-4-yl-pyridine-3-carboxylic acid amide;
349 N-(4,4-Dimethyl-pentyl)-2-(2-methoxy-ethoxy)-4-methyl-6-morpholin-4-yl-pyridine-3-carboxylic acid amide;
350 2-Ethylsulfanyl-4-methyl-N-[3-(1-methyl-cyclopropyl)-propyl]-6-morpholin-4-yl-pyridine-3-carboxylic acid amide;
351 2-Cyclopropyl-N-[[4-fluoro-3-(methoxymethyl)-phenyl]methyl]-4-methyl-6-morpholin-4-yl-pyridine-3-carboxylic acid amide;
352 2-Ethylsulfanyl-N-[[4-fluoro-3-(methoxymethyl)-phenyl]-methyl]-4-methyl-6-[(3R)-3-methyl-morpholin-4-yl]-pyridine-3-carboxylic acid amide;
353 2-Ethylsulfanyl-N-[[4-fluoro-3-(hydroxymethyl)-phenyl]-methyl]-4-methyl-6-morpholin-4-yl-pyridine-3-carboxylic acid amide;
354 N-(4,4-Dimethyl-pentyl)-2-(3-methoxy-propyl)-4-methyl-6-morpholin-4-yl-pyridine-3-carboxylic acid amide;
355 2-Cyclopropyl-N-[[3-fluoro-4-(methoxymethyl)-phenyl]methyl]-4-methyl-6-morpholin-4-yl-pyridine-3-carboxylic acid amide;
356 N-[(3-Fluorophenyl)-methyl]-2-(methoxymethyl)-4-methyl-6-morpholin-4-yl-pyridine-3-carboxylic acid amide;
357 N-[(4-Chlorophenyl)-methyl]-2,4-diisopropyl-6-morpholin-4-yl-pyridine-3-carboxylic acid amide;
358 N-(4,4-Dimethyl-pentyl)-2-(2-methoxy-ethyl)-4-methyl-6-morpholin-4-yl-pyridine-3-carboxylic acid amide;
359 N-[(4-Chlorophenyl)-methyl]-2,4-diethyl-6-morpholin-4-yl-pyridine-3-carboxylic acid amide;
362 N-(4,4-Dimethyl-pentyl)-4-methyl-6-morpholin-4-yl-2-tetrahydro-pyran-4-yl-pyridine-3-carboxylic acid amide,
respectively in the form of the free compounds; the racemate; the enantiomers, diastereomers, mixtures of the enantiomers or diastereomers in any mixing ratio or of an individual enantiomer or diastereomer; or in the form of the salts of physiologically acceptable acids or bases; or in the form of solvates, in particular hydrates.

One particularly preferred subgroup of the compounds of the invention of the aforementioned general formula (I) comprises compounds corresponding to the formula (X)

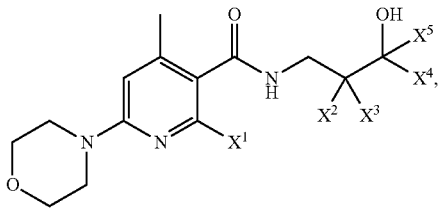

(X)

wherein
$X^1$ represents a $C_{2-6}$-aliphatic residue, unsubstituted or mono- or polysubstituted; or a $C_{3-6}$-cycloaliphatic residue or a 3 to 6 membered heterocycloaliphatic residue, in each case unsubstituted or mono- or polysubstituted, and in each case optionally bridged via a $C_{1-4}$ aliphatic group, which in turn may be unsubstituted or mono- or polysubstituted;
or represents $OX^6$, wherein
$X^6$ represents a $C_{1-6}$-aliphatic residue, unsubstituted or mono- or polysubstituted; or a $C_{3-6}$-cycloaliphatic residue, unsubstituted or mono- or polysubstituted;

$X^2$ and $X^3$ independently of one another represent H; F; Cl; Br; I; CN; $CH_2F$; $CHF_2$; $CF_3$; OH; $OCH_2F$; $OCHF_2$; $OCF_3$; $SCF_3$; a $C_{1-4}$-aliphatic residue, or an O—$C_{1-4}$ aliphatic residue, wherein the $C_{1-4}$ aliphatic residue may in each case be unsubstituted or mono- or polysubstituted; or a $C_{3-6}$-cycloaliphatic residue or a 3 to 6 membered heterocycloaliphatic residue, in each case unsubstituted or mono- or polysubstituted;
with the proviso that at least one of $X^2$ and $X^3$ denotes H or is linked via a carbon atom (to the remaining part of the superordinate structure, i.e. of general formula (X)),
$X^4$ and $X^5$ independently of one another represent H; $CH_2F$; $CHF_2$; $CF_3$; a $C_{1-4}$-aliphatic residue, wherein the $C_{1-4}$ aliphatic residue may be unsubstituted or mono- or polysubstituted; or a $C_{3-6}$-cycloaliphatic residue or a 3 to 6 membered heterocycloaliphatic residue, in each case unsubstituted or mono- or polysubstituted;
on the condition that if $X^4$ and/or $X^5$ denote(s) a 3 to 6 membered heterocycloaliphatic residue, the 3 to 6 membered heterocycloaliphatic residue is linked via a carbon atom (to the remaining part of the superordinate structure, i.e. of general formula (X)),
or
$X^2$ and $X^3$
and/or $X^4$ and $X^5$
in pairs, in each case independently of one another, together with the carbon atom connecting them, form a $C_{3-10}$-cycloaliphatic residue or a 3 to 10 membered heterocycloaliphatic residue, in each case unsubstituted or mono- or polysubstituted,
and the respective remaining substituents of $X^2$ and $X^3$ each independently of one another represent H; F; Cl; Br; I; CN; $CH_2F$; $CHF_2$; $CF_3$; OH; $OCH_2F$; $OCHF_2$; $OCF_3$; $SCF_3$; a $C_{1-4}$-aliphatic residue, or an O—$C_{1-4}$ aliphatic residue, wherein the $C_{1-4}$ aliphatic residue may in each case be unsubstituted or mono- or polysubstituted; or a $C_{3-6}$-cycloaliphatic residue or a 3 to 6 membered heterocycloaliphatic residue, in each case unsubstituted or mono- or polysubstituted,
with the proviso that at least one of $X^2$ and $X^3$ denotes H or is linked via a carbon atom,
and the respective remaining substituents of $X^4$ and $X^5$ each independently of one another represent H; $CH_2F$; $CHF_2$; $CF_3$; a $C_{1-4}$-aliphatic residue, wherein the $C_{1-4}$ aliphatic residue may be unsubstituted or mono- or polysubstituted; or a $C_{3-6}$-cycloaliphatic residue or a 3 to 6 membered heterocycloaliphatic residue, in each case unsubstituted or mono- or polysubstituted;
on the condition that if $X^4$ and/or $X^5$ denote(s) a 3 to 6 membered heterocycloaliphatic residue, the 3 to 6 membered heterocycloaliphatic residue is linked via a carbon atom,
or
$X^2$ and $X^4$ together with the carbon atoms connecting them, form a $C_{3-10}$-cycloaliphatic residue or a 3 to 10 membered heterocycloaliphatic residue, in each case unsubstituted or mono- or polysubstituted,
and $X^3$ represents H; F; Cl; Br; I; CN; $CH_2F$; $CHF_2$; $CF_3$; OH; $OCH_2F$; $OCHF_2$; $OCF_3$; $SCF_3$; a $C_{1-4}$-aliphatic residue, or an O—$C_{1-4}$ aliphatic residue, wherein the $C_{1-4}$ aliphatic residue may in each case be unsubstituted or mono- or polysubstituted; or a $C_{3-6}$-cycloaliphatic residue or a 3 to 6 membered heterocycloaliphatic residue, in each case unsubstituted or mono- or polysubstituted;
and $X^5$ represents H; $CH_2F$; $CHF_2$; $CF_3$; a $C_{1-4}$-aliphatic residue, wherein the $C_{1-4}$ aliphatic residue may be unsubstituted or mono- or polysubstituted; or a $C_{3-6}$-cycloaliphatic residue or a 3 to 6 membered heterocycloaliphatic residue, in each case unsubstituted or mono- or polysubstituted;

on the condition that if $X^5$ denotes a 3 to 6 membered heterocycloaliphatic residue, the 3 to 6 membered heterocycloaliphatic residue is linked via a carbon atom, in which an "aliphatic group" and an "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue)$_2$, a NH—C(=O)—$C_{1-4}$ aliphatic residue, a $N(C_{1-4}$-aliphatic residue)-C(=O)—$C_{1-4}$ aliphatic residue, a NH—S(=O)$_2$—$C_{1-4}$ aliphatic residue, a $N(C_{1-4}$-aliphatic residue)-S(=O)$_2$—$C_{1-4}$ aliphatic residue, =O, OH, $OCH_2F$, $OCHF_2$, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)—$C_{1-4}$-aliphatic residue, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, a S(=O)$_2$—N($C_{1-4}$-aliphatic residue)$_2$, CN, $CH_2F$, $CHF_2$, $CF_3$, CHO, COOH, a $C_{1-4}$-aliphatic residue, $CH_2OH$, $CH_2$—$OCH_3$, $C_2H_4$—OH, $C_2H_4$—$OCH_3$ $CH_2$—$CF_3$, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue)$_2$, a NH—C(=O)—$C_{1-4}$ aliphatic residue, a $N(C_{1-4}$-aliphatic residue)-C(=O)—$C_{1-4}$ aliphatic residue, a NH—S(=O)$_2$—$C_{1-4}$ aliphatic residue, a $N(C_{1-4}$-aliphatic residue)-S(=O)$_2$—$C_{1-4}$ aliphatic residue, =O, OH, $OCH_2F$, $OCHF_2$, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)—$C_{1-4}$-aliphatic residue, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, a S(=O)$_2$—N($C_{1-4}$-aliphatic residue)$_2$, CN, $CH_2F$, $CHF_2$, $CF_3$, CHO, COOH, a $C_{1-4}$-aliphatic residue, $CH_2OH$, $CH_2$—$OCH_3$, $C_2H_4$—OH, $C_2H_4$—$OCH_3$ $CH_2$—$CF_3$, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

optionally in the form of a single stereoisomer or a mixture of stereoisomers, in the form of the free compound and/or a physiologically acceptable salt thereof and/or a physiologically acceptable solvate, in particular hydrate, thereof.

Preferred substituents of "aliphatic residue" and "aliphatic group" with respect to compounds according to general formula (X) are selected from the group consisting of F, Cl, Br, I, $NO_2$, $NH_2$, an $NH(C_{1-4}$ aliphatic residue), an $N(C_{1-4}$ aliphatic residue)$_2$, =O, OH, $OCH_2F$, $OCHF_2$, $OCF_3$, a O—$C_{1-4}$-aliphatic residue, SH, $SCF_3$, a S—$C_{1-4}$-aliphatic residue, a S(=O)—$C_{1-4}$-aliphatic residue, a S(=O)$_2$—$C_{1-4}$-aliphatic residue, a S(=O)$_2$—NH—$C_{1-4}$-aliphatic residue, a S(=O)$_2$—N($C_{1-4}$-aliphatic residue)$_2$, CN, $CH_2F$, $CHF_2$, $CF_3$, a $C_{1-4}$-aliphatic residue, $CH_2OH$, $CH_2$—$OCH_3$, $C_2H_4$—OH, $C_2H_4$—$OCH_3$ $CH_2$—$CF_3$, a C(=O)—$C_{1-4}$-aliphatic residue, a C(=O)—O—$C_{1-4}$-aliphatic residue, $CONH_2$, a C(=O)—NH($C_{1-4}$ aliphatic residue), and a C(=O)—N($C_{1-4}$ aliphatic residue)$_2$.

Preferred substituents of "cycloaliphatic residue" and "heterocycloaliphatic residue" with respect to compounds according to general formula (X) are selected from the group consisting of F, Cl, Br, I, $NO_2$, $NH_2$, an $NH(C_{1-4}$ aliphatic residue), an $N(C_{1-4}$ aliphatic residue)$_2$, =O, OH, $OCH_2F$, $OCHF_2$, $OCF_3$, a O—$C_{1-4}$-aliphatic residue, SH, $SCF_3$, a S—$C_{1-4}$-aliphatic residue, a S(=O)—$C_{1-4}$-aliphatic residue, a S(=O)$_2$—$C_{1-4}$-aliphatic residue, a S(=O)$_2$—NH—$C_{1-4}$-aliphatic residue, a S(=O)$_2$—N($C_{1-4}$-aliphatic residue)$_2$, CN, $CH_2F$, $CHF_2$, $CF_3$, a $C_{1-4}$-aliphatic residue, $CH_2OH$, $CH_2$—$OCH_3$, $C_2H_4$—OH, $C_2H_4$—$OCH_3$ $CH_2$—$CF_3$, a C(=O)—$C_{1-4}$-aliphatic residue, a C(=O)—O—$C_{1-4}$-aliphatic residue, $CONH_2$, a C(=O)—NH($C_{1-4}$ aliphatic residue), and a C(=O)—N($C_{1-4}$ aliphatic residue)$_2$.

In a preferred embodiment of the compound according to general formula (X) the particular radicals $X^2$-$X^5$ have the meanings described herein in connection with the compounds according to the invention and preferred embodiments thereof and $X^1$ represents a $C_{2-6}$-aliphatic residue, unsubstituted or mono- or polysubstituted; or a $C_{3-6}$-cycloaliphatic residue, unsubstituted or mono- or polysubstituted, optionally bridged via a $C_{1-4}$ aliphatic group, which in turn may be unsubstituted or mono- or polysubstituted.

In another preferred embodiment of the compound according to general formula (X) the particular radicals $X^2$-$X^5$ have the meanings described herein in connection with the compounds according to the invention and preferred embodiments thereof and $X^1$ represents $OX^6$, wherein $X^6$ represents a $C_{1-6}$-aliphatic residue, unsubstituted or mono- or polysubstituted.

Preferred embodiments of the compound according to general formula (X) are compounds which have the general formulae (X-a) and/or (X-b):

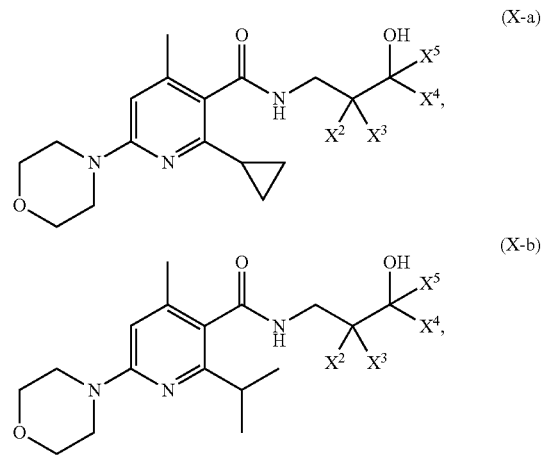

wherein the particular radicals $X^2$, $X^3$, $X^4$, and $X^5$, have the meanings described herein in connection with the compounds according to the invention and preferred embodiments thereof.

Another preferred embodiment of the compound according to general formula (X) is a compound which has the general formula (X-c),

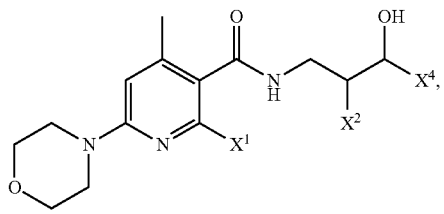

wherein the particular radicals $X^1$, $X^2$ and $X^4$ have the meanings described herein in connection with the compounds according to the invention and preferred embodiments thereof.

Further preferred embodiments of the compound according to general formula (X) are compounds which have the general formula (X-d) and/or (X-e),

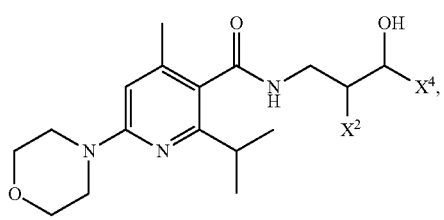

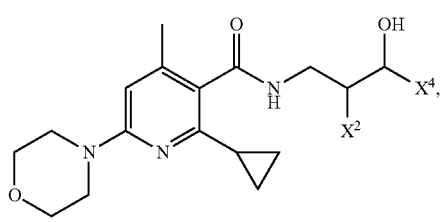

wherein the particular radicals $X^2$ and $X^4$ have the meanings described herein in connection with the compounds according to the invention and preferred embodiments thereof.

Further preferred embodiments of the compound according to general formula (X) are compounds which have the general formula (X-f) and/or (X-g),

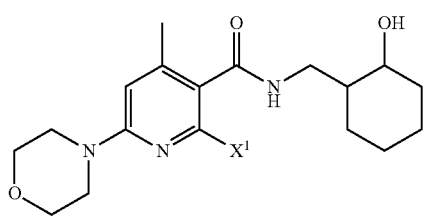

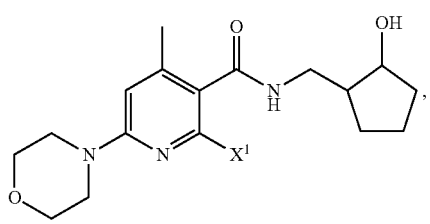

wherein the particular radical $X^1$ has the meanings described herein in connection with the compounds according to the invention and preferred embodiments thereof.

Yet another preferred embodiment of present invention is a compound according to general formula (X), wherein $X^1$ represents a $C_{2-6}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or represents a $C_{3-6}$-cycloaliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, and wherein the $C_{3-6}$-cycloaliphatic residue may optionally be bridged via a $C_{1-4}$ aliphatic group, which in turn may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or represents $OX^6$, wherein $X^6$ represents a $C_{1-6}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue;

wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, $X^2$ and $X^3$ independently of one another represent H; F; Cl; Br; I; CN; $CH_2F$; $CHF_2$; $CF_3$; OH; $OCH_2F$; $OCHF_2$; $OCF_3$; $SCF_3$; a $C_{1-4}$-aliphatic residue, or an O—$C_{1-4}$ aliphatic residue, wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or represent a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic residue, a S(=O)$_2$—C$_{1-4}$-aliphatic residue, CN, and a C$_{1-4}$-aliphatic residue,
    wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue,
with the proviso that at least one of X$^2$ and X$^3$ denotes H or is linked via a carbon atom,
X$^4$ and X$^5$ independently of one another represent H; CH$_2$F; CHF$_2$; CF$_3$; a C$_{1-4}$-aliphatic residue,
    wherein the C$_{1-4}$-aliphatic residue may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue,
or represent a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic residue, a S(=O)$_2$—C$_{1-4}$-aliphatic residue, CN, and a C$_{1-4}$-aliphatic residue,
    wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue,
on the condition that if X$^4$ and/or X$^5$ denote(s) a 3 to 6 membered heterocycloaliphatic residue, the 3 to 6 membered heterocycloaliphatic residue is linked via a carbon atom,
or
X$^2$ and X$^3$
and/or X$^4$ and X$^5$
in pairs, in each case independently of one another, together with the carbon atom connecting them, form a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic residue, a S(=O)$_2$—C$_{1-4}$-aliphatic residue, CN, and a C$_{1-4}$-aliphatic residue,
    wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—C$_{1-4}$-aliphatic residue,
and the respective remaining substituents of X$^2$ and X$^3$ each independently of one another represent H; F; Cl; Br; I; CN; CH$_2$F; CHF$_2$; CF$_3$; OH; OCH$_2$F; OCHF$_2$; OCF$_3$; SCF$_3$; a C$_{1-4}$-aliphatic residue, or an O—C$_{1-4}$ aliphatic residue,
    wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted aliphatic residue,
or represent a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic residue, a S(=O)$_2$—C$_{1-4}$-aliphatic residue, CN, and a C$_{1-4}$-aliphatic residue,
    wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted aliphatic residue,
with the proviso that at least one of X$^2$ and X$^3$ denotes H or is linked via a carbon atom,
and the respective remaining substituents of X$^4$ and X$^5$ each independently of one another represent H; CH$_2$F; CHF$_2$; CF$_3$; a C$_{1-4}$-aliphatic residue,
    wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted aliphatic residue,
or represent a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic residue, a S(=O)$_2$—C$_{1-4}$-aliphatic residue, CN, and a C$_{1-4}$-aliphatic residue,
    wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted aliphatic residue,
on the condition that if X$^4$ and/or X$^5$ denote(s) a 3 to 6 membered heterocycloaliphatic residue, the 3 to 6 membered heterocycloaliphatic residue is linked via a carbon atom,
or
X$^2$ and X$^4$ together with the carbon atoms connecting them, form a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCH$_2$F, OCHF$_2$, OCF$_3$, SH, SCF$_3$, a S—C$_{1-4}$-aliphatic residue, a S(=O)—C$_{1-4}$-aliphatic residue, a S(=O)$_2$—C$_{1-4}$-aliphatic residue, CN, and a C$_{1-4}$-aliphatic residue,
    wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted aliphatic residue,
and the remaining substituent X$^3$ represents H; F; Cl; Br; I; CN; CH$_2$F; CHF$_2$; CF$_3$; OH; OCH$_2$F; OCHF$_2$; OCF$_3$; SCF$_3$; a C$_{1-4}$-aliphatic residue, or an O—C$_{1-4}$ aliphatic residue,
    wherein the C$_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted aliphatic residue,
or represents a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted aliphatic residue, and the remaining substituent $X^5$ represents H; $CH_2F$; $CHF_2$; $CF_3$; a $C_{1-4}$-aliphatic residue,
wherein the $C_{1-4}$-aliphatic residue may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or represents a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted aliphatic residue, on the condition that if $X^5$ denotes a 3 to 6 membered heterocycloaliphatic residue, the 3 to 6 membered heterocycloaliphatic residue is linked via a carbon atom.

In another preferred embodiment of the compound according to general formula (X), the residue
$X^1$ represents a $C_{2-6}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue, or represents a $C_{3-6}$-cycloaliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue.

Preferably,
$X^1$ represents a $C_{2-6}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue is in each case unsubstituted, or represents a $C_{3-6}$-cycloaliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue is in each case unsubstituted, or represents $OX^6$, wherein
$X^6$ represents a $C_{1-6}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue is in each case unsubstituted.

More preferably,
$X^1$ represents a $C_{2-6}$-aliphatic residue, unsubstituted or mono- or polysubstituted with at least one substituent selected from the group consisting of F, Cl, Br, I, OH, and an unsubstituted O—$C_{1-4}$-aliphatic residue, or represents a $C_{3-6}$-cycloaliphatic residue, unsubstituted or mono- or polysubstituted with at least one substituent selected from the group consisting of F, Cl, Br, I, OH, and an unsubstituted O—$C_{1-4}$-aliphatic residue, or represents $OX^6$, wherein
$X^6$ represents a $C_{1-4}$-aliphatic residue, unsubstituted or mono- or polysubstituted with at least one substituent selected from the group consisting of F, Cl, Br, I, OH, and an unsubstituted O—$C_{1-4}$-aliphatic residue.

Even more preferably,
$X^1$ represents ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, ethenyl or propenyl (—$CH_2CH$=$CH_2$, —CH=CH—$CH_3$, —C(=$CH_2$)—$CH_3$), or represents a $C_{3-6}$-cycloaliphatic residue, preferably selected from the group consisting of cyclopropyl, cyclobutyl, cyclopentyl, and cyclohexyl, unsubstituted or mono- or polysubstituted with at least one substituent selected from the group consisting of F, Cl, Br, I, OH, and an unsubstituted $C_{1-4}$-aliphatic residue, preferably unsubstituted, or represents $OX^6$, wherein $X^6$ represents methyl, ethyl, n-propyl, 2-propyl, n-butyl, isobutyl, sec.-butyl, tert.-butyl, $CH_2OH$, $CH_2OCH_3$, $CH_2CH_2OH$, $CH_2CH_2OCH_3$, and $CH(OH)CH_2OH$.

In particular, $X^1$ represents ethyl, n-propyl, 2-propyl, n-butyl, isobutyl, sec.-butyl, tert.-butyl, cyclopropyl, cyclobutyl, cyclopentyl, or cyclohexyl, or represents $OX^6$, wherein $X^6$ represents methyl, ethyl, n-propyl, 2-propyl, n-butyl, isobutyl, sec.-butyl, or tert.-butyl, preferably represents ethyl, n-propyl, 2-propyl, n-butyl, isobutyl, sec.-butyl, tert.-butyl, cyclopropyl, cyclobutyl, cyclopentyl, or cyclohexyl.

Most preferred, $X^1$ represents ethyl, n-propyl, 2-propyl, tert.-butyl, or cyclopropyl.

In another preferred embodiment of the compound according to general formula (X), the residue $X^2$ and $X^3$ independently of one another represent H; F; Cl; Br; I; $CH_2F$; $CHF_2$; $CF_3$; OH; $OCH_2F$; $OCHF_2$; $OCF_3$; a $C_{1-4}$-aliphatic residue, or an O—$C_{1-4}$ aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, or represent a $C_{3-6}$-cycloaliphatic residue or a 3 to 6 membered heterocycloaliphatic residue, preferably a $C_{3-6}$-cycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, with the proviso that at least one of $X^2$ and $X^3$ denotes H or is linked via a carbon atom, $X^4$ and $X^5$ independently of one another represent H; $CH_2F$; $CHF_2$; $CF_3$; a $C_{1-4}$-aliphatic residue, wherein the $C_{1-4}$-aliphatic residue may be unsubstituted or mono- or polysubstituted with at least one substituent selected from the group consisting of F, Cl, Br, I, OH, and an unsubstituted O—$C_{1-4}$-aliphatic residue, or represent a $C_{3-6}$-cycloaliphatic residue or a 3 to 6 membered heterocycloaliphatic residue, preferably a $C_{3-6}$-cycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, on the condition that if $X^4$ and/or $X^5$ denote(s) a 3 to 6 membered heterocycloaliphatic residue, the 3 to 6 membered heterocycloaliphatic residue is linked via a carbon atom, or $X^2$ and $X^3$ and/or $X^4$ and $X^5$, preferably $X^2$ and $X^3$ or $X^4$ and $X^5$, in pairs, in each case independently of one another, together with the carbon atom connecting them, form a $C_{3-10}$-cycloaliphatic residue or a 3 to 10 membered heterocycloaliphatic residue, preferably a $C_{3-10}$-cycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, and the respective remaining substituents of $X^2$ and $X^3$ each independently of one another represent H; F; Cl; Br; I; $CH_2F$; $CHF_2$; $CF_3$; OH; $OCH_2F$; $OCHF_2$; $OCF_3$; a $C_{1-4}$-aliphatic residue, or an O—$C_{1-4}$ aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, or represent a $C_{3-6}$-cycloaliphatic residue or a 3 to 6 membered heterocycloaliphatic residue, preferably a $C_{3-6}$-cycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, with the proviso that at least one of $X^2$ and $X^3$ denotes H or is linked via a carbon atom, and the respective remaining substituents of $X^4$ and $X^5$ each independently of one another represent H; $CH_2F$; $CHF_2$; $CF_3$; a $C_{1-4}$-aliphatic residue, wherein the $C_{1-4}$-aliphatic residue may be unsubstituted or mono- or polysubstituted with at least one substituent selected from the group consisting of F, Cl, Br, I, OH, and an unsubstituted O—$C_{1-4}$-aliphatic residue, or represent a $C_{3-6}$-cycloaliphatic residue or a 3 to 6 membered heterocycloaliphatic residue, preferably a $C_{3-6}$-cycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, on the condition that if $X^4$ and/or $X^5$ denote(s) a 3 to 6 membered heterocycloaliphatic residue, the 3 to 6 membered heterocycloaliphatic residue is linked via a carbon atom, or $X^2$ and $X^4$ together with the carbon atoms connecting them, form a $C_{3-10}$-cycloaliphatic residue or a 3 to 10 membered heterocycloaliphatic residue, preferably a $C_{3-10}$-cycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, and the remaining substituent $X^3$ represents H; F; Cl; Br; I; $CH_2F$; $CHF_2$; $CF_3$; OH; $OCH_2F$; $OCHF_2$; $OCF_3$; a $C_{1-4}$-aliphatic residue, or an O—$C_{1-4}$ aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, or represents a $C_{3-6}$-cycloaliphatic residue or a 3 to 6 membered heterocycloaliphatic residue, preferably a $C_{3-6}$-cycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, and the remaining substituent $X^5$ represents H; $FCH_2F$; $CHF_2$; $CF_3$; a $C_{1-4}$-aliphatic residue, wherein the $C_{1-4}$-aliphatic residue may be unsubstituted or mono- or polysubstituted with at least one substituent selected from the group consisting of F, Cl, Br, I, OH, and an unsubstituted O—$C_{1-4}$-aliphatic residue, or represents a $C_{3-6}$-cycloaliphatic residue or a 3 to 6 membered heterocycloaliphatic residue, preferably a $C_{3-6}$-cycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, on the condition that if $X^5$ denotes a 3 to 6 membered heterocycloaliphatic residue, the 3 to 6 membered heterocycloaliphatic residue is linked via a carbon atom.

Preferably, $X^2$ and $X^3$ independently of one another represent H; F; Cl; Br; I; $CH_2F$; $CHF_2$; $CF_3$; OH; a $C_{1-4}$-aliphatic residue, or an O—$C_{1-4}$ aliphatic residue, wherein the $C_{1-4}$-aliphatic residue is in each case unsubstituted, or represent a $C_{3-6}$-cycloaliphatic residue or a 3 to 6 membered heterocycloaliphatic residue, preferably a $C_{3-6}$-cycloaliphatic residue, in each case unsubstituted, with the proviso that at least one of $X^2$ and $X^3$ denotes H or is linked via a carbon atom, $X^4$ and $X^5$ independently of one another represent H; $CH_2F$; $CHF_2$; $CF_3$; a $C_{1-4}$-aliphatic residue, wherein the $C_{1-4}$-aliphatic residue is unsubstituted, or represent a $C_{3-6}$-cycloaliphatic residue or a 3 to 6 membered heterocycloaliphatic residue, preferably a $C_{3-6}$-cycloaliphatic residue, in each case unsubstituted, on the condition that if $X^4$ and/or $X^5$ denote(s) a 3 to 6 membered heterocycloaliphatic residue, the 3 to 6 membered heterocycloaliphatic residue is linked via a carbon atom, or $X^2$ and $X^3$ and/or $X^4$ and $X^5$, preferably $X^2$ and $X^3$ or $X^4$ and $X^5$, in pairs, in each case independently of one another, together with the carbon atom connecting them, form a $C_{3-10}$-cycloaliphatic residue or a 3 to 10 membered heterocycloaliphatic residue, preferably a $C_{3-10}$-cycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, and a $C_{1-4}$-aliphatic residue, wherein the $C_{1-4}$-aliphatic residue is in each case unsubstituted, and the respective remaining substituents of $X^2$ and $X^3$ each independently of one another represent H; F; Cl; Br; I; $CH_2F$; $CHF_2$; $CF_3$; OH; a $C_{1-4}$-aliphatic residue, or an O—$C_{1-4}$ aliphatic residue, wherein the $C_{1-4}$-aliphatic residue is in each unsubstituted, or represent a $C_{3-6}$-cycloaliphatic residue or a 3 to 6 membered heterocycloaliphatic residue, preferably a $C_{3-6}$-cycloaliphatic residue, in each case unsubstituted, with the proviso that at least one of $X^2$ and $X^3$ denotes H or is linked via a carbon atom, and the respective remaining substituents of $X^4$ and $X^5$ each independently of one another represent H; $CH_2F$; $CHF_2$; $CF_3$; a $C_{1-4}$-aliphatic residue, wherein the $C_{1-4}$-aliphatic residue is in each unsubstituted, or represent a $C_{3-6}$-cycloaliphatic residue or a 3 to 6 membered heterocycloaliphatic residue, preferably a $C_{3-6}$-cycloaliphatic residue, in each case unsubstituted, on the condition that if $X^4$ and/or $X^5$ denote(s) a 3 to 6 membered heterocycloaliphatic residue, the 3 to 6 membered heterocycloaliphatic residue is linked via a carbon atom, or $X^2$ and $X^4$ together with the carbon atoms connecting them, form a $C_{3-10}$-cycloaliphatic residue or a 3 to 10 membered heterocycloaliphatic residue, preferably a $C_{3-10}$-cycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, and a $C_{1-4}$-aliphatic residue, wherein the $C_{1-4}$-aliphatic residue is in each case unsubstituted, and the remaining substituent $X^3$ represents H; F; Cl; Br; I; $CH_2F$; $CHF_2$; $CF_3$; OH; a $C_{1-4}$-aliphatic residue, or an O—$C_{1-4}$ aliphatic residue, wherein the $C_{1-4}$-aliphatic residue is in each case unsubstituted, or represents a $C_{3-6}$-cycloaliphatic residue or a 3 to 6 membered heterocycloaliphatic residue, preferably a $C_{3-6}$-cycloaliphatic residue, in each case unsubstituted, and the remaining substituent $X^5$ represents H; $CH_2F$; $CHF_2$; $CF_3$; a $C_{1-4}$-aliphatic residue, wherein the $C_{1-4}$-aliphatic residue is in each case unsubstituted, or represents a $C_{3-6}$-cycloaliphatic residue or a 3 to 6 membered heterocycloaliphatic residue, preferably a $C_{3-6}$-cycloaliphatic residue, in each case unsubstituted, on the condition that if $X^5$ denotes a 3 to 6 membered heterocycloaliphatic residue, the 3 to 6 membered heterocycloaliphatic residue is linked via a carbon atom.

More preferably, $X^2$ and $X^3$ independently of one another represent H; OH; an unsubstituted $C_{1-4}$-aliphatic residue, or an unsubstituted $O-C_{1-4}$ aliphatic residue, with the proviso that at least one of $X^2$ and $X^3$ denotes H or is linked via a carbon atom, $X^4$ and $X^5$ independently of one another represent H; $CH_2F$; $CHF_2$; $CF_3$; an unsubstituted $C_{1-4}$-aliphatic residue, or $X^2$ and $X^3$ or $X^4$ and $X^5$ in pairs, in each case independently of one another, together with the carbon atom connecting them, form a $C_{3-10}$-cycloaliphatic residue, preferably a $C_{3-6}$-cycloaliphatic residue, unsubstituted or mono- or polysubstituted with at least one substituent selected from the group consisting of F, Cl, Br, I, OH, $CH_2F$, $CHF_2$, $CF_3$, an unsubstituted $O-C_{1-4}$-aliphatic residue, and an unsubstituted $C_{1-4}$-aliphatic residue, and the respective remaining substituents of $X^2$ and $X^3$ each independently of one another represent H; OH; an unsubstituted $C_{1-4}$-aliphatic residue, or an unsubstituted $O-C_{1-4}$ aliphatic residue, with the proviso that at least one of $X^2$ and $X^3$ denotes H or is linked via a carbon atom, and the respective remaining substituents of $X^4$ and $X^5$ each independently of one another represent H; $CH_2F$; $CHF_2$; $CF_3$; an unsubstituted $C_{1-4}$-aliphatic residue, or $X^2$ and $X^4$ together with the carbon atoms connecting them, form a $C_{3-10}$-cycloaliphatic residue, preferably a $C_{3-6}$-cycloaliphatic residue, unsubstituted or mono- or polysubstituted with at least one substituent selected from the group consisting of F, Cl, Br, I, OH, an unsubstituted $O-C_{1-4}$-aliphatic residue, $CH_2F$, $CHF_2$, $CF_3$, and a an unsubstituted $C_{1-4}$-aliphatic residue, and the remaining substituent $X^3$ represents H; F; Cl; Br; I; OH; an unsubstituted $C_{1-4}$-aliphatic residue, or an unsubstituted $O-C_{1-4}$ aliphatic residue, and the remaining substituent $X^5$ represents H; $CH_2F$; $CHF_2$; $CF_3$; an unsubstituted $C_{1-4}$-aliphatic residue.

Even more preferably, $X^2$ and $X^3$ independently of one another represent H; OH; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $OCH_3$ or $OCH_2CH_3$, with the proviso that at least one of $X^2$ and $X^3$ denotes H or is linked via a carbon atom, preferably represent H; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $OCH_3$ or $OCH_2CH_3$, with the proviso that at least one of $X^2$ and $X^3$ denotes H or is linked via a carbon atom, $X^4$ and $X^5$ independently of one another represent H; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $CH_2F$; $CHF_2$; $CF_3$;

or $X^2$ and $X^3$ or $X^4$ and $X^5$ in pairs, in each case independently of one another, together with the carbon atom connecting them, form a $C_{3-6}$-cycloaliphatic residue selected from the group consisting of cyclopropyl, cyclobutyl, cyclopentyl and cyclohexyl, unsubstituted or mono- or polysubstituted with at least one substituent selected from the group consisting of F, Cl, Br, I, OH, methyl; ethyl, n-propyl, 2-propyl, n-butyl, isobutyl, sec.-butyl, tert.-butyl, $CH_2F$, $CHF_2$, $CF_3$, $OCH_3$ and $OCH_2CH_3$, and the respective remaining substituents of $X^2$ and $X^3$ each independently of one another represents H; OH; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $OCH_3$ or $OCH_2CH_3$, with the proviso that at least one of $X^2$ and $X^3$ denotes H or is linked via a carbon atom, preferably represent H; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $OCH_3$ or $OCH_2CH_3$, with the proviso that at least one of $X^2$ and $X^3$ denotes H or is linked via a carbon atom, and the respective remaining substituents of $X^4$ and $X^5$ each independently of one another represents H; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $CH_2F$; $CHF_2$; $CF_3$;

or $X^2$ and $X^4$ together with the carbon atoms connecting them, form a $C_{3-6}$-cycloaliphatic residue selected from the group consisting of cyclopropyl, cyclobutyl, cyclopentyl and cyclohexyl, unsubstituted or mono- or polysubstituted with at least one substituent selected from the group consisting of F, Cl, Br, I, OH, methyl; ethyl, n-propyl, 2-propyl, n-butyl, isobutyl, sec.-butyl, tert.-butyl, $CH_2F$, $CHF_2$, $CF_3$, $OCH_3$ and $OCH_2CH_3$, and $X^3$ represents H; OH; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $OCH_3$ or $OCH_2CH_3$, preferably represents H; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $OCH_3$ or $OCH_2CH_3$, and $X^5$ represents H; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $CH_2F$; $CHF_2$; $CF_3$.

Still more preferably, $X^2$ and $X^3$ independently of one another represent H; OH; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $OCH_3$ or $OCH_2CH_3$, with the proviso that at least one of $X^2$ and $X^3$ denotes H or is linked via a carbon atom, preferably represents H; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $OCH_3$ or $OCH_2CH_3$, with the proviso that at least one of $X^2$ and $X^3$ denotes H or is linked via a carbon atom, $X^4$ and $X^5$ independently of one another represent H; methyl; ethyl, n-propyl, 2-propyl, n-butyl, isobutyl, sec.-butyl, tert.-butyl, n-pentyl, isopentyl, neopentyl, n-hexyl, $CH_2—CH(CH_3)(C_2H_5)$, $C(CH_3)_2(C_2H_5)$, $CH_2F$; $CHF_2$; $CF_3$;

or $X^2$ and $X^4$ together with the carbon atoms connecting them, form a $C_{3-6}$-cycloaliphatic residue selected from the group consisting of cyclopropyl, cyclobutyl, cyclopentyl and cyclohexyl, unsubstituted or mono- or polysubstituted with at least one substituent selected from the group consisting of F, Cl, Br, I, OH, methyl; ethyl, n-propyl, 2-propyl, n-butyl, isobutyl, sec.-butyl, tert.-butyl, $CH_2F$, $CHF_2$, $CF_3$, $OCH_3$ and $OCH_2CH_3$, and the respective remaining substituent $X^3$ represents H; OH; methyl; ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, $OCH_3$ or $OCH_2CH_3$, preferably represent H; methyl; ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, $OCH_3$ or $OCH_2CH_3$, and the respective remaining substituents $X^5$ represents H; methyl; ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, $CH_2F$; $CHF_2$; $CF_3$.

In another preferred embodiment of the compound according to general formula (X), at least one of $X^2$, $X^3$, $X^4$ and $X^5$ denotes H, preferably at least two of $X^2$, $X^3$, $X^4$ and $X^5$ denote H.

In yet another preferred embodiment of the compound according to general formula (X), at least one of $X^3$ and $X^5$ denotes H, preferably both $X^3$ and $X^5$ denote H.

In a further preferred embodiment of the compound according to general formula (X), $X^1$ represents ethyl, n-propyl, 2-propyl, n-butyl, isobutyl, sec.-butyl, tert.-butyl, cyclopropyl, cyclobutyl, cyclopentyl, or cyclohexyl,
or represents $OX^6$, wherein
$X^6$ represents methyl, ethyl, n-propyl, 2-propyl, n-butyl, isobutyl, sec.-butyl, or tert.-butyl,
preferably represents ethyl, n-propyl, 2-propyl, n-butyl, isobutyl, sec.-butyl, tert.-butyl, cyclopropyl, cyclobutyl, cyclopentyl, or cyclohexyl, $X^2$ and $X^3$ independently of one another represent H; methyl; ethyl, n-propyl, 2-propyl, n-butyl, isobutyl, sec.-butyl, or tert.-butyl,
preferably $X^2$ is selected from the group consisting of methyl; ethyl, n-propyl, 2-propyl, n-butyl, isobutyl, sec.-butyl, or tert.-butyl, and $X^3$ denotes H, $X^4$ and $X^5$ independently of one another represent H; methyl; ethyl, n-propyl, 2-propyl, n-butyl, isobutyl, sec.-butyl, tert.-butyl, $CH_2F$, $CHF_2$, or $CF_3$;
preferably $X^4$ is selected from the group consisting of methyl; ethyl, n-propyl, 2-propyl, n-butyl, isobutyl, sec.-butyl, tert.-butyl, $CH_2F$, $CHF_2$, and $CF_3$; and $X^5$ denotes H,
or
$X^2$ and $X^3$ or $X^4$ and $X^5$
in pairs, in each case independently of one another, together with the carbon atom connecting them, form a $C_{3-6}$-cycloaliphatic residue selected from the group consisting of cyclopropyl, cyclobutyl, cyclopentyl and cyclohexyl, unsubstituted or mono- or polysubstituted with at least one substituent selected from the group consisting of OH, methyl; ethyl, n-propyl, 2-propyl, n-butyl, isobutyl, sec.-butyl, $CH_2F$, $CHF_2$, $CF_3$, $OCH_3$ and $OCH_2CH_3$, and the respective remaining substituents of $X^2$ and $X^3$ independently of one another represent H; methyl; ethyl, n-propyl, 2-propyl, n-butyl, isobutyl, sec.-butyl, or tert.-butyl,
preferably $X^2$ is selected from the group consisting of methyl; ethyl, n-propyl, 2-propyl, n-butyl, isobutyl, sec.-butyl, or tert.-butyl, and $X^3$ denotes H,
and the respective remaining substituents of $X^4$ and $X^5$ independently of one another represent H; methyl; ethyl, n-propyl, 2-propyl, n-butyl, isobutyl, sec.-butyl, tert.-butyl, $CH_2F$, $CHF_2$, or $CF_3$;

preferably $X^4$ is selected from the group consisting of methyl; ethyl, n-propyl, 2-propyl, n-butyl, isobutyl, sec.-butyl, tert.-butyl, $CH_2F$, $CHF_2$, and $CF_3$; and $X^5$ denotes H,
or
$X^2$ and $X^4$ together with the carbon atoms connecting them, form a $C_{3-6}$-cycloaliphatic residue selected from the group consisting of cyclopropyl, cyclobutyl, cyclopentyl and cyclohexyl, unsubstituted or mono- or polysubstituted with at least one substituent selected from the group consisting of OH, methyl; ethyl, n-propyl, 2-propyl, n-butyl, isobutyl, sec.-butyl, tert.-butyl, $CH_2F$, $CHF_2$, $CF_3$, $OCH_3$ and $OCH_2CH_3$,
and $X^3$ represents H; methyl; ethyl, n-propyl, 2-propyl, n-butyl, isobutyl, sec.-butyl, or tert.-butyl,
preferably $X^3$ denotes H,
and $X^5$ represents H; methyl; ethyl, n-propyl, 2-propyl, n-butyl, isobutyl, sec.-butyl, tert.-butyl, $CH_2F$, $CHF_2$, or $CF_3$,
preferably $X^5$ denotes H.

In a further preferred embodiment of the compound according to general formula (I), $X^1$ represents ethyl, n-propyl, 2-propyl, n-butyl, isobutyl, sec.-butyl, tert.-butyl, cyclopropyl, cyclobutyl, cyclopentyl, or cyclohexyl,
or represents $OX^6$, wherein
$X^6$ represents methyl, ethyl, n-propyl, 2-propyl, n-butyl, isobutyl, sec.-butyl, or tert.-butyl,
preferably represents ethyl, n-propyl, 2-propyl, n-butyl, isobutyl, sec.-butyl, tert.-butyl, cyclopropyl, cyclobutyl, cyclopentyl, or cyclohexyl, $X^2$ and $X^3$ independently of one another represent H; methyl; ethyl, n-propyl, 2-propyl, n-butyl, isobutyl, sec.-butyl, or tert.-butyl,
preferably $X^2$ is selected from the group consisting of methyl; ethyl, n-propyl, 2-propyl, n-butyl, isobutyl, sec.-butyl, or tert.-butyl, and $X^3$ denotes H, $X^4$ and $X^5$ independently of one another represent H; methyl; ethyl, n-propyl, 2-propyl, n-butyl, isobutyl, sec.-butyl, tert.-butyl, $CH_2F$, $CHF_2$, or $CF_3$;
preferably $X^4$ is selected from the group consisting of methyl; ethyl, n-propyl, 2-propyl, n-butyl, isobutyl, sec.-butyl, tert.-butyl, $CH_2F$, $CHF_2$, and $CF_3$, and $X^5$ denotes H.
or
$X^2$ and $X^4$ together with the carbon atoms connecting them, form a $C_{3-6}$-cycloaliphatic residue selected from the group consisting of cyclopropyl, cyclobutyl, cyclopentyl and cyclohexyl, unsubstituted or mono- or polysubstituted with at least one substituent selected from the group consisting of OH, methyl; ethyl, n-propyl, 2-propyl, n-butyl, isobutyl, sec.-butyl, tert.-butyl, $CH_2F$, $CHF_2$, $CF_3$, $OCH_3$ and $OCH_2CH_3$, and the respective remaining substituent $X^3$ represents H; methyl; ethyl, n-propyl, 2-propyl, n-butyl, isobutyl, sec.-butyl, or tert.-butyl, preferably $X^3$ denotes H,
and the respective remaining substituent $X^5$ represents H; methyl; ethyl, n-propyl, 2-propyl, n-butyl, isobutyl, sec.-butyl, tert.-butyl, $CH_2F$, $CHF_2$, and $CF_3$,
preferably $X^5$ denotes H.

Particularly preferred compounds of formula (X) are selected from the group consisting of:

X1 2-Cyclopropyl-N-(3-hydroxy-4,4-dimethyl-pentyl)-4-methyl-6-morpholin-4-yl-pyridine-3-carboxylic acid amide;

X2 2-Cyclopropyl-N-[[(1S,2R)-2-hydroxy-cyclohexyl]-methyl]-4-methyl-6-morpholin-4-yl-pyridine-3-carboxylic acid amide;

X3 2-Cyclopropyl-N-[[(1R,2S)-2-hydroxy-cyclohexyl]-methyl]-4-methyl-6-morpholin-4-yl-pyridine-3-carboxylic acid amide;

X4 2-Cyclopropyl-N-([2-hydroxy-cyclopentyl]-methyl)-4-methyl-6-morpholin-4-yl-pyridine-3-carboxylic acid amide;

X5 N-(3-Hydroxy-4,4-dimethyl-pentyl)-2-isopropyl-4-methyl-6-morpholin-4-yl-pyridine-3-carboxylic acid amide;

X6 2-Isopropyl-4-methyl-6-morpholin-4-yl-N-(4,4,4-trifluoro-3-hydroxy-butyl)-pyridine-3-carboxylic acid amide; and X7 N-[[(1S,2R)-2-Hydroxy-cyclohexyl]-methyl]-2-isopropyl-4-methyl-6-morpholin-4-yl-pyridine-3-carboxylic acid amide;

optionally in the form of a single stereoisomer or a mixture of stereoisomers, in the form of the free compound and/or a physiologically acceptable salt thereof.

The substituted compounds according to the invention of the aforementioned general formula (I) and corresponding stereoisomers and also the respective corresponding salts and solvates are toxicologically safe and are therefore suitable as pharmaceutical active ingredients in pharmaceutical compositions.

The present invention therefore further relates to a pharmaceutical composition containing at least one compound according to general formula (I), in each case if appropriate in the form of one of its pure stereoisomers, in particular enantiomers or diastereomers, its racemates or in the form of a mixture of stereoisomers, in particular the enantiomers and/or diastereomers, in any desired mixing ratio, or respectively in the form of a physiologically acceptable salt, or respectively in the form of a corresponding solvate, and also if appropriate one or more pharmaceutically acceptable auxiliaries.

These pharmaceutical compositions according to the invention are suitable in particular for the modulation of KCNQ2/3 K$^+$ channels, preferably for KCNQ2/3 K$^+$ channel inhibition and/or KCNQ2/3 K$^+$ channel stimulation, i.e. they exert an agonistic or antagonistic effect.

Likewise, the pharmaceutical compositions according to the invention are preferably suitable for the prophylaxis and/or treatment of disorders and/or diseases which are mediated, at least in part, by KCNQ2/3 K$^+$ channels.

The pharmaceutical composition according to the invention is suitable for administration to adults and children, including toddlers and babies.

The pharmaceutical composition according to the invention may be prepared as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one substituted compound of general formula (I), if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally may contain further physiologically acceptable pharmaceutical auxiliaries which, for example, can be selected from the group consisting of excipients, fillers, solvents, diluents, surface-active substances, dyes, preservatives, blasting agents, slip additives, lubricants, aromas and binders.

The selection of the physiologically acceptable auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository, in a dissolved form or in a plaster, and further agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention can be prepared with the aid of conventional means, devices, methods and process known in the art, such as are described for example in "Remington's Pharmaceutical Sciences", A. R. Gennaro (Editor), 17$^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula (I) may vary and is for example dependent on the patient's weight or age and also on the type of application, the indication and the severity of the disorder. Conventionally, 0.001 to 100 mg/kg, preferably 0.05 to 75 mg/kg, particularly preferably 0.05 to 50 mg of at least one compound according to the invention are applied per kg of the patient's body weight.

The pharmaceutical composition according to the invention is preferably suitable for the prophylaxis and/or treatment of disorders and/or diseases which are mediated, at least in part, by KCNQ2/3 K$^+$ channels. The pharmaceutical composition according to the invention is more preferably suitable for the treatment and/or prophylaxis of one or more diseases and/or disorders selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

The pharmaceutical composition according to the invention is suitable particularly preferably for the treatment of pain, more particularly preferably of acute pain, chronic pain, neuropathic pain, visceral pain, inflammatory pain and muscular pain, and most particularly for the treatment of neuropathic pain.

The pharmaceutical composition according to the invention is also preferably suitable for the treatment and/or prophylaxis of epilepsy.

The present invention further relates to at least one compound according to general formula (I) and also if appropriate of one or more pharmaceutically acceptable auxiliaries for use in the modulation of KCNQ2/3 K$^+$ channels, preferably for use in KCNQ2/3 K$^+$ channel inhibition and/or stimulation.

The present invention therefore further relates to at least one compound according to general formula (I) and also if appropriate of one or more pharmaceutically acceptable auxiliaries for use in the prophylaxis and/or treatment of disorders and/or diseases which are mediated, at least in part, by KCNQ2/3 K$^+$ channels.

Preference is given to at least one compound according to general formula (I) and optionally one or more pharmaceutically acceptable auxiliaries for use in the prophylaxis and/or treatment of disorders and/or diseases selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for use in the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for use in the prophylaxis and/or treatment of epilepsy.

The present invention further relates to at least one compound according to general formula (I) and also if appropriate of one or more pharmaceutically acceptable auxiliaries for the modulation of KCNQ2/3 K$^+$ channels, preferably for KCNQ2/3 K$^+$ channel inhibition and/or stimulation.

The present invention therefore further relates to at least one compound according to general formula (I) and also if appropriate of one or more pharmaceutically acceptable auxiliaries for the prophylaxis and/or treatment of disorders and/or diseases which are mediated, at least in part, by KCNQ2/3 K$^+$ channels.

Preference is given to at least one compound according to general formula (I) and optionally one or more pharmaceutically acceptable auxiliaries for the prophylaxis and/or treatment of disorders and/or diseases selected from the group consisting of pain, especially pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for the prophylaxis and/or treatment of epilepsy.

The present invention further relates to at least one compound according to general formula (I) and also if appropriate of one or more pharmaceutically acceptable auxiliaries for use in the preparation of a medicament for prophylaxis and/or treatment of disorders and/or diseases which are mediated, at least in part, by KCNQ2/3 K$^+$ channels.

Preference is given to at least one compound according to general formula (I) and optionally one or more pharmaceutically acceptable auxiliaries for use in the preparation of a medicament for the prophylaxis and/or treatment of disorders and/or diseases selected from the group consisting of pain, in particular pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias.

Particular preference is given to at least one compound according to general formula (I) and optionally one or more pharmaceutically acceptable auxiliaries for use in the preparation of a medicament for the prophylaxis and/or treatment of disorders and/or diseases selected from the group consisting of pain, in particular pain selected from the group consisting of acute pain, chronic pain, neuropathic pain, muscular pain, visceral pain and inflammatory pain, most particularly neuropathic pain.

Particular preference is also given to at least one compound according to general formula (I) and optionally one or more pharmaceutically acceptable auxiliaries for use in the preparation of a medicament for the prophylaxis and/or treatment of epilepsy.

Another aspect of the present invention is a method of treatment and/or prophylaxis of disorders and/or diseases, which are mediated, at least in part, by KCNQ2/3 K$^+$ channels, in a mammal, preferably of disorders and/or diseases selected from the group consisting of pain, preferably pain selected from the group consisting of acute pain, chronic pain, neuropathic pain, muscular pain, visceral pain and inflammatory pain, epilepsy, urinary incontinence, anxiety, dependency, mania, bipolar disorders, migraine, cognitive diseases and dystonia-associated dyskinesias, which comprises administering an effective amount of at least one compound of general formula (I) to the mammal.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74 79 (1941)) or by the formalin test (e.g. according to D. Dubuisson et al., Pain 1977, 4, 161-174). The effectiveness against epilepsy can be demonstrated, for example, in the DBA/2 mouse model (De Sarro et al., Naunyn-Schmiedeberg's Arch. Pharmacol. 2001, 363, 330-336).

The compounds according to the invention preferably have a $EC_{50}$ value of not more than 10000 nM or not more than 8000 nM, more preferably not more than 7000 nM or not more than 6000 nM, yet more preferably not more than 5000 nM or not more than 3000 nM, even more preferably not more than 2000 nM or not more than 1000 nM, yet even more preferably not more than 800 nM or not more than 700 nM, still more preferably not more than 600 nM or not more than 500 nM, yet still more preferably not more than 400 nM or not more than 300 nM, most preferably not more than 200 nM or not more than 150 nM and especially not more than 120 nM or not more than 100 nM. Methods for determining the $EC_{50}$ value are known to the person skilled in the art. The $EC_{50}$ value is preferably determined by fluorimetry, particularly preferably as described below under "pharmacological experiments".

The invention further provides processes for the preparation of the substituted compounds according to the invention.

The chemicals and reaction components used in the reactions and schemes described below are available commercially or in each case can be prepared by conventional methods known to the person skilled in the art.

The reactions described can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps described below, as well as the respective purification and/or isolation of intermediate or end products, can be carried out partly or completely under an inert gas atmosphere, preferably under a nitrogen atmosphere.

If the substituted compounds according to the invention of the aforementioned general formula (I) are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallisation processes. These processes allow individual enantiomers, for example diastereomeric salts formed by means of chiral stationary phase HPLC or by means of crystallisation with chiral acids, for example (+)-tartaric acid, (−)-tartaric acid or (+)-10-camphorsulphonic acid, to be separated from one another.

General reaction scheme I (synthesis of precursor SM01):

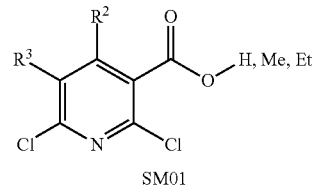

SM01

A plurality of syntheses of and synthesis paths to compounds of the general formula SM01 with a very broad substitution pattern for residues $R^2$ and $R^3$ are known in the current specialist literature. Previously unknown intermediates of the general formula SM01 with similar substitution patterns for residues $R^2$ and $R^3$ as outlined thereafter and whose syntheses are not described in greater detail, can be produced by the person skilled in the art according to these known methods or by combination of the known methods.

General reaction scheme II:

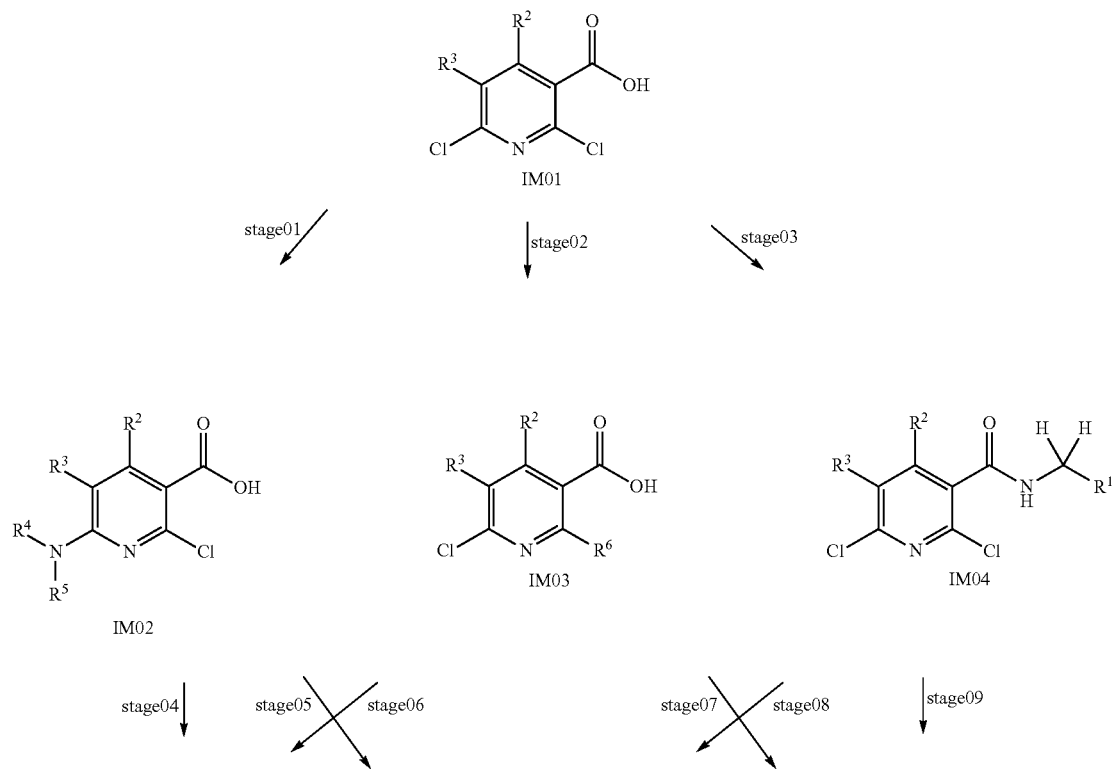

115

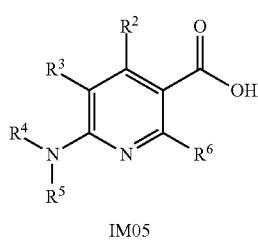

IM05

-continued

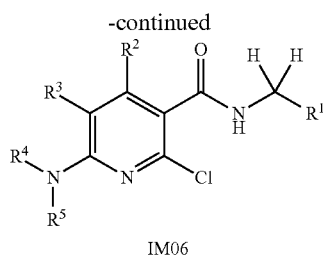

IM06

116

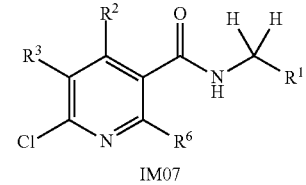

IM07 stage10 stage11 stage12

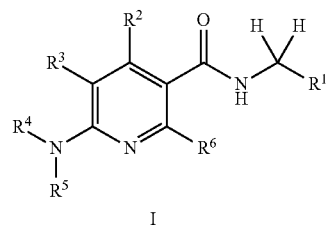

I

In stage03, stage05, stage07 and stage10, acids of the general formulae IM01, IM02, IM03 and IM05, respectively, can be transformed into amides of the general formulae IM04, IM06, IM07 and I respectively, with amines of the general formula $R^1$—$CH_2$—$NH_2$ according to methods known to the person skilled in the art, for example, using a suitable coupling reagent, for example HATU.

In stage01, stage06, stage08 and stage12, 6-chloro-pyridines of the general formulae IM01, IM03, IM04 and IM07 respectively, can be transformed into 6-amino-pyridines of the general formulae IM02, IM05, IM06 and I respectively, with amines of the general formula $HNR^4R^5$ according to methods known to the person skilled in the art, for example by conventional or microwave heating, neat or in solution, for example in MeCN, DMF or THF, optionally in the presence of a suitable base, for example $NEt_3$, DIPEA, $K_2CO_3$, $Cs_2CO_3$, NaOtBu or KOtBu, optionally by addition of a suitable coupling reagent, for example $Pd(PPh_3)_4$.

In stage02, stage04, stage09, and stage11, 2-chloro-pyridines of the general formulae IM01, IM02, IM04, and IM06 respectively, can be transformed into 2-substituted-pyridines of the general formulae IM03, IM05, IM07 and I respectively, with compounds of the general formula X—$R^6$, where X denotes H, a metal, for example sodium, or a residue to form an organometal reagent, for example MgBr or MgCl, according to methods known to the person skilled in the art, for example by conventional or microwave heating, neat or in solution, for example in MeCN, DMF, THF, MeOH or EtOH, optionally in the presence of a suitable base, for example $NEt_3$, DIPEA, $K_2CO_3$, $Cs_2CO_3$, NaOtBu or KOtBu, optionally by addition of a suitable coupling reagent, for example $Pd(PPh_3)_4$, $Ni(dppp)Cl_2$ or $Fe(acac)_3$.

General reaction scheme III:

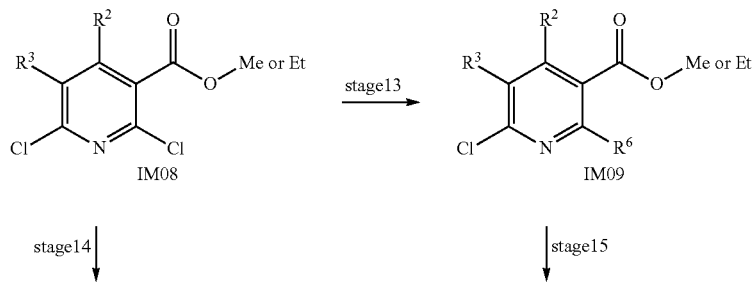

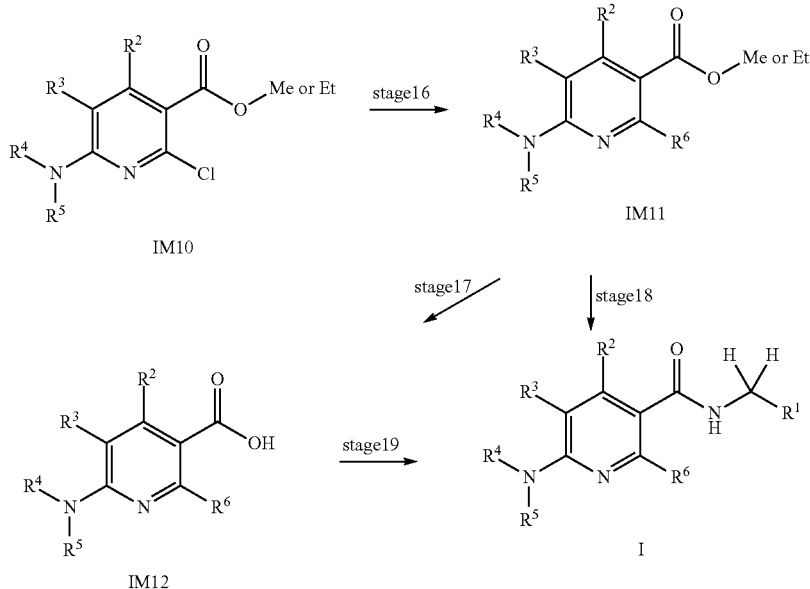

In stage13 and stage16, 2-chloro-pyridines of the general formulae IM108 and IM10 respectively, can be transformed into 2-substituted-pyridines of the general formulae IM109 and IM11 respectively, with compounds of the general formula X—$R^6$, where X denotes H, a metal, for example sodium, or a residue to form an organometal reagent, for example MgBr or MgCl, according to methods known to the person skilled in the art, for example by conventional or microwave heating, neat or in solution, for example in MeCN, DMF, THF, MeOH or EtOH, optionally in the presence of a suitable base, for example $NEt_3$, DIPEA, $K_2CO_3$, $Cs_2CO_3$, NaOtBu or KOtBu, optionally by addition of a suitable coupling reagent, for example $Pd(PPh_3)_4$, $Ni(dppp)Cl_2$ or $Fe(acac)_3$.

In stage14 and stage15, 6-chloro-pyridines of the general formulae IM108 and IM109 respectively, can be transformed into 6-Amino-pyridines of the general formulae IM10 and IM11 respectively, with amines of the general formula $HNR^4R^5$ according to methods known to the person skilled in the art, for example by conventional or microwave heating, neat or in solution, for example in MeCN, DMF or THF, optionally in the presence of a suitable base, for example $NEt_3$, DIPEA, $K_2CO_3$, $Cs_2CO_3$, NaOtBu or KOtBu, optionally by addition of a suitable coupling reagent, for example $Pd(PPh_3)_4$.

In stage17 esters of the general formula IM11 can be transformed into acids of the general formula IM12 according to methods known to the person skilled in the art, for example, by employing a base, for example lithium hydroxide.

In stage18 esters of the general formula IM11 can be converted to yield amides of the general formula I, with amines of the general formula $R^1$—$CH_2$—$NH_2$ according to methods known to the person skilled in the art, for example by the addition of trimethyl aluminium.

In stage19 acids of the general formula IM12 can be transformed into amides of the general formula I with amines of the general formula $R^1$—$CH_2$—$NH_2$ according to methods known to the person skilled in the art, for example, using a suitable coupling reagent, for example, HATU.

Thus obtained compounds of the general formula I can be further transformed to introduce and/or exchange one or more of the substituents $R^1$, $R^2$, $R^3$, $R^4$ $R^5$ and $R^6$ by simple derivatization reactions known to the person skilled in the art, for example, esterification, ester formation, amide formation, etherification, ether cleavage, oxidation, reduction, substitution or cross-coupling reactions.

General reaction scheme X-I:

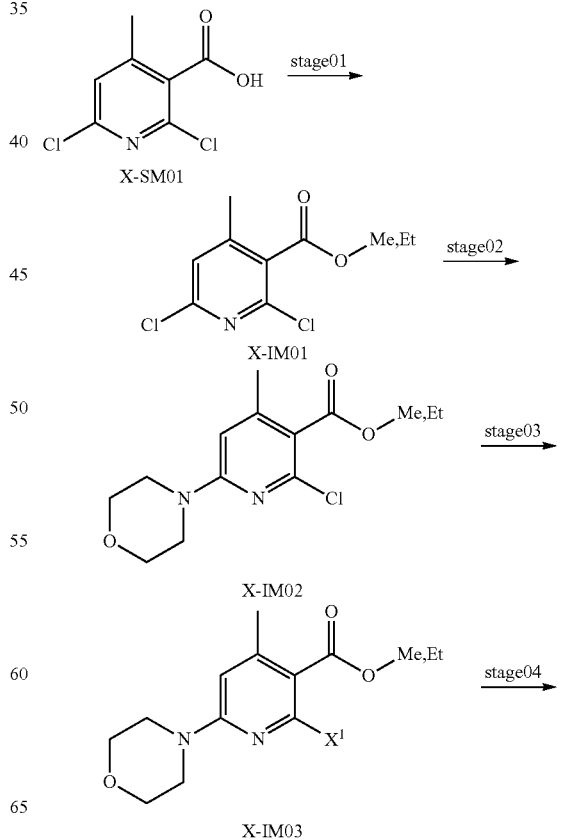

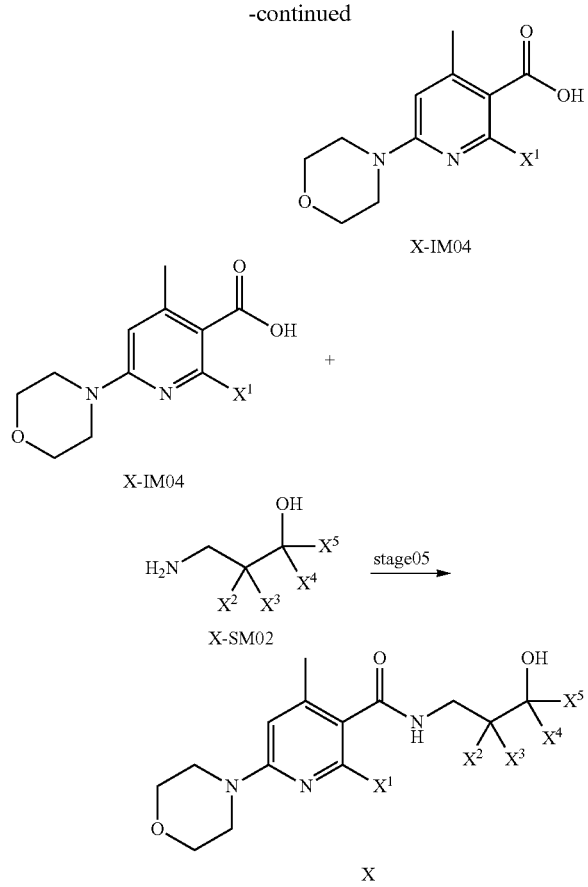

In stage01, 2, 6-dichloro-nicotinic acids of the general formula X-SM01 can be transformed into the corresponding esters of the general formula X-IM01 according to methods known to the person skilled in the art, for example using a suitable alkylation reagent, for example methyl iodide or ethyl iodide.

In stage02, 2, 6-dichloro-nicotinic acid esters of the general formula X-IM01 can be transformed into 2-chloro-6-morpholin-nicotinic acid esters of the general formula X-IM02 using morpholine according to methods known to the person skilled in the art, for example by conventional or microwave heating, neat or in solution, for example in acetonitrile, dimethylformamide, dioxane, N-methyl-2-pyrrolidone or tetrahydrofuran, optionally in the presence of a suitable base, for example triethylamine, N,N-diisopropylethylamine, potassium carbonate, caesium carbonate, sodium tert-butoxide or potassium tert-butoxide, optionally by addition of a suitable coupling reagent, for example tetrakis(triphenylphosphin)-palladium, bis(dibenzylideneacetone)-palladium(0), or tris(dibenzylideneacetone)-dipalladium(0), optionally in presence of an additional ligand, for example (2-biphenyl)di-tert-butylphosphine or 2'-bis(diphenylphosphino)-1,1'-binaphthyl.

In stage03 2-chloro-6-morpholin-nicotinic acid esters of the general formulae X-IM02 can be transformed into the intermediates of the general formula X-IM03 according to methods known to the person skilled in the art with compounds of the general formula Y—X$^1$, where Y denotes hydrogen, a metal or organometallic residue, for example sodium, magnesium bromide, magnesium chloride, tributyltin or boronic acid, or a residue to form an organometallic reagent, according to methods known to the person skilled in the art, for example by conventional or microwave heating, neat or in solution, for example in acetonitrile, dimethylformamide, dioxane, N-methyl-2-pyrrolidone, tetrahydrofuran, methanol or ethanol, optionally in the presence of a suitable base, for example triethylamine, N,N-diisopropylethylamine, potassium carbonate, caesium carbonate, sodium tert-butoxide or potassium tert-butoxide, optionally by addition of a suitable coupling reagent, for example tetrakis(triphenylphosphin)-palladium, bis(dibenzylideneacetone)-palladium(0), tris(dibenzylideneacetone)-dipalladium(0), [1,3-bis(diphenylphosphino)propane]-dichloronickel(II) or iron(III) acetylacetonate, optionally in presence of an additional ligand, for example (2-biphenyl)di-tert-butylphosphine or 2'-bis(diphenylphosphino)-1,1'-binaphthyl.

In stage04 nicotinic acid esters of the general formula X-IM03 can be transformed into the corresponding nicotinic acids of the general formula X-IM04 according to methods known to the person skilled in the art, for example by employing a base, for example sodium hydroxide.

In stage05 nicotinic acids of the general formula X-IM04 can be converted to yield amides of the general formula X with amines of the general formula X-SM02 according to methods known to the person skilled in the art, for example by using a suitable coupling reagent, for example O-(7-azabenzotriazol-1-yl)-N,N,N',N'-tetramethyluronium hexafluorophosphate.

General reaction scheme X-II:

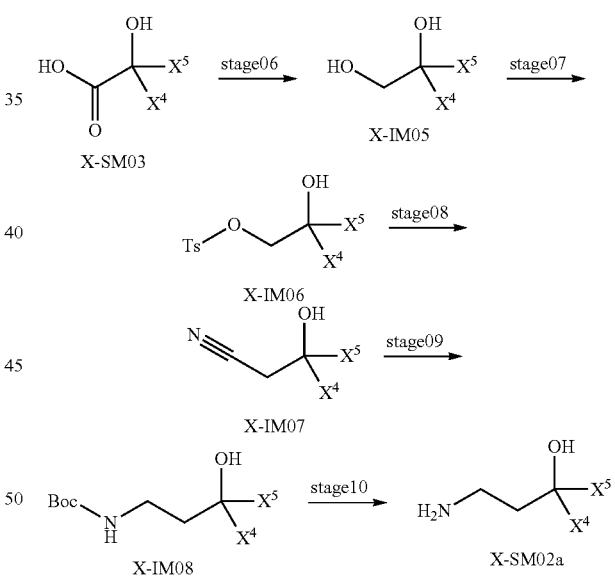

Amines of the general formula X-SM02, in which X$^2$ and X$^3$ denote hydrogen, herein thereafter referred to as X-SM02a can be prepared from substituted 2-hydroxyacetic acids of the general formula X-SM03, according to methods known to the person skilled in the art. Enantiomerically pure amines of the general formula X-SM02a can be obtained from enantiomerically pure 2-hydroxyacetic acids of the general formula X-SM03. In stage06, 2-hydroxyacetic acids of the general formula X-SM03 can be transformed into the corresponding diols of the general formula X-IM05 according to methods known to the person skilled in the art, for example by employing a reducing agent, for example lithium aluminium hydride. In stage07, diols of the general formula X-IM05 can be transformed into the corresponding p-toluenesulfonic acid esters of the general formula X-IM06 according to methods known to the person skilled in the art, for example by treating with 4-toluenesulfonyl chloride. In stage08, p-toluenesulfonic acid esters of the general formula X-IM06 can be transformed into the corresponding nitriles general formula X-IM07 according to methods known to the person skilled in the art, for example by treating with sodium cyanide. In stage09, nitriles general formula X-IM07 can be transformed into the corresponding tert-butyl carbamates of the general formula X-IM08 according to methods known to the person skilled in the art, for example by treating with nickel(II) chloride and sodium borohydride in the presence of di-tert-butyl dicarbonate. In stage10, tert-butyl carbamates of the general formula X-IM08 can be transformed into the corresponding amines of the general formula SM02a according to methods known to the person skilled in the art, for example by treating with hydrochloric acid.

General reaction scheme X-III:

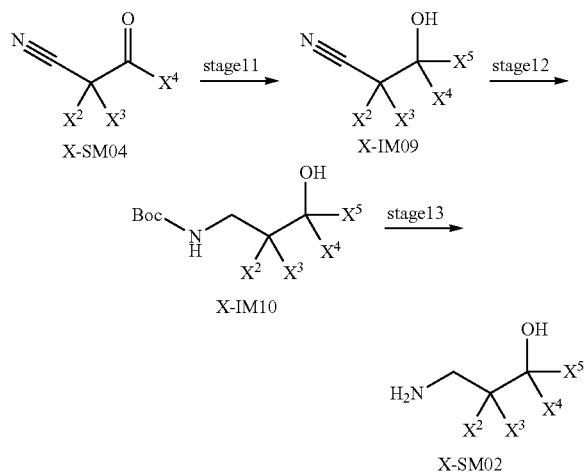

Alternatively, amines of the general formula X-SM02 can be prepared from substituted 3-oxopropanenitriles of the general formula X-SM04, according to methods known to the person skilled in the art. In stage11, 3-oxopropanenitriles of the general formula X-SM04 can be transformed into the corresponding 3-hydroxypropanenitriles of the general formula X-M09 according to methods known to the person skilled in the art, for example by employing a reducing agent, for example sodium borohydride, borane dimethyl sulfide complex or borane tetrahydrofuran complex (affording compounds in which $X^5$ denotes a hydrogen), optionally in presence of a suitable ligand, for example CBS-oxazaborolidines, or alternatively by treating with compounds of the general formula Y—$X^5$, where Y denotes a metal or organometallic residue, for example sodium, magnesium bromide, magnesium chloride, or a residue to form an organometallic reagent, according to methods known to the person skilled in the art (affording compounds in which $X^5$ denotes a substituted carbon). In stage12, 3-hydroxypropanenitriles of the general formula X-IM09 can be transformed into the corresponding tert-butyl carbamates of the general formula X-IM10 according to methods known to the person skilled in the art, for example by treating with nickel(II) chloride and sodium borohydride in the presence of di-tert-butyl dicarbonate. In stage13, tert-butyl carbamates of the general formula X-IM10 can be transformed into the corresponding amines of the general formula X-SM02 according to methods known to the person skilled in the art, for example by treating with hydrochloric acid.

A plurality of additional synthesis paths to compounds of the general formulae X-SM02, X-SM02a, X-SM03, X-SM04 with a very broad substitution pattern for residues $X^2$ to $X^5$ are known in the current specialist literature. Previously unknown intermediates of the general formulae X-SM02, X-SM02a, X-SM03, X-SM04 with similar substitution patterns for residues $X^2$ to $X^5$ as outlined above and whose syntheses are not described in greater detail can be produced by the person skilled in the art according to these known methods or by combination of the known methods.

The invention will be described hereinafter with the aid of a number of examples. This description is intended merely by way of example and does not limit the general idea of the invention.

EXAMPLES

The indication "equivalents" ("eq.") means molar equivalents, "RT" means room temperature (23±7° C.), "M" are indications of concentration in mol/l, "aq." means aqueous, "sat." means saturated, "sol." means solution, "conc." means concentrated.

Further abbreviations:
acac acetylacetone=2,4-pentanedione
AcOH acetic acid
d days
dppp 1,3-bis(diphenylphosphino)propane
brine saturated aqueous sodium chloride solution
CC column chromatography on silica gel
DCM dichloromethane
DIPEA N,N-diisopropylethylamine
DMF N,N-dimethylformamide
ether diethyl ether
EtOAc ethyl acetate
EtOH ethanol
h hour(s)
$H_2O$ water
HATU O-(7-aza-benzotriazol-1-yl)-N,N,N',N'-tetramethyluroniumhexafluorophosphate
m/z mass-to-charge ratio
MeOH methanol
MeCN acetonitrile
min minutes
MS mass spectrometry
N/A not available
$NEt_3$ triethylamine
NMP N-methyl-2-pyrrolidone
RM reaction mixture
THF tetrahydrofuran
v/v volume to volume
w/w weight in weight The yields of the compounds prepared were not optimized.
All temperatures are uncorrected.
All starting materials which are not explicitly described were either commercially available (the details of suppliers such as for example Acros, Avocado, Aldrich, Bachem, Fluka, Lancaster, Maybridge, Merck, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, N L or the SciFinder® Database of the ACS, Washington D.C., US, respectively, for example) or can be prepared using the conventional methods known to the person skilled in the art.

The stationary phase used for the column chromatography was silica gel 60 (0.04-0.063 mm) from E. Merck, Darmstadt.

For microwave reactions a Discover® microwave, from the CEM Corporation, Matthews, US, was used.

The mixing ratios of solvents or eluents for chromatography are specified in v/v.

All the intermediate products and exemplary compounds were analytically characterised by means of $^1$H-NMR spectroscopy. In addition, mass spectrometry tests (MS, m/z for [M+H]$^+$) were carried out for all the exemplary compounds and selected intermediate products.

Synthesis of Exemplary Compounds

Synthesis of Example 1

N-[(3,5-difluoro-phenyl)-methyl]-2-ethylsulfanyl-4-methyl-6-morpholin-4-yl-pyridine-3-carboxylic acid amide

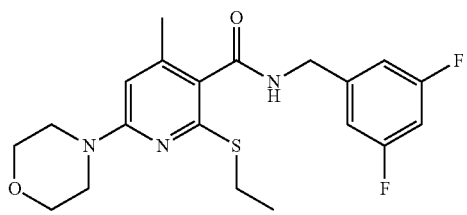 [SMILES: CCSc1nc(N2CCOCC2)cc(C)c1C(=O)NCc1cc(F)cc(F)c1]

a) Synthesis of 6-chloro-2-ethylsulfanyl-4-methyl-pyridine-3-carboxylic acid 6.1 g (153 mmol, 60% w/w in mineral oil) NaH were dissolved in THF (90 ml) at 0° C. At this temperature 3.4 g (54.7 mmol) ethane thiol were added. After stirring for 15 min at 0° C., 12.4 g (60.2 mmol) 2,6-dichloro-4-methyl-pyridine-3-carboxylic acid were added portionwise. The RM was allowed to warm to RT and stirring was continued at RT for 16 h. Then the reaction was quenched with a 2M aq. HCl and diluted with EtOAc. The organic layer was separated, dried over MgSO$_4$ and concentrated in vacuo. Crystallisation (DCM/hexane) of the residue yielded 12.0 g (51.7 mmol, 95%) 6-chloro-2-ethylsulfanyl-4-methyl-pyridine-3-carboxylic acid.

b) Synthesis of 2-ethylsulfanyl-4-methyl-6-morpholin-4-yl-pyridine-3-carboxylic acid A mixture of 12.0 g (51.7 mmol) 6-chloro-2-ethylsulfanyl-4-methyl-pyridine-3-carboxylic acid and 33.7 g (387 mmol) morpholine was heated to 105° C. for 5 d. After cooling to RT a 2M aq. NaOH sol. (200 ml) was added, followed by washing with ether (3×200 ml). The aqueous layer was then acidified with a 2M aq. HCl to pH 5 and extracted with EtOAc. In the same manner pH 4 was adjusted followed by extraction with EtOAc. The combined EtOAc extracts were dried over MgSO$_4$ and concentrated in vacuo. Crystallisation (DCM/hexane) of the residue yielded 7.2 g (25.3 mmol, 49%) 2-ethylsulfanyl-4-methyl-6-morpholin-4-yl-pyridine-3-carboxylic acid.

c) Synthesis of N-[(3,5-Difluoro-phenyl)-methyl]-2-ethylsulfanyl-4-methyl-6-morpholin-4-yl-pyridine-3-carboxylic acid amide To a solution of 250 mg (0.89 mmol) 2-ethylsulfanyl-4-methyl-6-morpholin-4-yl-pyridine-3-carboxylic acid in THF (7 ml), 124 μl (0.97 mmol) 3,5-difluorobenzylamine, 335 mg (0.89 mmol) HATU and 367 μl (2.66 mmol) NEt$_3$ were added and the RM was heated at 70° C. for 5d. Subsequently the mixture was diluted with EtOAc and washed with a 4M aq. NH$_4$Cl sol., a 1M aq. NaHCO$_3$ sol. and brine. The organic layer was dried over MgSO$_4$ and concentrated in vacuo. Purification of the residue by CC (hexane/EtOAc 3:2) provided 187 mg (0.46 mmol, 52%) N-[(3,5-difluoro-phenyl)-methyl]-2-ethylsulfanyl-4-methyl-6-morpholin-4-yl-pyridine-3-carboxylic acid amide (example 1). [M+H]$^+$408.1.

Synthesis of Example 2

2-ethylsulfanyl-N-[(3-fluorophenyl)-methyl]-4-methyl-6-morpholin-4-yl-pyridine-3-carboxylic acid amide

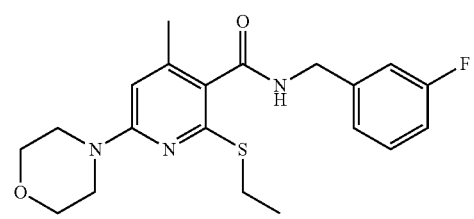

a) Synthesis of 2,6-dichloro-N-(3-fluorobenzyl)-4-methyl-pyridine-3-carboxylic acid amide To a solution of 17.4 g (84.4 mmol) of 2,6-dichloro-4-methyl-pyridine-3-carboxylic acid in THF (340 ml) were added 10.6 ml (92.9 mmol) 3-fluorobenzylamine, 32.0 g (84.4 mmol) HATU and 35.0 ml (253.3 mmol) NEt$_3$. The RM was then heated at 70° C. for 16. After dilution with EtOAc (350 ml) the mixture was washed with a 4M aq. NH$_4$Cl sol., a 1M aq. NaHCO$_3$ sol. and brine. The organic layer was dried over MgSO$_4$ and concentrated in vacuo. Purification of the residue by CC (hexane/EtOAc 3:2) provided 19.5 g (62.3 mmol, 74%) 2,6-dichloro-N-(3-fluorobenzyl)-4-methyl-pyridine-3-carboxylic acid amide.

b) Synthesis of 6-chloro-2-ethylsulfanyl-N-[(3-fluorophenyl)-methyl]-4-methyl-pyridine-3-carboxylic acid amide A solution of 4.0 g (12.8 mmol) 2,6-dichloro-N-(3,5-difluorobenzyl)-4-methyl-pyridine-3-carboxylic acid amide in DMF (30 ml) was treated with 2.6 g (19.2 mmol) K$_2$CO$_3$ and 1.2 ml (16.0 mmol) ethanethiol, followed by stirring in a closed vessel at RT for 16 h. Then water (35 ml) was added and the mixture was extracted with EtOAc (2×70 ml). The combined organic layers were washed with water, a 2M aq. NaOH sol. and brine, dried over MgSO$_4$ and concentrated in vacuo. Purification of the residue by CC (hexane/EtOAc 3:1) provided 3.3 g (9.7 mmol, 76%) 6-chloro-2-ethylsulfanyl-N-[(3-fluorophenyl)-methyl]-4-methyl-pyridine-3-carboxylic acid amide.

c) Synthesis of 2-Ethylsulfanyl-N-[(3-fluorophenyl)-methyl]-4-methyl-6-morpholin-4-yl-pyridine-3-carboxylic acid amide A mixture of 1.5 g (4.4 mmol) 6-chloro-2-ethylsulfanyl-N-[(3-fluorophenyl)-methyl]-4-methyl-pyridine-3-carboxylic acid amide and 1.9 ml (22.1 mmol) morpholine was heated in the microwave at 120° C. for 30 min. Subsequently the RM was diluted with water and EtOAc and the layers were separated. The organic layer was washed with a 1M aq. NaOH sol. and brine, dried over MgSO$_4$ and concentrated in vacuo. Crystallisation (hexane/EtOAc 3:1) of the residue yielded 1.3 g (3.3 mmol, 75%) 2-ethylsulfanyl-N-[(3-fluorophenyl)-methyl]-4-methyl-6-morpholin-4-yl-pyridine-3-carboxylic acid amide (example 2). [M+H]$^+$390.2.

Synthesis of Example 3

N-[(3,5-difluoro-phenyl)-methyl]-2-methoxy-4-methyl-6-morpholin-4-yl-pyridine-3-carboxylic acid amide

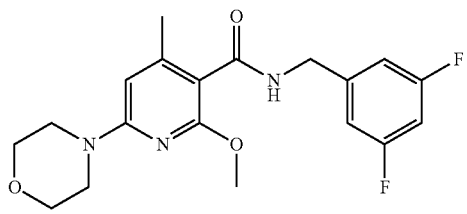 [SMILES: COc1nc(N2CCOCC2)cc(C)c1C(=O)NCc1cc(F)cc(F)c1]

a) Synthesis of 6-chloro-2-methoxy-4-methyl-pyridine-3-carboxylic acid

To a suspension of 9.3 g (231 mmol, 60% w/w in mineral oil) NaH in THF (200 ml) was added a solution of 3.8 ml (93 mmol) Methanol in THF (200 ml) while the temperature was kept at 10-20° C. Subsequently a solution of 20.0 g (97 mmol) of 2,6-dichloro-4-methyl-pyridine-3-carboxylic acid in THF (200 ml) was added and the RM was heated to 70° C. for 16 h. After cooling to RT the mixture was acidified with a 2M aq. HCl to pH 3-4 and was then extracted with EtOAc (2×600 ml). The combined organic layers were washed with water and brine, dried over MgSO$_4$ and concentrated in vacuo. The obtained crude 22.6 g 6-chloro-2-methoxy-4-methyl-pyridine-3-carboxylic acid was used in subsequent reactions without further purification.

b) Synthesis of 2-methoxy-4-methyl-6-morpholin-4-yl-pyridine-3-carboxylic acid

To a solution of 302 mg crude 6-chloro-2-methoxy-4-methyl-pyridine-3-carboxylic acid in THF (12 ml) were added 568 mg (1.5 mmol) HATU and 934 µl (6.8 mmol) NEt$_3$. The RM was stirred at 50° C. for 3 h followed by the addition of 268 mg (1.9 mmol) 3,5-difluorobenzylamine. Stirring was continued at 50° C. for 72 h. The RM was then diluted with EtOAc (50 ml) and subsequently washed with a 4M aq. NH$_4$Cl sol., a 1M aq. NaHCO$_3$ sol. and brine. The organic layer was dried over MgSO$_4$ and concentrated in vacuo. Purification of the residue by CC (hexane/EtOAc 3:1) provided 237 mg (0.7 mmol, 54% over 2 steps) 2-methoxy-4-methyl-6-morpholin-4-yl-pyridine-3-carboxylic acid.

c) Synthesis of N-[(3,5-Difluoro-phenyl)-methyl]-2-methoxy-4-methyl-6-morpholin-4-yl-pyridine-3-carboxylic acid amide A mixture of 237 mg (0.7 mmol) 2-methoxy-4-methyl-6-morpholin-4-yl-pyridine-3-carboxylic acid and 474 µl (5.4 mmol) morpholine was heated in the microwave at 90° C. for 150 min. Subsequently the RM was diluted EtOAc and the layers were separated. The organic layer was washed with a 1M aq. NaHCO$_3$ and brine, dried over MgSO$_4$ and concentrated in vacuo. Purification of the residue by CC (hexane/EtOAc 7:3) provided 100 mg (0.26 mmol, 38%) N-[(3,5-difluoro-phenyl)-methyl]-2-methoxy-4-methyl-6-morpholin-4-yl-pyridine-3-carboxylic acid amide (example 3). [M+H]$^+$378.2.

Synthesis of Example 4

2-ethylsulfanyl-N-[(4-fluorophenyl)-methyl]-4-methyl-6-morpholin-4-yl-pyridine-3-carboxylic acid amide

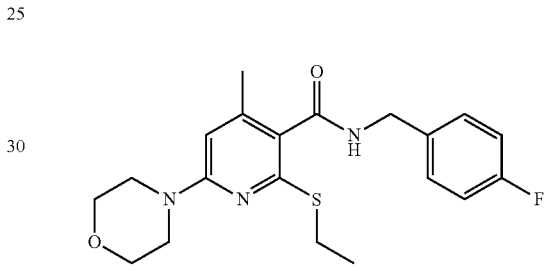

A solution of 254 mg (0.75 mmol) 6-chloro-2-ethylsulfanyl-N-[(4-fluorophenyl)-methyl]-4-methyl-pyridine-3-carboxylic acid amide (synthesized according to the methods described in sections a) and b) of example 2), 196 µl (2.25 mmol) morpholine and 392 µl (2.25 mmol) DIPEA in MeCN (2 ml) was heated in the microwave at 180° C. for 4 h. Subsequently the RM was diluted with water and EtOAc and the layers were separated. The organic layer was washed with water and brine, dried over MgSO$_4$ and concentrated in vacuo. Crystallisation (hexane/EtOAc 1:1) of the residue yielded 154 mg (0.40 mmol, 53%) 2-ethylsulfanyl-N-[(4-fluorophenyl)-methyl]-4-methyl-6-morpholin-4-yl-pyridine-3-carboxylic acid amide (example 4). [M+H]$^+$390.2.

Synthesis of Example 5

2-ethylsulfanyl-N-[(3-fluorophenyl)-methyl]-4-methyl-6-[methyl-(tetrahydro-pyran-2-yl-methyl)-amino]-pyridine-3-carboxylic acid amide

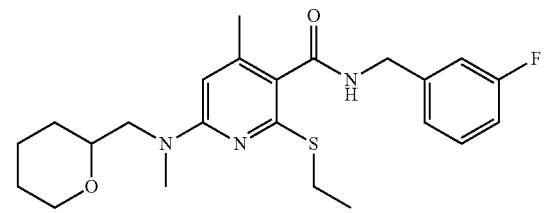 [SMILES: CCSc1nc(N(C)CC2CCCCO2)cc(C)c1C(=O)NCc1cccc(F)c1]

A solution of 254 mg (0.75 mmol) 6-chloro-2-ethylsulfanyl-N-[(3-fluorophenyl)-methyl]-4-methyl-pyridine-3-carboxylic acid amide (synthesis is described in section b) of example 2), 322 mg (2.25 mmol) N-methyl-1-(tetrahydro-2H-pyran-2-yl)methanamine and 392 μl (2.25 mmol) DIPEA in MeCN (2 ml) was heated in the microwave at 150° C. for 4.5 h. Subsequently the RM was diluted with a 2M aq. NaOH sol and EtOAc and the layers were separated. The organic layer was washed with water and brine, dried over MgSO$_4$ and concentrated in vacuo. Purification of the residue by CC (hexane/EtOAc 1:1) provided 122 mg (0.28 mmol, 38%) 2-ethylsulfanyl-N-[(3-fluorophenyl)-methyl]-4-methyl-6-[methyl-(tetrahydro-pyran-2-yl-methyl)-amino]-pyridine-3-carboxylic acid amide (example 5). [M+H]$^+$432.2.

Synthesis of Example 6

2-ethylsulfanyl-N-[(3-fluorophenyl)-methyl]-6-(3-methoxy-azetidine-1-yl)-4-methyl-pyridine-3-carboxylic acid amide

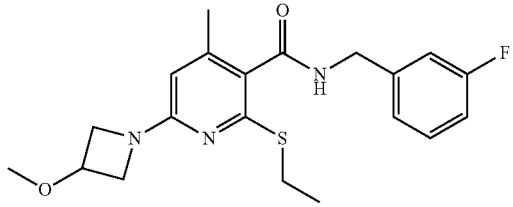 [SMILES: CCSc1nc(N2CC(OC)C2)cc(C)c1C(=O)NCc1cccc(F)c1]

A solution of 410 mg (1.2 mmol) 6-chloro-2-ethylsulfanyl-N-[(3-fluorophenyl)-methyl]-4-methyl-pyridine-3-carboxylic acid amide (synthesis is described in section b) of example 2), 125 mg (1.0 mmol) 3-methoxy-azetidine and 824 mg (2.53 mmol) Cs$_2$CO$_3$ in 1,4-dioxane (7 ml) was heated at 110° C. for 24 h. Subsequently the RM was concentrated in vacuo. The residue obtained was partitioned between water and EtOAc. The organic layer was separated, dried over MgSO$_4$ and concentrated in vacuo. Purification of the residue by CC (hexane/EtOAc 3:1) provided 122 mg (0.31 mmol, 31%) 2-ethylsulfanyl-N-[(3-fluorophenyl)-methyl]-6-(3-methoxy-azetidin-1-yl)-4-methyl-pyridine-3-carboxylic acid amide (example 6). [M+H]$^+$390.2.

Synthesis of Example 7

2-ethylsulfanyl-N-[(3-fluorophenyl)-methyl]-6-(3-hydroxy-azetidin-1-yl)-4-methyl-pyridine-3-carboxylic acid amide

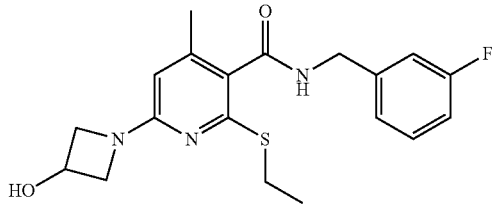 [SMILES: CCSc1nc(N2CC(O)C2)cc(C)c1C(=O)NCc1cccc(F)c1]

A mixture of 439 mg (1.2 mmol) 6-chloro-2-ethylsulfanyl-N-[(3-fluorophenyl)-methyl]-4-methyl-pyridine-3-carboxylic acid amide (synthesis is described in section b) of example 2), 284 mg (2.6 mmol) 3-hydroxy-azetidine, 2.1 g (6.5 mmol) Cs$_2$CO$_3$ and 149 mg (0.13 mmol) Pd(PPh$_3$)$_2$ in 1,4-dioxane (4 ml) was heated at 110° C. for 16 h. Subsequently the RM was diluted with brine (30 ml) and extracted with EtOAc (3×40 ml). The combined organic layers were dried over MgSO$_4$ and concentrated in vacuo. Purification of the residue by CC (hexane/EtOAc 1:1) and subsequent crystallization (hexane/EtOAc) provided 66 mg (0.18 mmol, 15%) 2-ethylsulfanyl-N-[(3-fluorophenyl)-methyl]-6-(3-hydroxy-azetidin-1-yl)-4-methyl-pyridine-3-carboxylic acid amide (example 7). [M+H]$^+$376.1.

Synthesis of Example 8

2-ethylsulfanyl-N-[(3-fluorophenyl)-methyl]-6-[(4-fluorophenyl)-methylamino]-4-methyl-pyridine-3-carboxylic acid amide

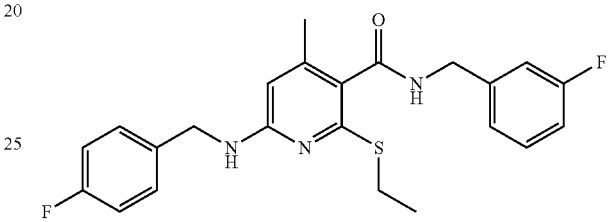

A mixture of 200 mg (0.59 mmol) 6-chloro-2-ethylsulfanyl-N-[(3-fluorophenyl)-methyl]-4-methyl-pyridine-3-carboxylic acid amide (synthesis is described in section b) of example 2), 340 μl (2.96 mmol) 3-fluorobenzylamine and 240 mg (1.77 mmol) K$_2$CO$_3$ were heated in a sealed tube at 160° C. for 16 h. Subsequently the RM was diluted with water (50 ml) and extracted with EtOAc (3×40 ml). The combined organic layers were washed with water and brine, dried over Na$_2$SO$_4$ and concentrated in vacuo. Purification of the residue by CC (hexane/EtOAc 3:1) provided 120 mg (0.28 mmol, 47%) 2-ethylsulfanyl-N-[(3-fluorophenyl)-methyl]-6-[(4-fluorophenyl)-methylamino]-4-methyl-pyridine-3-carboxylic acid amide (example 8). [M+H]$^+$428.2.

Synthesis of Example 9

(E)-N-(3-fluorobenzyl)-4-methyl-6-morpholino-2-(prop-1-enyl)-pyridine-3-carboxylic acid amide a) Synthesis of 6-chloro-N-[(3-fluorophenyl)-methyl]-4-methyl-2-morpholin-4-yl-pyridine-3-carboxylic acid amide and 2-chloro-N-[(3-fluorophenyl)-methyl]-4-methyl-6-morpholin-4-yl-pyridine-3-carboxylic acid amide To a solution of 2.0 g (6.4 mmol) 2,6-dichloro-N-(3-fluorobenzyl)-4-methyl-pyridine-3-carboxylic acid amide (synthesis is described in section a) of example 2) in DMF (19 ml) were added 1.32 g (9.6 mmol) K$_2$CO$_3$ and 660 mg (7.7 mmol) morpholine and the RM was stirred at 90° C. for 16 h. Then the RM was poured into ice water (40 ml), followed by extraction with EtOAc (3×40 ml). The combined organic layers were washed with water and brine, dried over Na$_2$SO$_4$ and concentrated in vacuo. Purification of the residue by CC (hexane/EtOAc 3:2) provided 1.14 g (3.2 mmol, 49%) 6-chloro-N-[(3-fluorophenyl)-methyl]-4-methyl-2-morpholin-4-yl-pyridine-3-carboxylic acid and 400 mg (1.1 mmol, 17%) 2-chloro-N-[(3-fluorophenyl)-methyl]-4-methyl-6-morpholin-4-yl-pyridine-3-carboxylic acid amide.

b) Synthesis of (E)-N-(3-fluorobenzyl)-4-methyl-6-morpholino-2-(prop-1-enyl)-pyridine-3-carboxylic acid amide To a solution of 400 mg (1.1 mmol) 2-chloro-N-[(3-fluorophenyl)-methyl]-4-methyl-6-morpholin-4-yl-pyridine-3-carboxylic acid amide in toluene (15 ml) were added 140 mg (1.7 mmol) (E)-prop-1-enylboronic acid, 1.1 g (3.3 mmol) CsCO₃ and EtOH (1.5 ml). After degassing with argon for 15 min 370 mg (0.32 mmol) Pd(PPh₃)₄ were added and the RM was heated to 110° C. for 5 h. Subsequently the RM was filtered through celite and the filtrate was concentrated in vacuo. Purification of the residue by CC (hexane/EtOAc 3:1) provided 300 mg (0.8 mmol, 74%) (E)-N-(3-fluorobenzyl)-4-methyl-6-morpholino-2-(prop-1-enyl)-pyridine-3-carboxylic acid amide (example 9). [M+H]⁺370.2.

Synthesis of Example 10

N-[(3-fluorophenyl)-methyl]-4-methyl-6-morpholin-4-yl-2-propyl-pyridine-3-carboxylic acid amide

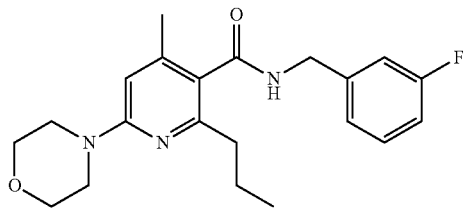

A solution of 300 mg (0.81 mmol) (E)-N-(3-fluorobenzyl)-4-methyl-6-morpholino-2-(prop-1-enyl)-pyridine-3-carboxylic acid amide (example 9) in MeOH (9 ml) was degassed with argon for 15 min. Then 0.065 g Pd/C (10% w/w) was added and the RM was stirred for 3 h under hydrogen atmosphere by use of an H₂ balloon. Subsequently the mixture was filtered through celite and the filtrate was concentrated in vacuo. Purification of the residue by CC (hexane/acetone 17:3) provided 170 mg (0.5 mmol, 56%) N-[(3-fluorophenyl)-methyl]-4-methyl-6-morpholin-4-yl-2-propyl-pyridine-3-carboxylic acid amide (example 10). [M+H]⁺ 372.2.

Synthesis of Example 11

2-ethylsulfanyl-N-[(3-fluorophenyl)-methyl]-6-morpholin-4-yl-4-(trifluoromethyl)-pyridine-3-carboxylic acid amide

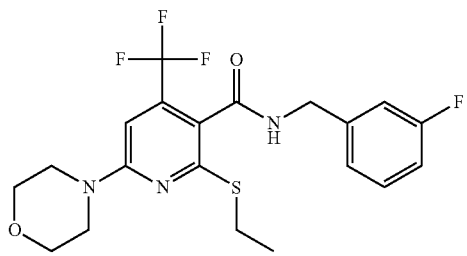 [SMILES: CCSc1nc(N2CCOCC2)cc(C(F)(F)F)c1C(=O)NCc1cccc(F)c1]

a) Synthesis of methyl 6-chloro-2-(ethylsulfanyl)-4-(trifluoromethyl)-pyridine-3-carboxylate To a solution of 2.5 g (9.1 mmol) methyl 2,6-dichloro-4-(trifluoromethyl)-pyridine-3-carboxylate in DMF (21 ml) were added 1.9 g (13.7 mmol) K₂CO₃ and 843 µl (11.4 mmol) ethanethiol. After stirring in a closed vessel at RT for 4 h, the RM was extracted twice with EtOAc. The combined organic layers were washed with water and a 2M aq. NaOH sol., dried over MgSO₄ and concentrated in vacuo. Purification of the residue by CC (hexane/EtOAc 99:1) provided 2.25 g of a ~1:1 mixture of methyl 6-chloro-2-(ethylsulfanyl)-4-(trifluoromethyl)-pyridine-3-carboxylate and methyl 2,6-bis(ethylsulfanyl)-4-(trifluoromethyl)-pyridine-3-carboxylate, which was used in the next step without further purification.

b) Synthesis of methyl 2-(ethylsulfanyl)-6-morpholin-4-yl-4-(trifluoromethyl)-pyridine-3-carboxylate A solution of 2 g of a ~1:1 mixture of methyl 6-chloro-2-(ethylsulfanyl)-4-(trifluoromethyl)-pyridine-3-carboxylate and methyl 2,6-bis(ethylsulfanyl)-4-(trifluoromethyl)-pyridine-3-carboxylate, 1.7 ml (20.0 mmol) morpholine and 3.5 ml (20.0 mmol) DIPEA in MeCN (10 ml) was heated in the microwave to 150° C. for 4 h. The RM was then diluted with water and EtOAc. The organic layer was separated, washed with water and brine, dried over MgSO₄ and concentrated in vacuo. Purification of the residue by CC (hexane/EtOAc 4:1) provided 440 mg (1.3 mmol, 16% over 2 steps) methyl 2-(ethylsulfanyl)-6-morpholin-4-yl-4-(trifluoromethyl)-pyridine-3-carboxylate.

c) Synthesis of 2-(ethylsulfanyl)-6-morpholin-4-yl-4-(trifluoromethyl)-pyridine-3-carboxylic acid A solution of 440 mg (1.3 mmol) methyl 2-(ethylsulfanyl)-6-morpholin-4-yl-4-(trifluoromethyl)-pyridine-3-carboxylate in a MeOH/THF mixture (6 ml, 1:1 v/v) was treated with a 2M aq. LiOH sol. (3 ml) and was then stirred at 60° C. for 5 d. After cooling to RT the RM was acidified with a 2M aq. HCl sol. to pH 2. Upon dilution with EtOAc the precipitate formed was filtered off to give 176 mg (0.5 mmol, 42%) 2-(ethylsulfanyl)-6-morpholin-4-yl-4-(trifluoromethyl)-pyridine-3-carboxylic acid, which was used in the next step without further purification.

d) Synthesis of 2-ethylsulfanyl-N-[(3-fluorophenyl)-methyl]-6-morpholin-4-yl-4-(trifluoromethyl)-pyridine-3-carboxylic acid amide To a solution of 170 mg (0.5 mmol) 2-(ethylsulfanyl)-6-morpholin-4-yl-4-(trifluoromethyl)-pyridine-3-carboxylic acid in THF (3 ml) were added 192 mg (0.5 mmol) HATU and 210 µl (1.5 mmol) NEt₃ and the RM was stirred at 50° C. for 90 min. Then 69 µl (0.6 mmol) 3-fluorobenzylamine were added and stirring was continued at 50° C. for 5d. After cooling to RT the mixture was partitioned between water and EtOAc. The organic layer was separated, washed with a 4N aq. NH₄Cl sol. and brine, dried over MgSO₄ and concentrated in vacuo. Purification of the residue by CC (hexae/EtOAc 3:1) provided 57 mg (0.13 mmol, 26%) 2-ethylsulfanyl-N-[(3-fluorophenyl)-methyl]-6-morpholin-4-yl-4-(trifluoromethyl)-pyridine-3-carboxylic acid amide (example 11). [M+H]⁺444.1.

Synthesis of Example 12

N-[(3-Fluorophenyl)-methyl]-4-methyl-2,6-dimorpholin-4-yl-pyridine-3-carboxylic acid amide

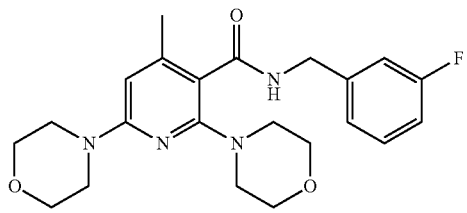 [SMILES: Cc1cc(N2CCOCC2)nc(N2CCOCC2)c1C(=O)NCc1cccc(F)c1]

A mixture of 300 mg (0.82 mmol) 6-chloro-N-[(3-fluorophenyl)-methyl]-4-methyl-2-morpholin-4-yl-pyridine-3-carboxylic acid (synthesis is described in section a) of example 9) and 1.4 g (16.5 mmol) morpholine was heated in the microwave to 120° C. for 2 h. The RM was then diluted with EtOAc and a 2M aq. NaOH sol. was added. The organic layer was separated, washed with water and brine, dried over MgSO$_4$ and concentrated in vacuo. Purification of the residue by CC (hexane/EtOAc 3:2) provided 253 mg (0.61 mmol, 74%) N-[(3-Fluorophenyl)-methyl]-4-methyl-2,6-dimorpholin-4-yl-pyridine-3-carboxylic acid amide (example 12). [M+H]$^+$415.2.

Synthesis of Example 14

1-[6-Ethylsulfanyl-5-[(3-fluorophenyl)-methyl-carbamoyl]-4-methyl-pyridin-2-yl]-piperidine-4-carboxylic acid

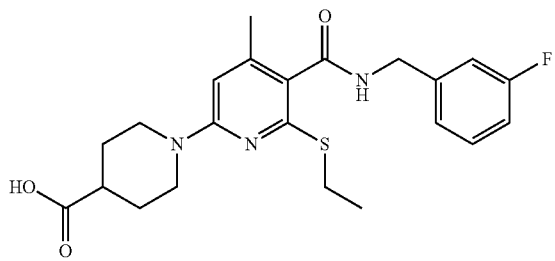 [SMILES: CCSc1nc(N2CCC(C(=O)O)CC2)cc(C)c1C(=O)NCc1cccc(F)c1]

A solution of 146 mg (0.32 mmol) 1-[6-Ethylsulfanyl-5-[(3-fluorophenyl)-methyl-carbamoyl]-4-methyl-pyridin-2-yl]-piperidine-4-carboxylic acid methyl ester (example 13) in a MeOH/THF mixture (1:1 v/v, 2 ml) was treated with 1 ml (2.0 mmol) 2M aq. LiOH sol. and heated to 70° C. for 16 h. Subsequently pH 3-4 was adjusted with a 2M aq. HCl sol., followed by extraction with EtOAc. The organic layer was washed with brine, dried over MgSO$_4$ and concentrated in vacuo. As residue 112 mg (0.26 mmol, 79%) 1-[6-Ethylsulfanyl-5-[(3-fluorophenyl)-methyl-carbamoyl]-4-methyl-pyridin-2-yl]-piperidine-4-carboxylic acid (example 14) were obtained. [M+H]$^+$432.2.

Synthesis of Example 16

2-Ethylsulfanyl-N-[(3-fluorophenyl)-methyl]-4-methyl-6-(4-oxo-piperidin-1-yl)-pyridine-3-carboxylic acid amide

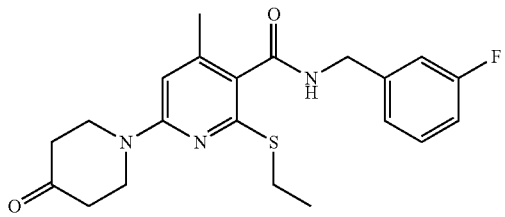 [SMILES: CCSc1nc(N2CCC(=O)CC2)cc(C)c1C(=O)NCc1cccc(F)c1]

A solution of 201 mg (0.5 mmol) 2-Ethylsulfanyl-N-[(3-fluorophenyl)-methyl]-6-(4-hydroxy-piperidin-1-yl)-4-methyl-pyridine-3-carboxylic acid amide (example 15) in DCM (7 ml) was treated with 1.84 g (0.65 mmol, 15% w/w in DCM) Dess-Martin periodinane and stirred at RT for 3 h. The RM was then quenched by addition of a 10% (w/w) aq. Na$_2$S$_2$O$_3$ sol. and diluted with DCM (30 ml). The organic layer was separated, washed with a 2M aq. NaOH sol. and brine, dried over MgSO$_4$ and concentrated in vacuo. Purification of the residue by CC (hexane/EtOAc 1:1) provided 88 mg (0.22 mmol, 44%) 2-Ethylsulfanyl-N-[(3-fluorophenyl)-methyl]-4-methyl-6-(4-oxo-piperidin-1-yl)-pyridine-3-carboxylic acid amide (example 16). [M+H]$^+$402.2.

Synthesis of Example 18

2-Ethylsulfanyl-N-[(4-fluoro-2-hydroxy-phenyl)-methyl]-4-methyl-6-morpholin-4-yl-pyridine-3-carboxylic acid amide

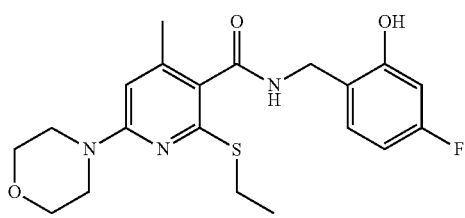 [SMILES: CCSc1nc(N2CCOCC2)cc(C)c1C(=O)NCc1ccc(F)cc1O]

To a cooled solution of 209 mg (0.5 mmol) 2-Ethylsulfanyl-N-[(4-fluoro-2-methoxy-phenyl)-methyl]-4-methyl-6-morpholin-4-yl-pyridine-3-carboxylic acid amide (example 17) in DCM (7 ml) were added dropwise 5 ml (5.0 mmol, 1M in DCM) BBr$_3$ at −50° C. The RM was then allowed to reach 0° C. and stirring was continued at this temperature for 3 h. Then a 1M aq. NaHCO$_3$ sol. (15 ml) was added at 0° C. and the mixture was diluted with MeOH (10 ml) and DCM (10 ml). The layers were separated and the aqueous layer was extracted with EtOAc. The combined organic layers were dried over MgSO$_4$ and concentrated in vacuo. Purification of the residue by CC (hexane/EtOAc 7:3) provided 81 mg (0.2 mmol, 40%) 2-Ethylsulfanyl-N-[(4-fluoro-2-hydroxy-phenyl)-methyl]-4-methyl-6-morpholin-4-yl-pyridine-3-carboxylic acid amide (example 18). [M+H]⁺406.2.

Synthesis of Example 19

N-[(3-Fluorophenyl)-methyl]-2-methoxy-4-methyl-6-morpholin-4-yl-pyridine-3-carboxylic acid amide

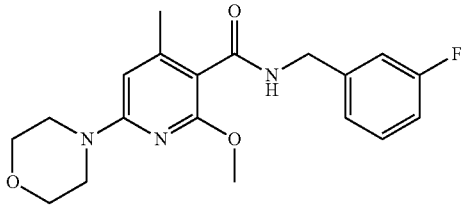 [SMILES: COc1nc(N2CCOCC2)cc(C)c1C(=O)NCc1cccc(F)c1]

a) Synthesis of 6-Chloro-N-[(3-Fluorophenyl)-methyl]-2-methoxy-4-methyl-pyridine-3-carboxylic acid amide 330 mg (8.3 mmol, 60% w/w in mineral oil) NaH were slowly added to Methanol (30 ml) at RT and stirring was continued at RT for 45 min. Then 2.35 g (7.5 mmol) 2,6-dichloro-N-(3-fluorobenzyl)-4-methyl-pyridine-3-carboxylic acid amide (synthesis is described in section a) of example 2) were added and the RM was heated to 70° C. for 24 h. After cooling to RT water (10 ml) was added and most of the MeOH was removed in vacuo. The mixture was then extracted with EtOAc and the organic layer was washed twice with brine, dried over MgSO₄ and concentrated in vacuo. Crystallisation (hexane/EtOAc 3:1) of the residue yielded 1.24 g (0.4 mmol, 54%) 6-Chloro-N-[(3-Fluorophenyl)-methyl]-2-methoxy-4-methyl-pyridine-3-carboxylic acid amide.

b) Synthesis of N-[(3-Fluorophenyl)-methyl]-2-methoxy-4-methyl-6-morpholin-4-yl-pyridine-3-carboxylic acid amide and N-[(3-Fluorophenyl)-methyl]-2-hydroxy-4-methyl-6-morpholin-4-yl-pyridine-3-carboxylic acid amide A mixture of 1.37 g (4.4 mmol) 6-Chloro-N-[(3-Fluorophenyl)-methyl]-2-methoxy-4-methyl-pyridine-3-carboxylic acid amide and 2.9 ml (33.2 mmol) morpholine was heated in the microwave to 120° C. for 30 min. The RM was then diluted with EtOAc (50 ml) and a 1M aq. NaOH sol. (20 ml) was added. The precipitate formed was filtered off to give 715 mg (2.0 mmol, 47%) N-[(3-Fluorophenyl)-methyl]-2-hydroxy-4-methyl-6-morpholin-4-yl-pyridine-3-carboxylic acid amide. The organic layer was separated from the filtrate, washed with water and brine, dried over MgSO₄ and concentrated in vacuo. Purification of the residue by CC (hexane/EtOAc 3:2) provided 397 mg (1.1 mmol, 25%) N-[(3-Fluororophenyl)-methyl]-2-methoxy-4-methyl-6-morpholin-4-yl-pyridine-3-carboxylic acid amide (example 19). [M+H]⁺360.2.

Synthesis of Example 20

2-Ethylamino-N-[(3-fluorophenyl)-methyl]-4-methyl-6-morpholin-4-yl-pyridine-3-carboxylic acid amide

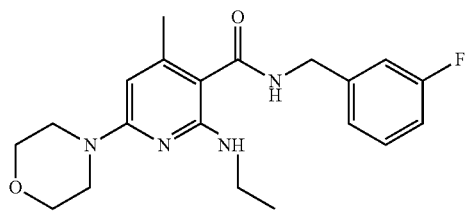 [SMILES: CCNc1nc(N2CCOCC2)cc(C)c1C(=O)NCc1cccc(F)c1]

a) Synthesis of 6-chloro-2-ethylamino-N-[(3-fluorophenyl)-methyl]-4-methyl-pyridine-3-carboxylic acid amide A suspension of 626 mg (2.0 mmol) 2,6-dichloro-N-(3-fluorobenzyl)-4-methyl-pyridine-3-carboxylic acid amide (synthesis is described in section a) of example 2), 244 mg (2.4 mmol) ethylamine hydrochloride and 689 mg (5.0 mmol) K₂CO₃ in DMF (6 ml) was heated to 100° C. for 3 d. Then the RM was poured into ice water (10 ml), followed by extraction with EtOAc (3×15 ml). The combined organic layers were washed with water and brine, dried over Na₂SO₄ and concentrated in vacuo. Purification of the residue by CC (hexane/EtOAc 1:1) provided 84 mg (0.26 mmol, 13%) 6-chloro-2-ethylamino-N-[(3-fluorophenyl)-methyl]-4-methyl-pyridine-3-carboxylic acid amide.

b) Synthesis of 2-Ethylamino-N-[(3-fluorophenyl)-methyl]-4-methyl-6-morpholin-4-yl-pyridine-3-carboxylic acid amide A mixture of 80 mg (0.25 mmol) 6-chloro-2-ethylamino-N-[(3-fluorophenyl)-methyl]-4-methyl-pyridine-3-carboxylic acid amide and 433 mg (5.0 mmol) morpholine was heated in the microwave to 120° C. for 10 h. After cooling to RT, purification of the residue by CC (hexane/EtOAc 2:1) provided 73 mg (0.2 mmol, 78%) 2-Ethylamino-N-[(3-fluorophenyl)-methyl]-4-methyl-6-morpholin-4-yl-pyridine-3-carboxylic acid amide (example 20). [M+H]⁺373.2.

Synthesis of Example 21

N-[(3-Fluorophenyl)-methyl]-2-(2-methoxy-ethoxy)-4-methyl-6-morpholin-4-yl-pyridine-3-carboxylic acid amide

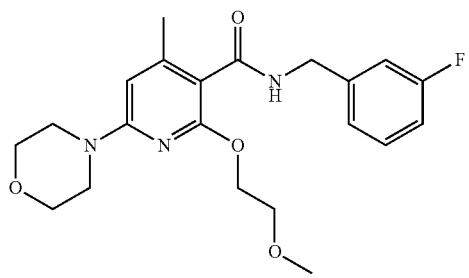 [SMILES: COCCOc1nc(N2CCOCC2)cc(C)c1C(=O)NCc1cccc(F)c1]

To a solution of 200 mg (0.58 mmol) N-[(3-Fluorophenyl)-methyl]-2-hydroxy-4-methyl-6-morpholin-4-yl-pyridine-3-carboxylic acid amide (synthesis is described in section b) of example 19) in DMF (8 ml) 15 mg (0.64 mmol, 60% w/w in mineral oil) NaH were added, followed by stirring at RT for 30 min. Then 88 mg (0.64 mmol) 2-bromoethyl-methylether were added and the RM was heated to 50° C. for 16 h. Subsequently water (10 ml) and EtOAc were added and the layers were separated. The aqueous layer was extracted with EtOAc. The combined organic layers were washed with brine, dried over MgSO$_4$ and concentrated in vacuo. Purification of the residue by CC (hexane/EtOAc 3:7) provided 90 mg (0.22 mmol, 39%) N-[(3-Fluorophenyl)-methyl]-2-(2-methoxy-ethoxy)-4-methyl-6-morpholin-4-yl-pyridine-3-carboxylic acid amide (example 21). [M+H]$^+$404.2.

Synthesis of Example 22

2-Ethyl-N-[(3-fluorophenyl)-methyl]-4-methyl-6-morpholin-4-yl-pyridine-3-carboxylic acid amide

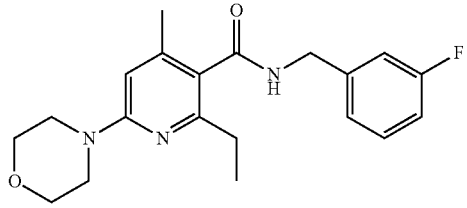 [SMILES: CCc1nc(N2CCOCC2)cc(C)c1C(=O)NCc1cccc(F)c1]

To a solution of 200 mg (0.55 mmol) 2-chloro-N-[(3-fluorophenyl)-methyl]-4-methyl-6-morpholin-4-yl-pyridine-3-carboxylic acid amide (synthesis is described in section a) of example 9) in THF (5 ml) were added 30 mg (0.055 mmol) Ni(dppp)Cl$_2$ and 330 µl (0.66 mmol, 2M in THF) ethylmagnesiumbromide. The RM was heated to 80° C. for 8 h, followed by quenching with a sat. aq. NH$_4$Cl sol. and extraction with EtOAc (3×20 ml). The combined organic layers were washed with water and brine, dried over Na$_2$SO$_4$ and concentrated in vacuo. Purification of the residue by CC (hexane/EtOAc 7:3) provided 50 mg (0.14 mmol, 25%) Ethyl-N-[(3-fluorophenyl)-methyl]-4-methyl-6-morpholin-4-yl-pyridine-3-carboxylic acid amide (example 22). [M+H]$^+$ 358.2.

Synthesis of Example 23

N-[(3-Fluorophenyl)-methyl]-2-isopropyl-4-methyl-6-morpholin-4-yl-pyridine-3-carboxylic acid amide

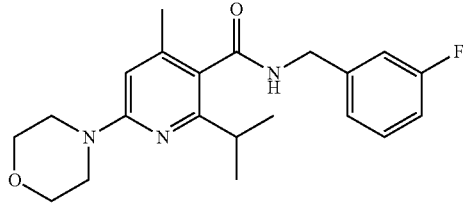 [SMILES: Cc1cc(N2CCOCC2)nc(C(C)C)c1C(=O)NCc1cccc(F)c1]

A solution of 300 mg (0.83 mmol) 2-chloro-N-[(3-fluorophenyl)-methyl]-4-methyl-6-morpholin-4-yl-pyridine-3-carboxylic acid amide (synthesis is described in section a) of example 9) in THF/NMP (6:1 v/v, 14 ml) was cooled to −30° C. At this temperature were successively added 58 mg (0.16 mmol) Fe(acac)$_3$ and 6 ml (12.0 mmol, 2M in THF) isopropyl-magnesium-chloride. The RM was then allowed to warm to 0° C. within 1 h. Then sat. aq. NH$_4$Cl sol. was added the mixture was extracted with EtOAc (3×20 ml). The combined organic layers were washed with water and brine, dried over Na$_2$SO$_4$ and concentrated in vacuo. Purification of the residue by CC (hexane/EtOAc 7:3) provided 110 mg (0.30 mmol, 36%) N-[(3-Fluorophenyl)-methyl]-2-isopropyl-4-methyl-6-morpholin-4-yl-pyridine-3-carboxylic acid amide (example 23). [M+H]$^+$372.2.

Synthesis of Example 24

N-[(3-Fluorophenyl)-methyl]-4-methyl-6-morpholin-4-yl-2-pyrrolidin-1-yl-pyridine-3-carboxylic acid amide

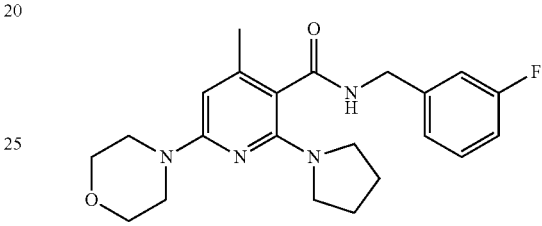

To a solution of 254 mg (0.7 mmol) 2-chloro-N-[(3-fluorophenyl)-methyl]-4-methyl-6-morpholin-4-yl-pyridine-3-carboxylic acid amide (synthesis is described in section a) of example 9) in MeCN (0.5 ml) were added 115 µl (1.4 mmol) pyrrolidine and 290 µl (2.1 mmol) NEt$_3$. The RM was heated in the microwave to 120° C. for 30 min and subsequently to 140° C. for 45 min. Then the mixture was filtered through celite and concentrated in vacuo. Purification of the residue by CC (hexane/EtOAc 2:1), followed by crystallization (hexane/EtOAc) provided 164 mg (0.41 mmol, 59%) N-[(3-Fluorophenyl)-methyl]-4-methyl-6-morpholin-4-yl-2-pyrrolidin-1-yl-pyridine-3-carboxylic acid amide (example 24). [M+H]$^+$399.2.

Synthesis of Example 117

2-Methoxy-4-methyl-6-morpholin-4-yl-N-[[4-(trifluoro-methyl)-phenyl]-methyl]pyridine-3-carboxylic acid amide

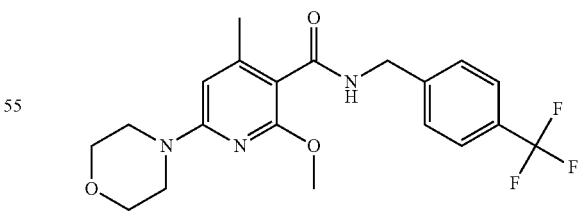

a) Synthesis of 6-chloro-2-methoxy-4-methylpyridine-3-carboxylic acid methylester A solution of 8.8 (43.7 mmol) 6-chloro-2-methoxy-4-methyl-3-carboxylic acid amide (synthesis is described in section a) of example 3) in DMF (110 ml) was treated with 9.0 g (65.5 mmol) K₂CO₃ and subsequently stirred at RT for 30 min. Then 5.4 ml (65.5 mmol) Iodomethan were added and stirring was continued at RT for 16 h. After quenching with water the mixture was extracted twice with EtOAc and the combined organic layer was washed with brine, dried over MgSO₄ and concentrated in vacuo. As residue 9.1 g (39.6 mmol, 91%) 6-chloro-2-methoxy-4-methylpyridine-3-carboxylic acid methylester was obtained which was used in next step without further purification.

b) Synthesis of 2-methoxy-4-methyl-6-morpholino-pyridine-3-carboxylic acid methylester A solution of 5.0 g (21.8 mmol) 6-chloro-2-methoxy-4-methylpyridine-3-carboxylic acid methylester, 2.0 g (24.0 mmol) morpholine and 6.0 ml (43.5 mmol) NEt₃ in NMP (21 ml) was heated at 90° C. for 2 d. After cooling to RT the mixture was partiotionated between EtOAc and a 1M aq. NaHCO₃ sol. The organic layer was separated, dried over MgSO₄ and concentrated in vacuo. Purification of the residue by CC (hexane/EtOAc 4:1) provided 2.7 g (9.8 mmol, 45%) 2-methoxy-4-methyl-6-morpholino-pyridine-3-carboxylic acid methylester.

c) Synthesis of 2-Methoxy-4-methyl-6-morpholin-4-yl-N-[[4-(trifluoro-methyl)-phenyl]-methyl]-pyridine-3-carboxylic acid amide 2-methoxy-4-methyl-6-morpholino-pyridine-3-carboxylic acid amide (example 117), [M+H]⁺410.2) was synthesized from 2-methoxy-4-methyl-6-morpholino-pyridine-3-carboxylic acid methylester according to the methods described in sections c) of example 11 and section c) of example 1.

Synthesis of Example 120

2-Ethylsulfanyl-6-[(4-fluoro-benzoyl)-methyl-amino]-N-[(3-fluorophenyl)-methyl]-4-methyl-pyridine-3-carboxylic acid amide

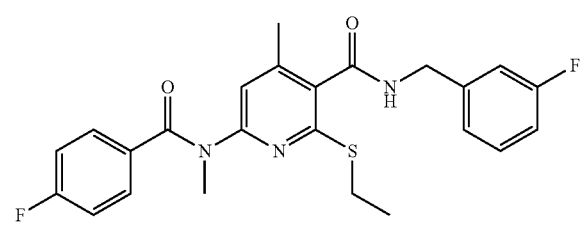 [SMILES: CCSc1nc(N(C)C(=O)c2ccc(F)cc2)cc(C)c1C(=O)NCc1cccc(F)c1]

To a solution of 150 mg (0.45 mmol) 2-ethylsulfanyl-N-[(3-fluorophenyl)-methyl]-6-(methyl-amino)-4-methyl-pyridine-3-carboxylic acid amide (synthesis is described in section a) of example 123) in DCM (3 ml) and THF (3 ml) was added 160 µl (0.95 mmol) DIPEA. At 0° C. 56 µl (0.47 mmol) 4-fluoro-benzoylchloride was added dropwise and stirring was continued at 0° C. for 2 h and RT for 16 h. Then the mixture was partiotionated between EtOAc and a 1M aq. NaHCO₃ sol. The organic layer was separated, dried over MgSO₄ and concentrated in vacuo. Purification of the residue by CC (hexane/EtOAc 1:1) provided 171 mg (0.38 mmol, 83%) 2-Ethylsulfanyl-6-[(4-fluoro-benzoyl)-methyl-amino]-N-[(3-fluorophenyl)-methyl]-4-methyl-pyridine-3-carboxylic acid amide (example 120). [M+H]⁺456.1

Synthesis of Example 123

6-(Acetyl-methyl-amino)-2-ethylsulfanyl-N-[(3-fluorophenyl)-methyl]-4-methyl-pyridine-3-carboxylic acid amide

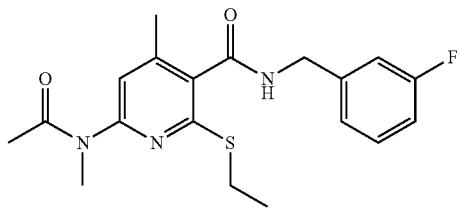 [SMILES: CCSc1nc(N(C)C(C)=O)cc(C)c1C(=O)NCc1cccc(F)c1]

a) Synthesis of 2-ethylsulfanyl-N-[(3-fluorophenyl)-methyl]-6-(methyl-amino)-4-methyl-pyridine-3-carboxylic acid amide A mixture of 750 mg (2.2 mmol) and 2.7 ml (22.1 mmol, 33% w/w in H₂O) was heated to 150° C. in the MW for 3 h. The mixture was then diluted with EtOAc and water and the organic layer was separated, washed with a 2M aq. NaOH sol. and brine, dried over MgSO₄ and concentrated in vacuo. Purification of the residue by CC (hexane/EtOAc 1:1) and subsequent crystallization (hexane/EtOAc) provided 454 mg (1.36 mmol, 62%) 2-ethylsulfanyl-N-[(3-fluorophenyl)-methyl]-6-(methyl-amino)-4-methyl-pyridine-3-carboxylic acid amide.

b) Synthesis of 2-ethylsulfanyl-N-[(3-fluorophenyl)-methyl]-6-(methyl-amino)-4-methyl-pyridine-3-carboxylic acid amide To a solution of 250 mg (0.75 mmol) 2-ethylsulfanyl-N-[(3-fluorophenyl)-methyl]-6-(methyl-amino)-4-methyl-pyridine-3-carboxylic acid amide in DCM (5 ml) and THF (5 ml) was added 267 µl (1.58 mmol) DIPEA. At 0° C. 74 µl (0.79 mmol) acetanhydride was added dropwise and stirring was continued at RT for 16 h. Then another 297 µl (3.2 mmol) acetanhydride and 535 µl (3.2 mmol) DIPEA were added at RT and the mixture was stirred at 35° C. for 2 d. The solution was diluted with water and a 1M aq. NaOH sol. The organic layer was separated, dried over MgSO₄ and concentrated in vacuo. Purification of the residue by CC (hexane/EtOAc 3:2) provided 226 mg (0.6 mmol, 80%) 6-(Acetyl-methyl-amino)-

2-ethylsulfanyl-N-[(3-fluorophenyl)-methyl]-4-methyl-pyridine-3-carboxylic acid amide (example 123). [M+H]⁺376.1

Synthesis of Example 138 & 139

2-Ethylsulfanyl-N-[(3-fluorophenyl)-methyl]-4-methyl-6-[(2S)-2-methyl-morpholin-4-yl]-pyridine-3-carboxylic acid amide & 2-Ethylsulfanyl-N-[(3-fluorophenyl)-methyl]-4-methyl-6-[(2R)-2-methyl-morpholin-4-yl]-pyridine-3-carboxylic acid amide

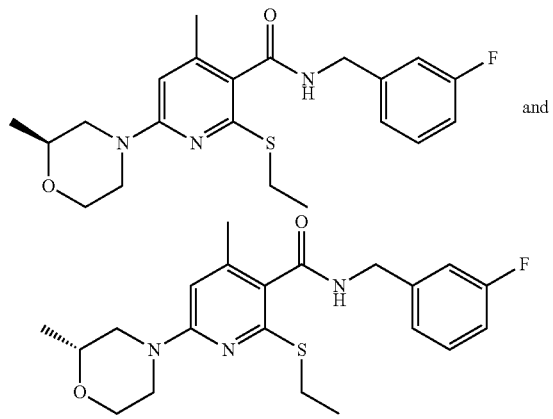

558 mg racemic 2-Ethylsulfanyl-N-[(3-fluorophenyl)-methyl]-4-methyl-6-(2-methyl-morpholin-4-yl)-pyridine-3-carboxylic acid amide (example 48) was separated by chiral HPLC to provide 183 mg 2-Ethylsulfanyl-N-[(3-fluorophenyl)-methyl]-4-methyl-6-[(2S)-2-methyl-morpholin-4-yl]-pyridine-3-carboxylic acid amide (example 138), [M+H]⁺ 404.2 and 184 mg 2-Ethylsulfanyl-N-[(3-fluorophenyl)-methyl]-4-methyl-6-[(2R)-2-methyl-morpholin-4-yl]-pyridine-3-carboxylic acid amide (example 139), [M+H]⁺ 404.2

Synthesis of Example 154

N-[(4-Fluorophenyl)-methyl]-4-methyl-2-methylsulfanyl-6-morpholin-4-yl-pyridine-3-carboxylic acid amide

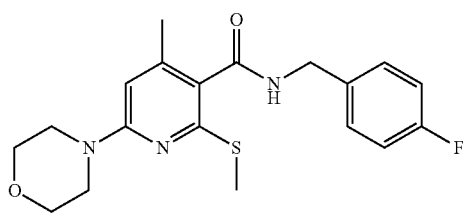 [SMILES: CSc1nc(N2CCOCC2)cc(C)c1C(=O)NCc1ccc(F)cc1]

a) Synthesis of 6-chloro-2-methylsulfanyl-4-methyl-pyridine-3-carboxylic acid

To a cooled (ice-bath) solution of 3.8 g (54.7 mmol) NaSMe in THF (85 ml) 12.4 g (60.2 mmol) 2,6-dichloro-4-methyl-pyridine-3-carboxylic acid was added. After stirring at RT for 2 h, 1.3 g (xx mmol) NaH (60% w/w in mineral oil, 32.5 mmol) and 1.6 g (23.0 mmol) NaSMe were added and stirring was continued at RT for 16 h. Then the mixture was diluted with THF (45 ml) and again 1.3 g (xx mmol) NaH (60% w/w in mineral oil, 32.5 mmol) and 3.4 g (48.9 mmol) NaSMe were added and stirring was continued at RT for 16 h. Then the reaction was quenched with a 2M aq. HCl and diluted with EtOAc. The organic layer was separated, dried over MgSO₄ and concentrated in vacuo. Crystallisation (DCM/hexane) of the residue yielded 7.34 g (33.7 mmol, 62%) 6-chloro-2-methylsulfanyl-4-methyl-pyridine-3-carboxylic acid.

b) Synthesis of N-[(4-Fluorophenyl)-methyl]-4-methyl-2-methylsulfanyl-6-morpholin-4-yl-pyridine-3-carboxylic acid amide N-[(4-Fluorophenyl)-methyl]-4-methyl-2-methylsulfanyl-6-morpholin-4-yl-pyridine-3-carboxylic acid amide (example 154), [M+H]⁺376.1, was synthesized from 6-chloro-2-methylsulfanyl-4-methyl-pyridine-3-carboxylic acid according to the methods described in sections b) & c) of example 1.

Synthesis of Example 169

N-[(4-Fluorophenyl)-methyl]-2-isopropyl-4-methyl-6-[(3R)-3-methyl-morpholin-4-yl]-pyridine-3-carboxylic acid amide

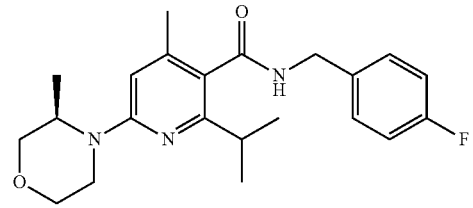 [SMILES: Cc1cc(N2CCOC[C@H]2C)nc(C(C)C)c1C(=O)NCc1ccc(F)cc1]

a) Synthesis of 2-chloro-N-(4-fluorobenzyl)-4-methyl-6-[(3R)-3-methylmorpholino]-pyridine-3-carboxylic amide A mixture of 6.0 g (19.2 mmol) 2,6-dichloro-N-(4-fluorobenzyl)-4-methyl-pyridine-3-carboxylic amide (synthesized according to the methods described in section a) of example 2), 3.9 g (28.7 mmol) (R)-3-methylmorpholine hydrochloride, 13.0 ml (76.6 mmol) and NMP (18.4 ml) was heated in the MW to 180° C. for 16 h. After cooling to RT the mixture was partiotionated between EtOAc and a 2M aq. NaOH sol. The organic layer was separated, dried over MgSO₄ and concentrated in vacuo. Purification of the residue by CC (hexane/EtOAc 1:1) provided 1.4 g (3.7 mmol, 20%) 2-chloro-N-(4-fluorobenzyl)-4-methyl-6-[(3R)-3-methylmorpholino]-pyridine-3-carboxylic amide.

b) Synthesis of N-[(4-Fluorophenyl)-methyl]-2-isopropyl-4-methyl-6-[(3R)-3-methyl-morpholin-4-yl]-pyridine-3-carboxylic acid amide 2-chloro-N-(4-fluorobenzyl)-4-methyl-6-[(3R)-3-methylmorpholino]-pyridine-3-carboxylic amide was converted into N-[(4-Fluorophenyl)-methyl]-2-isopropyl-4-methyl-6-

[(3R)-3-methyl-morpholin-4-yl]-pyridine-3-carboxylic acid amide (example 169), [M+H]⁺386.2, according to the method described for example 23.

Synthesis of Example 171

2-Ethylsulfanyl-N-[(3-fluorophenyl)-methyl]-4-methyl-6-(methyl-pyridin-3-yl-amino)-pyridine-3-carboxylic acid amide

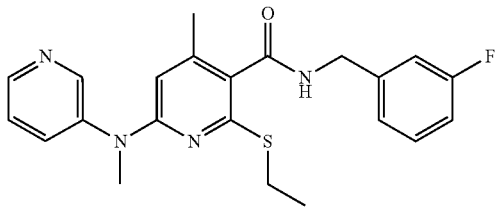 [SMILES: CCSc1nc(N(C)c2cccnc2)cc(C)c1C(=O)NCc1cccc(F)c1]

A mixture of 338 mg (1.0 mmol) 6-chloro-2-ethylsulfanyl-N-[(3-fluorophenyl)-methyl]-4-methyl-pyridine-3-carboxylic acid amide (synthesis is described in section b) of example 2), 237 mg (2.2 mmol) 2-methylamino-pyridine, 1.8 g (5.4 mmol) Cs$_2$CO$_3$ and 125 mg (0.11 mmol) Pd(PPh$_3$)$_2$ in 1,4-dioxane (4 ml) was heated at 110° C. for 2 h and stirred at RT for 16 h. The mixture was then filtered through celite and concentrated in vacuo. Purification of the residue by CC (hexane/EtOAc 1:1) provided 243 mg (0.59 mmol, 59%) 2-ethylsulfanyl-N-[(3-fluorophenyl)-methyl]-4-methyl-6-(methyl-pyridin-3-yl-amino)-pyridine-3-carboxylic acid amide (example 171). [M+H]⁺411.2

Synthesis of Example 172

2-Dimethylamino-N-[(4-fluorophenyl)-methyl]-4-methyl-6-[(3R)-3-methyl-morpholin-4-yl]-pyridine-3-carboxylic acid amide

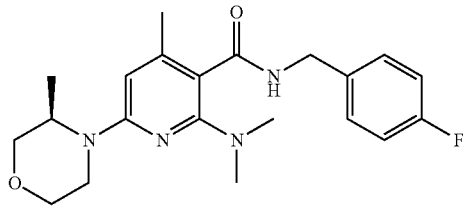 [SMILES: Cc1cc(N2CCOC[C@H]2C)nc(N(C)C)c1C(=O)NCc1ccc(F)cc1]

2-chloro-N-(4-fluorobenzyl)-4-methyl-6-[(3R)-3-methyl-morpholino]-pyridine-3-carboxylic amide (synthesis is described in section a) of example 169) was converted with a 2M solution of dimethylamine in THF into 2-dimethylamino-N-[(4-fluorophenyl)-methyl]-4-methyl-6-[(3R)-3-methyl-morpholin-4-yl]-pyridine-3-carboxylic acid amide (example 172), [M+H]⁺387.2, according to the method described for example 24.

Synthesis of Example 174

2-(Ethyl-methyl-amino)-N-[(4-fluorophenyl)-methyl]-4-methyl-6-morpholin-4-yl-pyridine-3-carboxylic acid amide

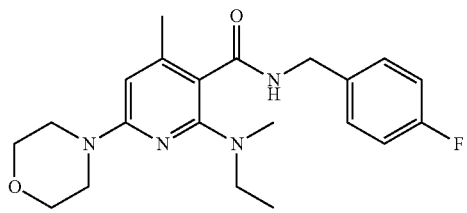 [SMILES: CCN(C)c1nc(N2CCOCC2)cc(C)c1C(=O)NCc1ccc(F)cc1]

a) Synthesis of 6-chloro-2-(ethyl(methyl)amino)-4-methyl-pyridine-3-carboxylic acid ethylester A mixture of 8.2 g (35.0 mmol) 2,6-dichloro-4-methyl-pyridine-3-carboxylic acid ethylester, 3.7 ml (43.8 mmol) N-methylethylamine and 8.9 ml (52.5 mmol) DIPEA in NMP (25 ml) was heated in the MW to 90° C. for 1 h. Then the solution was diluted with water, a 1M aq. NaOH sol. and EtOAc. The organic layer was separated, dried over MgSO$_4$ and concentrated in vacuo. Purification of the residue by CC (hexane/EtOAc 9:1) provided 4.0 g (15.6 mmol, 44%) 6-chloro-2-(ethyl(methyl)amino)-4-methyl-pyridine-3-carboxylic acid ethylester.

b) Synthesis of 2-(ethyl(methyl)amino)-4-methyl-6-morpholino-pyridine-3-carboxylic acid ethylester A mixture of 4.0 g (15.6 mmol) 6-chloro-2-(ethyl(methyl)amino)-4-methyl-pyridine-3-carboxylic acid ethylester and 13.6 ml (155.8 mmol) morpholine was heated in the MW to 135° C. for 2 h. Then the mixture was diluted with a 1M aq. NaOH sol. and EtOAc. The organic layer was separated, washed with brine, dried over MgSO$_4$ and concentrated in vacuo. Purification of the residue by CC (hexane/EtOAc 9:1) provided 2.0 g (6.4 mmol, 41%) 2-(ethyl(methyl)amino)-4-methyl-6-morpholino-pyridine-3-carboxylic acid ethylester.

c) Synthesis of -(Ethyl-methyl-amino)-N-[(4-fluorophenyl)-methyl]-4-methyl-6-morpholin-4-yl-pyridine-3-carboxylic acid amide A solution of 249 mg (0.81 mmol) 2-(ethyl(methyl)amino)-4-methyl-6-morpholino-pyridine-3-carboxylic acid ethylester and 924 μl (8.1 mmol) 4-fluoro-benzylamine in toluene (17 ml) was treated with 2.85 ml (2M in toluene, 5.7 mmol) AlMe$_3$ and was subsequently heated to 120° C. for 4 d. Then the solution was diluted with water, a 1M aq. NaOH sol. and EtOAc. The organic layer was separated, washed with a 2M aq. NaOH sol. and brine, dried over MgSO$_4$ and concentrated in vacuo. Purification of the residue by CC (hexane/EtOAc 3:1) provided 127 mg (0.33 mmol, 40%) 2-(Ethyl-methyl-amino)-N-[(4-fluorophenyl)-methyl]-4-methyl-6-morpholin-4-yl-pyridine-3-carboxylic acid amide (example 174). [M+H]⁺387.2

Synthesis of Example 176

N-[(4-Fluorophenyl)-methyl]-4-methyl-6-[(3R)-3-methyl-morpholin-4-yl]-2-methylsulfanyl-pyridine-3-carboxylic acid amide

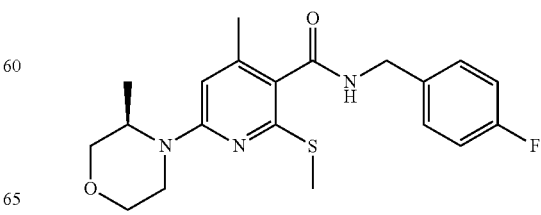

To a solution of 200 mg (0.52 mmol) 2-chloro-N-(4-fluorobenzyl)-4-methyl-6-[(3R)-3-methylmorpholino]-pyridine-3-carboxylic amide (synthesis is described in section a) of example 169) in THF (3 ml) was added 46 µg (0.66 mmol) NaSMe. The reaction mixture was stirred in a closed vessel at 80° C. for 3 d. Subsequently the mixture was diluted with water and a 2M aq. NaOH sol. and extracted twice with EtOAc. The combined organic layers were washed with water, dried over MgSO₄ and concentrated in vacuo. Crystallisation (EtOAc/pentane) of the residue yielded 128 mg (0.33 mmol, 62%) N-[(4-Fluorophenyl)-methyl]-4-methyl-6-[(3R)-3-methyl-morpholin-4-yl]-2-methylsulfanyl-pyridine-3-carboxylic acid amide (example 176). [M+H]⁺ 390.2

Synthesis of Example 214

N-[(3-Fluorophenyl)-methyl]-2-methoxy-4-methyl-6-[(3R)-3-methyl-morpholin-4-yl]-pyridine-3-carboxylic acid amide

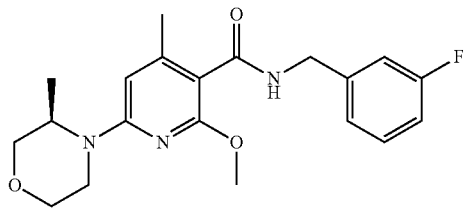 [SMILES: COc1nc(N2CCOC[C@H]2C)cc(C)c1C(=O)NCc1cccc(F)c1]

6-Chloro-N-[(3-Fluorophenyl)-methyl]-2-methoxy-4-methyl-pyridine-3-carboxylic acid amide (synthesis is described in section b) of example 19) was converted with (R)-3-methylmorpholine into N-[(3-Fluorophenyl)-methyl]-2-methoxy-4-methyl-6-[(3R)-3-methyl-morpholin-4-yl]-pyridine-3-carboxylic acid amide (example 214), [M+H]⁺ 374.2, according to the method described for example 171.

Synthesis of Example 253

2-Ethylsulfanyl-N-[(3-fluorophenyl)-methyl]-4-methyl-6-[methyl-(2-oxo-propyl)-amino]-pyridine-3-carboxylic acid amide

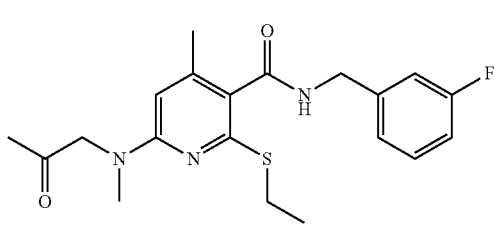 [SMILES: CCSc1nc(N(C)CC(C)=O)cc(C)c1C(=O)NCc1cccc(F)c1]

To a solution of 150 mg (0.45 mmol) 2-ethylsulfanyl-N-[(3-fluorophenyl)-methyl]-6-(methyl-amino)-4-methyl-pyridine-3-carboxylic acid amide (synthesis is described in section a) of example 123) in NMP (1 ml) were added 229 µl (1.35 mmol) DIPEA and 39 µl (0.50 mmol) chloroacetone. The mixture was heated in the MW to 140° C. for 40 min and subsequently partiotionated between a 1M aq. NaOH sol and EtOAc. The organic layer was separated, washed with a 1M aq. NaOH sol, water and brine, dried over MgSO₄ and concentrated in vacuo. Purification of the residue by CC (hexane/EtOAc 13:7) provided 53 mg (0.14 mmol, 30%) 2-Ethylsulfanyl-N-[(3-fluorophenyl)-methyl]-4-methyl-6-[methyl-(2-oxo-propyl)-amino]-pyridine-3-carboxylic acid amide (example 253). [M+H]⁺390.2

Synthesis of Example 258

2-Ethylsulfanyl-N-[(3-fluorophenyl)-methyl]-4-methyl-6-(methyl-tetrahydro-pyran-4-yl-amino)-pyridine-3-carboxylic acid amide

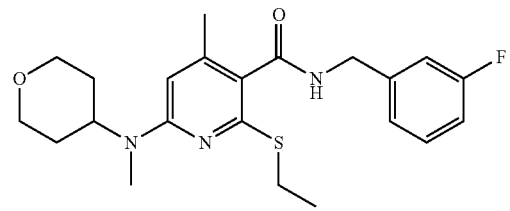 [SMILES: CCSc1nc(N(C)C2CCOCC2)cc(C)c1C(=O)NCc1cccc(F)c1]

A solution of 338 mg (1.0 mmol) 6-chloro-2-ethylsulfanyl-N-[(3-fluorophenyl)-methyl]-4-methyl-pyridine-3-carboxylic acid amide (synthesis is described in section b) of example 2), 172 mg (1.5 mmol) N-methyl-tetrahydro-2H-pyran-4-amine and 509 µl (3.0 mmol) DIPEA in NMP (1 ml) was heated in the microwave at 180° C. for 2 h. Subsequently the RM was diluted with a 2M aq. NaOH sol, water and EtOAc and the layers were separated. The organic layer was washed with water and brine, dried over MgSO₄ and concentrated in vacuo. Purification of the residue by CC (hexane/EtOAc 13:7) provided 77 mg (0.18 mmol, 18%) 2-Ethylsulfanyl-N-[(3-fluorophenyl)-methyl]-4-methyl-6-(methyl-tetrahydro-pyran-4-yl-amino)-pyridine-3-carboxylic acid amide (example 258). [M+H]⁺418.2

Synthesis of Example 263

2-Ethylsulfanyl-N-[(3-fluorophenyl)-methyl]-6-[(3S)-3-(hydroxymethyl)-morpholin-4-yl]-4-methyl-pyridine-3-carboxylic acid amide

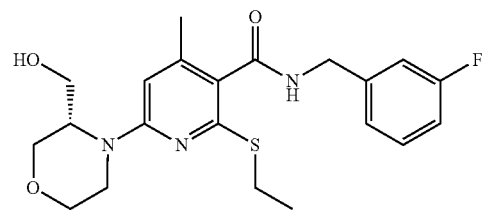 [SMILES: CCSc1nc(N2CCOC[C@@H]2CO)cc(C)c1C(=O)NCc1cccc(F)c1]

To a cooled (ice-bath) solution of 450 mg (1.32 mmol) (S)-morpholin-3-yl-methanol in THF (5 ml) were added at 0° C. 570 µl (2.78 mmol) 1,1,1,3,3,3 hexamethyldisilazane and 33 µl (0.26 mmol) trimethylchlorosilane. The mixture was then stirred at RT for 1 h. Then another 33 µl (0.26 mmol) trimethylchlorosilane was added and stirring was continued at RT for 1 h followed by concentration in vacuo. The residue, 450 mg (1.3 mmol) 6-chloro-2-ethylsulfanyl-N-[(3-fluorophenyl)-methyl]-4-methyl-pyridine-3-carboxylic acid amide (synthesis is described in section b) of example 2) and 903 µl (5.3 mmol) DIPEA were suspended in NMP (1.5 ml). Then the reaction mixture was heated at 180° C. for 32 h and stirred at RT for 72 h. Subsequently a 1M hydrochlorid acid was added and the mixture was stirred at RT for 15 min. After neutralization with a sat. aq. NaHCO₃ sol. EtOAc was added and the layers were separated. The organic layer was washed with water and brine, dried over MgSO₄ and concentrated in vacuo. Purification of the residue by CC (cyclohexane/EtOAc 1:1) provided mg (0.17 mmol, 13%) 2-Ethylsulfanyl-N-[(3-fluorophenyl)-methyl]-6-[(3S)-3-(hydroxymethyl)-morpholin-4-yl]-4-methyl-pyridine-3-carboxylic acid amide (example 263). [M+H]⁺420.2

Synthesis of Example 285

N-[(4-Chlorophenyl)-methyl]-2-isopropyl-6-[(2S)-2-(methoxymethyl)-morpholin-4-yl]-4-methyl-pyridine-3-carboxylic acid amide

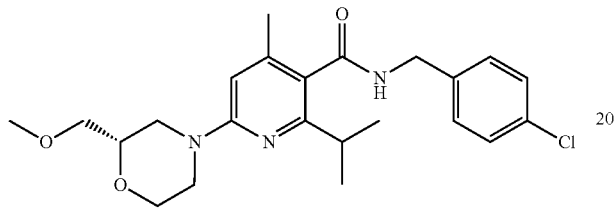

a) Synthesis of 6-chloro-N-(4-chlorobenzyl)-2-isopropyl-4-methyl-pyridine-3-carboxylic amide A solution of 6.0 g (18.3 mmol) 2,6-dichloro-N-(4-chlorobenzyl)-4-methyl-pyridine-3-carboxylic acid amide (synthesized according to the method described in section a) of example 2) in THF (180 ml) and NMP (60 ml) was degassed for 30 min followed by the addition of 1.3 g (3.7 mmol) Fe(acac)₃. This mixture was degassed again for 20 min. At −40° C. 137 ml (2M in THF, 274 mmol) isopropylmagnesiumchloride was added dropwise over 1 h. The reaction mixture was allowed to reach 0° C. and was quenched at this temperature with a sat. aq. NH₄Cl sol. followed by stirring at 10° C. for 30 min. Then the mixture was diluted with EtOAc and the organic layer was separated, washed with water and brine, dried over Na₂SO₄ and concentrated in vacuo. Purification of the residue by CC (hexane/EtOAc 9:1) provided 2.45 g (7.3 mmol, 40%) 6-chloro-N-(4-chlorobenzyl)-2-isopropyl-4-methyl-pyridine-3-carboxylic amide.

b) Synthesis of N-[(4-Chlorophenyl)-methyl]-2-isopropyl-6-[(2S)-2-(methoxymethyl)-morpholin-4-yl]-4-methyl-pyridine-3-carboxylic acid amide 6-chloro-N-(4-chlorobenzyl)-2-isopropyl-4-methyl-pyridine-3-carboxylic amide was converted into N-[(4-Chlorophenyl)-methyl]-2-isopropyl-6-[(2S)-2-(methoxymethyl)-morpholin-4-yl]-4-methyl-pyridine-3-carboxylic acid amide (example 285), [M+H]⁺432.2, according to the method described for example 258.

Synthesis of Example 298

6-(1,1-Dioxo-[1,4]thiazinan-4-yl)-2-ethylsulfanyl-N-[(3-fluorophenyl)-methyl]-4-methyl-pyridine-3-carboxylic acid amide

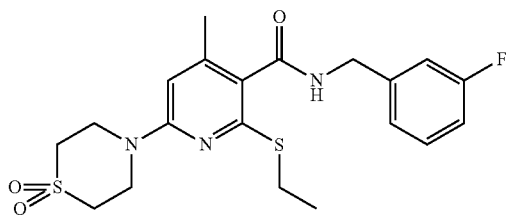 [SMILES: CCSc1nc(N2CCS(=O)(=O)CC2)cc(C)c1C(=O)NCc1cccc(F)c1]

a) Synthesis of 2-chloro-N-(3-fluorobenzyl)-4-methyl-6-thiomorpholino-pyridine-3-carboxylic acid amide A solution of 700 mg (2.24 mmol) 2,6-dichloro-N-(3-fluorobenzyl)-4-methyl-pyridine-3-carboxylic acid amide (synthesis is described in section a) of example 2), 280 µl (2.9 mmol) thiomorpholine and 3.95 g (12.1 mmol) Cs₂CO₃ in dioxane (60 ml) was degassed for 30 min followed by the addition of 285 mg (0.25 mmol) Pd(PPh₃)₄. Subsequently the reaction solution was heated to 120° C. for 16 h. Then the mixture was filtered through celite and concentrated in vacuo. Purification of the residue by CC (hexane/EtOAc 19:1) provided 420 mg (1.1 mmol, 49%) 2-chloro-N-(3-fluorobenzyl)-4-methyl-6-thiomorpholino-pyridine-3-carboxylic acid amide.

b) Synthesis of 2-chloro-6-(1,1-Dioxo-[1,4]thiazinan-4-yl)-2-N-[(3-fluorophenyl)-methyl]-4-methyl-pyridine-3-carboxylic acid amide To a solution of 420 mg (1.1 mmol) 2-chloro-N-(3-fluorobenzyl)-4-methyl-6-thiomorpholino-pyridine-3-carboxylic acid amide in DCM (13 ml) was added 640 mg (60% pure, 2.2 mmol) mCPBA at 0° C. and stirring was continued at this temperature for 2 h. The mixture was then diluted with DCM and washed with a sat. aq. Na₂CO₃ sol., water and brine, dried over Na₂SO₄ and concentrated in vacuo. The obtained crude 450 mg 2-chloro-6-(1,1-Dioxo-[1,4]thiazinan-4-yl)-2-N-[(3-fluorophenyl)-methyl]-4-methyl-pyridine-3-carboxylic acid amide was used in subsequent reactions without further purification.

c) Synthesis of 6-(1,1-Dioxo-[1,4]thiazinan-4-yl)-2-ethylsulfanyl-N-[(3-fluorophenyl)-methyl]-4-methyl-pyridine-3-carboxylic acid amide A solution of 450 mg (crude, ~1.1 mmol) 2-chloro-6-(1,1-Dioxo-[1,4]thiazinan-4-yl)-2-N-[(3-fluorophenyl)-methyl]-4-methyl-pyridine-3-carboxylic acid amide, 750 mg (5.5 mmol) K₂CO₃ and 400 µL (5.5 mmol) ethylmercaptane in DMF (4 ml) was heated to 60° C. for 2 h. Subsequently the mixture was poured into water. The mixture was extracted with EtOAc and the organic layer was washed with water and brine, dried over Na₂SO₄ and concentrated in vacuo. Purification of the residue by CC (hexane/EtOAc 1:1) provided 205 mg (0.47 mmol, 43%) 6-(1,1-Dioxo-[1,4]thiazinan-4-yl)-2-ethylsulfanyl-N-[(3-fluorophenyl)-methyl]-4-methyl-pyridine-3-carboxylic acid amide. [M+H]⁺438.1

Synthesis of Example 307

2-Ethylsulfanyl-N-[(3-fluorophenyl)-methyl]-6-[(3-methoxy-cyclohexyl)-methyl-amino]-4-methyl-pyridine-3-carboxylic acid amide

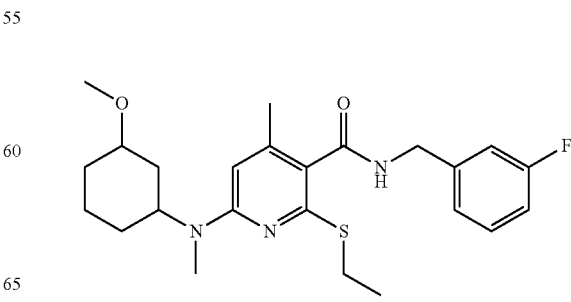

a) Synthesis of 2-chloro-N-(3-fluorobenzyl)-6-((3-methoxycyclohexyl)(methyl)amino)-4-methyl-pyridine-3-carboxylic acid amide To a solution of 1.19 g (3.8 mmol) 2,6-dichloro-N-(3-fluorobenzyl)-4-methyl-pyridine-3-carboxylic acid amide (synthesis is described in section a) of example 2) in DMF (12 ml) were added 1.05 g (7.6 mmol) K$_2$CO$_3$ and 683 mg (3.8 mmol) 3-methoxy-N-methylcyclohexanamine and the reaction mixture was heated at 110° C. for 16 h. The mixture was then poured into water and extracted with EtOAc. The organic layer was washed with water and brine, dried over Na$_2$SO$_4$ and concentrated in vacuo. Purification of the residue by CC (hexane/EtOAc 4:1) provided 850 mg (2.7 mmol, 32%) 2-chloro-N-(3-fluorobenzyl)-6-((3-methoxycyclohexyl)(methyl)amino)-4-methyl-pyridine-3-carboxylic acid amide.

b) Synthesis of 2-Ethylsulfanyl-N-[(3-fluorophenyl)-methyl]-6-[(3-methoxy-cyclohexyl)-methyl-amino]-4-methyl-pyridine-3-carboxylic acid amide To a solution of 148 mg (0.35 mmol) 2-chloro-N-(3-fluorobenzyl)-6-((3-methoxy-cyclohexyl)(methyl)amino)-4-methyl-pyridine-3-carboxylic acid amide in DM (1 ml) were added 488 mg (3.53 mmol) K$_2$CO$_3$ and 260 μl (3.53 mmol) mmol) ethylmercaptane and the reaction mixture was heated at 80° C. for 16 h. The mixture was then poured into water and extracted with EtOAc. The organic layer was washed with water and brine, dried over Na$_2$SO$_4$ and concentrated in vacuo. Purification of the residue by CC (hexane/EtOAc 17:3) provided 90 mg (0.2 mmol, 58%) 2-Ethylsulfanyl-N-[(3-fluorophenyl)-methyl]-6-[(3-methoxy-cyclohexyl)-methyl-amino]-4-methyl-pyridine-3-carboxylic acid amide (example 307). [M+H]$^+$446.2

Synthesis of Example 312

2-Ethylsulfanyl-N-[(3-fluorophenyl)-methyl]-4-methyl-6-(3-oxo-morpholin-4-yl)-pyridine-3-carboxylic acid amide

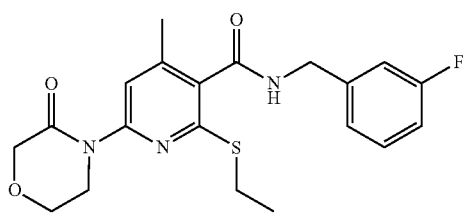 [SMILES: CCSc1nc(N2CCOCC2=O)cc(C)c1C(=O)NCc1cccc(F)c1]

A solution of 1.0 g (2.95 mmol) 6-chloro-2-ethylsulfanyl-N-[(3-fluorophenyl)-methyl]-4-methyl-pyridine-3-carboxylic acid amide (synthesis is described in section b) of example 2) in propionitrile (20 ml) was treated with 1.33 g (8.87 mmol) NaI and 1.0 ml (8.28 mmol) trichloromethylsilane. Subsequently the solution was heated at 110° C. for 16 h. The mixture was then partitioned between a 2M aq. NaOH sol and EtOAc. The organic layer was separated, washed with brine, dried over Na$_2$SO$_4$ and concentrated in vacuo. The residue was dissolved in dioxane (10 ml) and 2.26 g (7.0 mmol) Cs$_2$CO$_3$ and 114 mg (0.92 mmol) picolinic acid were added. This mixture was degassed for 30 min followed by the addition of 88 mg (0.46 mmol) CuI and 470 mg (4.65 mmol) 3-morpholinone. The reaction solution was then heated to 100° C. for 16 h and subsequently concentrated in vacuo. The residue was dissolved in water and was extracted with EtOAc. The organic layer was washed with water and brine, dried over Na$_2$SO$_4$ and concentrated in vacuo. Purification of the residue by CC (hexane/EtOAc 7:3) provided 60 mg (0.15 mmol, 5%) 2-Ethylsulfanyl-N-[(3-fluorophenyl)-methyl]-4-methyl-6-(3-oxo-morpholin-4-yl)-pyridine-3-carboxylic acid amide (example 312). [M+H]$^+$404.1.

Synthesis of Example 317

N-[(3-Fluorophenyl)-methyl]-4-methyl-6-morpholin-4-yl-2-(oxetan-3-yloxy)-pyridine-3-carboxylic acid amide

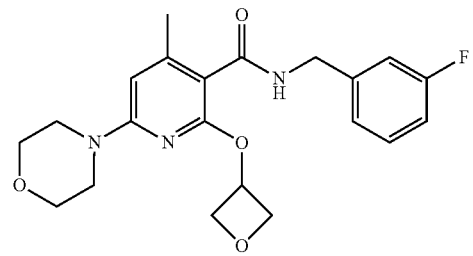 [SMILES: Cc1cc(N2CCOCC2)nc(OC2COC2)c1C(=O)NCc1cccc(F)c1]

A solution of 209 mg (2.82 mmol) 3-hydroxy-oxetane in THF (6 ml) was treated with 316 mg (2.81 mmol) KOtBu and was heated at 50° C. for 15 min. After cooling to RT a solution of 205 mg (0.56 mmol) 2-chloro-N-[(3-fluorophenyl)-methyl]-4-methyl-6-morpholin-4-yl-pyridine-3-carboxylic acid amide (synthesis is described in section a) of example 9) in THF (3 ml) was added and the mixture was heated at 80° C. for 8 h. The mixture was then poured into water and extracted with EtOAc. The organic layer was washed with water and brine, dried over Na$_2$SO$_4$ and concentrated in vacuo. Purification of the residue by CC (hexane/EtOAc 7:3) provided 190 mg (0.47 mmol, 84%) N-[(3-Fluorophenyl)-methyl]-4-methyl-6-morpholin-4-yl-2-(oxetan-3-yloxy)-pyridine-3-carboxylic acid amide (example 317). [M+H]$^+$402.2.

Synthesis of Example 336

2-Ethylsulfanyl-N-[(3-fluorophenyl)-methyl]-4-methoxy-6-morpholin-4-yl-pyridine-3-carboxylic acid amide

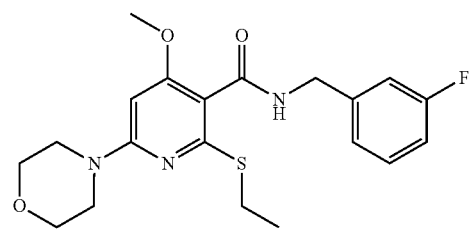 [SMILES: CCSc1nc(N2CCOCC2)cc(OC)c1C(=O)NCc1cccc(F)c1]

a) Synthesis of 2,6-dichloro-4-methoxy-pyridine-3-carboxylic acid

To a solution of 4.0 g (22.5 mmol) 2,6-dichloro-4-methoxy-pyridine in THF (20 ml) was added 10.0 ml (2.47 M in hexane, 24.7 mmol) n-butyllithium at −78° C. After stirring for 1 h at −78° C. excess dry ice was added and the mixture was allowed to warm to RT. Then the mixture was acidified with 6N aqueous hydrochlorid acid to pH 3-4 followed by extraction with EtOAc. The organic layer was dried over Na₂SO₄ and concentrated in vacuo. Purification of the residue by CC (hexane/EtOAc 4:1) provided 3.5 g (15.8 mmol, 70%) 2,6-dichloro-4-methoxy-pyridine-3-carboxylic acid.

b) Synthesis of 2-Ethylsulfanyl-N-[(3-fluorophenyl)-methyl]-4-methoxy-6-morpholin-4-yl-pyridine-3-carboxylic acid amide 2,6-dichloro-4-methoxy-pyridine-3-carboxylic acid was converted into 2-Ethylsulfanyl-N-[(3-fluorophenyl)-methyl]-4-methoxy-6-morpholin-4-yl-pyridine-3-carboxylic acid amide (example 336), [M+H]⁺406.2, according to the methods described for example 2.

Synthesis of Example 341

2-(Acetyl-methyl-amino)-N-[(3-fluorophenyl)-methyl]-4-methyl-6-morpholin-4-yl-pyridine-3-carboxylic acid amide

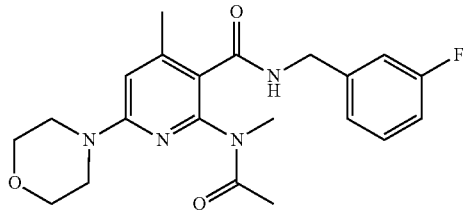 [SMILES: CC(=O)N(C)c1nc(N2CCOCC2)cc(C)c1C(=O)NCc1cccc(F)c1]

a) Synthesis of 6-chloro-N-(3-fluorobenzyl)-4-methyl-2-(N-methylacetamido)-pyridine-3-carboxylic acid amide To a solution of 240 µl (1.69 mmol) diisopropylamine in THF (5 ml) was added 680 µl (2.47 M in hexane, 1.69 mmol) n-butyllithium at −78° C. After stirring for 15 min at −78° C. a solution of 520 mg (1.69 mmol) 6-chloro-2-methylamino-N-[(3-fluorophenyl)-methyl]-4-methyl-pyridine-3-carboxylic acid amide (synthesized according to the method described in section a) of example 20) in THF (5 ml) was added at −78° C. The mixture was then allowed to warm to 0° C. At this temperature 160 µl (1.69 mmol) acetanhydride was added and stirring was continued at RT for 4 h. After quenching with a sat. aq. NH₄Cl sol the mixture was extracted with EtOAc. The organic layer was washed with water and brine, dried over Na₂SO₄ and concentrated in vacuo. Purification of the residue by CC (hexane/EtOAc 13:7) provided 200 mg (0.57 mmol, 34%) 6-chloro-N-(3-fluorobenzyl)-4-methyl-2-(N-methylacetamido)-pyridine-3-carboxylic acid amide.

b) Synthesis of 2-(Acetyl-methyl-amino)-N-[(3-fluorophenyl)-methyl]-4-methyl-6-morpholin-4-yl-pyridine-3-carboxylic acid amide 6-chloro-N-(3-fluorobenzyl)-4-methyl-2-(N-methylacetamido)-pyridine-3-carboxylic acid amide was converted into 2-(Acetyl-methyl-amino)-N-[(3-fluorophenyl)-methyl]-4-methyl-6-morpholin-4-yl-pyridine-3-carboxylic acid amide (example 341), [M+H]⁺401.2, according to the method described for example 258.

Synthesis of Example 346

2-Ethylsulfanyl-N-[(3-fluorophenyl)-methyl]-4-(methoxymethyl)-6-morpholin-4-yl-pyridine-3-carboxylic acid amide

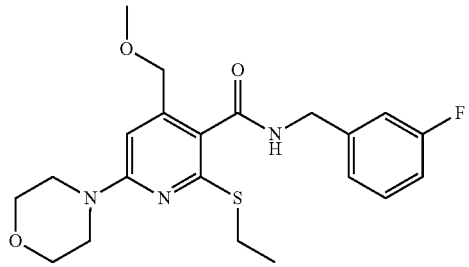 [SMILES: CCSc1nc(N2CCOCC2)cc(COC)c1C(=O)NCc1cccc(F)c1]

a) Synthesis of 4-(bromomethyl)-2,6-dichloro-pyridine-3-carboxylic acid methylester To a solution of 5.3 g (24.1 mmol) 2,6-dichloro-4-methyl-pyridine-3-carboxylic acid methylester in CCl₄ (92 ml) were added 3.1 g (26.5 mmol) N-Bromosuccinimide, 395 mg (2.4 mmol) AIBN and 1.45 ml (25.3 mmol) acetic acid. The mixture was irradiated with a 200 W Wolfram lamp at 60° C. for 24 h. Subsequently the mixture was filtered through celite and the filtrate was concentrated in vacuo. Purification of the residue by CC (hexane/EtOAc 97:3) provided 5.2 g of a mixture of 2,6-dichloro-4-methyl-pyridine-3-carboxylic acid methylester and 4-(bromomethyl)-2,6-dichloro-pyridine-3-carboxylic acid methylester which was used in subsequent reactions without further purification.

b) Synthesis of 2,6-dichloro-4-(methoxymethyl)-pyridine-3-carboxylic acid methylester 320 mg Sodium was dissolved in MeOH (40 ml) at 0° C. followed by the addition of a solution of 5.2 g of the crude mixture from section a) in MeOH (30 ml) at 0° C. The reaction solution was stirred at RT for 2 h and was then poured into water. This mixture was extracted with EtOAc and the organic layer was washed with water and brine, dried over Na₂SO₄ and concentrated in vacuo. Purification of the residue by CC (hexane/EtOAc 97:3) provided 830 mg (11.9 mmol, 10% over 2 steps) 2,6-dichloro-4-(methoxymethyl)-pyridine-3-carboxylic acid methylester.

c) Synthesis of 2,6-dichloro-4-(methoxymethyl)-pyridine-3-carboxylic acid

To a solution of 630 mg (2.5 mmol) 2,6-dichloro-4-(methoxymethyl)-pyridine-3-carboxylic acid methylester in dioxane (16 ml) was added a aq. 1M NaOH sol. and the reaction solution was heated to 100° C. for 4 h. The mixture was then diluted with water and washed with EtOAc. The aqueous layer was acidified with 2M HCl to pH 3 to 4 and was extracted with DCM. The organic layer was dried over Na₂SO₄ and concentrated in vacuo. The obtained 520 mg (2.4 mmol, 94%) 2,6-dichloro-4-(methoxymethyl)-pyridine-3-carboxylic acid was used in subsequent reactions without further purification.

d) Synthesis of 2-Ethylsulfanyl-N-[(3-fluorophenyl)-methyl]-4-(methoxymethyl)-6-morpholin-4-yl-pyridine-3-carboxylic acid amide 2,6-dichloro-4-(methoxymethyl)-pyridine-3-carboxylic acid was converted into 2-ethylsulfanyl-N-[(3-fluorophenyl)-methyl]-4-(methoxymethyl)-6-morpholin-4-yl-pyridine-3-carboxylic acid amide (example 346), [M+H]$^+$420.2, according to the method described for example 2.

Synthesis of Example 354

N-(4,4-Dimethyl-pentyl)-2-(3-methoxy-propyl)-4-methyl-6-morpholin-4-yl-pyridine-3-carboxylic acid amide

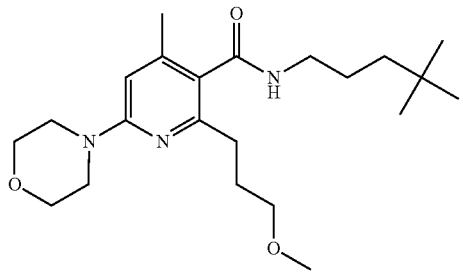 [SMILES: COCCCc1nc(N2CCOCC2)cc(C)c1C(=O)NCCCC(C)(C)C]

a) Synthesis of 2,6-dichloro-4-methyl-pyridine-3-carboxylic acid methylester

To a solution of 5.0 g (24.3 mmol) 2,6-dichloro-4-methyl-pyridine-3-carboxylic acid in DMF (73 ml) were added 5.0 g (36.4 mmol) K$_2$CO$_3$ and 7.6 ml (121.3 mmol) iodomethane at 0° C. The reaction mixture was stirred at RT for 3 h and was subsequently poured into water. This mixture was extracted with EtOAc and the organic layer was washed with water and brine, dried over Na$_2$SO$_4$ and concentrated in vacuo. Purification of the residue by CC (hexane/EtOAc 19:1) provided 5.2 g (23.7 mmol, 98%) 2,6-dichloro-4-methyl-pyridine-3-carboxylic acid methylester.

b) Synthesis of 2-chloro-4-methyl-6-morpholino-pyridine-3-carboxylic acid methylester A solution of 5.2 g (23.7 mmol) 2,6-dichloro-4-methyl-pyridine-3-carboxylic acid methylester, 3.94 g (28.5 mmol) K$_2$CO$_3$ and 2.06 ml (23.7 mmol) morpholine in DMF (48 ml) was heated to 60° C. for 16 h. Then the mixture was poured into water and extracted with EtOAc. The organic layer was washed with water and brine, dried over Na$_2$SO$_4$ and concentrated in vacuo. Purification of the residue by CC (hexane/EtOAc 4:1) provided 1.95 g (7.2 mmol, 30%) 2-chloro-4-methyl-6-morpholino-pyridine-3-carboxylic acid methylester.

c) Synthesis of 2-(3-methoxyprop-1-ynyl)-4-methyl-6-morpholino-pyridine-3-carboxylic acid methylester To a solution of 700 mg (2.6 mmol) 2-chloro-4-methyl-6-morpholino-pyridine-3-carboxylic acid methylester and 1.39 g (3.9 mmol) tributyl(3-methoxyprop-1-ynyl)stannane in dioxane (10 ml) was added 273 mg (0.39 mmol) PdCl$_2$(PPh$_3$)$_2$. Then the reaction solution was heated at 100° C. for 16 h. After cooling to RT the mixture was filtered through celite and the filtrate was concentrated in vacuo. The residue was dissolved in EtOAc and washed with water. The organic layer was dried over Na$_2$SO$_4$ and concentrated in vacuo. Purification of the residue by CC (5% KF-silica, hexane/EtOAc 19:1) provided 500 mg (1.64 mmol, 63%) 2-(3-methoxyprop-1-ynyl)-4-methyl-6-morpholino-pyridine-3-carboxylic acid methylester.

d) Synthesis of 2-(3-methoxypropyl)-4-methyl-6-morpholino-pyridine-3-carboxylic acid methylester To a solution of 500 mg (1.64 mmol) 2-(3-methoxyprop-1-ynyl)-4-methyl-6-morpholino-pyridine-3-carboxylic acid methylester in MeOH (30 ml) was added 170 mg 10%-Pd/C. The reaction solution was stirred under hydrogen atmosphere (balloon) at RT for 16 h. Then the mixture was filtered through celite and the filtrate was concentrated in vacuo. Purification of the residue by CC (hexane/EtOAc 9:1) provided 480 mg (1.55 mmol, 95%) 2-(3-methoxypropyl)-4-methyl-6-morpholino-pyridine-3-carboxylic acid methylester.

e) Synthesis of N-(4,4-Dimethyl-pentyl)-2-(3-methoxy-propyl)-4-methyl-6-morpholin-4-yl-pyridine-3-carboxylic acid amide 2-(3-methoxypropyl)-4-methyl-6-morpholino-pyridine-3-carboxylic acid methylester was converted into N-(4,4-Dimethyl-pentyl)-2-(3-methoxy-propyl)-4-methyl-6-morpholin-4-yl-pyridine-3-carboxylic acid amide (example 354), [M+H]$^+$392.3, according to the methods described in sections c) and d) of example 11.

Synthesis of Example 355

2-Cyclopropyl-N-[[3-fluoro-4-(methoxymethyl)-phenyl]-methyl]-4-methyl-6-morpholin-4-yl-pyridine-3-carboxylic acid amide

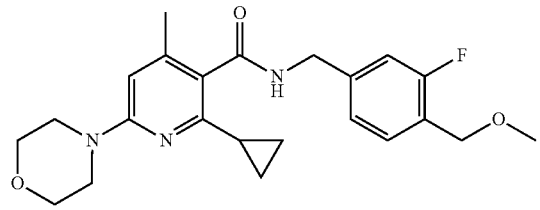 [SMILES: COCc1ccc(CNC(=O)c2c(C)cc(N3CCOCC3)nc2C2CC2)cc1F]

a) Synthesis of 2-cyclopropyl-4-methyl-6-morpholino-pyridine-3-carboxylic acid methylester To a solution of 1.0 g (3.69 mmol) 2-chloro-4-methyl-6-morpholino-pyridine-3-carboxylic acid methylester (synthesis is described in section b) of example 354) in toluene (20 ml) were added 634 mg (7.38 mmol) cyclopropyl boronic acid, 2.74 g (12.9 mmol) K$_3$PO$_4$, 104 mg (0.37 mmol) tricyclohexyl-phosphine and water (1 ml). After degassing for 30 min 82 mg (0.37 mmol) Pd(OAc)$_2$ were added and the reaction solution was heated at 120° C. for 16 h. The mixture was then poured into water and extracted with EtOAc. The organic layer was washed with water and brine, dried over Na₂SO₄ and concentrated in vacuo. Purification of the residue by CC (hexane/EtOAc 17:3) provided 500 mg (1.84 mmol, 80%) 2-cyclopropyl-4-methyl-6-morpholino-pyridine-3-carboxylic acid methylester b) Synthesis of 2-Cyclopropyl-N-[[3-fluoro-4-(methoxymethyl)-phenyl]methyl]-4-methyl-6-morpholin-4-yl-pyridine-3-carboxylic acid amide 2-Cyclopropyl-4-methyl-6-morpholin-4-yl-pyridine-3-carboxylic acid methylester was converted into 2-Cyclopropyl-N-[[3-fluoro-4-(methoxymethyl)-phenyl]-methyl]-4-methyl-6-morpholin-4-yl-pyridine-3-carboxylic acid amide (example 355), [M+H]⁺414.2, according to the methods described in sections c) and d) of example 11.

Synthesis of Example 356

N-[(3-Fluorophenyl)-methyl]-2-(methoxymethyl)-4-methyl-6-morpholin-4-yl-pyridine-3-carboxylic acid amide

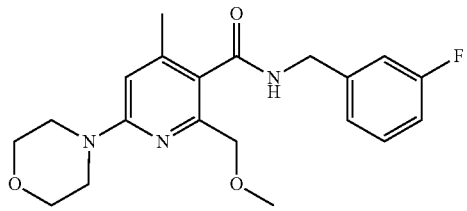 [SMILES: COCc1nc(N2CCOCC2)cc(C)c1C(=O)NCc1cccc(F)c1]

a) Synthesis of 2-(methoxymethyl)-4-methyl-6-morpholin-4-yl-pyridine-3-carboxylic acid methylester To a solution of 710 mg, (3.6 mmol) 6-chloro-2,4-dimethyl-pyridine-3-carboxylic acid methylester in CCl₄ (16 ml) were added 688 mg (3.90 mmol) N-bromosuccinimide, 59 mg (0.36 mmol) AIBN and 210 μl (3.72 mmol) acetic acid. The reaction mixture was irradiated with a 200 W Wolfram lamp at 60° C. for 24 h. The mixture was then filtered through celite, washed with CCl₄ and concentrated in vacuo. After CC (hexane/EtOAc 97:3) of the residue a mixture of 6-chloro-2,4-dimethyl-pyridine-3-carboxylic acid methylester, 4-(bromomethyl)-6-chloro-2-methyl-pyridine-3-carboxylic acid methylester and 2-(bromomethyl)-6-chloro-4-methyl-pyridine-3-carboxylic acid methylester was obtained. This mixture was dissolved in dioxane (10 ml) and added at 0° C. to a solution prepared by dissolving 594 mg (25.8 mmol) sodium in MeOH (11 ml) at 0° C. This reaction mixture was stirred at RT for 3 h. Then the reaction solution was poured into water and extracted with EtOAc. The organic layer was washed with water and brine, dried over Na₂SO₄ and concentrated in vacuo. After CC (hexane/EtOAc 97:3) of the residue again a mixture of 6-chloro-4-(methoxymethyl)-2-methyl-pyridine-3-carboxylic acid methylester and 6-chloro-2-(methoxymethyl)-4-methyl-pyridine-3-carboxylic acid methylester was obtained. This material was dissolved in NMP (7.8 ml) and 860 μl (9.85 mmol) morpholine and 1.36 g (9.85 mmol) K₂CO₃ were added followed by heating at 100° C. for 5 h. Then the mixture was poured into water and extracted with EtOAc. The organic layer was washed with water and brine, dried over Na₂SO₄ and concentrated in vacuo. Purification of the residue by CC (hexane/EtOAc 9:1) provided 90 mg (0.32 mmol, 9%) 2-(methoxymethyl)-4-methyl-6-morpholin-4-yl-pyridine-3-carboxylic acid methylester.

b) Synthesis of N-[(3-Fluorophenyl)-methyl]-2-(methoxymethyl)-4-methyl-6-morpholin-4-yl-pyridine-3-carboxylic acid amide 2-(methoxymethyl)-4-methyl-6-morpholin-4-yl-pyridine-3-carboxylic acid methylester was converted into N-[(3-Fluorophenyl)-methyl]-2-(methoxymethyl)-4-methyl-6-morpholin-4-yl-pyridine-3-carboxylic acid amide (example 356), [M+H]⁺373.2, according to the methods described in sections c) and d) of example 11.

Synthesis of Example 357

N-[(4-Chlorophenyl)-methyl]-2,4-diisopropyl-6-morpholin-4-yl-pyridine-3-carboxylic acid amide

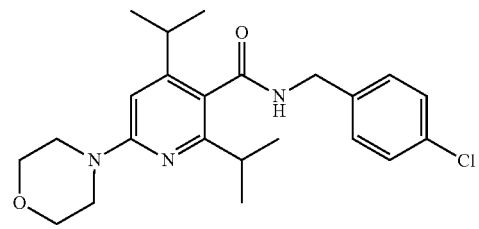 [SMILES: CC(C)c1cc(N2CCOCC2)nc(C(C)C)c1C(=O)NCc1ccc(Cl)cc1]

a) Synthesis of 2,4-diisopropyl-6-oxo-1,6-dihydropyridine-3-carboxylic acid ethylester To a solution of 20.0 g, (126.4 mmol) ethyl 4-methyl-3-oxopentanoate in methanol (100 ml) was added 48.72 g, (632.2 mmol) ammonium acetate. The reaction mixture was stirred at RT for 3 d. Then the mixture was concentrated in vacuo. The residue was taken up with DCM (300 ml) and filtered. The filtrate is water and brine, dried over Na₂SO₄ and concentrated in vacuo. This residue was dissolved in toluene (100 ml), followed by the addition of HCl (saturated solution in dioxane, 65 ml) at 0° C. The reaction mixture was heated at 120° C. for 20 h and subsequently filtered and the solid is washed with toluene. The filtrate was concentrated in vacuo. Purification of the residue by CC (hexane/EtOAc 3:2) provided 2.2 g (8.76 mmol, 7%) 2,4-diisopropyl-6-oxo-1,6-dihydropyridine-3-carboxylic acid ethylester.

b) Synthesis of 6-chloro-2,4-diisopropyl-pyridine-3-carboxylic acid ethylester

A solution of 2.2 g (8.76 mmol) 2,4-diisopropyl-6-oxo-1,6-dihydropyridine-3-carboxylic acid ethylester in POCl₃ (43.8 ml) was stirred at 120° C. for 2 h. Then excess POCl₃ was evaporated. The residue was dissolved in EtOAc (60 ml) and the solution was washed with a sat. NaHCO₃ sol, water and brine. The organic layer was dried over Na₂SO₄ and concentrated in vacuo. Purification of this residue by CC (hexane/EtOAc 97:3) provided 2.0 g (7.43 mmol, 85%) 6-chloro-2,4-diisopropyl-pyridine-3-carboxylic acid ethylester.

c) Synthesis of N-[(4-Chlorophenyl)-methyl]-2,4-diisopropyl-6-morpholin-4-yl-pyridine-3-carboxylic acid amide 6-chloro-2,4-diisopropyl-pyridine-3-carboxylic acid ethylester was converted into N-[(4-Chlorophenyl)-methyl]-2,4-diisopropyl-6-morpholin-4-yl-pyridine-3-carboxylic acid amide (example 357), [M+H]$^+$415.2, according to the methods described in sections b) of example 117 followed by the methods described in section c) and d) of example 11.

Synthesis of Example 358

N-(4,4-Dimethyl-pentyl)-2-(2-methoxy-ethyl)-4-methyl-6-morpholin-4-yl-pyridine-3-carboxylic acid amide

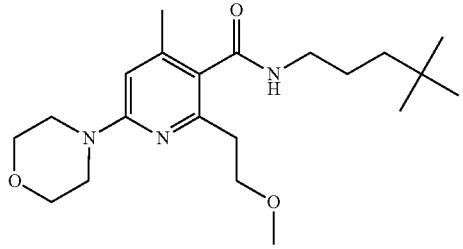 [SMILES: COCCc1nc(N2CCOCC2)cc(C)c1C(=O)NCCCC(C)(C)C]

To a solution of 750 mg, (2.17 mmol) N-(4,4-dimethylpentyl)-4-methyl-6-morpholino-2-vinyl-pyridine-3-carboxylic acid amide (synthesized according to the methods described for example 9) in THF (10 ml) was added dropwise 730 µl (7.6 mmol) at 0° C. and the resulting mixture was stirred at RT for 16 h. The reaction mixture was cooled to 0° C. and a 1N aq. NaOH sol (4 ml) was added dropwise over a period of 0.5 h, followed by the addition of H$_2$O$_2$ (30% in water, 4 ml). Then the reaction mixture was stirred at RT for 4 h and was then extracted with EtOAc. The organic layer was dried over Na$_2$SO$_4$ and concentrated in vacuo. After CC (hexane/EtOAc 3:7) a mixture of N-(4,4-dimethylpentyl)-2-(2-hydroxy-ethyl)-4-methyl-6-morpholino-pyridine-3-carboxylic acid amide and N-(4,4-dimethylpentyl)-2-(1-hydroxyethyl)-4-methyl-6-morpholino-pyridine-3-carboxylic acid amide was obtained. This mixture was dissolved in THF (6 ml) and benzene (6 ml) and 24 mg, 0.0716 mmol) TBAHS was added at RT followed by the addition of a 25% aq. NaOH sol (6 ml) and 0.450 µl (7.16 mmol) iodomethane. Then the reaction mixture was slowly heated to 70° C. and stirred at the same temperature for 3 h. The additional 0.450 µl (7.16 mmol) iodomethane was added and stirring was continued at 70° C. for another 3 h. Then the organic layer was separated and the aq. layer was extracted with EtOAc. The combined organic layer was washed with water, and brine, dried over Na$_2$SO$_4$ and concentrated in vacuo. Purification of this residue by CC (hexane/EtOAc 3:2) provided 60 mg (0.16 mmol, 6%) N-(4,4-Dimethyl-pentyl)-2-(2-methoxy-ethyl)-4-methyl-6-morpholin-4-yl-pyridine-3-carboxylic acid amide (example 358). [M+H]$^+$377.3

Synthesis of Example 359

N-[(4-Chlorophenyl)-methyl]-2,4-diethyl-6-morpholin-4-yl-pyridine-3-carboxylic acid amide

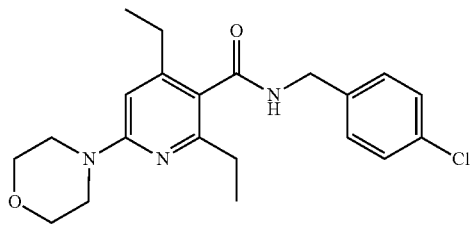 [SMILES: CCc1cc(N2CCOCC2)nc(CC)c1C(=O)NCc1ccc(Cl)cc1]

a) Synthesis of 6-chloro-2,4-diethyl-pyridine-3-carboxylic acid ethylester

To a solution of 2.73 g (14.12 mmol) 2,4-diethyl-pyridine-3-carboxylic acid ethylester in chloroform (109 ml) was added 6.97 g, (70% pure, 28.29 mmol) mCPBA at 0° C. The reaction mixture was stirred at RT for 6 h and was then diluted with chloroform and washed with a sat. NaHCO$_3$ sol and brine. The organic layer was dried over Na$_2$SO$_4$ and concentrated in vacuo. The residue was dissolved in POCl$_3$ (70 ml) and the reaction mixture was heated at 110° C. for 6.5 h. Then excess POCl$_3$ was evaporated and cold water was added to the residue. The mixture was basified with a sat. NaHCO$_3$ sol to pH ~10 and was extracted EtOAc. The organic layer was washed with water and brine, dried over Na$_2$SO$_4$ and concentrated in vacuo. Purification of this residue by CC (hexane/EtOAc 9:1) provided 1.6 g (7.02 mmol, 20%) 6-chloro-2,4-diethyl-pyridine-3-carboxylic acid ethylester.

b) Synthesis of N-[(4-Chlorophenyl)-methyl]-2,4-diethyl-6-morpholin-4-yl-pyridine-3-carboxylic acid amide 6-chloro-2,4-diethyl-pyridine-3-carboxylic acid ethylester was converted into N-[(4-Chlorophenyl)-methyl]-2,4-diethyl-6-morpholin-4-yl-pyridine-3-carboxylic acid amide (example 359), [M+H]$^+$387.2, according to the methods described in sections b) of example 117 followed by the methods described in section c) and d) of example 11.

Synthesis of Example X1

2-Cyclopropyl-N-(3-hydroxy-4,4-dimethyl-pentyl)-4-methyl-6-morpholin-4-yl-pyridine-3-carboxylic acid amide

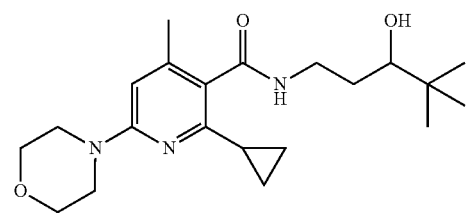 [SMILES: Cc1cc(N2CCOCC2)nc(C2CC2)c1C(=O)NCCC(O)C(C)(C)C]

a) Synthesis of 2,6-dichloro-4-methyl-pyridine-3-carboxylic acid ethyl ester A mixture of 2,6-dichlor-4-methylpyridin-3-carboxylic acid (100 g, 485 mmol) and potassium carbonate (100 g, 728 mmol) in dimethylformamide (1.25 l) is stirred for 30 h at RT before ethyl iodide (59.5 ml, 728 mmol) is added and stirring is continued for 18 h. After completion of the reaction, water is added and the mixture is extracted with ethyl acetate (3×). The combined organic layers are washed with water (2×) and brine (1×), dried over magnesium sulphate and evaporated to dryness to yield 2,6-dichloro-4-methyl-pyridine-3-carboxylic acid ethyl ester (112 g), which was used without further purification.

b) Synthesis of 2-chloro-4-methyl-6-morpholin-4-yl-pyridine-3-carboxylic acid ethyl ester A mixture of 2,6-dichloro-4-methyl-pyridine-3-carboxylic acid ethyl ester (29.7 g, 127 mmol), potassium carbonate (26.3 g, 190 mmol), and morpholine (13.3 g, 152 mmol) in dimethylformamide (350 ml) is stirred for 18 h at 95° C. After completion of the reaction, water is added and the mixture is extracted with diethyl ether (3×). The combined organic layers are washed with water (2×) and brine (1×), dried over magnesium sulphate and evaporated to dryness. The crude product is purified by flash chromatography (silica gel, 25% ethyl acetate/cyclohexane) to yield 2-chloro-4-methyl-6-morpholin-4-yl-pyridine-3-carboxylic acid ethyl ester (10.5 g, 36.9 mmol, 29%).

c) Synthesis of 2-cyclopropyl-4-methyl-6-morpholin-4-yl-pyridine-3-carboxylic acid ethyl ester To a solution 2-chloro-4-methyl-6-morpholin-4-yl-pyridine-3-carboxylic acid ethyl ester (7.0 g, 24.6 mmol) in tetrahydrofuran-N-methyl-2-pyrrolidone (2:3) (250 ml) is added iron(III) acetylacetonate (1.74 g, 4.92 mmol) and the mixture is cooled to −20° C. At this temperature, a solution of cyclopropylmagnesium bromide (0.7 M in tetrahydrofuran) (105 ml, 73.8 mmol) is slowly added and the mixture is warmed to 0° C. within 30 min. After completion of the reaction, 10% aqueous ammonium chloride is added and the mixture is extracted with ethyl acetate (2×). The combined organic layers are washed with water and brine, dried over magnesium sulphate and evaporated to dryness. The reaction is repeated once and the combined crude products are purified by flash chromatography (silica gel, 75% ethyl acetate/cyclohexane) to yield 2-cyclopropyl-4-methyl-6-morpholin-4-yl-pyridine-3-carboxylic acid ethyl ester (15.1 g).

d) Synthesis of 2-cyclopropyl-4-methyl-6-morpholin-4-yl-pyridine-3-carboxylic acid A solution of 2-cyclopropyl-4-methyl-6-morpholin-4-yl-pyridine-3-carboxylic acid ethyl ester (16.8 g, 57.8 mmol) in methanol-tetrahydrofuran (1:1) (90 ml) is treated for 3 days with a 2M aqueous solution of sodium hydroxide at reflux. The organic solvent is distilled off and the aqueous layer treated with 2M hydrochloric acid, and extracted with ethyl acetate. The combined organic layers are dried over magnesium sulphate and evaporated to dryness. The crude product is purified by flash chromatography (silica gel, 75% ethyl acetate/cyclohexane) to yield 2-cyclopropyl-4-methyl-6-morpholin-4-yl-pyridine-3-carboxylic acid (10.4 g, 39.6 mmol, 69%).

e) Synthesis of 2-cyclopropyl-N-(3-hydroxy-4,4-dimethyl-pentyl)-4-methyl-6-morpholin-4-yl-pyridine-3-carboxylic acid amide To a solution of 2-cyclopropyl-4-methyl-6-morpholin-4-yl-pyridine-3-carboxylic acid (1.90 g, 7.24 mmol) in tetrahydrofuran (60 ml) are added triethylamine (3.0 ml, 21.7 mol) and O-(7-azabenzotriazol-1-yl)N,N,N',N'-tetramethyluronium hexafluorophosphate (2.75 g, 7.24 mmol).

The mixture is stirred for 15 min at RT, before 1-amino-4,4-dimethylpentan-3-ol (1.05 g, 7.97 mmol) is added and stirring is continued for 18 h. After completion of the reaction, the mixture is diluted with ethyl acetate and 10% aqueous ammonium chloride. The organic layer is separated and washed with saturated sodium hydrogencarbonate solution and brine, dried over magnesium sulphate and evaporated to dryness. The crude product is purified by flash chromatography (silica gel, 50% ethyl acetate/cyclohexane) to yield 2-cyclopropyl-N-(3-hydroxy-4,4-dimethyl-pentyl)-4-methyl-6-morpholin-4-yl-pyridine-3-carboxylic acid amide (example X1) (1.74 g, 4.63 mmol, 64%). [M+H]$^+$376.4.

Examples X1a and X1b: 2-Cyclopropyl-N-(3-hydroxy-4,4-dimethyl-pentyl)-4-methyl-6-morpholin-4-yl-pyridine-3-carboxylic acid amide (1.64 g) was resolved into its corresponding enantiomers using chiral HPLC with the following conditions. Column, Chiralpak AD-H, 5μ, 250×20 mm; mobile phase, n-heptane/iso-propanol=90:10 (v/v); flow rate, 19 ml/min; detection, UV (254 nm), 180 separations with 10 mg racemic material each. Analytical HPLC conditions. Column, Chiralpak AD-H, 250×4.6 mm; mobile phase, n-heptane/iso-propanol=90:10 (v/v); flow rate, 1 ml/min; detection, UV (254 nm). Retention time (min): first eluting enantiomer, 8.59 (>99% ee); second eluting enantiomer, 10.45 (94% ee). Separation by chiral HPLC affords the first eluting enantiomer of 2-cyclopropyl-N-(3-hydroxy-4,4-dimethyl-pentyl)-4-methyl-6-morpholin-4-yl-pyridine-3-carboxylic acid amide (example X1a) (0.49 g; [M+H]$^+$376.4) and the second eluting enantiomer of 2-cyclopropyl-N-(3-hydroxy-4,4-dimethyl-pentyl)-4-methyl-6-morpholin-4-yl-pyridine-3-carboxylic acid amide (example X1b) (0.49 g; [M+H]$^+$376.4) as white solids.

Synthesis of Example X2

2-Cyclopropyl-N-[[(1S,2R)-2-hydroxy-cyclohexyl]-methyl]-4-methyl-6-morpholin-4-yl-pyridine-3-carboxylic acid amide

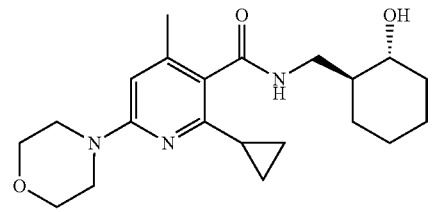 [SMILES: Cc1cc(N2CCOCC2)nc(C2CC2)c1C(=O)NC[C@@H]1CCCC[C@H]1O]

To a solution of 2-cyclopropyl-4-methyl-6-morpholin-4-yl-pyridine-3-carboxylic acid (synthesized according to the methods described in sections a) to d) of example X1) (0.15 g, 0.57 mmol) in dichloromethane (10 ml) are added N-ethyl-diisopropylamine (0.24 ml, 1.43 mmol), 1-ethyl-3-(3-dimethylaminopropyl) carbodiimide (0.13 g, 0.69 mmol), and 1-hydroxybenzotriazole hydrate (0.015 g, 0.11 mmol). The mixture is stirred for 15 min at RT, and then cooled to 0° C., before (1R,2S)-2-(aminomethyl)cyclohexanol (0.07 g, 0.57 mmol) is added and stirring is continued for 3 days. After completion of the reaction, the mixture is diluted with ethyl acetate and 10% aqueous ammonium chloride. The organic layer is separated and washed with saturated sodium hydrogencarbonate solution and brine, dried over magnesium sulphate and evaporated to dryness. The crude product is purified by flash chromatography (silica gel, 30% ethyl acetate/cyclohexane) to yield 2-cyclopropyl-N-[[(1S,2R)-2-hydroxy-cyclohexyl]-methyl]-4-methyl-6-morpholin-4-yl-pyridine-3-carboxylic acid amide (example X2) (0.21 g, 0.56 mmol, 98%). [M+H]⁺374.2.

Synthesis of Example X3

2-Cyclopropyl-N-[[(1R,2S)-2-hydroxy-cyclohexyl]-methyl]-4-methyl-6-morpholin-4-yl-pyridine-3-carboxylic acid amide

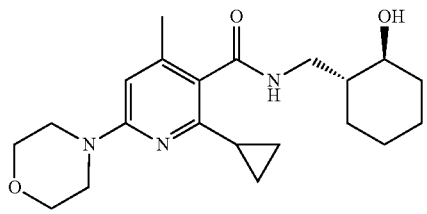 [SMILES: Cc1cc(N2CCOCC2)nc(C2CC2)c1C(=O)NC[C@H]1CCCC[C@@H]1O]

To a solution of 2-cyclopropyl-4-methyl-6-morpholin-4-yl-pyridine-3-carboxylic acid (synthesized according to the methods described in sections a) to d) of example X1) (0.15 g, 0.57 mmol) in dichloromethane (10 ml) are added N-ethyldiisopropylamine (0.24 ml, 1.43 mmol), 1-ethyl-3-(3-dimethylaminopropyl) carbodiimide (0.13 g, 0.69 mmol), and 1-hydroxybenzotriazole hydrate (0.015 g, 0.11 mmol). The mixture is stirred for 15 min at RT, and then cooled to 0° C., before (1S,2R)-2-(aminomethyl)cyclohexanol (0.07 g, 0.57 mmol) is added and stirring is continued for 3 days. After completion of the reaction, the mixture is diluted with ethyl acetate and 10% aqueous ammonium chloride. The organic layer is separated and washed with saturated sodium hydrogencarbonate solution and brine, dried over magnesium sulphate and evaporated to dryness. The crude product is purified by flash chromatography (silica gel, 60% ethyl acetate/cyclohexane) to yield 2-cyclopropyl-N-[[(1R,2S)-2-hydroxy-cyclohexyl]-methyl]-4-methyl-6-morpholin-4-yl-pyridine-3-carboxylic acid amide (example X3) (0.17 g, 0.45 mmol, 80%). [M+H]⁺374.3.

Synthesis of Example X4

2-Cyclopropyl-N-([2-hydroxy-cyclopentyl]-methyl)-4-methyl-6-morpholin-4-yl-pyridine-3-carboxylic acid amide

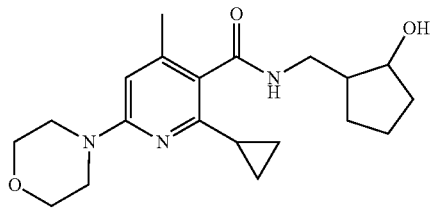 [SMILES: Cc1cc(N2CCOCC2)nc(C2CC2)c1C(=O)NCC1CCCC1O]

To a solution of 2-cyclopropyl-4-methyl-6-morpholin-4-yl-pyridine-3-carboxylic acid (synthesized according to the methods described in sections a) to d) of example X1) (0.50 g, 1.91 mmol) in dichloromethane (20 ml) are added N-ethyldiisopropylamine (0.81 ml, 4.77 mmol), 1-ethyl-3-(3-dimethylaminopropyl) carbodiimide hydrochloride (0.42 g, 2.29 mmol), and 1-hydroxybenzotriazole hydrate (0.05 g, 0.38 mmol). The mixture is stirred for 15 min at RT, and then cooled to 0° C., before 2-(aminomethyl)cyclopentanol (0.22 g, 1.91 mmol) is added and stirring is continued for 3 days. After completion of the reaction, the mixture is diluted with ethyl acetate and 10% aqueous ammonium chloride. The organic layer is separated and washed with saturated sodium hydrogencarbonate solution and brine, dried over magnesium sulphate and evaporated to dryness affording example X4 as crude product. The crude product is purified by flash chromatography (silica gel, 50% ethyl acetate/cyclohexane) to yield the first eluting diastereomer of 2-cyclopropyl-N-([2-hydroxy-cyclopentyl]-methyl)-4-methyl-6-morpholin-4-yl-pyridine-3-carboxylic acid amide (example X4a) (0.34 g, 0.95 mmol, [M+H]⁺360.2) and the second eluting diastereomer of 2-cyclopropyl-N-([2-hydroxy-cyclopentyl]-methyl)-4-methyl-6-morpholin-4-yl-pyridine-3-carboxylic acid amide (example X4b) (0.27 g, 0.75 mmol, [M+H]⁺360.2) as white solids.

Synthesis of Example X5

N-(3-Hydroxy-4,4-dimethyl-pentyl)-2-isopropyl-4-methyl-6-morpholin-4-yl-pyridine-3-carboxylic acid amide

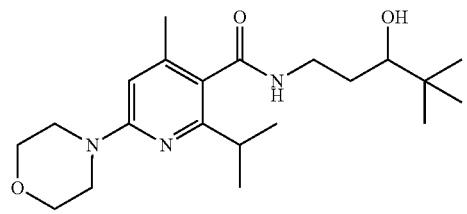 [SMILES: Cc1cc(N2CCOCC2)nc(C(C)C)c1C(=O)NCCC(O)C(C)(C)C]

To a solution of 2-isopropyl-4-methyl-6-morpholin-4-yl-pyridine-3-carboxylic acid (synthesized similar to the methods described in sections a) to d) of example X1) (1.86 g, 7.05 mmol) in tetrahydrofuran (60 ml) are added triethylamine (2.9 ml, 21.1 mol) and 0-(7-azabenzotriazol-1-yl)N,N,N',N'-tetramethyluronium hexafluorophosphate (2.69 g, 7.05 mmol). The mixture is stirred for 15 min at RT, before 1-amino-4,4-dimethylpentan-3-ol (1.02 g, 7.76 mmol) is added and stirring is continued for 18 h. After completion of the reaction, the mixture is diluted with ethyl acetate and 10% aqueous ammonium chloride. The organic layer is separated and washed with saturated sodium hydrogencarbonate solution and brine, dried over magnesium sulphate and evaporated to dryness. The crude product is purified by flash chromatography (silica gel, 30% ethyl acetate/cyclohexane) to yield N-(3-hydroxy-4,4-dimethyl-pentyl)-2-isopropyl-4-methyl-6-morpholin-4-yl-pyridine-3-carboxylic acid amide (example X5) (1.30 g, 3.44 mmol, 49%). [M+H]⁺378.3.

Examples X5a and X5b: N-(3-Hydroxy-4,4-dimethyl-pentyl)-2-isopropyl-4-methyl-6-morpholin-4-yl-pyridine-3-carboxylic acid amide (1.1 g) was resolved into its corresponding enantiomers using chiral HPLC with the following conditions. Column, Chiralpak AD-H, 5µ, 250×20 mm; mobile phase, n-heptane/iso-propanol=90:10 (v/v); flow rate, 19 ml/min; detection, UV (254 nm), 80 separations with 15 mg racemic material each. Analytical HPLC conditions. Column, Chiralpak AD-H, 250×4.6 mm; mobile phase, n-heptane/iso-propanol=90:10 (v/v); flow rate, 1 ml/min; detection, UV (254 nm). Retention time (min): first eluting enantiomer, 6.07 (94% ee); second eluting enantiomer, 8.40

(99% ee). Separation by chiral HPLC affords the first eluting enantiomer of N-(3-hydroxy-4,4-dimethyl-pentyl)-2-isopropyl-4-methyl-6-morpholin-4-yl-pyridine-3-carboxylic acid amide (example X5a) (0.44 g; [M+H]$^+$378.3) and the second eluting enantiomer of N-(3-hydroxy-4,4-dimethyl-pentyl)-2-isopropyl-4-methyl-6-morpholin-4-yl-pyridine-3-carboxylic acid amide (example X5b) (0.42 g; [M+H]$^+$378.3) as white solids.

Synthesis of Example X6

2-Isopropyl-4-methyl-6-morpholin-4-yl-N-(4,4,4-trifluoro-3-hydroxy-butyl)-pyridine-3-carboxylic acid amide

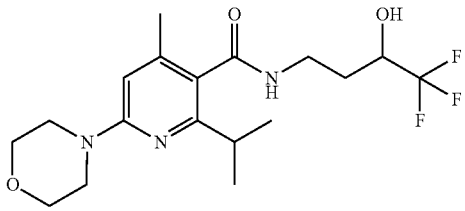 [SMILES: Cc1cc(N2CCOCC2)nc(C(C)C)c1C(=O)NCCC(O)C(F)(F)F]

To a solution of 2-isopropyl-4-methyl-6-morpholin-4-yl-pyridine-3-carboxylic acid (synthesized similar to the methods described in sections a) to d) of example X1) (1.40 g, 5.30 mmol) in tetrahydrofuran (40 ml) are added triethylamine (2.9 ml, 21.2 mol) and 0-(7-azabenzotriazol-1-yl)N,N,N',N'-tetramethyluronium hexafluorophosphate (2.9 g, 5.3 mmol). The mixture is stirred for 15 min at RT, before 4-amino-1,1,1-trifluorobutan-2-ol hydrochloride (1.05 g, 5.8 mmol) is added and stirring is continued for 18 h. After completion of the reaction, the mixture is diluted with ethyl acetate and 10% aqueous ammonium chloride. The organic layer is separated and washed with saturated sodium hydrogencarbonate solution and brine, dried over magnesium sulphate and evaporated to dryness. The crude product is purified by flash chromatography (silica gel, 50% ethyl acetate/cyclohexane) to yield 2-Isopropyl-4-methyl-6-morpholin-4-yl-N-(4,4,4-trifluoro-3-hydroxy-butyl)-pyridine-3-carboxylic acid amide (example X6) (1.24 g, 3.18 mmol, 60%). [M+H]$^+$390.2.

Examples X6a and X6b: 2-Isopropyl-4-methyl-6-morpholin-4-yl-N-(4,4,4-trifluoro-3-hydroxy-butyl)-pyridine-3-carboxylic acid amide was resolved into its corresponding enantiomers using chiral HPLC with the following conditions. Column, Chiralpak AD-H, 5µ, 250×20 mm; mobile phase, n-heptane/iso-propanol=90:10 (v/v); flow rate, 19 ml/min; detection, UV (254 nm). Analytical HPLC conditions. Column, Chiralpak AD-H, 250×4.6 mm; mobile phase, n-heptane/ethanol=95:5 (v/v); flow rate, 1 ml/min; detection, UV (254 nm). Retention time (min): first eluting enantiomer, 9.60 (example X6a); second eluting enantiomer, 12.21 (example X6b).

Synthesis of Example X7

N-[[(1S,2R)-2-Hydroxy-cyclohexyl]-methyl]-2-isopropyl-4-methyl-6-morpholin-4-yl-pyridine-3-carboxylic acid amide

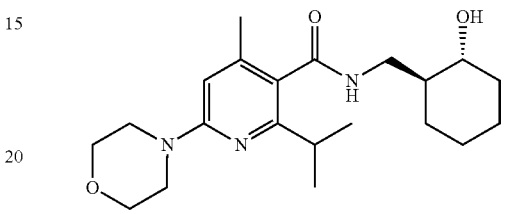

To a solution of 2-isopropyl-4-methyl-6-morpholin-4-yl-pyridine-3-carboxylic acid (synthesized similar to the methods described in sections a) to d) of example X1) (0.20 g, 0.76 mmol) in dichloromethane (15 ml) are added N-ethyl-diisopropylamine (0.32 ml, 0.89 mmol), 1-ethyl-3-(3-dimethylaminopropyl) carbodiimide hydrochloride (0.17 g, 0.91 mmol), and 1-hydroxybenzotriazole hydrate (0.02 g, 0.15 mmol). The mixture is stirred for 15 min at RT, and then cooled to 0° C., before (1R,2S)-2-(aminomethyl)cyclohexanol (0.09 g, 0.76 mmol) is added and stirring is continued for 18 h. After completion of the reaction, the mixture is diluted with ethyl acetate and 10% aqueous ammonium chloride. The organic layer is separated and washed with saturated sodium hydrogencarbonate solution and brine, dried over magnesium sulphate and evaporated to dryness. The crude product is purified by flash chromatography (silica gel, 50% ethyl acetate/cyclohexane) to yield N-[[(1S,2R)-2-hydroxy-cyclohexyl]-methyl]-2-isopropyl-4-methyl-6-morpholin-4-yl-pyridine-3-carboxylic acid amide (example X7) (0.18 g, 0.48 mmol, 63%). [M+H]$^+$376.3.

Synthesis of Further Examples

The synthesis of further examples was carried out according to the methods already described. Table 1 shows which compound was produced according to which method. It is evident to the person skilled in the art which deducts and reagents were used in each case.

TABLE 1

| Example | Chemical name | Preparation according to example | MS m/z [M + H]$^+$ |
| --- | --- | --- | --- |
| 13 | 1-[6-Ethylsulfanyl-5-[(3-fluorophenyl)-methyl-carbamoyl]-4-methyl-pyridin-2-yl]-piperidine-4-carboxylic acid methyl ester | 5 | 446.2 |
| 15 | 2-Ethylsulfanyl-N-[(3-fluorophenyl)-methyl]-6-(4-hydroxy-piperidin-1-yl)-4-methyl-pyridine-3-carboxylic acid amide | 5 | 404.2 |
| 17 | 2-Ethylsulfanyl-N-[(4-fluoro-2-methoxy-phenyl)-methyl]-4-methyl-6-morpholin-4-yl-pyridine-3-carboxylic acid amide | 1 | 420.2 |

TABLE 1-continued

| Example | Chemical name | Preparation according to example | MS m/z [M + H]+ |
|---|---|---|---|
| 25 | 2-Ethylsulfanyl-N-[(3-fluorophenyl)-methyl]-4-methyl-6-pyrrolidin-1-yl-pyridine-3-carboxylic acid amide | 8 | 374.2 |
| 26 | 2-Ethylsulfanyl-N-[(3-fluorophenyl)-methyl]-4-methyl-6-(1,2,3,4-tetrahydro-isoquinolin-2-yl)-pyridine-3-carboxylic acid amide | 8 | 436.2 |
| 27 | 2-Ethylsulfanyl-N-[(3-fluorophenyl)-methyl]-4-methyl-6-[6-(trifluoromethyl)-1,2,3,4-tetrahydro-isoquinolin-2-yl]-pyridine-3-carboxylic acid amide | 5 | 504.2 |
| 28 | (E)-N-(4-fluorobenzyl)-4-methyl-6-morpholino-2-(prop-1-enyl)-pyridine-3-carboxylic acid amide | 9 | 370.2 |
| 29 | N-[(4-Fluorophenyl)-methyl]-4-methyl-6-morpholin-4-yl-2-propyl-pyridine-3-carboxylic acid amide | 10 | 372.2 |
| 30 | 2-Ethylsulfanyl-N-[(3-fluorophenyl)-methyl]-6-(3-methoxy-pyrrolidin-1-yl)-4-methyl-pyridine-3-carboxylic acid amide | 6 | 404.2 |
| 31 | 2-Ethylsulfanyl-N-[(3-fluorophenyl)-methyl]-4-methyl-6-(4-methyl-piperazin-1-yl)-pyridine-3-carboxylic acid amide | 4 | 403.2 |
| 32 | 2-Ethylsulfanyl-N-[(3-fluorophenyl)-methyl]-4-methyl-6-piperidin-1-yl-pyridine-3-carboxylic acid amide | 4 | 388.2 |
| 33 | 6-Dimethylamino-2-ethylsulfanyl-N-[(3-fluorophenyl)-methyl]-4-methyl-pyridine-3-carboxylic acid amide | 4 | 348.1 |
| 34 | 2-Ethylsulfanyl-N-[(3-fluorophenyl)-methyl]-4-methyl-6-methylamino-pyridine-3-carboxylic acid amide | 4 | 334.1 |
| 35 | 2-Ethylsulfanyl-N-[(3-fluorophenyl)-methyl]-6-(2-methoxy-ethyl-methyl-amino)-4-methyl-pyridine-3-carboxylic acid amide | 4 | 392.2 |
| 36 | 2-Ethylsulfanyl-N-[(3-fluorophenyl)-methyl]-6-(2-methoxy-ethylamino)-4-methyl-pyridine-3-carboxylic acid amide | 4 | 378.2 |
| 37 | N-[(3-Fluorophenyl)-methyl]-2-(isopropylsulfanyl)-4-methyl-6-morpholin-4-yl-pyridine-3-carboxylic acid amide | 2 | 404.2 |
| 38 | 2-Ethoxy-N-[(3-fluorophenyl)-methyl]-4-methyl-6-morpholin-4-yl-pyridine-3-carboxylic acid amide | 19 | 374.2 |
| 39 | N-[(4-Fluorophenyl)-methyl]-2-methoxy-4-methyl-6-morpholin-4-yl-pyridine-3-carboxylic acid amide | 19 | 360.2 |
| 40 | N-[(3-Fluorophenyl)-methyl]-4-methyl-2-methylsulfanyl-6-morpholin-4-yl-pyridine-3-carboxylic acid amide | 2 | 376.1 |
| 41 | N-[(3,4-Difluoro-phenyl)-methyl]-2-ethylsulfanyl-4-methyl-6-morpholin-4-yl-pyridine-3-carboxylic acid amide | 1 | 408.1 |
| 42 | 2-Ethylsulfanyl-4-methyl-N-(3-methyl-butyl)-6-morpholin-4-yl-pyridine-3-carboxylic acid amide | 1 | 352.2 |
| 43 | N-(Cyclopentyl-methyl)-2-ethylsulfanyl-4-methyl-6-morpholin-4-yl-pyridine-3-carboxylic acid amide | 1 | 364.2 |
| 44 | N-(2-Cyclopentyl-ethyl)-2-ethylsulfanyl-4-methyl-6-morpholin-4-yl-pyridine-3-carboxylic acid amide | 1 | 378.2 |
| 45 | 2-Ethylsulfanyl-N-[(6-fluoro-pyridin-2-yl)-methyl]-4-methyl-6-morpholin-4-yl-pyridine-3-carboxylic acid amide | 1 | 391.2 |
| 46 | 2-Ethylsulfanyl-N-[(5-fluoro-pyridin-2-yl)-methyl]-4-methyl-6-morpholin-4-yl-pyridine-3-carboxylic acid amide | 1 | 391.2 |
| 47 | N-(2,2-Dimethyl-propyl)-2-ethylsulfanyl-4-methyl-6-morpholin-4-yl-pyridine-3-carboxylic acid amide | 1 | 352.2 |
| 48 | 2-Ethylsulfanyl-N-[(3-fluorophenyl)-methyl]-4-methyl-6-(2-methyl-morpholin-4-yl)-pyridine-3-carboxylic acid amide | 5 | 404.2 |
| 49 | 2-Ethylsulfanyl-N-[(3-fluorophenyl)-methyl]-6-(4-methoxy-piperidin-1-yl)-4-methyl-pyridine-3-carboxylic acid amide | 4 | 418.2 |

TABLE 1-continued

| Example | Chemical name | Preparation according to example | MS m/z [M + H]+ |
|---|---|---|---|
| 50 | 2-Ethylsulfanyl-4-methyl-6-morpholin-4-yl-N-[(2-phenyl-phenyl)-methyl]-pyridine-3-carboxylic acid amide | 1 | 448.2 |
| 51 | 2-Ethylsulfanyl-4-methyl-6-morpholin-4-yl-N-[[2-(trifluoromethyl)-phenyl]-methyl]-pyridine-3-carboxylic acid amide | 1 | 440.2 |
| 52 | 2-Ethylsulfanyl-N-[(3-fluorophenyl)-methyl]-6-[(4-fluorophenyl)-methyl-methyl-amino]-4-methyl-pyridine-3-carboxylic acid amide | 4 | 442.2 |
| 53 | 2-Ethylsulfanyl-4-methyl-6-morpholin-4-yl-N-(3-phenyl-propyl)-pyridine-3-carboxylic acid amide | 1 | 400.2 |
| 54 | 2-Ethylsulfanyl-4-methyl-6-morpholin-4-yl-N-phenethyl-pyridine-3-carboxylic acid amide | 1 | 386.2 |
| 55 | N-Benzyl-2-ethylsulfanyl-4-methyl-6-morpholin-4-yl-pyridine-3-carboxylic acid amide | 1 | 372.2 |
| 56 | N-[(3-Fluorophenyl)-methyl]-4-methyl-6-morpholin-4-yl-2-(propylsulfanyl)-pyridine-3-carboxylic acid amide | 2 | 404.2 |
| 57 | 2-(Butylsulfanyl)-N-[(3-fluorophenyl)-methyl]-4-methyl-6-morpholin-4-yl-pyridine-3-carboxylic acid amide | 2 | 418.2 |
| 58 | 2-Ethylsulfanyl-5-fluoro-N-[(3-fluorophenyl)-methyl]-4-methyl-6-morpholin-4-yl-pyridine-3-carboxylic acid amide | 2 | 408.1 |
| 59 | 2-Ethylsulfanyl-4-methyl-6-morpholin-4-yl-N-[[3-(trifluoromethyl)phenyl]-methyl]-pyridine-3-carboxylic acid amide | 1 | 440.2 |
| 60 | 2-Ethylsulfanyl-4-methyl-6-morpholin-4-yl-N-[[4-(trifluoromethyl)-phenyl]-methyl]-pyridine-3-carboxylic acid amide | 1 | 440.2 |
| 61 | 2-Ethylsulfanyl-N-[(3-fluorophenyl)-methyl]-4-methyl-6-[methyl-(tetrahydro-pyran-4-yl-methyl)-amino]-pyridine-3-carboxylic acid amide | 5 | 432.2 |
| 62 | N-[(3-Fluorophenyl)-methyl]-4-methyl-2-(2-methyl-propylsulfanyl)-6-morpholin-4-yl-pyridine-3-carboxylic acid amide | 2 | 418.2 |
| 63 | N-[(3-Fluorophenyl)-methyl]-2-(2-methoxy-ethylsulfanyl)-4-methyl-6-morpholin-4-yl-pyridine-3-carboxylic acid amide | 2 | 420.2 |
| 64 | 2-Ethoxy-N-[(4-fluorophenyl)-methyl]-4-methyl-6-morpholin-4-yl-pyridine-3-carboxylic acid amide | 19 | 374.2 |
| 65 | 2-Dimethylamino-N-[(3-fluorophenyl)-methyl]-4-methyl-6-morpholin-4-yl-pyridine-3-carboxylic acid amide | 24 | 373.2 |
| 66 | 6-(2,6-Dimethyl-morpholin-4-yl)-2-ethylsulfanyl-N-[(3-fluorophenyl)-methyl]-4-methyl-pyridine-3-carboxylic acid amide | 5 | 418.2 |
| 67 | N-(4,4-Dimethyl-pentyl)-2-ethylsulfanyl-4-methyl-6-morpholin-4-yl-pyridine-3-carboxylic acid amide | 1 | 380.2 |
| 68 | 2-Ethylsulfanyl-4-methyl-6-morpholin-4-yl-N-(2-tetrahydro-pyran-2-yl-ethyl)-pyridine-3-carboxylic acid amide | 1 | 394.2 |
| 69 | 2-Ethylsulfanyl-4-methyl-6-morpholin-4-yl-N-(tetrahydro-pyran-2-yl-methyl)-pyridine-3-carboxylic acid amide | 1 | 380.2 |
| 70 | 2-Ethylsulfanyl-N-[(3-fluorophenyl)-methyl]-4-methyl-6-(4-methyl-piperidin-1-yl)-pyridine-3-carboxylic acid amide | 5 | 402.2 |
| 71 | 2-Ethylsulfanyl-N-[[2-(4-fluorophenyl)-phenyl]-methyl]-4-methyl-6-morpholin-4-yl-pyridine-3-carboxylic acid amide | 1 | 466.2 |
| 72 | 2-[[6-Ethylsulfanyl-5-[(3-fluorophenyl)-methyl-carbamoyl]-4-methyl-pyridin-2-yl]-methyl-amino]-acetic acid ethyl ester | 5 | 420.2 |
| 73 | 6-(4-Cyclopropyl-piperazin-1-yl)-2-ethylsulfanyl-N-[(3-fluorophenyl)-methyl]-4-methyl-pyridine-3-carboxylic acid amide | 5 | 429.2 |
| 74 | 6-(4,4-Dimethyl-piperidin-1-yl)-2-ethylsulfanyl-N-[(3-fluorophenyl)-methyl]-4-methyl-pyridine-3-carboxylic acid amide | 5 | 416.2 |

TABLE 1-continued

| Example | Chemical name | Preparation according to example | MS m/z [M + H]+ |
|---|---|---|---|
| 75 | 2-Ethylsulfanyl-4-methyl-6-morpholin-4-yl-N-[[4-(trifluoromethylsulfanyl)-phenyl]-methyl]-pyridine-3-carboxylic acid amide | 1 | 472.1 |
| 76 | N-(Cyclohexyl-methyl)-2-ethylsulfanyl-4-methyl-6-morpholin-4-yl-pyridine-3-carboxylic acid amide | 1 | 378.2 |
| 77 | 2-Ethylsulfanyl-N-(2-methoxy-ethyl)-4-methyl-6-morpholin-4-yl-pyridine-3-carboxylic acid amide | 1 | 340.2 |
| 78 | 2-Ethylsulfanyl-N-(3-methoxy-propyl)-4-methyl-6-morpholin-4-yl-pyridine-3-carboxylic acid amide | 1 | 354.2 |
| 79 | 2-Ethylsulfanyl-4-methyl-N-(4-methyl-pentyl)-6-morpholin-4-yl-pyridine-3-carboxylic acid amide | 1 | 366.2 |
| 80 | N-Butyl-2-ethylsulfanyl-4-methyl-6-morpholin-4-yl-pyridine-3-carboxylic acid amide | 1 | 338.2 |
| 81 | 2-Ethylsulfanyl-4-methyl-6-morpholin-4-yl-N-pentyl-pyridine-3-carboxylic acid amide | 1 | 352.2 |
| 82 | 2-Ethylsulfanyl-N-[[4-fluoro-3-(trifluoromethyl)-phenyl]-methyl]-4-methyl-6-morpholin-4-yl-pyridine-3-carboxylic acid amide | 1 | 458.1 |
| 83 | N-(2-tert-Butoxy-ethyl)-2-ethylsulfanyl-4-methyl-6-morpholin-4-yl-pyridine-3-carboxylic acid amide | 1 | 382.2 |
| 84 | 2-Ethylsulfanyl-4-methyl-6-morpholin-4-yl-N-(4,4,4-trifluoro-butyl)-pyridine-3-carboxylic acid amide | 1 | 392.2 |
| 85 | 2-Ethylsulfanyl-N-[[4-fluoro-2-(4-fluorophenyl)-phenyl]-methyl]-4-methyl-6-morpholin-4-yl-pyridine-3-carboxylic acid amide | 1 | 484.2 |
| 86 | N-(4,4-Dimethyl-pentyl)-2-methoxy-4-methyl-6-morpholin-4-yl-pyridine-3-carboxylic acid amide | 3 | 350.2 |
| 87 | N-[(3,4-Difluoro-phenyl)-methyl]-2-methoxy-4-methyl-6-morpholin-4-yl-pyridine-3-carboxylic acid amide | 3 | 378.2 |
| 88 | 2-Methoxy-4-methyl-6-morpholin-4-yl-N-[(2-phenyl-phenyl)-methyl]-pyridine-3-carboxylic acid amide | 3 | 418.2 |
| 89 | N-(4,4-Dimethyl-pentyl)-2-ethoxy-4-methyl-6-morpholin-4-yl-pyridine-3-carboxylic acid amide | 3 | 364.3 |
| 90 | N-[(3,5-Difluoro-phenyl)-methyl]-2-ethoxy-4-methyl-6-morpholin-4-yl-pyridine-3-carboxylic acid amide | 3 | 392.2 |
| 91 | N-[(3,4-Difluoro-phenyl)-methyl]-2-ethoxy-4-methyl-6-morpholin-4-yl-pyridine-3-carboxylic acid amide | 3 | 392.2 |
| 92 | 2-Ethoxy-4-methyl-6-morpholin-4-yl-N-[(2-phenyl-phenyl)-methyl]-pyridine-3-carboxylic acid amide | 3 | 432.2 |
| 93 | 2-Ethylsulfanyl-N-[[3-fluoro-5-(trifluoromethyl)-phenyl]-methyl]-4-methyl-6-morpholin-4-yl-pyridine-3-carboxylic acid amide | 1 | 458.1 |
| 94 | 2-Ethylsulfanyl-N-[[2-fluoro-3-(trifluoromethyl)-phenyl]-methyl]-4-methyl-6-morpholin-4-yl-pyridine-3-carboxylic acid amide | 1 | 458.1 |
| 95 | 2-Ethylsulfanyl-N-[[2-fluoro-5-(trifluoromethyl)-phenyl]-methyl]-4-methyl-6-morpholin-4-yl-pyridine-3-carboxylic acid amide | 1 | 458.1 |
| 96 | 2-Ethylsulfanyl-N-[(3-fluorophenyl)-methyl]-4-methyl-6-([1,4]oxazepane-4-yl)-pyridine-3-carboxylic acid amide | 5 | 404.2 |
| 97 | 2-Ethylsulfanyl-4-methyl-6-morpholin-4-yl-N-[[4-(trifluoromethyloxy)-phenyl]-methyl]-pyridine-3-carboxylic acid amide | 1 | 456.1 |
| 98 | N-[(3-Fluorophenyl)-methyl]-2-methoxy-4-methyl-6-([1,4]oxazepan-4-yl)-pyridine-3-carboxylic acid amide | 5 | 374.2 |
| 99 | 2-Ethoxy-N-[(3-fluorophenyl)-methyl]-4-methyl-6-([1,4]oxazepan-4-yl)-pyridine-3-carboxylic acid amide | 5 | 388.2 |
| 100 | N-[(2,3-Difluoro-phenyl)-methyl]-2-ethylsulfanyl-4-methyl-6-morpholin-4-yl-pyridine-3-carboxylic acid amide | 1 | 408.1 |

TABLE 1-continued

| Example | Chemical name | Preparation according to example | MS m/z [M + H]+ |
|---|---|---|---|
| 101 | N-[(2,5-Difluoro-phenyl)-methyl]-2-ethylsulfanyl-4-methyl-6-morpholin-4-yl-pyridine-3-carboxylic acid amide | 1 | 408.1 |
| 102 | N-[(3-Cyano-phenyl)-methyl]-2-ethylsulfanyl-4-methyl-6-morpholin-4-yl-pyridine-3-carboxylic acid amide | 1 | 397.2 |
| 103 | 2-Ethylsulfanyl-N-(2-isopropoxy-ethyl)-4-methyl-6-morpholin-4-yl-pyridine-3-carboxylic acid amide | 1 | 368.2 |
| 104 | N-(3,3-Dimethyl-butyl)-2-ethylsulfanyl-4-methyl-6-morpholin-4-yl-pyridine-3-carboxylic acid amide | 1 | 366.2 |
| 105 | N-(3-Cyclopentyl-propyl)-2-ethylsulfanyl-4-methyl-6-morpholin-4-yl-pyridine-3-carboxylic acid amide | 1 | 392.2 |
| 106 | N-(2-Cyclohexyl-ethyl)-2-ethylsulfanyl-4-methyl-6-morpholin-4-yl-pyridine-3-carboxylic acid amide | 1 | 392.2 |
| 107 | N-[(2,4-Difluoro-phenyl)-methyl]-2-ethylsulfanyl-4-methyl-6-morpholin-4-yl-pyridine-3-carboxylic acid amide | 1 | 408.1 |
| 108 | 2-Ethylsulfanyl-N-[3-(4-fluorophenyl)-propyl]-4-methyl-6-morpholin-4-yl-pyridine-3-carboxylic acid amide | 1 | 418.2 |
| 109 | 2-Ethylsulfanyl-4-methyl-6-morpholin-4-yl-N-(3-pyridin-2-yl-propyl)-pyridine-3-carboxylic acid amide | 1 | 401.2 |
| 110 | 2-Butoxy-N-[(3-fluorophenyl)-methyl]-4-methyl-6-morpholin-4-yl-pyridine-3-carboxylic acid amide | 21 | 402.2 |
| 111 | N-[(3-Fluorophenyl)-methyl]-4-methyl-6-morpholin-4-yl-2-propoxy-pyridine-3-carboxylic acid amide | 21 | 388.2 |
| 112 | 2-Ethylsulfanyl-N-[(3-fluorophenyl)-methyl]-4-methyl-6-(3-oxo-azetidin-1-yl)-pyridine-3-carboxylic acid amide | 16 | 374.1 |
| 113 | 2-Ethylsulfanyl-N-[3-(3-fluorophenyl)-propyl]-4-methyl-6-morpholin-4-yl-pyridine-3-carboxylic acid amide | 1 | 418.2 |
| 114 | 2-Ethylsulfanyl-4-methyl-6-morpholin-4-yl-N-(3-pyridin-3-yl-propyl)-pyridine-3-carboxylic acid amide | 1 | 401.2 |
| 115 | 2-Ethylsulfanyl-4-methyl-6-morpholin-4-yl-N-(3-pyridin-4-yl-propyl)-pyridine-3-carboxylic acid amide | 1 | 401.2 |
| 116 | N-(5,5-Dimethyl-hexyl)-2-ethylsulfanyl-4-methyl-6-morpholin-4-yl-pyridine-3-carboxylic acid amide | 1 | 394.2 |
| 118 | 2-Ethylsulfanyl-N-[(3-fluorophenyl)-methyl]-4-methyl-6-[methyl-(pyridin-4-yl-methyl)-amino]-pyridine-3-carboxylic acid amide | 5 | 425.2 |
| 119 | 2-Ethylsulfanyl-N-[(3-fluorophenyl)-methyl]-4-methyl-6-[methyl-(pyridin-3-yl-methyl)-amino]-pyridine-3-carboxylic acid amide | 5 | 425.2 |
| 121 | 2-Ethylsulfanyl-N-[(3-fluorophenyl)-methyl]-4-methyl-6-[methyl-(pyridin-2-yl-methyl)-amino]-pyridine-3-carboxylic acid amide | 5 | 425.2 |
| 122 | 2-Ethylsulfanyl-N-[(3-fluorophenyl)-methyl]-4-methyl-6-(pyridin-3-yl-methylamino)-pyridine-3-carboxylic acid amide | 5 | 411.2 |
| 124 | N-[(4-Chlorophenyl)-methyl]-2-ethylsulfanyl-4-methyl-6-morpholin-4-yl-pyridine-3-carboxylic acid amide | 1 | 406.1 |
| 125 | N-[(3-Chlorophenyl)-methyl]-2-ethylsulfanyl-4-methyl-6-morpholin-4-yl-pyridine-3-carboxylic acid amide | 1 | 406.1 |
| 126 | 6-[Bis(2-methoxy-ethyl)-amino]-2-ethylsulfanyl-N-[(3-fluorophenyl)-methyl]-4-methyl-pyridine-3-carboxylic acid amide | 5 | 436.2 |
| 127 | 2-(Ethyl-methyl-amino)-N-[(3-fluorophenyl)-methyl]-4-methyl-6-morpholin-4-yl-pyridine-3-carboxylic acid amide | 20 | 387.2 |
| 128 | 2-Ethylsulfanyl-N-[(3-fluorophenyl)-methyl]-6-(3-methoxy-propyl-methyl-amino)-4-methyl-pyridine-3-carboxylic acid amide | 5 | 406.2 |

TABLE 1-continued

| Example | Chemical name | Preparation according to example | MS m/z [M + H]+ |
|---|---|---|---|
| 129 | 2-Ethylsulfanyl-N-[3-(2-fluorophenyl)-propyl]-4-methyl-6-morpholin-4-yl-pyridine-3-carboxylic acid amide | 1 | 418.2 |
| 130 | 2-Ethylsulfanyl-4-methyl-6-morpholin-4-yl-N-[[3-(trifluoromethyloxy)-phenyl]-methyl]-pyridine-3-carboxylic acid amide | 1 | 456.1 |
| 131 | 2-Ethylsulfanyl-N-[[3-(methoxymethyl)-phenyl]-methyl]-4-methyl-6-morpholin-4-yl-pyridine-3-carboxylic acid amide | 1 | 416.2 |
| 132 | 2-Ethoxy-4-methyl-6-morpholin-4-yl-N-[[4-(trifluoromethyl)-phenyl]-methyl]-pyridine-3-carboxylic acid amide | 117 | 424.2 |
| 133 | 2-Ethoxy-4-methyl-6-morpholin-4-yl-N-(4,4,4-trifluoro-butyl)-pyridine-3-carboxylic acid amide | 117 | 376.2 |
| 134 | N-(1,3-Benzodioxol-5-yl-methyl)-2-ethylsulfanyl-4-methyl-6-morpholin-4-yl-pyridine-3-carboxylic acid amide | 1 | 416.2 |
| 135 | 2-Ethylsulfanyl-N-[[2-fluoro-4-(trifluoromethyl)-phenyl]-methyl]-4-methyl-6-morpholin-4-yl-pyridine-3-carboxylic acid amide | 1 | 458.1 |
| 136 | 6-(Azepan-1-yl)-2-ethylsulfanyl-N-[(3-fluorophenyl)-methyl]-4-methyl-pyridine-3-carboxylic acid amide | 5 | 402.2 |
| 137 | 2-Ethylsulfanyl-N-[(4-methoxyphenyl)-methyl]-4-methyl-6-morpholin-4-yl-pyridine-3-carboxylic acid amide | 1 | 402.2 |
| 140 | 2-Methoxy-4-methyl-6-morpholin-4-yl-N-(4,4,4-trifluoro-butyl)-pyridine-3-carboxylic acid amide | 117 | 362.2 |
| 141 | N-(3-Cyclopropyl-propyl)-2-ethylsulfanyl-4-methyl-6-morpholin-4-yl-pyridine-3-carboxylic acid amide | 1 | 364.2 |
| 142 | 2-Ethylsulfanyl-N-[[3-fluoro-4-(trifluoromethyl)-phenyl]-methyl]-4-methyl-6-morpholin-4-yl-pyridine-3-carboxylic acid amide | 1 | 458.1 |
| 143 | 2-Ethylsulfanyl-N-[(3-fluorophenyl)-methyl]-4-methyl-6-(3-oxo-piperazin-1-yl)-pyridine-3-carboxylic acid amide | 258 | 403.2 |
| 144 | 6-(4-Acetyl-piperazin-1-yl)-2-ethylsulfanyl-N-[(3-fluorophenyl)-methyl]-4-methyl-pyridine-3-carboxylic acid amide | 258 | 431.2 |
| 145 | N-[(4-Cyano-phenyl)-methyl]-2-ethylsulfanyl-4-methyl-6-morpholin-4-yl-pyridine-3-carboxylic acid amide | 1 | 397.2 |
| 146 | 2-Ethylsulfanyl-N-[[4-(methoxymethyl)-phenyl]-methyl]-4-methyl-6-morpholin-4-yl-pyridine-3-carboxylic acid amide | 1 | 416.2 |
| 147 | 2-Ethylsulfanyl-N-[[3-fluoro-4-(methoxymethyl)-phenyl]-methyl]-4-methyl-6-morpholin-4-yl-pyridine-3-carboxylic acid amide | 1 | 434.2 |
| 148 | N-[(4-Dimethylaminophenyl)-methyl]-2-ethylsulfanyl-4-methyl-6-morpholin-4-yl-pyridine-3-carboxylic acid amide | 1 | 415.2 |
| 149 | 2-Ethylsulfanyl-N-[[4-fluoro-3-(methoxymethyl)-phenyl]-methyl]-4-methyl-6-morpholin-4-yl-pyridine-3-carboxylic acid amide | 1 | 434.2 |
| 150 | 2-Ethylsulfanyl-N-[(3-fluorophenyl)-methyl]-4-methyl-6-(4-methyl-3-oxo-piperazin-1-yl)-pyridine-3-carboxylic acid amide | 5 | 417.2 |
| 151 | 2-Ethylsulfanyl-N-[(3-fluorophenyl)-methyl]-4-methyl-6-(6-oxa-2-azaspiro[3.3]heptan-2-yl)-pyridine-3-carboxylic acid amide | 5 | 402.2 |
| 152 | N-(4,4-Dimethyl-pentyl)-4-methyl-2-methylsulfanyl-6-morpholin-4-yl-pyridine-3-carboxylic acid amide | 1 | 366.2 |
| 153 | 4-Methyl-2-methylsulfanyl-6-morpholin-4-yl-N-(4,4,4-trifluoro-butyl)-pyridine-3-carboxylic acid amide | 1 | 378.1 |
| 155 | N-[(3,4-Difluoro-phenyl)-methyl]-4-methyl-2-methylsulfanyl-6-morpholin-4-yl-pyridine-3-carboxylic acid amide | 154 | 394.1 |

TABLE 1-continued

| Example | Chemical name | Preparation according to example | MS m/z [M + H]+ |
|---|---|---|---|
| 156 | N-[(3,5-Difluoro-phenyl)-methyl]-4-methyl-2-methylsulfanyl-6-morpholin-4-yl-pyridine-3-carboxylic acid amide | 154 | 394.1 |
| 157 | 4-Methyl-2-methylsulfanyl-6-morpholin-4-yl-N-[[4-(trifluoromethyl)-phenyl]-methyl]-pyridine-3-carboxylic acid amide | 154 | 426.1 |
| 158 | 2-Ethylsulfanyl-N-[(3-fluorophenyl)-methyl]-4-methyl-6-(6-oxo-2,3,4,7,8,8a-hexahydro-1H-pyrrolo[1,2-a]pyrazin-2-yl)-pyridine-3-carboxylic acid amide | 5 | 443.2 |
| 159 | 2-Ethylsulfanyl-N-[(3-fluorophenyl)-methyl]-4-methyl-6-(3-oxa-6-azabicyclo[2.2.1]heptan-6-yl)-pyridine-3-carboxylic acid amide | 5 | 402.2 |
| 160 | N-(3-Cyano-propyl)-2-ethylsulfanyl-4-methyl-6-morpholin-4-yl-pyridine-3-carboxylic acid amide | 1 | 349.2 |
| 161 | 2-Ethylsulfanyl-4-methyl-6-morpholin-4-yl-N-(p-tolyl-methyl)-pyridine-3-carboxylic acid amide | 1 | 386.2 |
| 162 | 2-Ethylsulfanyl-4-methyl-N-(3-methylsulfonyl-propyl)-6-morpholin-4-yl-pyridine-3-carboxylic acid amide | 1 | 402.1 |
| 163 | N-(4-Cyano-butyl)-2-ethylsulfanyl-4-methyl-6-morpholin-4-yl-pyridine-3-carboxylic acid amide | 1 | 363.2 |
| 164 | 2-Ethylsulfanyl-4-methyl-6-morpholin-4-yl-N-(m-tolyl-methyl)-pyridine-3-carboxylic acid amide | 1 | 386.2 |
| 165 | N-[(4-Chlorophenyl)-methyl]-2-methoxy-4-methyl-6-morpholin-4-yl-pyridine-3-carboxylic acid amide | 117 | 376.1 |
| 166 | N-[(4-Chlorophenyl)-methyl]-2-ethoxy-4-methyl-6-morpholin-4-yl-pyridine-3-carboxylic acid amide | 117 | 390.2 |
| 167 | 6-(2-Ethyl-morpholin-4-yl)-2-ethylsulfanyl-N-[(3-fluorophenyl)-methyl]-4-methyl-pyridine-3-carboxylic acid amide | 5 | 418.2 |
| 168 | N-[(4-Chlorophenyl)-methyl]-4-methyl-2-methylsulfanyl-6-morpholin-4-yl-pyridine-3-carboxylic acid amide | 154 | 392.1 |
| 170 | 2-Ethylsulfanyl-N-[(3-fluorophenyl)-methyl]-4-methyl-6-(methyl-pyridin-2-yl-amino)-pyridine-3-carboxylic acid amide | 5 | 411.2 |
| 173 | 2-(Ethyl-methyl-amino)-N-[(4-fluorophenyl)-methyl]-4-methyl-6-[(3R)-3-methyl-morpholin-4-yl]-pyridine-3-carboxylic acid amide | 172 | 401.2 |
| 175 | 2-Ethylsulfanyl-N-[(3-fluorophenyl)-methyl]-4-methyl-6-[methyl-(tetrahydro-pyran-3-yl-methyl)-amino]-pyridine-3-carboxylic acid amide | 5 | 432.2 |
| 177 | 2-Ethylsulfanyl-N-[(4-fluorophenyl)-methyl]-4-methyl-6-[(3R)-3-methyl-morpholin-4-yl]-pyridine-3-carboxylic acid amide | 176 | 404.2 |
| 178 | 6-(3-Ethyl-morpholin-4-yl)-2-ethylsulfanyl-N-[(3-fluorophenyl)-methyl]-4-methyl-pyridine-3-carboxylic acid amide | 258 | 418.2 |
| 179 | 2-Ethylsulfanyl-N-[(3-fluorophenyl)-methyl]-6-[(3R)-3-(methoxymethyl)-morpholin-4-yl]-4-methyl-pyridine-3-carboxylic acid amide | 258 | 434.2 |
| 180 | 2-Ethylsulfanyl-N-[(3-fluorophenyl)-methyl]-6-[(3S)-3-(methoxymethyl)-morpholin-4-yl]-4-methyl-pyridine-3-carboxylic acid amide | 258 | 434.2 |
| 181 | N-[(4-Fluorophenyl)-methyl]-2-methoxy-4-methyl-6-[(3R)-3-methyl-morpholin-4-yl]-pyridine-3-carboxylic acid amide | 176 | 374.2 |
| 182 | 2-Ethoxy-N-[(4-fluorophenyl)-methyl]-4-methyl-6-[(3R)-3-methyl-morpholin-4-yl]-pyridine-3-carboxylic acid amide | 176 | 388.2 |
| 183 | 2-Dimethylamino-N-(4,4-dimethyl-pentyl)-4-methyl-6-[(3R)-3-methyl-morpholin-4-yl]-pyridine-3-carboxylic acid amide | 172 | 377.3 |
| 184 | N-(4,4-Dimethyl-pentyl)-2-(ethyl-methyl-amino)-4-methyl-6-[(3R)-3-methyl-morpholin-4-yl]-pyridine-3-carboxylic acid amide | 172 | 391.3 |

TABLE 1-continued

| Example | Chemical name | Preparation according to example | MS m/z [M + H]+ |
|---|---|---|---|
| 185 | N-(4,4-Dimethyl-pentyl)-2-isopropyl-4-methyl-6-[(3R)-3-methyl-morpholin-4-yl]-pyridine-3-carboxylic acid amide | 169 | 376.3 |
| 186 | N-(4,4-Dimethyl-pentyl)-2-methoxy-4-methyl-6-[(3R)-3-methyl-morpholin-4-yl]-pyridine-3-carboxylic acid amide | 176 | 364.3 |
| 187 | N-(4,4-Dimethyl-pentyl)-2-ethoxy-4-methyl-6-[(3R)-3-methyl-morpholin-4-yl]-pyridine-3-carboxylic acid amide | 176 | 378.3 |
| 188 | 2-(Ethyl-methyl-amino)-4-methyl-6-morpholin-4-yl-N-[[4-(trifluoromethyl)-phenyl]-methyl]-pyridine-3-carboxylic acid amide | 174 | 437.2 |
| 189 | N-(4,4-Dimethyl-pentyl)-2-(ethyl-methyl-amino)-4-methyl-6-morpholin-4-yl-pyridine-3-carboxylic acid amide | 174 | 377.3 |
| 190 | 2-(Ethyl-methyl-amino)-4-methyl-6-morpholin-4-yl-N-(4,4,4-trifluoro-butyl)-pyridine-3-carboxylic acid amide | 174 | 389.2 |
| 191 | N-[(4-Chlorophenyl)-methyl]-2-(ethyl-methyl-amino)-4-methyl-6-morpholin-4-yl-pyridine-3-carboxylic acid amide | 174 | 403.2 |
| 192 | N-(4,4-Dimethyl-pentyl)-4-methyl-6-[(3R)-3-methyl-morpholin-4-yl]-2-methylsulfanyl-pyridine-3-carboxylic acid amide | 176 | 380.2 |
| 193 | N-(4,4-Dimethyl-pentyl)-2-ethylsulfanyl-4-methyl-6-[(3R)-3-methyl-morpholin-4-yl]-pyridine-3-carboxylic acid amide | 176 | 394.2 |
| 194 | N-[(4-Fluorophenyl)-methyl]-4-methyl-6-[(3R)-3-methyl-morpholin-4-yl]-2-(1-methyl-propyl)-pyridine-3-carboxylic acid amide | 169 | 400.2 |
| 195 | N-(4,4-Dimethyl-pentyl)-4-methyl-6-[(3R)-3-methyl-morpholin-4-yl]-2-(1-methyl-propyl)-pyridine-3-carboxylic acid amide | 169 | 390.3 |
| 196 | 2-Cyclopropyl-N-[(4-fluorophenyl)-methyl]-4-methyl-6-[(3R)-3-methyl-morpholin-4-yl]-pyridine-3-carboxylic acid amide | 169 | 384.2 |
| 197 | N-[(4-Fluorophenyl)-methyl]-4-methyl-6-[(3R)-3-methyl-morpholin-4-yl]-2-propyl-pyridine-3-carboxylic acid amide | 169 | 386.2 |
| 198 | 2-Cyclopropyl-N-(4,4-dimethyl-pentyl)-4-methyl-6-[(3R)-3-methyl-morpholin-4-yl]-pyridine-3-carboxylic acid amide | 169 | 374.3 |
| 199 | N-(4,4-Dimethyl-pentyl)-4-methyl-6-[(3R)-3-methyl-morpholin-4-yl]-2-propyl-pyridine-3-carboxylic acid amide | 169 | 376.3 |
| 200 | 2-Ethylsulfanyl-N-[(3-fluorophenyl)-methyl]-4-methyl-6-(methyl-pyridin-4-yl-amino)-pyridine-3-carboxylic acid amide | 171 | 411.2 |
| 201 | 2-Ethylsulfanyl-N-[(4-fluoro-3-methyl-phenyl)-methyl]-4-methyl-6-morpholin-4-yl-pyridine-3-carboxylic acid amide | 1 | 404.2 |
| 202 | 2-Ethylsulfanyl-N-(2-hydroxy-3-phenyl-propyl)-4-methyl-6-morpholin-4-yl-pyridine-3-carboxylic acid amide | 1 | 416.2 |
| 203 | N-[(3,4-Difluoro-phenyl)-methyl]-2-(ethyl-methyl-amino)-4-methyl-6-morpholin-4-yl-pyridine-3-carboxylic acid amide | 174 | 405.2 |
| 204 | N-[(3,5-Difluoro-phenyl)-methyl]-2-(ethyl-methyl-amino)-4-methyl-6-morpholin-4-yl-pyridine-3-carboxylic acid amide | 174 | 405.2 |
| 205 | 2-Dimethylamino-N-[(4-fluorophenyl)-methyl]-4-methyl-6-morpholin-4-yl-pyridine-3-carboxylic acid amide | 174 | 373.2 |
| 206 | N-[(3,4-Difluoro-phenyl)-methyl]-2-dimethylamino-4-methyl-6-morpholin-4-yl-pyridine-3-carboxylic acid amide | 174 | 391.2 |
| 207 | N-[(4-Chlorophenyl)-methyl]-2-ethylsulfanyl-4-methyl-6-[(3R)-3-methyl-morpholin-4-yl]-pyridine-3-carboxylic acid amide | 5 | 420.1 |
| 208 | N-[(3,5-Dimethyl-phenyl)-methyl]-2-ethylsulfanyl-4-methyl-6-morpholin-4-yl-pyridine-3-carboxylic acid amide | 1 | 400.2 |
| 209 | 2-Ethylsulfanyl-N-heptyl-4-methyl-6-morpholin-4-yl-pyridine-3-carboxylic acid amide | 1 | 380.2 |

TABLE 1-continued

| Example | Chemical name | Preparation according to example | MS m/z [M + H]+ |
|---|---|---|---|
| 210 | 6-Dimethylamino-N-(4,4-dimethyl-pentyl)-2-ethylsulfanyl-4-methyl-pyridine-3-carboxylic acid amide | 5 | 338.2 |
| 211 | N-(4,4-Dimethyl-pentyl)-2-ethylsulfanyl-6-(2-methoxy-ethyl-methyl-amino)-4-methyl-pyridine-3-carboxylic acid amide | 5 | 382.2 |
| 212 | N-(4,4-Dimethyl-pentyl)-2-ethylsulfanyl-6-(3-methoxy-propyl-methyl-amino)-4-methyl-pyridine-3-carboxylic acid amide | 5 | 396.3 |
| 213 | 2-Ethylsulfanyl-N-[(3-fluorophenyl)-methyl]-4-methyl-6-(3-propyl-morpholin-4-yl)-pyridine-3-carboxylic acid amide | 258 | 432.2 |
| 215 | N-[(4-Chlorophenyl)-methyl]-2-methoxy-4-methyl-6-[(3R)-3-methyl-morpholin-4-yl]-pyridine-3-carboxylic acid amide | 214 | 390.2 |
| 216 | N-[(3-Fluorophenyl)-methyl]-4-methyl-2-(1-methyl-propyl)-6-morpholin-4-yl-pyridine-3-carboxylic acid amide | 23 | 386.2 |
| 217 | 2-Ethylsulfanyl-N-hexyl-4-methyl-6-morpholin-4-yl-pyridine-3-carboxylic acid amide | 1 | 366.2 |
| 218 | N-(4,4-Dimethyl-pentyl)-2-ethylsulfanyl-4-methyl-6-(methyl-tetrahydro-furan-3-yl-amino)-pyridine-3-carboxylic acid amide | 5 | 394.2 |
| 219 | N-(4,4-Dimethyl-pentyl)-2-ethylsulfanyl-4-methyl-6-(2-methyl-morpholin-4-yl)-pyridine-3-carboxylic acid amide | 5 | 394.2 |
| 220 | 2-tert-Butyl-N-(4,4-dimethyl-pentyl)-4-methyl-6-morpholin-4-yl-pyridine-3-carboxylic acid amide | 23 | 376.3 |
| 221 | N-(4,4-Dimethyl-pentyl)-4-methyl-2-(1-methyl-propyl)-6-morpholin-4-yl-pyridine-3-carboxylic acid amide | 23 | 376.3 |
| 222 | 2-Ethylsulfanyl-N-[(3-fluorophenyl)-methyl]-4-methyl-6-(2-oxa-6-azaspiro[3.4]octan-6-yl)-pyridine-3-carboxylic acid amide | 5 | 416.2 |
| 223 | 2-Ethylsulfanyl-N-[(3-fluorophenyl)-methyl]-6-[(2R)-2-(methoxymethyl)-morpholin-4-yl]-4-methyl-pyridine-3-carboxylic acid amide | 5 | 434.2 |
| 224 | 2-Ethylsulfanyl-N-[(3-fluorophenyl)-methyl]-6-[(2S)-2-(methoxymethyl)-morpholin-4-yl]-4-methyl-pyridine-3-carboxylic acid amide | 5 | 434.2 |
| 225 | N-[(3,4-Difluoro-phenyl)-methyl]-2-ethylsulfanyl-4-methyl-6-[(3R)-3-methyl-morpholin-4-yl]-pyridine-3-carboxylic acid amide | 176 | 422.2 |
| 226 | N-[(3,4-Difluoro-phenyl)-methyl]-2-methoxy-4-methyl-6-[(3R)-3-methyl-morpholin-4-yl]-pyridine-3-carboxylic acid amide | 176 | 392.2 |
| 227 | 2-Ethylsulfanyl-N-(3-hydroxy-3-phenyl-propyl)-4-methyl-6-morpholin-4-yl-pyridine-3-carboxylic acid amide | 1 | 416.2 |
| 228 | 2-Ethylsulfanyl-N-(2-hydroxy-4-methyl-pentyl)-4-methyl-6-morpholin-4-yl-pyridine-3-carboxylic acid amide | 1 | 382.2 |
| 229 | 2-Ethylsulfanyl-N-[(3-fluorophenyl)-methyl]-6-[2-(2-methoxy-ethyl)-morpholin-4-yl]-4-methyl-pyridine-3-carboxylic acid amide | 5 | 448.2 |
| 230 | 2-Ethylsulfanyl-N-(5-hydroxy-4,4-dimethyl-pentyl)-4-methyl-6-morpholin-4-yl-pyridine-3-carboxylic acid amide | 1 | 396.2 |
| 231 | 2-Ethylsulfanyl-4-methyl-N-[(3-methylsulfonyl-phenyl)-methyl]-6-morpholin-4-yl-pyridine-3-carboxylic acid amide | 1 | 450.1 |
| 232 | 2-Ethylsulfanyl-N-[(3-fluorophenyl)-methyl]-4-methyl-6-[2-(trifluoromethyl)-5,6,7,8-tetrahydro-[1,6]naphthyridin-6-yl]-pyridine-3-carboxylic acid amide | 258 | 505.2 |
| 233 | N-[(3,5-Difluoro-phenyl)-methyl]-2-ethylsulfanyl-4-methyl-6-[(3R)-3-methyl-morpholin-4-yl]-pyridine-3-carboxylic acid amide | 176 | 422.2 |
| 234 | N-[(3,5-Difluoro-phenyl)-methyl]-2-methoxy-4-methyl-6-[(3R)-3-methyl-morpholin-4-yl]-pyridine-3-carboxylic acid amide | 176 | 392.2 |

TABLE 1-continued

| Example | Chemical name | Preparation according to example | MS m/z [M + H]+ |
|---|---|---|---|
| 235 | 2-Ethylsulfanyl-4-methyl-6-[(3R)-3-methyl-morpholin-4-yl]-N-(4,4,4-trifluoro-butyl)-pyridine-3-carboxylic acid amide | 176 | 406.2 |
| 236 | 2-Methoxy-4-methyl-6-[(3R)-3-methyl-morpholin-4-yl]-N-(4,4,4-trifluoro-butyl)-pyridine-3-carboxylic acid amide | 176 | 376.2 |
| 237 | 2-Ethylsulfanyl-4-methyl-6-[(3R)-3-methyl-morpholin-4-yl]-N-[[4-(trifluoromethyl)-phenyl]-methyl]-pyridine-3-carboxylic acid amide | 176 | 454.2 |
| 238 | 2-Methoxy-4-methyl-6-[(3R)-3-methyl-morpholin-4-yl]-N-[[4-(trifluoromethyl)-phenyl]-methyl]-pyridine-3-carboxylic acid amide | 176 | 424.2 |
| 239 | 2-Ethylsulfanyl-N-[(3-fluorophenyl)-methyl]-6-[3-(methoxymethyl)-azetidin-1-yl]-4-methyl-pyridine-3-carboxylic acid amide | 5 | 404.2 |
| 240 | 6-(2,5-Dimethyl-morpholin-4-yl)-2-ethylsulfanyl-N-[(3-fluorophenyl)-methyl]-4-methyl-pyridine-3-carboxylic acid amide | 258 | 418.2 |
| 241 | 2-Dimethylamino-4-methyl-6-morpholin-4-yl-N-[[4-(trifluoromethyl)-phenyl]-methyl]-pyridine-3-carboxylic acid amide | 174 | 423.2 |
| 242 | N-[(3,5-Difluoro-phenyl)-methyl]-2-dimethylamino-4-methyl-6-morpholin-4-yl-pyridine-3-carboxylic acid amide | 174 | 391.2 |
| 243 | 2-Ethylsulfanyl-N-[(3-fluorophenyl)-methyl]-4-methyl-6-[2-(trifluoromethyl)-5,6,7,8-tetrahydro-imidazo[1,2-a]pyrazin-7-yl]-pyridine-3-carboxylic acid amide | 5 | 494.2 |
| 244 | N-[(4-Chlorophenyl)-methyl]-2-dimethylamino-4-methyl-6-morpholin-4-yl-pyridine-3-carboxylic acid amide | 174 | 389.2 |
| 245 | 2-Dimethylamino-N-(4,4-dimethyl-pentyl)-4-methyl-6-morpholin-4-yl-pyridine-3-carboxylic acid amide | 174 | 363.3 |
| 246 | 2-Dimethylamino-4-methyl-6-morpholin-4-yl-N-(4,4,4-trifluoro-butyl)-pyridine-3-carboxylic acid amide | 174 | 375.2 |
| 247 | 2-Ethylsulfanyl-4-methyl-N-[(4-methylsulfonyl-phenyl)-methyl]-6-morpholin-4-yl-pyridine-3-carboxylic acid amide | 1 | 450.1 |
| 248 | 2-Ethylsulfanyl-N-[(4-fluorophenyl)-methyl]-6-[(3R)-3-(methoxymethyl)-morpholin-4-yl]-4-methyl-pyridine-3-carboxylic acid amide | 258 | 434.2 |
| 249 | 2-Ethylsulfanyl-N-[(4-fluorophenyl)-methyl]-6-[(3S)-3-(methoxymethyl)-morpholin-4-yl]-4-methyl-pyridine-3-carboxylic acid amide | 258 | 434.2 |
| 250 | 2-tert-Butyl-N-[(3-fluorophenyl)-methyl]-4-methyl-6-morpholin-4-yl-pyridine-3-carboxylic acid amide | 23 | 386.2 |
| 251 | 2-Ethylsulfanyl-N-[(3-fluorophenyl)-methyl]-4-methyl-6-[4-(2,2,2-trifluoro-ethyl)-piperazin-1-yl]-pyridine-3-carboxylic acid amide | 258 | 471.2 |
| 252 | 6-(2,2-Dimethyl-morpholin-4-yl)-2-ethylsulfanyl-N-[(3-fluorophenyl)-methyl]-4-methyl-pyridine-3-carboxylic acid amide | 258 | 418.2 |
| 254 | N-[(4-Chlorophenyl)-methyl]-2-ethylsulfanyl-6-[(2R)-2-(methoxymethyl)-morpholin-4-yl]-4-methyl-pyridine-3-carboxylic acid amide | 258 | 450.2 |
| 255 | N-[(4-Chlorophenyl)-methyl]-2-ethylsulfanyl-6-[(2S)-2-(methoxymethyl)-morpholin-4-yl]-4-methyl-pyridine-3-carboxylic acid amide | 258 | 450.2 |
| 256 | N-[(4-Chlorophenyl)-methyl]-2-ethylsulfanyl-6-[(3R)-3-(methoxymethyl)-morpholin-4-yl]-4-methyl-pyridine-3-carboxylic acid amide | 258 | 450.2 |
| 257 | N-[(4-Chlorophenyl)-methyl]-2-ethylsulfanyl-6-[(3S)-3-(methoxymethyl)-morpholin-4-yl]-4-methyl-pyridine-3-carboxylic acid amide | 258 | 450.2 |
| 259 | 2-Ethylsulfanyl-N-[(3-fluorophenyl)-methyl]-6-[(4-methoxy-cyclohexyl)-methyl-amino]-4-methyl-pyridine-3-carboxylic acid amide | 258 | 446.2 |
| 260 | 2-Ethylsulfanyl-N-[(3-fluorophenyl)-methyl]-4-methyl-6-[2-(trifluoromethyl)-morpholin-4-yl]-pyridine-3-carboxylic acid amide | 258 | 458.1 |
| 261 | 2-Ethylsulfanyl-N-[(3-fluorophenyl)-methyl]-4-methyl-6-(methyl-tetrahydro-pyran-3-yl-amino)-pyridine-3-carboxylic acid amide | 258 | 418.2 |

TABLE 1-continued

| Example | Chemical name | Preparation according to example | MS m/z [M + H]+ |
|---|---|---|---|
| 262 | 6-(3,5-Dimethyl-morpholin-4-yl)-2-ethylsulfanyl-N-[(3-fluorophenyl)-methyl]-4-methyl-pyridine-3-carboxylic acid amide | 258 | 418.2 |
| 264 | 2-Ethylsulfanyl-N-[(3-fluorophenyl)-methyl]-6-[(3R)-3-(hydroxymethyl)-morpholin-4-yl]-4-methyl-pyridine-3-carboxylic acid amide | 263 | 420.2 |
| 265 | N-[(4-Chlorophenyl)-methyl]-2-isopropyl-4-methyl-6-[(3R)-3-methyl-morpholin-4-yl]-pyridine-3-carboxylic acid amide | 169 | 402.2 |
| 266 | N-[(4-Chlorophenyl)-methyl]-4-methyl-6-[(3R)-3-methyl-morpholin-4-yl]-2-propyl-pyridine-3-carboxylic acid amide | 169 | 402.2 |
| 267 | 2-Ethylsulfanyl-N-(3-hydroxy-4,4-dimethyl-pentyl)-4-methyl-6-morpholin-4-yl-pyridine-3-carboxylic acid amide | 1 | 396.2 |
| 268 | N-[(4-Cyano-3-fluoro-phenyl)-methyl]-2-ethylsulfanyl-4-methyl-6-morpholin-4-yl-pyridine-3-carboxylic acid amide | 1 | 415.2 |
| 269 | N-[(4-Chlorophenyl)-methyl]-2-(2-fluoro-ethoxy)-4-methyl-6-morpholin-4-yl-pyridine-3-carboxylic acid amide | 176 | 408.1 |
| 270 | N-[(4-Chlorophenyl)-methyl]-2-(2,2-difluoro-ethoxy)-4-methyl-6-morpholin-4-yl-pyridine-3-carboxylic acid amide | 176 | 426.1 |
| 271 | N-[(4-Chlorophenyl)-methyl]-2-(cyclopropyl-methoxy)-4-methyl-6-morpholin-4-yl-pyridine-3-carboxylic acid amide | 176 | 416.2 |
| 272 | 2-(2,2-Difluoro-ethoxy)-N-[(4-fluorophenyl)-methyl]-4-methyl-6-morpholin-4-yl-pyridine-3-carboxylic acid amide | 176 | 410.2 |
| 273 | N-[(4-Chlorophenyl)-methyl]-2-ethoxy-4-methyl-6-[(3R)-3-methyl-morpholin-4-yl]-pyridine-3-carboxylic acid amide | 176 | 404.2 |
| 274 | N-(4,4-Dimethyl-pentyl)-2-ethylsulfanyl-4-methyl-6-[(2S)-2-methyl-morpholin-4-yl]-pyridine-3-carboxylic acid amide | 138 | 394.2 |
| 275 | N-(4,4-Dimethyl-pentyl)-2-ethylsulfanyl-4-methyl-6-[(2R)-2-methyl-morpholin-4-yl]-pyridine-3-carboxylic acid amide | 139 | 394.2 |
| 276 | 2-(Cyclopropyl-methoxy)-N-[(4-fluorophenyl)-methyl]-4-methyl-6-morpholin-4-yl-pyridine-3-carboxylic acid amide | 176 | 400.2 |
| 277 | N-[(4-Chlorophenyl)-methyl]-2-isopropyl-6-[(3S)-3-(methoxymethyl)-morpholin-4-yl]-4-methyl-pyridine-3-carboxylic acid amide | 258 | 432.2 |
| 278 | N-(4,4-Dimethyl-pentyl)-4-methyl-2-(2-methyl-butyl)-6-morpholin-4-yl-pyridine-3-carboxylic acid amide | 23 | 390.3 |
| 279 | N-(4,4-Dimethyl-pentyl)-2-(1,1-dimethyl-propyl)-4-methyl-6-morpholin-4-yl-pyridine-3-carboxylic acid amide | 23 | 390.3 |
| 280 | N-(4,4-Dimethyl-pentyl)-2-ethylsulfanyl-4-methyl-6-(methyl-tetrahydro-pyran-3-yl-amino)-pyridine-3-carboxylic acid amide | 258 | 408.3 |
| 281 | 2-Ethylsulfanyl-4-methyl-6-morpholin-4-yl-N-[(4-nitrophenyl)-methyl]-pyridine-3-carboxylic acid amide | 1 | 417.2 |
| 282 | N-[(4-Chlorophenyl)-methyl]-2-cyclopropyl-4-methyl-6-[(3R)-3-methyl-morpholin-4-yl]-pyridine-3-carboxylic acid amide | 169 | 400.2 |
| 283 | N-[(4-Chlorophenyl)-methyl]-2-(2-dimethylaminoethyloxy)-4-methyl-6-morpholin-4-yl-pyridine-3-carboxylic acid amide | 176 | 433.2 |
| 284 | 2-Ethylsulfanyl-N-[(4-fluoro-3-methoxy-phenyl)-methyl]-4-methyl-6-morpholin-4-yl-pyridine-3-carboxylic acid amide | 1 | 420.2 |
| 286 | 2-Ethylsulfanyl-N-(3-hydroxy-4-methyl-pentyl)-4-methyl-6-morpholin-4-yl-pyridine-3-carboxylic acid amide | 1 | 382.2 |
| 287 | 2-Ethylsulfanyl-N-[(3-fluoro-4-methoxy-phenyl)-methyl]-4-methyl-6-morpholin-4-yl-pyridine-3-carboxylic acid amide | 1 | 420.2 |
| 288 | N-[[4-(Difluoro-methoxy)-phenyl]-methyl]-2-ethylsulfanyl-4-methyl-6-morpholin-4-yl-pyridine-3-carboxylic acid amide | 1 | 438.2 |

TABLE 1-continued

| Example | Chemical name | Preparation according to example | MS m/z [M + H]+ |
|---|---|---|---|
| 289 | N-(1,3-Dihydro-isobenzofuran-5-yl-methyl)-2-ethylsulfanyl-4-methyl-6-morpholin-4-yl-pyridine-3-carboxylic acid amide | 1 | 414.2 |
| 290 | N-[(4-Chlorophenyl)-methyl]-2-cyclopropyl-6-[(2S)-2-(methoxymethyl)-morpholin-4-yl]-4-methyl-pyridine-3-carboxylic acid amide | 285 | 430.2 |
| 291 | 2-Ethylsulfanyl-N-[(3-fluorophenyl)-methyl]-6-[(2S)-2-(hydroxymethyl)-morpholin-4-yl]-4-methyl-pyridine-3-carboxylic acid amide | 263 | 420.2 |
| 292 | 2-Ethylsulfanyl-N-[(3-fluorophenyl)-methyl]-6-[(2R)-2-(hydroxymethyl)-morpholin-4-yl]-4-methyl-pyridine-3-carboxylic acid amide | 263 | 420.2 |
| 294 | 2-Ethylsulfanyl-N-[(3-fluorophenyl)-methyl]-4-methyl-6-[methyl-(tetrahydro-furan-2-yl-methyl)-amino]-pyridine-3-carboxylic acid amide | 5 | 418.2 |
| 295 | 2-Ethylsulfanyl-N-[(3-fluorophenyl)-methyl]-4-methyl-6-[(3R)-3-methyl-morpholin-4-yl]-pyridine-3-carboxylic acid amide | 171 | 404.2 |
| 296 | 2-Ethylsulfanyl-N-[(3-fluorophenyl)-methyl]-4-methyl-6-[(3S)-3-methyl-morpholin-4-yl]-pyridine-3-carboxylic acid amide | 171 | 404.2 |
| 297 | 2-Ethylsulfanyl-N-[(3-fluorophenyl)-methyl]-4-methyl-6-[methyl-[[4-(trifluoromethyl)-phenyl]-methyl]-amino]-pyridine-3-carboxylic acid amide | 171 | 492.2 |
| 299 | 6-(Azetidin-1-yl)-2-ethylsulfanyl-N-[(3-fluorophenyl)-methyl]-4-methyl-pyridine-3-carboxylic acid amide | 293 | 360.1 |
| 301 | 2-Ethylsulfanyl-N-[(3-fluorophenyl)-methyl]-4-methyl-6-(methyl-tetrahydro-furan-3-yl-amino)-pyridine-3-carboxylic acid amide | 171 | 404.2 |
| 302 | 2-Ethylsulfanyl-N-[(3-fluorophenyl)-methyl]-4-methyl-6-(N-methyl-anilino)-pyridine-3-carboxylic acid amide | 171 | 410.2 |
| 303 | 6-(2,3-Dihydro-1H-isoindol-2-yl)-2-ethylsulfanyl-N-[(3-fluorophenyl)-methyl]-4-methyl-pyridine-3-carboxylic acid amide | 171 | 422.2 |
| 304 | 2-Ethylsulfanyl-N-[(3-fluorophenyl)-methyl]-4-methyl-6-(1,2,3,4-tetrahydro-quinolin-1-yl)-pyridine-3-carboxylic acid amide | 171 | 436.2 |
| 305 | 6-(2,3-Dihydro-1H-indol-1-yl)-2-ethylsulfanyl-N-[(3-fluorophenyl)-methyl]-4-methyl-pyridine-3-carboxylic acid amide | 171 | 422.2 |
| 306 | 2-Ethylsulfanyl-4-methyl-6-morpholin-4-yl-N-(2,4,4-trimethyl-pentyl)-pyridine-3-carboxylic acid amide | 1 | 394.2 |
| 308 | N-(4,4-Difluoro-pentyl)-2-ethylsulfanyl-4-methyl-6-morpholin-4-yl-pyridine-3-carboxylic acid amide | 1 | 388.2 |
| 309 | N-[(4-Fluorophenyl)-methyl]-2-isopropyl-4-methyl-6-morpholin-4-yl-pyridine-3-carboxylic acid amide | 23 | 372.2 |
| 310 | N-[(3,4-Difluoro-phenyl)-methyl]-2-isopropyl-4-methyl-6-morpholin-4-yl-pyridine-3-carboxylic acid amide | 23 | 390.2 |
| 311 | 2-Isopropyl-4-methyl-6-morpholin-4-yl-N-[[4-(trifluoromethyl)-phenyl]-methyl]-pyridine-3-carboxylic acid amide | 23 | 422.2 |
| 313 | N-(4,4-Dimethyl-pentyl)-4-methyl-6-morpholin-4-yl-2-propyl-pyridine-3-carboxylic acid amide | 23 | 362.3 |
| 314 | N-(4,4-Dimethyl-pentyl)-2-isopropyl-4-methyl-6-morpholin-4-yl-pyridine-3-carboxylic acid amide | 23 | 362.3 |
| 315 | 2-Isopropyl-4-methyl-6-morpholin-4-yl-N-(4,4,4-trifluoro-butyl)-pyridine-3-carboxylic acid amide | 23 | 374.2 |
| 316 | N-[(3,5-Difluoro-phenyl)-methyl]-2-isopropyl-4-methyl-6-morpholin-4-yl-pyridine-3-carboxylic acid amide | 23 | 390.2 |
| 318 | 2-Ethylsulfanyl-N-(4-methoxy-4-methyl-pentyl)-4-methyl-6-morpholin-4-yl-pyridine-3-carboxylic acid amide | 1 | 396.2 |
| 319 | 2-Ethylsulfanyl-N-(4-fluoro-4-methyl-pentyl)-4-methyl-6-morpholin-4-yl-pyridine-3-carboxylic acid amide | 1 | 384.2 |

TABLE 1-continued

| Example | Chemical name | Preparation according to example | MS m/z [M + H]+ |
|---|---|---|---|
| 320 | 4-Methyl-6-morpholin-4-yl-2-propyl-N-(4,4,4-trifluoro-butyl)-pyridine-3-carboxylic acid amide | 23 | 374.2 |
| 321 | N-[(3,4-Difluoro-phenyl)-methyl]-4-methyl-6-morpholin-4-yl-2-propyl-pyridine-3-carboxylic acid amide | 23 | 390.2 |
| 322 | N-[(3,5-Difluoro-phenyl)-methyl]-4-methyl-6-morpholin-4-yl-2-propyl-pyridine-3-carboxylic acid amide | 23 | 390.2 |
| 323 | 4-Methyl-6-morpholin-4-yl-2-propyl-N-[[4-(trifluoromethyl)-phenyl]-methyl]-pyridine-3-carboxylic acid amide | 23 | 422.2 |
| 324 | N-(4,4-Dimethyl-2-oxo-pentyl)-2-ethylsulfanyl-4-methyl-6-morpholin-4-yl-pyridine-3-carboxylic acid amide | 1 | 394.2 |
| 325 | 2-Ethylsulfanyl-N-[(3-fluorophenyl)-methyl]-4-methyl-6-(8-oxa-3-azabicyclo[3.2.1]octan-3-yl)-pyridine-3-carboxylic acid amide | 258 | 416.2 |
| 326 | N-[(4-Chlorophenyl)-methyl]-4-methyl-6-morpholin-4-yl-2-propyl-pyridine-3-carboxylic acid amide | 23 | 388.2 |
| 327 | N-[(4-Chlorophenyl)-methyl]-2-isopropyl-4-methyl-6-morpholin-4-yl-pyridine-3-carboxylic acid amide | 23 | 388.2 |
| 328 | 2-Cyclopropyl-N-(4,4-dimethyl-pentyl)-4-methyl-6-morpholin-4-yl-pyridine-3-carboxylic acid amide | 355 | 360.3 |
| 329 | 2-Cyclopropyl-4-methyl-6-morpholin-4-yl-N-(4,4,4-trifluoro-butyl)-pyridine-3-carboxylic acid amide | 355 | 372.2 |
| 330 | 2-Cyclopropyl-N-[(3-fluorophenyl)-methyl]-4-methyl-6-morpholin-4-yl-pyridine-3-carboxylic acid amide | 355 | 370.2 |
| 331 | 2-Cyclopropyl-N-[(4-fluorophenyl)-methyl]-4-methyl-6-morpholin-4-yl-pyridine-3-carboxylic acid amide | 355 | 370.2 |
| 332 | 2-Cyclopropyl-N-[(3,4-difluoro-phenyl)-methyl]-4-methyl-6-morpholin-4-yl-pyridine-3-carboxylic acid amide | 355 | 388.2 |
| 333 | 2-Cyclopropyl-N-[(3,5-difluoro-phenyl)-methyl]-4-methyl-6-morpholin-4-yl-pyridine-3-carboxylic acid amide | 355 | 388.2 |
| 334 | 2-Cyclopropyl-4-methyl-6-morpholin-4-yl-N-[[4-(trifluoromethyl)-phenyl]-methyl]-pyridine-3-carboxylic acid amide | 355 | 420.2 |
| 335 | N-[(4-Chlorophenyl)-methyl]-2-cyclopropyl-4-methyl-6-morpholin-4-yl-pyridine-3-carboxylic acid amide | 355 | 386.2 |
| 337 | N-(4,4-Dimethyl-pentyl)-2-(2-methoxy-ethylsulfanyl)-4-methyl-6-morpholin-4-yl-pyridine-3-carboxylic acid amide | 2 | 410.2 |
| 338 | 2-Ethylsulfanyl-N-[(3-fluorophenyl)-methyl]-6-[(4-fluorophenyl)-methyl-(3-methoxy-propyl)-amino]-4-methyl-pyridine-3-carboxylic acid amide | 258 | 500.2 |
| 339 | 2-Ethylsulfanyl-4-methyl-6-morpholin-4-yl-N-(3,4,4-trimethyl-pentyl)-pyridine-3-carboxylic acid amide | 1 | 394.2 |
| 340 | 2-Ethylsulfanyl-N-[(3-fluorophenyl)-methyl]-6-[3-(2-methoxy-ethyl)-morpholin-4-yl]-4-methyl-pyridine-3-carboxylic acid amide | 258 | 448.2 |
| 342 | 2-Ethylsulfanyl-N-[(3-fluorophenyl)-methyl]-6-[(4-fluorophenyl)-methyl-(2-methoxy-ethyl)-amino]-4-methyl-pyridine-3-carboxylic acid amide | 258 | 486.2 |
| 343 | 2-Ethylsulfanyl-4-methyl-N-[3-(3-methyl-oxetan-3-yl)-propyl]-6-morpholin-4-yl-pyridine-3-carboxylic acid amide | 1 | 394.2 |
| 344 | N-(4,4-Dimethyl-pent-2-ynyl)-2-ethylsulfanyl-4-methyl-6-morpholin-4-yl-pyridine-3-carboxylic acid amide | 1 | 376.2 |
| 345 | 2-Ethylsulfanyl-N-[(3-fluorophenyl)-methyl]-4-methyl-6-(3-oxa-8-azabicyclo[3.2.1]octan-8-yl)-pyridine-3-carboxylic acid amide | 258 | 416.2 |

TABLE 1-continued

| Example | Chemical name | Preparation according to example | MS m/z [M + H]+ |
|---|---|---|---|
| 347 | N-[(4-Chlorophenyl)-methyl]-4-methyl-2-(1-methyl-propyl)-6-morpholin-4-yl-pyridine-3-carboxylic acid amide | 23 | 402.2 |
| 348 | N-(4,4-Dimethyl-hexyl)-2-ethylsulfanyl-4-methyl-6-morpholin-4-yl-pyridine-3-carboxylic acid amide | 1 | 394.2 |
| 349 | N-(4,4-Dimethyl-pentyl)-2-(2-methoxy-ethoxy)-4-methyl-6-morpholin-4-yl-pyridine-3-carboxylic acid amide | 176 | 394.3 |
| 350 | 2-Ethylsulfanyl-4-methyl-N-[3-(1-methyl-cyclopropyl)-propyl]-6-morpholin-4-yl-pyridine-3-carboxylic acid amide | 1 | 378.2 |
| 351 | 2-Cyclopropyl-N-[[4-fluoro-3-(methoxymethyl)-phenyl]-methyl]-4-methyl-6-morpholin-4-yl-pyridine-3-carboxylic acid amide | 355 | 414.2 |
| 352 | 2-Ethylsulfanyl-N-[[4-fluoro-3-(methoxymethyl)-phenyl]-methyl]-4-methyl-6-[(3R)-3-methyl-morpholin-4-yl]-pyridine-3-carboxylic acid amide | 1 | 448.2 |
| 353 | 2-Ethylsulfanyl-N-[[4-fluoro-3-(hydroxymethyl)-phenyl]-methyl]-4-methyl-6-morpholin-4-yl-pyridine-3-carboxylic acid amide | 1 | 420.2 |
| 362 | N-(4,4-Dimethyl-pentyl)-4-methyl-6-morpholin-4-yl-2-tetrahydro-pyran-4-yl-pyridine-3-carboxylic acid amide | 354 | 403.3 |

Pharmacological Experiments

Method I. Fluorescence Assay Using a Voltage Sensitive Dye (Fluorimetry)

The modulation of the KCNQ opening state (and consequently the voltage potential of a cell) by test compounds such as compounds according to the present invention results in an increased or reduced amount of a voltage-sensitive dye in the cytoplasm of the cells tested. These voltage-sensitive dyes are fluorescent dyes and, therefore, are forming the link between cell potential influenced by KCNQ modulation and fluorescence intensity. A KCNQ agonist leads to an opening of the channel, potassium and dye efflux, a following hyperpolarization and a reduction of the inner fluorescence intensity in a kinetic protocol. If applying an ion jump by KCl depolarization, KCNQ agonists increase the ΔF/F value. An antagonist performs vice versa, respectively.

The 'fluorimetry $EC_{50}$' is the half maximum effective concentration ($EC_{50}$), where the concentration of a drug/compound induces a response halfway between the baseline and maximum plateau effect. In other words, said value represents the concentration of a compound, where 50% of its maximal effect in the fluorimetric assay is observed if the substance concentration is graphed against the corresponding ΔF/F values (for which the calculation method is described below). Therefore, 'fluorimetry $EC_{50}$' is a measure for the compound potency. The compound efficacy is mirrored by 'fluorimetry % efficacy' ('% Efficacy') and refers to the maximum response achievable by the test compound, i.e. the plateau effect. This drug's plateau effect is related to the plateau effect, which can be achieved by applying a saturated concentration of a reference compound, e.g. Retigabine (50 μM), in independent wells of the same experimental plate or series. A compound showing 100% efficacy is as efficacious as the reference compound (Retigabine) with a saturated concentration. This calculation '% Efficacy' method was introduced in order to normalize the ΔF/F values of different experiments to a common comparator compound, and make the test drug effects comparable.

Human CHO-K1 cells expressing KCNQ2/3 channels are cultivated adherently at 37° C., 5% $CO_2$ and 95% humidity in cell culture bottles (e.g. 80 $cm^2$ TC flasks, Nunc) with DMEM-high glucose (Sigma Aldrich, D7777) including 10% FCS (PAN Biotech, e.g. 3302-P270521) or alternatively MEM Alpha Medium (1×, liquid, Invitrogen, #22571), 10% fetal calf serum (FCS) (Invitrogen, #10270-106, heat-inactivated) and the necessary selection antibiotics.

Before being sown out for the measurements, the cells are washed with 1×DPBS buffer $Ca^{2+}/Mg^{2+}$-free (e.g. Invitrogen, #14190-094) and detached from the bottom of the culture vessel by using Accutase (PAA Laboratories, #L11-007) (incubation with Accutase for 15 min at 37° C.). The cell number is determined using a CASY™ cell counter (TCC, Schärfe System). Depending on the optimal density for each individual cell line, 20,000-30,000 cells/well/100 μl are seeded onto 96-well Corning™ CellBIND™ assay plates (Flat Clear Bottom Black Polystyrene Microplates, #3340). Freshly seeded cells are then left to settle for one hour at room temperature, followed by incubation for 24 hours at 37° C., 5% $CO_2$ and 95% humidity.

The voltage-sensitive fluorescent dye from the Membrane Potential Assay Kit (Red™ Bulk format part R8123 for FLIPR, MDS Analytical Technologies™) is prepared by dissolving the contents of one vessel Membrane Potential Assay Kit Red Component A in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed once with 200 μl of ES buffer, then loaded for 45 min at room temperature in 100 μl of dye solution in the dark.

Fluorescence measurements are carried out in a BMG Labtech FLUOstar™, BMG Labtech NOVOstar™ or BMG Labtech POLARstar™ instrument (525 nm excitation, 560 nm emission, Bottom Read mode). After incubation with the dye, 50 μl of the test substances in the desired concentrations, or 50 μl of ES buffer for control purposes, are applied to the wells of the assay plate and incubated for 30 min at room temperature while being shielded from light. The fluorescence intensity of the dye is then measured for 5 min and the fluorescence value $F_1$ of each well is thus determined at a given, constant time. 15 µl of a KCl solution are then added to each well (final concentration of potassium ions 92 mM). The change in fluorescence intensity is subsequently monitored until all the relevant values have been obtained (mainly 5-30 min). At a given time post KCl application, a fluorescence value $F_2$ is determined, in this case at the time of the fluorescence peak.

For calculation, the fluorescence intensity $F_2$ is corrected for the fluorescence intensity $F_1$, and the activity ($\Delta F/F$) of the target compound on the potassium channel is determined as follows:

$$\left(\frac{F_2 - F_1}{F_1}\right) \times 100 = \frac{\Delta F}{F}(\%)$$

In order to determine whether a substance has agonistic activity, $$\frac{\Delta F}{F}$$

can be related to $$\left(\frac{\Delta F}{F}\right)_K$$

of control wells.

$$\left(\frac{\Delta F}{F}\right)_K$$

is determined by adding to the well only the buffer solution instead of the test substance, determining the value $F_{1K}$ of the fluorescence intensity, adding the potassium ions as described above, and measuring a value $F_{2K}$ of the fluorescence intensity. $F_{2K}$ and $F_{1K}$ are then calculated as follows:

$$\left(\frac{F_{2K} - F_{1K}}{F_{1K}}\right) \times 100 = \left(\frac{\Delta F}{F}\right)_K(\%)$$

A substance has an agonistic activity on the potassium channel if $$\frac{\Delta F}{F}$$

is greater than $$\left(\frac{\Delta F}{F}\right)_K : \frac{\Delta F}{F}\left(\frac{\Delta F}{F}\right)_K$$

Independently of the comparison of $$\frac{\Delta F}{F}$$

with $$\left(\frac{\Delta F}{F}\right)_K$$

it is possible to conclude that a target compound has agonistic activity if $$\frac{\Delta F}{F}$$

increases dose dependently.

Calculations of $EC_{50}$ and $IC_{50}$ values are carried out with the aid of 'Prism v4.0' software (GraphPad Software™)

Method II. Low-Intensity Tail Flick Test (Rat)

In the low-intensity tail flick test, the determination of the antinociceptive effect of the compounds according to the invention towards an acute noxious thermal stimulus is carried out by measuring the withdrawal reflex of the rat tail (tail flick) in response to a radiant heat beam (analgesia meter; model 2011 of the company Rhema Labortechnik, Hofheim, Germany) according to the method described by D'Amour and Smith (J. Pharm. Exp. Ther. 72, 74 79 (1941). To this end, the rats were placed in a plexiglass restrainer, and a low-intensity radiant heat beam (48° C.) was focused onto the dorsal surface of the tail root. The stimulus intensity was adjusted to result in a mean pre-drug control withdrawal latency of about 7 s, thus also allowing a supraspinal modulation of the spinally mediated acute nociceptive reflex. A cutoff time of 30 s was applied to avoid tissue damage. Male Sprague-Dawley rats (Janvier, Le Genest St. Isle, Frankreich) with weights of 200-250 g were used. 10 rats were used per group. Before administration of a compound according to the invention, the animals were pre-tested twice in the course of five minutes and the mean of these measurements was calculated as the pre-test mean. The antinociceptive effect was determined at 20, 40 and 60 min after peroral compound administration. The antinociceptive effect was calculated based on the increase in the tail withdrawal latency according to the following formula and is expressed as percentage of the maximum possible effect (MPE [%]):

$$\text{MPE} = [(T_1 - T_0)/(T_2 - T_0)] \ast 100$$

In this, $T_0$ is the control latency time before and $T_1$ the latency time after administration of the compound, $T_2$ is the cutoff time and MPE is the maximum possible effect. Employing variant analysis (repeated measures ANOVA) allowed testing of statistically significant differences between the compounds according to the invention and the vehicle group. The significance level was set to $p \leq 0.05$. To determine the dose dependency, the particular compound according to the invention was administered in 3-5 logarithmically increasing doses, including a threshold dose and a maximum effective dose, and the $ED_{50}$ values were determined with the aid of regression analysis. The $ED_{50}$ calculation was performed at the time of maximum efficacy (usually 20 min after administration of the compounds).

Pharmacological Data

The pharmacological effects of the compounds according to the invention were determined as described hereinbefore (pharmacological experiments, methods I and II respectively).

The corresponding pharmacological data are summarized in Tables 2 and 3.

TABLE 2

| Example | Fluorimetry % efficacy (retigabine = 100%) | Fluorimetry $EC_{50}/IC_{50}$ [nM] | Low intensity tail flick, rat, peroral, $ED_{50}$ or MPE (dose) [mg/kg] |
|---|---|---|---|
| 1 | 160 | 56 | 78 (4.64) |
| 2 | 171 | 134 | 4.3 |
| 3 | 132 | 233 | |
| 4 | 158 | 124 | 94 (10) |
| 5 | 111 | 269 | |
| 6 | 140 | 3875 | |
| 7 | 44 | | |
| 8 | 71 | 442 | |
| 9 | 174 | 740 | |
| 10 | 176 | 181 | 81 (10) |
| 11 | 41 | 175 | |
| 12 | 210 | 2010 | |
| 13 | 145 | 1094 | |
| 14 | 16 | | |
| 15 | 93 | 7063 | |
| 16 | 149 | 2521 | |
| 17 | 21 | | |
| 18 | 224 | 98 | |
| 19 | 155 | 736 | 79 (10) |
| 20 | 140 | 782 | |
| 21 | 146 | 1221 | |
| 22 | 166 | 790 | |
| 23 | 182 | 113 | |
| 24 | 210 | 308 | |
| 25 | 162 | 211 | |
| 26 | 155 | 132 | |
| 27 | 132 | 151 | |
| 29 | 185 | 236 | |
| 30 | 144 | 1315 | |
| 31 | 23 | | |
| 32 | 166 | 132 | |
| 33 | 110 | 639 | |
| 34 | 37 | 1832 | |
| 35 | 153 | 635 | |
| 36 | 125 | 6001 | |
| 37 | 148 | 99 | |
| 38 | 144 | 219 | 61 (10) |
| 39 | 143 | 645 | |
| 40 | 168 | 587 | 84 (10) |
| 41 | 169 | 69 | 92 (6.81) |
| 42 | 169 | 571 | |
| 43 | 189 | 679 | |
| 44 | 116 | 87 | |
| 45 | 151 | 3136 | |
| 46 | 143 | 4834 | |
| 47 | 119 | 2607 | |
| 48 | 145 | 217 | |
| 49 | 143 | 1463 | |
| 50 | -97 | 63 | |
| 51 | -84 | 541 | |
| 52 | 122 | 235 | |
| 53 | 191 | 248 | |
| 54 | 103 | 2123 | |
| 55 | 162 | 260 | |
| 56 | 167 | 77 | |
| 57 | 169 | 47 | |
| 58 | 173 | 2286 | |
| 59 | 128 | 70 | |
| 60 | 128 | 126 | |
| 61 | 110 | 528 | |
| 62 | 164 | 47 | |
| 63 | 157 | 585 | |
| 64 | 137 | 216 | |
| 65 | 238 | 1058 | |
| 66 | 109 | 983 | |
| 67 | 244 | 42 | 100 (10) |
| 68 | 134 | 7371 | |
| 69 | 160 | 4479 | |
| 70 | 175 | 163 | |
| 71 | -102 | 275 | |
| 72 | 93 | 2085 | |
| 73 | 67 | 3008 | |
| 74 | 70 | 702 | |
| 75 | 135 | 61 | |
| 76 | 179 | 91 | |
| 77 | 40 | | |
| 78 | 31 | | |
| 79 | 215 | 206 | 46 (10) |
| 80 | 147 | 2168 | |
| 81 | 163 | 662 | |
| 82 | 117 | 118 | |
| 83 | 182 | 2804 | |
| 84 | 203 | 357 | |
| 85 | -61 | 107 | |
| 86 | 236 | 172 | |
| 87 | 138 | 311 | |
| 88 | -83 | 253 | |
| 89 | 268 | 138 | |
| 90 | 134 | 122 | |
| 91 | 127 | 117 | |
| 92 | -79 | 128 | |
| 93 | 103 | 54 | |
| 94 | 111 | 39 | |
| 95 | 62 | 56 | |
| 96 | 173 | 1098 | |
| 97 | 136 | 67 | |
| 98 | 146 | 2310 | |
| 99 | 134 | 899 | |
| 100 | 98 | 118 | |
| 101 | 100 | 133 | |
| 102 | 138 | 1223 | |
| 103 | 142 | 4522 | |
| 104 | 100 | 1401 | |
| 105 | 207 | 179 | |
| 106 | 160 | 172 | |
| 107 | 90 | 88 | |
| 108 | 203 | 317 | |
| 109 | 53 | | |
| 110 | 163 | 71 | |
| 111 | 153 | 109 | |
| 112 | 130 | 2742 | |
| 113 | 192 | 212 | |
| 114 | 126 | 9381 | |
| 115 | 96 | 7972 | |
| 116 | 210 | 131 | |
| 117 | 128 | 268 | |
| 118 | 3 | | |
| 119 | 91 | 2422 | |
| 120 | 10 | | |
| 121 | 35 | | |
| 122 | 68 | 8894 | |
| 123 | 67 | | |
| 124 | 149 | 82 | |
| 125 | 152 | 87 | |
| 126 | 145 | 2093 | |
| 127 | 238 | 385 | |
| 128 | 142 | 785 | |
| 129 | 206 | 221 | |
| 130 | 148 | 74 | |
| 131 | 137 | 1247 | |
| 132 | 122 | 110 | |
| 133 | 235 | 392 | |
| 134 | 159 | 1137 | |
| 135 | 43 | 54 | |
| 136 | 171 | 108 | |
| 137 | 151 | 1066 | |
| 138 | 125 | 170 | |
| 139 | 146 | 770 | |
| 140 | 227 | 1121 | |
| 141 | 167 | 242 | |

TABLE 2-continued

| Example | Fluorimetry % efficacy (retigabine = 100%) | Fluorimetry $EC_{50}/IC_{50}$ [nM] | Low intensity tail flick, rat, peroral, $ED_{50}$ or MPE (dose) [mg/kg] |
|---|---|---|---|
| 142 | 125 | 38 | |
| 143 | 28 | | |
| 144 | 59 | | |
| 145 | 145 | 673 | |
| 146 | 159 | 2493 | |
| 147 | 153 | 530 | |
| 148 | 105 | 3624 | |
| 149 | 136 | 451 | |
| 150 | 98 | 9647 | |
| 151 | 92 | 12116 | |
| 152 | 249 | 63 | |
| 153 | 210 | 676 | |
| 154 | 154 | 394 | |
| 155 | 158 | 152 | |
| 156 | 167 | 157 | |
| 157 | 127 | 166 | |
| 158 | 60 | | |
| 159 | 149 | 1258 | |
| 160 | 70 | | |
| 161 | 143 | 366 | |
| 162 | 21 | | |
| 163 | 73 | | |
| 164 | 122 | 237 | |
| 165 | 135 | 230 | |
| 166 | 134 | 117 | |
| 167 | 137 | 113 | |
| 168 | 149 | 132 | |
| 169 | 197 | 24 | |
| 170 | 84 | 1238 | |
| 171 | 62 | 1944 | |
| 172 | 246 | 378 | |
| 173 | 259 | 201 | |
| 174 | 221 | 422 | |
| 175 | 114 | 870 | |
| 176 | 215 | 136 | |
| 177 | 174 | 97 | |
| 178 | 147 | 54 | |
| 179 | 190 | 243 | |
| 180 | 123 | 86 | |
| 181 | 167 | 255 | |
| 182 | 146 | 125 | |
| 183 | 221 | 168 | |
| 184 | 228 | 221 | |
| 185 | 238 | 15 | |
| 186 | 240 | 63 | |
| 187 | 242 | 49 | |
| 188 | 154 | 343 | |
| 189 | 225 | 284 | |
| 190 | 207 | 2504 | |
| 191 | 214 | 265 | |
| 192 | 236 | 46 | |
| 193 | 246 | 29 | |
| 194 | 189 | 31 | |
| 195 | 242 | 13 | |
| 196 | 197 | 103 | |
| 197 | 211 | 142 | |
| 198 | 246 | 19 | |
| 199 | 232 | 50 | |
| 200 | 22 | | |
| 201 | 127 | 135 | |
| 202 | 129 | 5986 | |
| 203 | 220 | 219 | |
| 204 | 239 | 141 | |
| 205 | 205 | 898 | |
| 206 | 207 | 402 | |
| 207 | 183 | 69 | |
| 208 | 61 | 281 | |
| 209 | 192 | 234 | |
| 210 | 223 | 187 | |
| 211 | 225 | 143 | |
| 212 | 200 | 152 | |
| 213 | 131 | 49 | |
| 214 | 194 | 224 | |
| 215 | 191 | 147 | |
| 216 | 181 | 69 | |
| 217 | 181 | 407 | |
| 218 | 194 | 272 | |
| 219 | 212 | 91 | |
| 220 | 166 | 682 | |
| 221 | 259 | 22 | |
| 222 | 56 | 7306 | |
| 223 | 137 | 3662 | |
| 224 | 136 | 693 | |
| 225 | 173 | 71 | |
| 226 | 186 | 129 | |
| 227 | 165 | 4193 | |
| 228 | 180 | 2451 | |
| 229 | 132 | 719 | |
| 230 | 131 | 12909 | |
| 231 | 61 | 10432 | |
| 232 | 131 | 112 | |
| 233 | 196 | 70 | |
| 234 | 195 | 124 | |
| 235 | 235 | 196 | |
| 236 | 227 | 469 | |
| 237 | 148 | 56 | |
| 238 | 164 | 102 | |
| 239 | 125 | 1820 | |
| 240 | 174 | 394 | |
| 241 | 160 | 558 | |
| 242 | 214 | 366 | |
| 243 | 105 | 1284 | |
| 245 | 225 | 345 | |
| 246 | 173 | 4103 | |
| 247 | 38 | | |
| 248 | 223 | 313 | |
| 249 | 129 | 82 | |
| 250 | 196 | 371 | |
| 251 | 97 | 1591 | |
| 252 | 137 | 274 | |
| 253 | 79 | 5737 | |
| 254 | 113 | 943 | |
| 255 | 121 | 169 | |
| 256 | 221 | 101 | |
| 257 | 125 | 23 | |
| 258 | 170 | 301 | |
| 259 | 133 | 298 | |
| 260 | 127 | 149 | |
| 261 | 96 | 786 | |
| 262 | 182 | 374 | |
| 263 | 114 | 4142 | |
| 264 | 184 | 1562 | |
| 265 | 206 | 28 | |
| 266 | 210 | 57 | |
| 267 | 223 | 247 | |
| 268 | 142 | 286 | |
| 269 | 119 | 147 | |
| 270 | 97 | 24 | |
| 271 | 128 | 93 | |
| 272 | 96 | 78 | |
| 273 | 163 | 137 | |
| 274 | 217 | 234 | |
| 275 | 208 | 63 | |
| 276 | 102 | 143 | |
| 277 | 129 | 17 | |
| 278 | 225 | 36 | |
| 279 | 172 | 430 | |
| 280 | 165 | 302 | |
| 281 | 109 | 311 | |
| 282 | 182 | 40 | |
| 283 | 22 | | |
| 284 | 94 | 648 | |
| 285 | 126 | 157 | |
| 286 | 198 | 1754 | |
| 287 | 153 | 971 | |
| 288 | 138 | 435 | |
| 289 | 129 | 2816 | |
| 290 | 136 | 314 | |
| 291 | 53 | 7952 | |
| 292 | 32 | | |

TABLE 2-continued

| Example | Fluorimetry % efficacy (retigabine = 100%) | Fluorimetry $EC_{50}/IC_{50}$ [nM] | Low intensity tail flick, rat, peroral, $ED_{50}$ or MPE (dose) [mg/kg] |
|---|---|---|---|
| 293 | 125 | 488 | |
| 294 | 129 | 1034 | |
| 295 | 188 | 50 | |
| 296 | 222 | 189 | |
| 297 | 125 | 177 | |
| 298 | 127 | 4585 | |
| 299 | 104 | 920 | |
| 301 | 132 | 767 | |
| 302 | 93 | 278 | |
| 303 | 54 | 1148 | |
| 304 | 81 | 348 | |
| 305 | 57 | | |
| 306 | 33 | | |
| 307 | 104 | 178 | |
| 308 | 249 | 397 | |
| 309 | 168 | 71 | |
| 310 | 174 | 43 | |
| 311 | 146 | 45 | |
| 312 | 135 | 6699 | |
| 313 | 229 | 62 | |
| 314 | 242 | 18 | |
| 315 | 187 | 314 | |
| 316 | 160 | 29 | |
| 317 | 116 | 1123 | |
| 318 | 193 | 2880 | |
| 319 | 233 | 348 | |
| 320 | 192 | 826 | |
| 321 | 162 | 83 | |
| 322 | 193 | 80 | |
| 323 | 130 | 102 | |
| 324 | 166 | 834 | |
| 325 | 153 | 282 | |
| 326 | 163 | 59 | |
| 327 | 173 | 50 | |
| 328 | 230 | 44 | |
| 329 | 170 | 763 | |
| 330 | 156 | 168 | |
| 331 | 144 | 148 | |
| 332 | 166 | 109 | |
| 333 | 169 | 98 | |
| 334 | 124 | 96 | |
| 335 | 162 | 85 | |
| 336 | 183 | 430 | |
| 337 | 237 | 117 | |
| 338 | 73 | 320 | |
| 339 | 202 | 37 | |
| 340 | 152 | 274 | |
| 341 | 22 | | |
| 342 | 124 | 291 | |
| 343 | 163 | 6843 | |
| 344 | 253 | 41 | |
| 345 | 200 | 122 | |
| 346 | 157 | 729 | |
| 347 | 156 | 41 | |
| 348 | 228 | 22 | |
| 349 | 216 | 284 | |
| 350 | 226 | 79 | |
| 351 | 118 | 489 | |
| 352 | 166 | 287 | |
| 353 | 46 | | |
| 354 | 204 | 1535 | |
| 355 | 167 | 721 | |
| 356 | 140 | 6322 | |
| 357 | 17 | | |
| 358 | 234 | 1126 | |
| 359 | 141 | 237 | |

TABLE 3

| Example | Fluorimetry % efficacy (retigabine = 100%) | Fluorimetry $EC_{50}/IC_{50}$ [nM] | Low intensity tail flick, rat, peroral, $ED_{50}$ or MPE (dose) [mg/kg] |
|---|---|---|---|
| X1 | 237 | 529 | |
| X1a | 242 | 961 | |
| X1b | 224 | 318 | |
| X2 | 245 | 483 | 67 (10) |
| X3 | 99 | 8545 | |
| X5 | 230 | 156 | |
| X6 | 150 | 1987 | |
| X7 | 243 | 185 | |

The invention claimed is:

1. A substituted compound of formula (X):

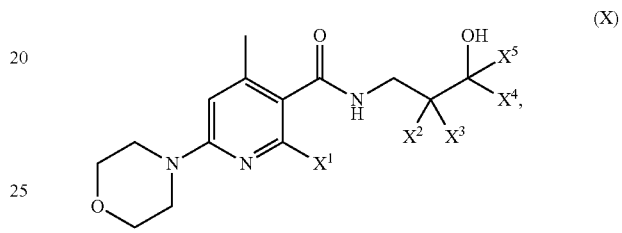

wherein $X^1$ represents a $C_{2-6}$-aliphatic residue, unsubstituted or mono- or polysubstituted; or a $C_{3-6}$-cycloaliphatic residue or a 3 to 6 membered heterocycloaliphatic residue, in each case unsubstituted or mono- or polysubstituted, and in each case optionally bridged via a $C_{1-4}$ aliphatic group, which in turn may be unsubstituted or mono- or polysubstituted;

or represents $OX^6$, wherein $X^6$ represents a $C_{1-6}$-aliphatic residue, unsubstituted or mono- or polysubstituted; or a $C_{3-6}$-cycloaliphatic residue, unsubstituted or mono- or polysubstituted;

$X^2$, $X^3$, $X^4$ and $X^5$ satisfy one of the clauses I, II or III below:

I, $X^2$ and $X^3$ independently of one another represent H; F; Cl; Br; I; CN; $CH_2F$; $CHF_2$; $CF_3$; OH; $OCH_2F$; $OCHF_2$; $OCF_3$; $SCF_3$; a $C_{1-4}$-aliphatic residue, or an O—$C_{1-4}$ aliphatic residue, wherein the $C_{1-4}$ aliphatic residue may in each case be unsubstituted or mono- or polysubstituted; or a $C_{3-6}$-cycloaliphatic residue or a 3 to 6 membered heterocycloaliphatic residue, in each case unsubstituted or mono- or polysubstituted, with the proviso that at least one of $X^2$ and $X^3$ denotes H or at least one of $X^2$ and $X^3$ denotes CN; $CH_2F$; $CHF_2$; $CF_3$; a $C_{1-4}$-aliphatic residue, wherein the $C_{1-4}$ aliphatic residue may be unsubstituted or mono- or polysubstituted; or a $C_{3-6}$-cycloaliphatic residue or a 3 to 6 membered heterocycloaliphatic residue linked via a carbon atom, in each case unsubstituted or mono- or polysubstituted;

$X^4$ and $X^5$ independently of one another represent H; $CH_2F$; $CHF_2$; $CF_3$; a $C_{1-4}$-aliphatic residue, wherein the $C_{1-4}$ aliphatic residue may be unsubstituted or mono- or polysubstituted; or a $C_{3-6}$-cycloaliphatic residue or a 3 to 6 membered heterocycloaliphatic residue, in each case unsubstituted or mono- or polysubstituted;

on the condition that if $X^4$ and/or $X^5$ denote(s) a 3 to 6 membered heterocycloaliphatic residue, the 3 to 6 membered heterocycloaliphatic residue is linked via a carbon atom, or

II, $X^2$ and $X^3$ and/or $X^4$ and $X^5$ in pairs, in each case independently of one another, together with the carbon atom connecting them, form a $C_{3-10}$-cycloaliphatic residue or a 3 to 10 membered heterocycloaliphatic residue, in each case unsubstituted or mono- or polysubstituted, and, if $X^2$ and $X^3$ together with the carbon atom connecting them do not form a $C_{3-10}$-cycloaliphatic residue or a 3 to 10 membered heterocycloaliphatic residue, in each case unsubstituted or mono- or polysubstituted, then $X^2$ and $X^3$ each independently of one another represent H; F; Cl; Br; I; CN; $CH_2F$; $CHF_2$; $CF_3$; OH; $OCH_2F$; $OCHF_2$; $OCF_3$; $SCF_3$; a $C_{1-4}$-aliphatic residue, or an O—$C_{1-4}$ aliphatic residue, wherein the $C_{1-4}$ aliphatic residue may in each case be unsubstituted or mono- or polysubstituted; or a $C_{3-6}$-cycloaliphatic residue or a 3 to 6 membered heterocycloaliphatic residue, in each case unsubstituted or mono- or polysubstituted, with the proviso that at least one of $X^2$ and $X^3$ denotes H or at least one of $X^2$ and $X^3$ denotes CN; $CH_2F$; $CHF_2$; $CF_3$; a $C_{1-4}$-aliphatic residue, wherein the $C_{1-4}$ aliphatic residue may be unsubstituted or mono- or polysubstituted; or a $C_{3-6}$-cycloaliphatic residue or a 3 to 6 membered heterocycloaliphatic residue linked via a carbon atom, in each case unsubstituted or mono- or polysubstituted, and, if $X^4$ and $X^5$ together with the carbon atom connecting them do not form a $C_{3-10}$-cycloaliphatic residue or a 3 to 10 membered heterocycloaliphatic residue, in each case unsubstituted or mono- or polysubstituted, then $X^4$ and $X^5$ each independently of one another represent H; $CH_2F$; $CHF_2$; $CF_3$; a $C_{1-4}$-aliphatic residue, wherein the $C_{1-4}$ aliphatic residue may be unsubstituted or mono- or polysubstituted; or a $C_{3-6}$-cycloaliphatic residue or a 3 to 6 membered heterocycloaliphatic residue, in each case unsubstituted or mono- or polysubstituted;

on the condition that if $X^4$ and/or $X^5$ denote(s) a 3 to 6 membered heterocycloaliphatic residue, the 3 to 6 membered heterocycloaliphatic residue is linked via a carbon atom, or

III, $X^2$ and $X^4$ together with the carbon atoms connecting them, form a $C_{3-10}$-cycloaliphatic residue or a 3 to 10 membered heterocycloaliphatic residue, in each case unsubstituted or mono- or polysubstituted, and $X^3$ represents H; F; Cl; Br; I; CN; $CH_2F$; $CHF_2$; $CF_3$; OH; $OCH_2F$; $OCHF_2$; $OCF_3$; $SCF_3$; a $C_{1-4}$-aliphatic residue, or an O—$C_{1-4}$ aliphatic residue, wherein the $C_{1-4}$ aliphatic residue may in each case be unsubstituted or mono- or polysubstituted; or a $C_{3-6}$-cycloaliphatic residue or a 3 to 6 membered heterocycloaliphatic residue, in each case unsubstituted or mono- or polysubstituted;

and $X^5$ represents H; $CH_2F$; $CHF_2$; $CF_3$; a $C_{1-4}$-aliphatic residue, wherein the $C_{1-4}$ aliphatic residue may be unsubstituted or mono- or polysubstituted; or a $C_{3-6}$-cycloaliphatic residue or a 3 to 6 membered heterocycloaliphatic residue, in each case unsubstituted or mono- or polysubstituted;

on the condition that if $X^5$ denotes a 3 to 6 membered heterocycloaliphatic residue, the 3 to 6 membered heterocycloaliphatic residue is linked via a carbon atom, wherein in $X^1$-$X^6$:

an "aliphatic group" and an "aliphatic residue" can in each case be branched or unbranched, saturated or unsaturated, a "cycloaliphatic residue" and a "heterocycloaliphatic residue" can in each case be saturated or unsaturated, "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue)$_2$, a NH—C(=O)—$C_{1-4}$ aliphatic residue, a N($C_{1-4}$-aliphatic residue)-C(=O)—$C_{1-4}$ aliphatic residue, a NH—S(=O)$_2$—$C_{1-4}$ aliphatic residue, a N($C_{1-4}$-aliphatic residue)-S(=O)$_2$—$C_{1-4}$ aliphatic residue, =O, OH, $OCH_2F$, $OCHF_2$, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)—$C_{1-4}$-aliphatic residue, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, a S(=O)$_2$—N($C_{1-4}$-aliphatic residue)$_2$, CN, $CH_2F$, $CHF_2$, $CF_3$, CHO, COOH, a $C_{1-4}$-aliphatic residue, $CH_2OH$, $CH_2$—$OCH_3$, $C_2H_4$—OH, $C_2H_4$—$OCH_3$ $CH_2$—$CF_3$, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

"mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue)$_2$, a NH—C(=O)—$C_{1-4}$ aliphatic residue, a N($C_{1-4}$-aliphatic residue)-C(=O)—$C_{1-4}$ aliphatic residue, a NH—S(=O)$_2$—$C_{1-4}$ aliphatic residue, a N($C_{1-4}$-aliphatic residue)-S(=O)$_2$—$C_{1-4}$ aliphatic residue, =O, OH, $OCH_2F$, $OCHF_2$, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)—$C_{1-4}$-aliphatic residue, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, a S(=O)$_2$—N($C_{1-4}$-aliphatic residue)$_2$, CN, $CH_2F$, $CHF_2$, $CF_3$, CHO, COOH, a $C_{1-4}$-aliphatic residue, $CH_2OH$, $CH_2$—$OCH_3$, $C_2H_4$—OH, $C_2H_4$—$OCH_3$ $CH_2$—$CF_3$, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

said compound being in the form of a free compound, the racemate, a mixture of enantiomers, diastereomers, or of enantiomers and diastereomers in any mixing ratio, or of an individual enantiomer or diastereomer, or in the form of a salt of physiologically acceptable acids or bases.

2. The compound according to claim 1, wherein $X^1$ represents a $C_{2-6}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
or represents a $C_{3-6}$-cycloaliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
and wherein the $C_{3-6}$-cycloaliphatic residue may optionally be bridged via a $C_{1-4}$ aliphatic group, which in turn may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
or represents $OX^6$, wherein
$X^6$ represents a $C_{1-6}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue;
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
$X^2$, $X^3$, $X^4$ and $X^5$ satisfy one of the clauses I, II or III below:
I,
$X^2$ and $X^3$ independently of one another represent H; F; Cl; Br; I; CN; $CH_2F$; $CHF_2$; $CF_3$; OH; $OCH_2F$; $OCHF_2$; $OCF_3$; $SCF_3$; a $C_{1-4}$-aliphatic residue, or an O—$C_{1-4}$ aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
or represent a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
with the proviso that at least one of $X^2$ and $X^3$ denotes H or at least one of $X^2$ and $X^3$ denotes CN; $CH_2F$; $CHF_2$; $CF_3$; a $C_{1-4}$-aliphatic residue, wherein the $C_{1-4}$-aliphatic residue may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue; or a $C_{3-6}$-cycloaliphatic residue or a 3 to 6 membered heterocycloaliphatic residue linked via a carbon atom, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
$X^4$ and $X^5$ independently of one another represent H; $CH_2F$; $CHF_2$; $CF_3$; or a $C_{1-4}$-aliphatic residue,
wherein the $C_{1-4}$-aliphatic residue may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
or represent a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
on the condition that if $X^4$ and/or $X^5$ denote(s) a 3 to 6 membered heterocycloaliphatic residue, the 3 to 6 membered heterocycloaliphatic residue is linked via a carbon atom,
wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
or
II,
$X^2$ and $X^3$
and/or $X^4$ and $X^5$
in pairs, in each case independently of one another, together with the carbon atom connecting them, form a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
and if $X^2$ and $X^3$ together with the carbon atom connecting them do not form a $C_{3-10}$-cycloaliphatic residue or a 3 to 10 membered heterocycloaliphatic residue, in each case unsubstituted or mono- or polysubstituted, then $X^2$ and $X^3$ each independently of one another represent H; F; Cl; Br; I; CN; $CH_2F$; $CHF_2$; $CF_3$; OH; $OCH_2F$; $OCHF_2$; $OCF_3$; $SCF_3$; a $C_{1-4}$-aliphatic residue, or an O—$C_{1-4}$ aliphatic residue,
  wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
or represent a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
with the proviso that at least one of $X^2$ and $X^3$ denotes H or at least one of $X^2$ and $X^3$ denotes CN; $CH_2F$; $CHF_2$; $CF_3$; a $C_{1-4}$-aliphatic residue, wherein the $C_{1-4}$-aliphatic residue may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue; or represent a $C_{3-6}$-cycloaliphatic residue or a 3 to 6 membered heterocycloaliphatic residue linked via a carbon atom, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
and if $X^4$ and $X^5$ together with the carbon atom connecting them do not form a $C_{3-10}$-cycloaliphatic residue or a 3 to 10 membered heterocycloaliphatic residue, in each case unsubstituted or mono- or polysubstituted, then $X^4$ and $X^5$ each independently of one another represent H; $CH_2F$; $CHF_2$; $CF_3$; a $C_{1-4}$-aliphatic residue,
  wherein the $C_{1-4}$-aliphatic residue may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
or represent a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
  on the condition that if $X^4$ and/or $X^5$ denote(s) a 3 to 6 membered heterocycloaliphatic residue, the 3 to 6 membered heterocycloaliphatic residue is linked via a carbon atom,
  wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
or
III,
$X^2$ and $X^4$ together with the carbon atoms connecting them, form a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
and the remaining substituent $X^3$ represents H; F; Cl; Br; I; CN; $CH_2F$; $CHF_2$; $CF_3$; OH; $OCH_2F$; $OCHF_2$; $OCF_3$; $SCF_3$; a $C_{1-4}$-aliphatic residue, or an O—$C_{1-4}$ aliphatic residue,
  wherein the $C_{1-4}$-aliphatic residue in each case may be unsubstituted or mono- or polysubstituted with at least one substituent selected from the group consisting of F, Cl, Br, I, OH, $OCH_2F$, $OCHF_2$, $OCF_3$, $CH_2F$, $CHF_2$, $CF_3$ and an unsubstituted O—$C_{1-4}$-aliphatic residue,
or represents a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCH_2F$, $OCHF_2$, $OCF_3$, SH, $SCF_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—$C_{1-4}$-aliphatic residue,
and the remaining substituent $X^5$ represents H; CH$_2$F; CHF$_2$; CF$_3$; OCH$_2$F; OCHF$_2$; OCF$_3$; SCF$_3$; a $C_{1-4}$-aliphatic residue,
  wherein the $C_{1-4}$-aliphatic residue may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—$C_{1-4}$-aliphatic residue,
  or represents a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$-aliphatic residue, OCH$_2$F, OCHF$_2$, OCF$_3$, SH, SCF$_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
  on the condition that if $X^5$ denotes a 3 to 6 membered heterocycloaliphatic residue, the 3 to 6 membered heterocycloaliphatic residue is linked via a carbon atom,
    wherein the $C_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—$C_{1-4}$-aliphatic residue.

3. The compound according to claim 1, wherein
$X^1$ represents a $C_{2-6}$-aliphatic residue, unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$-aliphatic residue, OCH$_2$F, OCHF$_2$, OCF$_3$, SH, SCF$_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—$C_{1-4}$-aliphatic residue,
  or represents a $C_{3-6}$-cycloaliphatic residue, unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$-aliphatic residue, OCH$_2$F, OCHF$_2$, OCF$_3$, SH, SCF$_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
    wherein the $C_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—$C_{1-4}$-aliphatic residue,
  or represents OX$^6$, wherein
    $X^6$ represents a $C_{1-6}$-aliphatic residue, unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$-aliphatic residue, OCH$_2$F, OCHF$_2$, OCF$_3$, SH, SCF$_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
      wherein the $C_{1-4}$-aliphatic residue in each case may be unsubstituted or mono- or polysubstituted with at least one substituent selected from the group consisting of F, Cl, Br, I, OH, OCH$_2$F, OCHF$_2$, OCF$_3$, CH$_2$F, CHF$_2$, CF$_3$ and an unsubstituted O—$C_{1-4}$-aliphatic residue.

4. The compound according to claim 1, wherein
$X^1$ represents a $C_{2-6}$-aliphatic residue, unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$-aliphatic residue, OCH$_2$F, OCHF$_2$, OCF$_3$, SH, SCF$_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
  wherein the $C_{1-4}$-aliphatic residue is in each case unsubstituted,
  or represents a $C_{3-6}$-cycloaliphatic residue, unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$-aliphatic residue, OCH$_2$F, OCHF$_2$, OCF$_3$, SH, SCF$_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
  wherein the $C_{1-4}$-aliphatic residue is in each case unsubstituted,
  or represents OX$^6$, wherein
    $X^6$ represents a $C_{1-6}$-aliphatic residue, unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$-aliphatic residue, OCH$_2$F, OCHF$_2$, OCF$_3$, SH, SCF$_3$, a S—$C_{1-4}$-aliphatic residue, a S(=O)—$C_{1-4}$-aliphatic residue, a S(=O)$_2$—$C_{1-4}$-aliphatic residue, CN, and a $C_{1-4}$-aliphatic residue,
      wherein the $C_{1-4}$-aliphatic residue is in each case unsubstituted.

5. The compound according to claim 1, wherein
$X^1$ represents a $C_{2-6}$-aliphatic residue, unsubstituted or mono- or polysubstituted with at least one substituent selected from the group consisting of F, Cl, Br, I, OH, and an unsubstituted O—$C_{1-4}$-aliphatic residue,
  or represents a $C_{3-6}$-cycloaliphatic residue, unsubstituted or mono- or polysubstituted with at least one substituent selected from the group consisting of F, Cl, Br, I, OH, and an unsubstituted O—$C_{1-4}$-aliphatic residue,
  or represents OX$^6$, wherein
    $X^6$ represents a $C_{1-4}$-aliphatic residue, unsubstituted or mono- or polysubstituted with at least one substituent selected from the group consisting of F, Cl, Br, I, OH, and an unsubstituted O—$C_{1-4}$-aliphatic residue.

6. The compound according to claim 1, wherein
$X^1$ represents ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, ethenyl or propenyl (—$CH_2CH$=$CH_2$, —CH=CH—$CH_3$, —C(=$CH_2$)—$CH_3$),
cyclopropyl, cyclobutyl, cyclopentyl, or cyclohexyl,
or represents $OX^6$, wherein
$X^6$ represents methyl, ethyl, n-propyl, 2-propyl, n-butyl, isobutyl, sec.-butyl, tert.-butyl, $CH_2OH$, $CH_2OCH_3$, $CH_2CH_2OH$, $CH_2CH_2OCH_3$, and $CH(OH)CH_2OH$.

7. The compound according to claim 1, wherein $X^2$, $X^3$, $X^4$ and $X^5$ satisfy one of the clauses I, II or III below:

I, $X^2$ and $X^3$ independently of one another represent H; F; Cl; Br; I; $CH_2F$; $CHF_2$; $CF_3$; OH; $OCH_2F$; $OCHF_2$; $OCF_3$; a $C_{1-4}$-aliphatic residue, or an O—$C_{1-4}$ aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, or represent a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, with the proviso that at least one of $X^2$ and $X^3$ denotes H or at least one of $X^2$ and $X^3$ denotes $CH_2F$; $CHF_2$; $CF_3$; a $C_{1-4}$-aliphatic residue, wherein the $C_{1-4}$-aliphatic residue may be unsubstituted or mono- or polysubstituted with at least one substituent selected from the group consisting of F, Cl, Br, I, OH, and an unsubstituted O—$C_{1-4}$-aliphatic residue; or a $C_{3-6}$-cycloaliphatic residue or a 3 to 6 membered heterocycloaliphatic residue linked via a carbon atom, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, $X^4$ and $X^5$ independently of one another represent H; $CH_2F$; $CHF_2$; $CF_3$; a $C_{1-4}$-aliphatic residue,
wherein the $C_{1-4}$-aliphatic residue may be unsubstituted or mono- or polysubstituted with at least one substituent selected from the group consisting of F, Cl, Br, I, OH, and an unsubstituted O—$C_{1-4}$-aliphatic residue, or represent a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, on the condition that if $X^4$ and/or $X^5$ denote(s) a 3 to 6 membered heterocycloaliphatic residue, the 3 to 6 membered heterocycloaliphatic residue is linked via a carbon atom, or

II, $X^2$ and $X^3$ and/or $X^4$ and $X^5$ in pairs, in each case independently of one another, together with the carbon atom connecting them, form a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, and if $X^2$ and $X^3$ together with the carbon atom connecting them do not form a $C_{3-10}$-cycloaliphatic residue or a 3 to 10 membered heterocycloaliphatic residue, in each case unsubstituted or mono- or polysubstituted, then $X^2$ and $X^3$ each independently of one another represent H; F; Cl; Br; I; $CH_2F$; $CHF_2$; $CF_3$; OH; $OCH_2F$; $OCHF_2$; $OCF_3$; a $C_{1-4}$-aliphatic residue, or an O—$C_{1-4}$ aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, or represent a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, with the proviso that at least one of $X^2$ and $X^3$ denotes H or at least one of $X^2$ and $X^3$ denotes $CH_2F$; $CHF_2$; $CF_3$; a $C_{1-4}$-aliphatic residue, wherein the $C_{1-4}$-aliphatic residue may be unsubstituted or mono- or polysubstituted with at least one substituent selected from the group consisting of F, Cl, Br, I, OH, and an unsubstituted O—$C_{1-4}$-aliphatic residue; or a $C_{3-6}$-cycloaliphatic residue or a 3 to 6 membered heterocycloaliphatic residue linked via a carbon atom, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, $OCH_2F$, $OCHF_2$, $OCF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, and if $X^4$ and $X^5$ together with the carbon atom connecting them do not form a $C_{3-10}$-cycloaliphatic residue or a 3 to 10 membered heterocycloaliphatic residue, in each case unsubstituted or mono- or polysubstituted, then X⁴ and X⁵ each independently of one another represent H; CH₂F; CHF₂; CF₃; a C₁₋₄-aliphatic residue,
wherein the C₁₋₄-aliphatic residue may be unsubstituted or mono- or polysubstituted with at least one substituent selected from the group consisting of F, Cl, Br, I, OH, and an unsubstituted O—C₁₋₄-aliphatic residue,
or represent a C₃₋₆-cycloaliphatic residue or a 3 to 6 membered heterocycloaliphatic residue, in each case unsubstituted or mono- or polysubstituted with at least one substituent selected from the group consisting of F, Cl, Br, I, OH, an O—C₁₋₄-aliphatic residue, CH₂F, CHF₂, CF₃, OCH₂F, OCHF₂, OCF₃, and a C₁₋₄-aliphatic residue,
on the condition that if X⁴ and/or X⁵ denote(s) a 3 to 6 membered heterocycloaliphatic residue, the 3 to 6 membered heterocycloaliphatic residue is linked via a carbon atom,
wherein the C₁₋₄-aliphatic residue in each case may be unsubstituted or mono- or polysubstituted with at least one substituent selected from the group consisting of F, Cl, Br, I, OH, and an unsubstituted O—C₁₋₄-aliphatic residue,
or
III,
X² and X⁴ together with the carbon atoms connecting them, form a C₃₋₁₀-cycloaliphatic residue or a 3 to 10 membered heterocycloaliphatic residue, in each case unsubstituted or mono- or polysubstituted with at least one substituent selected from the group consisting of F, Cl, Br, I, OH, an O—C₁₋₄-aliphatic residue, CH₂F, CHF₂, CF₃, OCH₂F, OCHF₂, OCF₃, and a C₁₋₄-aliphatic residue,
wherein the C₁₋₄-aliphatic residue in each case may be unsubstituted or mono- or polysubstituted with at least one substituent selected from the group consisting of F, Cl, Br, I, OH, and an unsubstituted O—C₁₋₄-aliphatic residue,
and the remaining substituent X³ represents H; F; Cl; Br; I; CH₂F; CHF₂; CF₃; OH; OCH₂F; OCHF₂; OCF₃; a C₁₋₄-aliphatic residue, or an O—C₁₋₄ aliphatic residue,
wherein the C₁₋₄-aliphatic residue in each case may be unsubstituted or mono- or polysubstituted with at least one substituent selected from the group consisting of F, Cl, Br, I, OH, and an unsubstituted O—C₁₋₄-aliphatic residue,
or represents a C₃₋₆-cycloaliphatic residue or a 3 to 6 membered heterocycloaliphatic residue, in each case unsubstituted or mono- or polysubstituted with at least one substituent selected from the group consisting of F, Cl, Br, I, OH, an O—C₁₋₄-aliphatic residue, CH₂F, CHF₂, CF₃, OCH₂F, OCHF₂, OCF₃, and a C₁₋₄-aliphatic residue,
wherein the C₁₋₄-aliphatic residue in each case may be unsubstituted or mono- or polysubstituted with at least one substituent selected from the group consisting of F, Cl, Br, I, OH, and an unsubstituted O—C₁₋₄-aliphatic residue,
and the remaining substituent X⁵ represents H; CH₂F; CHF₂; CF₃; a C₁₋₄-aliphatic residue,
wherein the C₁₋₄-aliphatic residue may be unsubstituted or mono- or polysubstituted with at least one substituent selected from the group consisting of F, Cl, Br, I, OH, and an unsubstituted O—C₁₋₄-aliphatic residue,
or represents a C₃₋₆-cycloaliphatic residue or a 3 to 6 membered heterocycloaliphatic residue, in each case unsubstituted or mono- or polysubstituted with at least one substituent selected from the group consisting of F, Cl, Br, I, OH, an O—C₁₋₄-aliphatic residue, CH₂F, CHF₂, CF₃, OCH₂F, OCHF₂, OCF₃, and a C₁₋₄-aliphatic residue,
on the condition that if X⁵ denotes a 3 to 6 membered heterocycloaliphatic residue, the 3 to 6 membered heterocycloaliphatic residue is linked via a carbon atom,
wherein the C₁₋₄-aliphatic residue in each case may be unsubstituted or mono- or polysubstituted with at least one substituent selected from the group consisting of F, Cl, Br, I, OH, and an unsubstituted O—C₁₋₄-aliphatic residue.

8. The compound according to claim 1, wherein X², X³, X⁴ and X⁵ satisfy one of the clauses I, II or III below:
I,
X² and X³ independently of one another represent H; F; Cl; Br; I; CH₂F; CHF₂; CF₃; OH; a C₁₋₄-aliphatic residue, or an O—C₁₋₄ aliphatic residue,
wherein the C₁₋₄-aliphatic residue is in each case unsubstituted,
or represent a C₃₋₆-cycloaliphatic residue or a 3 to 6 membered heterocycloaliphatic residue, in each case unsubstituted,
with the proviso that at least one of X² and X³ denotes H or at least one of X² and X³ denotes CH₂F; CHF₂; CF₃; a C₁₋₄-aliphatic residue, wherein the C₁₋₄-aliphatic residue is unsubstituted, or represent a C₃₋₆-cycloaliphatic residue or a 3 to 6 membered heterocycloaliphatic residue linked via a carbon atom, in each case unsubstituted,
X⁴ and X⁵ independently of one another represent H; CH₂F; CHF₂; CF₃; a C₁₋₄-aliphatic residue,
wherein the C₁₋₄-aliphatic residue is unsubstituted,
or represent a C₃₋₆-cycloaliphatic residue or a 3 to 6 membered heterocycloaliphatic residue, in each case unsubstituted,
on the condition that if X⁴ and/or X⁵ denote(s) a 3 to 6 membered heterocycloaliphatic residue, the 3 to 6 membered heterocycloaliphatic residue is linked via a carbon atom,
or
II,
X² and X³
and/or X⁴ and X⁵
in pairs, in each case independently of one another, together with the carbon atom connecting them, form a C₃₋₁₀-cycloaliphatic residue or a 3 to 10 membered heterocycloaliphatic residue, in each case unsubstituted or mono- or polysubstituted with at least one substituent selected from the group consisting of F, Cl, Br, I, OH, an O—C₁₋₄-aliphatic residue, CH₂F, CHF₂, CF₃, and a C₁₋₄-aliphatic residue,
wherein the C₁₋₄-aliphatic residue is in each case unsubstituted,
and if X² and X³ together with the carbon atom connecting them do not form a C₃₋₁₀-cycloaliphatic residue or a 3 to 10 membered heterocycloaliphatic residue, in each case unsubstituted or mono- or polysubstituted, then X² and X³ each independently of one another represent H; F; Cl; Br; I; CH₂F; CHF₂; CF₃; OH; a C₁₋₄-aliphatic residue, or an O—C₁₋₄ aliphatic residue,
wherein the C₁₋₄-aliphatic residue is in each unsubstituted,
or represent a C₃₋₆-cycloaliphatic residue or a 3 to 6 membered heterocycloaliphatic residue, in each case unsubstituted, with the proviso that at least one of $X^2$ and $X^3$ denotes H or at least one of $X^2$ and $X^3$ denotes $CH_2F$; $CHF_2$; $CF_3$; a $C_{1-4}$-aliphatic residue, wherein the $C_{1-4}$-aliphatic residue is unsubstituted; or a $C_{3-6}$-cycloaliphatic residue or a 3 to 6 membered heterocycloaliphatic residue linked via a carbon atom, in each case unsubstituted, and if $X^4$ and $X^5$ together with the carbon atom connecting them do not form a $C_{3-10}$-cycloaliphatic residue or a 3 to 10 membered heterocycloaliphatic residue, in each case unsubstituted or mono- or polysubstituted, then $X^4$ and $X^5$ each independently of one another represent H; $CH_2F$; $CHF_2$; $CF_3$; a $C_{1-4}$-aliphatic residue,
  wherein the $C_{1-4}$-aliphatic residue is unsubstituted,
or represent a $C_{3-6}$-cycloaliphatic residue or a 3 to 6 membered heterocycloaliphatic residue, in each case unsubstituted,
  on the condition that if $X^4$ and/or $X^5$ denote(s) a 3 to 6 membered heterocycloaliphatic residue, the 3 to 6 membered heterocycloaliphatic residue is linked via a carbon atom, or

III, $X^2$ and $X^4$ together with the carbon atoms connecting them, form a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, an O—$C_{1-4}$-aliphatic residue, $CH_2F$, $CHF_2$, $CF_3$, and a $C_{1-4}$-aliphatic residue,
  wherein the $C_{1-4}$-aliphatic residue is in each case unsubstituted,
and the remaining substituent $X^3$ represents H; F; Cl; Br; I; $CH_2F$; $CHF_2$; $CF_3$; OH; a $C_{1-4}$-aliphatic residue, or an O—$C_{1-4}$ aliphatic residue,
  wherein the $C_{1-4}$-aliphatic residue is in each case unsubstituted,
or represents a $C_{3-6}$-cycloaliphatic residue or a 3 to 6 membered heterocycloaliphatic residue, in each case unsubstituted,
and the remaining substituent $X^5$ represents H; $CH_2F$; $CHF_2$; $CF_3$; a $C_{1-4}$-aliphatic residue,
  wherein the $C_{1-4}$-aliphatic residue is unsubstituted,
or represents a $C_{3-6}$-cycloaliphatic residue or a 3 to 6 membered heterocycloaliphatic residue, in each case unsubstituted,
  on the condition that if $X^5$ denotes a 3 to 6 membered heterocycloaliphatic residue, the 3 to 6 membered heterocycloaliphatic residue is linked via a carbon atom.

9. The compound according to claim 1, wherein $X^2$, $X^3$, $X^4$ and $X^5$ satisfy one of the clauses I, II or III below:

I, $X^2$ and $X^3$ independently of one another represent H; OH; an unsubstituted $C_{1-4}$-aliphatic residue, or an unsubstituted O—$C_{1-4}$ aliphatic residue, with the proviso that at least one of $X^2$ and $X^3$ denotes H or at least one of $X^2$ and $X^3$ denotes an unsubstituted $C_{1-4}$-aliphatic residue, $X^4$ and $X^5$ independently of one another represent H; $CH_2F$; $CHF_2$; $CF_3$; an unsubstituted $C_{1-4}$-aliphatic residue, or

II, $X^2$ and $X^3$
or $X^4$ and $X^5$
  in pairs, in each case independently of one another, together with the carbon atom connecting them, form a $C_{3-10}$-cycloaliphatic residue, unsubstituted or mono- or polysubstituted with at least one substituent selected from the group consisting of F, Cl, Br, I, OH, $CH_2F$, $CHF_2$, $CF_3$, an unsubstituted O—$C_{1-4}$-aliphatic residue, and an unsubstituted $C_{1-4}$-aliphatic residue,
and if $X^2$ and $X^3$ together with the carbon atom connecting them do not form a $C_{3-10}$-cycloaliphatic residue, unsubstituted or mono- or polysubstituted, then $X^2$ and $X^3$ each independently of one another represent H; OH; an unsubstituted $C_{1-4}$-aliphatic residue, or an unsubstituted O—$C_{1-4}$ aliphatic residue, with the proviso that at least one of $X^2$ and $X^3$ denotes H or at least one of $X^2$ and $X^3$ denotes an unsubstituted $C_{1-4}$-aliphatic residue,
and if $X^4$ and $X^5$ together with the carbon atom connecting them do not form a $C_{3-10}$-cycloaliphatic residue, unsubstituted or mono- or polysubstituted, then $X^4$ and $X^5$ each independently of one another represent H; $CH_2F$; $CHF_2$; $CF_3$; an unsubstituted $C_{1-4}$-aliphatic residue, or

III, $X^2$ and $X^4$ together with the carbon atoms connecting them, form a $C_{3-10}$-cycloaliphatic residue, unsubstituted or mono- or polysubstituted with at least one substituent selected from the group consisting of F, Cl, Br, I, OH, an unsubstituted O—$C_{1-4}$-aliphatic residue, $CH_2F$, $CHF_2$, $CF_3$, and a an unsubstituted $C_{1-4}$-aliphatic residue,
and the remaining substituent $X^3$ represents H; F; Cl; Br; I; OH; an unsubstituted $C_{1-4}$-aliphatic residue, or an unsubstituted O—$C_{1-4}$ aliphatic residue,
and the remaining substituent $X^5$ represents H; $CH_2F$; $CHF_2$; $CF_3$; an unsubstituted $C_{1-4}$-aliphatic residue.

10. The compound according to claim 1, wherein $X^2$, $X^3$, $X^4$ and $X^5$ satisfy one of the clauses I, II or III below:

I, $X^2$ and $X^3$ independently of one another represent H; methyl; ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, $OCH_3$ or $OCH_2CH_3$, with the proviso that at least one of $X^2$ and $X^3$ denotes H or at least one of $X^2$ and $X^3$ denotes methyl; ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, or $C(CH_3)_2(C_2H_5)$, $X^4$ and $X^5$ independently of one another represent H; methyl; ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, $CH_2F$; $CHF_2$; $CF_3$;

or

II, $X^2$ and $X^3$
or $X^4$ and $X^5$
  in pairs, in each case independently of one another, together with the carbon atom connecting them, form a $C_{3-6}$-cycloaliphatic residue selected from the group consisting of cyclopropyl, cyclobutyl, cyclopentyl and cyclohexyl, unsubstituted or mono- or polysubstituted with at least one substituent selected from the group consisting of F, Cl, Br, I, OH, methyl; ethyl, n-propyl, 2-propyl, n-butyl, isobutyl, sec.-butyl, tert.-butyl, $CH_2F$, $CHF_2$, $CF_3$, $OCH_3$ and $OCH_2CH_3$,
and if $X^2$ and $X^3$ together with the carbon atom connecting them do not form a cyclopropyl, cyclobutyl, cyclopentyl or cyclohexyl, in each case unsubstituted or mono- or polysubstituted, then $X^2$ and $X^3$ each independently of one another represents H;

methyl; ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, OCH$_3$ or OCH$_2$CH$_3$, with the proviso that at least one of X$^2$ and X$^3$ denotes H or at least one of X$^2$ and X$^3$ denotes methyl; ethyl, n-propyl, 2-propyl, n-butyl, isobutyl, sec.-butyl, tert.-butyl, n-pentyl, isopentyl, neopentyl, n-hexyl, CH$_2$—CH(CH$_3$)(C$_2$H$_5$), or C(CH$_3$)$_2$(C$_2$H$_5$), and if X$^4$ and X$^5$ together with the carbon atom connecting them do not form a cyclopropyl, cyclobutyl, cyclopentyl or cyclohexyl, in each case unsubstituted or mono- or polysubstituted, then X$^4$ and X$^5$ each independently of one another represents H; methyl; ethyl, n-propyl, 2-propyl, n-butyl, isobutyl, sec.-butyl, tert.-butyl, n-pentyl, isopentyl, neopentyl, n-hexyl, CH$_2$—CH(CH$_3$)(C$_2$H$_5$), C(CH$_3$)$_2$(C$_2$H$_5$), CH$_2$F; CHF$_2$; CF$_3$;

or

III,

X$^2$ and X$^4$ together with the carbon atoms connecting them, form a C$_{3-6}$-cycloaliphatic residue selected from the group consisting of cyclopropyl, cyclobutyl, cyclopentyl and cyclohexyl, unsubstituted or mono- or polysubstituted with at least one substituent selected from the group consisting of F, Cl, Br, I, OH, methyl; ethyl, n-propyl, 2-propyl, n-butyl, isobutyl, sec.-butyl, tert.-butyl, CH$_2$F, CHF$_2$, CF$_3$, OCH$_3$ and OCH$_2$CH$_3$, and the respective remaining substituent of X$^3$ represents H; methyl; ethyl, n-propyl, 2-propyl, n-butyl, isobutyl, sec.-butyl, tert.-butyl, n-pentyl, isopentyl, neopentyl, n-hexyl, CH$_2$—CH(CH$_3$)(C$_2$H$_5$), C(CH$_3$)$_2$(C$_2$H$_5$), OCH$_3$ or OCH$_2$CH$_3$, and the respective remaining substituent X$^5$ represents H; methyl; ethyl, n-propyl, 2-propyl, n-butyl, isobutyl, sec.-butyl, tert.-butyl, n-pentyl, isopentyl, neopentyl, n-hexyl, CH$_2$—CH(CH$_3$)(C$_2$H$_5$), C(CH$_3$)$_2$(C$_2$H$_5$), CH$_2$F; CHF$_2$; CF$_3$.

11. The compound according to claim 1, wherein

X$^1$ represents ethyl, n-propyl, 2-propyl, n-butyl, isobutyl, sec.-butyl, tert.-butyl, cyclopropyl, cyclobutyl, cyclopentyl, or cyclohexyl, or represents OX$^6$, wherein X$^6$ represents methyl, ethyl, n-propyl, 2-propyl, n-butyl, isobutyl, sec.-butyl, or tert.-butyl, X$^2$, X$^3$, X$^4$ and X$^5$ satisfy one of the clauses I, II or III below:

I,

X$^2$ and X$^3$ independently of one another represent H; methyl; ethyl, n-propyl, 2-propyl, n-butyl, isobutyl, sec.-butyl, or tert.-butyl, X$^4$ and X$^5$ independently of one another represent H; methyl; ethyl, n-propyl, 2-propyl, n-butyl, isobutyl, sec.-butyl, tert.-butyl, CH$_2$F, CHF$_2$, or CF$_3$;

or

II,

X$^2$ and X$^3$ or X$^4$ and X$^5$ in pairs, in each case independently of one another, together with the carbon atom connecting them, form a C$_{3-6}$-cycloaliphatic residue selected from the group consisting of cyclopropyl, cyclobutyl, cyclopentyl and cyclohexyl, unsubstituted or mono- or polysubstituted with at least one substituent selected from the group consisting of OH, methyl; ethyl, n-propyl, 2-propyl, n-butyl, isobutyl, sec.-butyl, CH$_2$F, CHF$_2$, CF$_3$, OCH$_3$ and OCH$_2$CH$_3$, and if X$^2$ and X$^3$ together with the carbon atom connecting them do not form a cyclopropyl, cyclobutyl, cyclopentyl or cyclohexyl, in each case unsubstituted or mono- or polysubstituted, then X$^2$ and X$^3$ in dependently of one another represent H; methyl; ethyl, n-propyl, 2-propyl, n-butyl, isobutyl, sec.-butyl, or tert.-butyl, and if X$^4$ and X$^5$ together with the carbon atom connecting them do not form a cyclopropyl, cyclobutyl, cyclopentyl or cyclohexyl, in each case unsubstituted or mono- or polysubstituted, then X$^4$ and X$^5$ independently of one another represent H; methyl; ethyl, n-propyl, 2-propyl, n-butyl, isobutyl, sec.-butyl, tert.-butyl, CH$_2$F, CHF$_2$, or CF$_3$;

or

III,

X$^2$ and X$^4$ together with the carbon atoms connecting them, form a C$_{3-6}$-cycloaliphatic residue selected from the group consisting of cyclopropyl, cyclobutyl, cyclopentyl and cyclohexyl, unsubstituted or mono- or polysubstituted with at least one substituent selected from the group consisting of OH, methyl; ethyl, n-propyl, 2-propyl, n-butyl, isobutyl, sec.-butyl, tert.-butyl, CH$_2$F, CHF$_2$, CF$_3$, OCH$_3$ and OCH$_2$CH$_3$, and X$^3$ represents H; methyl; ethyl, n-propyl, 2-propyl, n-butyl, isobutyl, sec.-butyl, or tert.-butyl, and X$^5$ represents H; methyl; ethyl, n-propyl, 2-propyl, n-butyl, isobutyl, sec.-butyl, tert.-butyl, CH$_2$F, CHF$_2$, or CF$_3$.

12. The compound according to claim 1, which is selected from the group consisting of 1  2-Cyclopropyl-N-(3-hydroxy-4,4-dimethyl-pentyl)-4-methyl-6-morpholin-4-yl-pyridine-3-carboxylic acid amide;

2  2-Cyclopropyl-N-[[(1S,2R)-2-hydroxy-cyclohexyl]-methyl]-4-methyl-6-morpholin-4-yl-pyridine-3-carboxylic acid amide;

3  2-Cyclopropyl-N-[[(1R,2S)-2-hydroxy-cyclohexyl]-methyl]-4-methyl-6-morpholin-4-yl-pyridine-3-carboxylic acid amide;

4  2-Cyclopropyl-N-([2-hydroxy-cyclopentyl]-methyl)-4-methyl-6-morpholin-4-yl-pyridine-3-carboxylic acid amide;

5  N-(3-Hydroxy-4,4-dimethyl-pentyl)-2-isopropyl-4-methyl-6-morpholin-4-yl-pyridine-3-carboxylic acid amide;

6  2-Isopropyl-4-methyl-6-morpholin-4-yl-N-(4,4,4-trifluoro-3-hydroxy-butyl)-pyridine-3-carboxylic acid amide; and 7  N-[[(1S,2R)-2-Hydroxy-cyclohexyl]-methyl]-2-isopropyl-4-methyl-6-morpholin-4-yl-pyridine-3-carboxylic acid amide;

optionally in the form of a single stereoisomer or a mixture of stereoisomers, in the form of the free compound and/or a physiologically acceptable salt thereof.

13. A pharmaceutical composition comprising at least one compound according to claim 1, optionally in the form of a single stereoisomer or a mixture of stereoisomers, in the form of the free compound and/or a physiologically acceptable salt thereof, and optionally at least one pharmaceutically acceptable auxiliary.

14. A method for the treatment of a disorder and/or a disease that is mediated, at least in part, by KCNQ2/3 K$^+$ channels, said disorder and/or disease being selected from the group consisting of pain, acute pain, chronic pain, neuropathic pain, muscular pain, visceral pain and inflammatory pain, and epilepsy, and said method comprising administering to a patient in need of such treatment an effective amount therefor of a compound according to claim 1.

* * * * *